United States Patent
Crosignani et al.

(10) Patent No.: US 9,758,505 B2
(45) Date of Patent: Sep. 12, 2017

(54) 3-(INDOL-3-YL)-PYRIDINE DERIVATIVES, PHARMACEUTICAL COMPOSITIONS AND METHODS FOR USE

(71) Applicant: ITEOS THERAPEUTICS, Charleroi (BE)

(72) Inventors: Stefano Crosignani, Nivelles (BE); Sandra Cauwenberghs, Halle (BE); Gregory Driessens, Watermael-Boitsfort (BE); Frederik Deroose, Destelbergen (BE)

(73) Assignee: iTeos Therapeutics, Charleroi (BE)

( * ) Notice: Subject to any disclaimer, the term of this patent is extended or adjusted under 35 U.S.C. 154(b) by 0 days.

(21) Appl. No.: 14/619,589

(22) Filed: Feb. 11, 2015

(65) Prior Publication Data

US 2015/0225367 A1 Aug. 13, 2015

Related U.S. Application Data

(60) Provisional application No. 61/996,974, filed on Feb. 12, 2014.

(30) Foreign Application Priority Data

Feb. 12, 2014 (EP) .................................... 14154911
Nov. 6, 2014 (BE) .................................... 2014/0774

(51) Int. Cl.
| | | |
|---|---|---|
| *C07D 401/04* | (2006.01) |
| *A61K 31/4439* | (2006.01) |
| *A61K 31/496* | (2006.01) |
| *C07D 401/14* | (2006.01) |
| *C07D 498/04* | (2006.01) |
| *C07D 471/04* | (2006.01) |
| *C07D 413/14* | (2006.01) |
| *C07D 405/14* | (2006.01) |

(52) U.S. Cl.
CPC ......... *C07D 401/04* (2013.01); *C07D 401/14* (2013.01); *C07D 405/14* (2013.01); *C07D 413/14* (2013.01); *C07D 471/04* (2013.01); *C07D 498/04* (2013.01)

(58) Field of Classification Search
None
See application file for complete search history.

(56) References Cited

U.S. PATENT DOCUMENTS

| | | |
|---|---|---|
| 7,151,108 B2 | 12/2006 | Prudhomme |
| 2005/0165005 A1 | 7/2005 | Genevois |
| 2011/0166143 A1 | 7/2011 | Bretschneider |

FOREIGN PATENT DOCUMENTS

| | | |
|---|---|---|
| CN | 101265259 A | 9/2008 |
| EP | 1411057 A1 | 4/2004 |
| WO | WO00/43393 A1 | 7/2000 |
| WO | WO-03/082869 | 10/2003 |
| WO | WO2005/058035 A1 | 6/2005 |
| WO | WO2006/005608 A1 | 1/2006 |
| WO | WO2007/039580 A1 | 4/2007 |
| WO | WO2007/045622 A1 | 4/2007 |
| WO | WO2007/050963 A1 | 5/2007 |
| WO | WO2008/073306 A1 | 6/2008 |
| WO | WO2008/094992 A2 | 8/2008 |
| WO | WO2008/115804 A1 | 9/2008 |
| WO | WO2010/008427 A1 | 1/2010 |
| WO | WO2010/096389 A1 | 8/2010 |
| WO | WO2010/136491 A1 | 12/2010 |
| WO | WO2011/038163 A1 | 3/2011 |
| WO | WO2012/161877 A1 | 11/2012 |

OTHER PUBLICATIONS

Chen et al. Synthesis and antiproliferative activity of novel 2-aryl-4-benzoyl-imidazole derivatives targeting tubulin polymerization. Bioorganic & Medicinal Chemistry. vol. 19(16):4782-4795. Aug. 2011.

Comings et al. Exon and intron variants in the human tryptophan 2,3-dioxygenase gene: potential association with Tourette syndrome, substance abuse and other disorders. Pharmacogenetics and Genomics. vol. 6(4):307-318. Aug. 1996.

Fuvesi et al. The role of kynurenines in the pathomechanism of amyotrophic lateral sclerosis and multiple sclerosis: therapeutic implications. Journal of Neural Transmission. vol. 199(2):225-234. Feb. 2012.

(Continued)

*Primary Examiner* — Emily Bernhardt
(74) *Attorney, Agent, or Firm* — Howson & Howson LLP; David Rubin; Cathy Kodroff

(57) ABSTRACT

The present invention relates to compound of Formula I

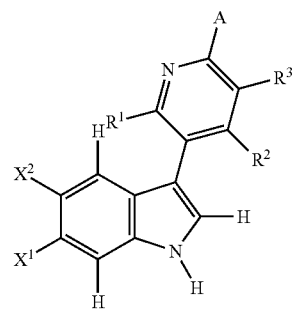

or pharmaceutically acceptable enantiomers, salts or solvates thereof. The invention further relates to the use of the compounds of Formula I as TDO2 inhibitors. The invention also relates to the use of the compounds of Formula I for the treatment and/or prevention of cancer, neurodegenerative disorders such as Parkinson's disease, Alzheimer's disease and Huntington's disease, chronic viral infections such as HCV and HIV, depression, and obesity. The invention also relates to a process for manufacturing compounds of Formula I.

15 Claims, No Drawings

(56) References Cited

OTHER PUBLICATIONS

Guo et al. Solubility-Driven Optimization of (Pyridin-3-yl) Benzoxazinyl-oxazolidinones Leading to a Promising Antibacterial Agent. Journal of Medicinal Chemistry. vol. 56(6):2642-2650. Feb. 2013.
Lahdou et al. Increased serum levels of quinolinic acid indicate enhanced severity of hepatic dysfunction in patients with liver cirrhosis. Human Immunology. vol. 74(1):60-66. Jun. 2012.
Manna et al. UPLC-MS-based Urine Metabolomics Reveals Indole-3-lactic Acid and Phenyllactic Acid as Conserved Biomarkers for Alcohol-induced Liver Disease in the Ppara-null Mouse Model. vol. 10(9):4120-4133. Jul. 2011.
Martin et al. Synthesis of Novel Analogs of Acetyl Coenzyme A: Mimics of Enzyme Reaction Intermediates. Journal of the American Chemical Society. vol. 116(11):4660-4668. Jun. 1994.
Miller et al. Expression of the kynurenine pathway enzyme tryptophan 2,3-dioxygenase is increased in the frontal cortex of individuals with schizophrenia. Neurobiology of Disease. vol. 15(3):618-629. Apr. 2004.
Ohta et al. Relationship between the level of serum L-tryptophan and its hepatic uptake and metabolism in rats with carbon tetrachloride-induced liver cirrhosis. Amino Acids. vol. 10(4):369-378. Dec. 1996.
Sperner-Unterweger et al. Enhanced tryptophan degradation in patients with ovarian carcinoma correlates with several serum soluble immune activation markers. Immunobiology. vol. 216(3):269-301. Mar. 2011.
Turiso et al. Discovery and in Vivo Evaluation of Dual PI3Kβ/δ Inhibitors. Journal of Medicinal Chemistry. vol. 55(17):7667-7685. Aug. 2012.
Widner et al. Increased neopterin production and tryptophan degradation in advanced Parkinson's disease. Journal of Neural Transmission. vol. 109(2):191-189. Feb. 2002.
Baroni, Synthesis of 3-Heteroaryloxindoles through t-BuOC1-Mediated Oxidation of 3-Heteroarylindoels, Synthesis, vol. 2010(23):4075-4081, Oct. 7, 2010.
Beevers, Low molecular weight indole fragments as IMPDH inhibitors, Bioorganic & Medicinal Chemistry Letters, vol. 16(9):2535-2538, May 2006.
Dolusic, Indoleamine 2, 3-dioxygen inhibitors: a patent review (2008-2012), Expert Opinion on Therapeutic Patents, vol. 23(10):1367-1381, Oct. 1, 2013.
Dolusic, Tryptophan 2, 3-Dioxygenase (TDO) Inhibitors. 3-(2-(Pyridyl)ethenyl)indoles as Potential Anticancer Immunomodulators, Journal of Medicinal Chemistry, vol. 54(15):5320-5334, Aug. 11, 2011.
Fallarino, T cell apoptosis by tryptophan catabolism, Cell Death and Differentiation, vol. 9:1069-1077, Apr. 2002.
Gupton, Preparation of Indole containing building blocks for the regiospecific constructions of indole appended pyrazoles and pyrroles, Tetrahedron, vol. 69(20):5829-5840, Jul. 1, 2013.
Henon, Expedited Synthesis of Substituted Dipyrrolo [3,4-a:3,4-c] carbazole-1,3,4,6-tetraones Structrually Related to Granulatimide, Synthesis, vol. 2006(4):711-715, Jan. 1, 2006.
Henon, Synthesis and biological evaluation of new dipyrrolo [3,4-a:3,4-c] carbazole-1,3,4,6-tetraones, substituted with various saturated and unsaturated side chains via palladium catalyzed cross-coupling reactions, Bioorganic & Medicinal Chemistry, vol. 14(11):3825-3834, Jun. 1, 2006.
Holmgaard, Indoleamine 2 3-dioxygenase is a critical resistance mechanism in antitumor T cell ummunotherapy targeting CTLA-4, J. Exp. Med., vol. 210(7):1389-1402, Jun. 2013.
Jakse, Application of alkyl 3-dimethylamino-2-)1H-indol-3-yl)propenoates in the synthesis of 3-heteroarylindoles, Tetrahedron, vol. 60(21):4601-4608, May 17, 2004.
Jimenez, 4-(1-Phenyl-1-pyrazol-4-yl) quinolones as novel, selective and brain penetrant metabotropic glutamate receptor 4 positive allosteric modulators, Bioorganic & Medicinal Chemistry Letters, vol. 22(9):3235-3239, Mar. 17, 2012.
Mahboobi, 3-Bromo-4-(1H-3-indolyl)-2, 5-dihydro-1H-2, 5-pyrroledione derivatives as new lead compounds for antibacterially active substances, European Journal of Medicinal Chemistry, vol. 41(2):176-191, Feb. 1, 2006.
Macor, A Direct Synthesis of 3-(Pyrrolidin-3-yl) Indoles for Use as Conformationally Restricted Analogs of Tryptamines, Synthesis, 1997(4):443-449, Apr. 4, 1007.
Mellor, Creating immune privilege: active local suppression that benefits friends, but protects foes, Nat. Rev. Immunol, vol. 8:74-80, Jan. 2008.
Muller, Chronic inflammation that facilitates tumor progression creates local immune suppression by inducing indoleamine 2, 3dioxygenase, PNAS, vol. 105(44):17073-17078, Nov. 2008.
Munn, Inhibition of T Cell Proliferation by Macrophage Tryptophan Catabolism, J. Exp. Med, vol. 189(9):1363-1372, May 1999.
Munn, Prevention of Allogeneic Fetal Rejection by Tryptophan Catabolism, Science, vol. 281:1191-1193, Aug. 1998.
Opitz, An endogenous tumour-promoting ligand of the human aryl hydrocarbon receptor, Nature, vol. 478(7368):197-203, Oct. 2011.
Pilotte, Reversal of tumoral immune resistance by inhibition of tryptophan 2,3-dioxygenase, PNAS, vol. 109(7):2497-2502, Feb. 2012.
Shigemitsu, Synthesis of 3-Methylthio-4-aryl-3-pyrroline-2, 5-diones and 3-Arylpyrrolidine-2, 5-diones by Reaction of Nitroketene Dithioacetal with Arylacetonitriles, Heterocycles, vol. 55(12):2257-2260, Jan. 1, 2001.
Uyttenhove, Evidence for a tumoral immune resistance mechanism based on tryptophan degradation by indoleamine 2, 3-dioxygenase, Nat. Med., vol. 9(10):1269-1274, Oct. 2003.
Chemical Abstracts Service, Database Registry Accession No. 859666-30-1, Aug. 11, 2005.
Chemical Abstracts Service, Database Registry Accession No. 1125444-69-0, Mar. 23, 2009.
Chemical Abstract Service, Database Registry Accession No. 1309341-94-3 (RN, Jun. 14, 2011.
Cavallo, 2011: The Immune Hallmarks of Cancer, Cancer Immunology Immunotherapy, vol. 60(3):319-326, Nov. 26, 2011.
Hanahan, Hallmarks of Cancer: The Next Generation, Cell, vol. 144:646-674, Mar. 4, 2011.
Hanahan, The Hallmarks of Cancer, Cell, vol. 100:57-70, Jan. 7, 2000.
Kyrgidia, Melanoma: Stem cells, sun exposure and hallmarks for carcinogenesis, molecular concepts and future clinical implications, Journal of Carcinogenesis, vol. 9(1):1-16, Feb. 16, 2010.
Sahm et al. The Endogenous Tryptophan Metabolite and NAD Precursor Quinolinic Acid Confers Resistance of Gliomas to Oxidative Stress. Cancer Research. vol. 73(11):3225-3234. Jun. 2013.
Stone et al. The kynurenine pathway as a therapeutic target in cognitive and neurodegenerative disorders. British Journal of Pharmacology. vol. 169(6):1211-1227. Jul. 2013.
Wu et al. Expression of Tryptophan 2,3-Dioxygenase and Production of Kynurenine Pathway Metabolites in Triple Transgenic Mice and Human Alzheimer's Disease Brain. PLOS One. vol. 8(4):e59749. Apr. 2013.
Forrest et al. Blood levels of kynurenines, interleukin-23 and soluble human leucocyte antigen-G at different stages of Huntington's disease. Journal of Neurochemistry. vol. 112(1):112-122. Jan. 2010.
Davies et al. Tryptophan, Neurodegeneration and HIV-Associated Neurocognitive Disorder. International Journal of Tryptophan Research. vol. 3:121-140. Jun. 2010.
Tilman et al. Human periostin gene expression in normal tissues, tumors and melanoma: evidences for periostin production by both stromal and melanoma cells. Molecular Cancer. vol. 1 6(80):1-13. Dec. 2007.
U.S. Appl. No. 14/076,016, filed Nov. 8, 2013.
U.S. Appl. No. 14/660,082, filed Mar. 17, 2015.
U.S. Appl. No. 61/996,974, filed Feb. 12, 2014.
U.S. Appl. No. 61/996,976, filed May 15, 2014.
U.S. Appl. No. 61/996,975, filed Feb. 27, 2015.

(56) References Cited

OTHER PUBLICATIONS

European Search Report issued on European Application No. 13192224, dated Jan. 14, 2014.
European Search Report issued on European Application No. 14154911, dated Aug. 29, 2014.
European Search Report issued on European Application No. 14160578, dated May 20, 2014.
European Search Report issued on European Application No. 14168534, dated Oct. 21, 2014.
International Search Report and Written Opinion, dated May 18, 2015, issued on corresponding International Patent Application No. PCT/IB2015/051036.

3-(INDOL-3-YL)-PYRIDINE DERIVATIVES, PHARMACEUTICAL COMPOSITIONS AND METHODS FOR USE

CROSS-REFERENCE TO RELATED APPLICATION

This application claims the benefit of the priority of U.S. Provisional Patent Application No. 61/996,974, filed Feb. 12, 2014, which application is hereby incorporated herein by reference.

FIELD OF INVENTION

The present invention relates to novel 3-(indol-3-yl)-pyridine derivatives, including pharmaceutically acceptable enantiomers, salts and solvates thereof. Compounds of the invention are inhibitors of TDO2 (tryptophan 2,3-dioxygenase) and are useful as therapeutic compounds, particularly in the treatment and/or prevention of cancers.

BACKGROUND OF INVENTION

Two decades after the importance of tryptophan catabolism for maintaining the immune privilege of the placenta was discovered (Munn, D. H. et al., Science, 1998, 281, 1191-1193), increasing evidence is extending its biological relevance beyond immune tolerance to non-self. According to the generally accepted concept, tryptophan, an essential amino acid, is catabolized in the local microenvironment of tumors, immune-privileged sites, or sites of inflammation (Mellor A L and Munn D H., Nat Rev Immunol, 2008, 8, 74-80). In these tissues, cancer cells, immune cells, or specialized epithelial cells (e.g., syncytiotrophoblasts in the placenta) create an immunosuppressive environment in tumors that shuts down antitumor immune responses in tumors and in tumor-draining lymph nodes by inducing T-cell anergy and apoptosis through depletion of tryptophan and accumulation of immunosuppressive tryptophan catabolites (Munn D H et al., J Exp Med., 1999, 189, 1363-1372; Fallarino F et al., Cell Death Differ., 2002, 9, 1069-1077).

It has recently been discovered that a key enzyme in tryptophan catabolism, tryptophan 2,3-dioxygenase (TDO2), which is considered responsible for regulating systemic tryptophan levels in the liver, is constitutively expressed in a wide variety of cancers, such as for example in bladder carcinoma, hepatocarcinoma, melanoma, mesothelioma, neuroblastoma, sarcoma, breast carcinoma, leukemia, renal cell carcinoma, colorectal carcinoma, head and neck carcinoma, lung carcinoma, brain tumor, glioblastoma, astrocytoma, myeloma, and pancreatic carcinoma (Pilotte L et al., Proc Natl Acad Sci USA, 2012, 109(7), 2497-502). TDO2 expression in tumor cells prevents tumor surveillance by the immune system and thus prevents tumor rejection by locally degrading tryptophan (Opitz C A et al., Nature, 2011, 478(7368), 197-203). The first evidence for this was provided through inhibition of TDO2 by a small molecule which inhibited tumor growth in a P815 mastocytoma tumor model with a prophylactic vaccination approach (Pilotte L et al., Proc Natl Acad Sci USA, 2012, 109(7), 2497-502). P815mTDO2 expressing tumors were rejected less in comparison to P815 tumors transfected with an empty vector, clearly demonstrating a growth benefit for TDO2 expressing tumors. Inhibition with a TDO2 inhibitor strongly decreased tumor growth in P815mTDO2 implanted tumors. Anti-tumor activity with the TDO2 inhibitor was equally observed in the P815 control implanted tumors negative for TDO2, thus providing evidence for an effect of TDO2 expressed in the immune system of the animal. These experiments for the first time provided clear evidence for a role of TDO2 in regulating tumor growth through expression in the cancer cell as well as immune compartment.

In line with its expression profile in liver, TDO2 was found predominantly in hepatocellular carcinoma (HCC) (Pilotte L et al., Proc Natl Acad Sci USA, 2012, 109(7), 2497-502). Inhibition of tryptophan catabolism and thus restoration of tryptophan concentration and decreased production of downstream metabolites could prove beneficial in the context of liver disease progressing to the stage of liver carcinoma. More particularly: (i) several reports have shown evidence that increased availability of tryptophan through supplementation is beneficial for example, cirrhotic livers, allowing the direct use of tryptophan for protein synthesis (Ohta et al., Amino Acids, 1996, 10(4), 369-78); (ii) there is a correlation between increased downstream serum tryptophan metabolites, such as quinolinic acid, and hepatic dysfunction in patients with liver cirrhosis (Landou et al., Hum Immunol, 2013, 74(1), 60-6) and (iii) increased secretion of another tryptophan metabolite, indole-3-lactic acid, has been associated with alcohol-induced liver disease in mice (Manna et al., J Proteome Res, 2011, 10(9), 4120-33). In the context of liver carcinoma itself, very high RNA expression is a good indication for therapeutic evaluation of TDO2 inhibitors (Pilotte L et al., Proc Natl Acad Sci USA, 2012, 109(7), 2497-502). The above thus provides a clear rationale for TDO2 activity modulation in the control of liver tumor development.

In addition to expression in liver, TDO2 is expressed in neurons, microglia and astrocytes and the potential benefit of TDO2 inhibition in the context of glioma was shown in another animal model. Platten and collaborators demonstrated that the tryptophan catabolite kynurenine produced by TDO expressed in the tumor cells suppresses antitumour immune responses and promotes tumor-cell survival and motility through the AHR in an autocrine/paracrine fashion (Opitz C A et al., Nature, 2011, 478(7368), 197-203). The TDO-AHR pathway is active in human brain tumors and is associated with malignant progression and poor survival. Further evidence came from the accumulation of a downstream metabolite, quinolinic acid which accumulates in human gliomas and was associated with a malignant phenotype (Sahm et al., Cancer Res, 2013, 73(11), 3225-34). Here tryptophan catabolism was shown to occur in microglia cells as well. The above data thus provides evidence for TDO2 targeting in glioma with brain-penetrant small molecules.

Other tumor types in which TDO2 mRNA was found are breast carcinoma, bladder, renal cell, pancreatic, colorectal, head & neck carcinoma and lung carcinoma as well as melanoma thus broadening the scope of TDO2 targeting beyond HCC and glioma (Pilotte L et al., Proc Natl Acad Sci USA, 2012, 109(7), 2497-502).

The enhanced Tryptophan degradation observed in patients with gynecological cancers (ovarian carcinoma, cervical cancer, endometrial cancer) provides additional rationale for TDO2 targeting in those cancers (Sperner-Unterweger B et al, Immunology, 2011, 216 (3); 296-301).

The tryptophan catabolism in some cancers might be also increased by the expression of indoleamine 2,3-dioxygenase (IDO1) by tumor cells (Uyttenhove, C. et al., Nat. Med., 2003, 9, 1269-1274).

Because tryptophan catabolism is induced by inflammatory mediators, notably IFN-gamma, it is thought to represent an endogenous mechanism that restricts excessive immune responses, thereby preventing immunopathology. However in the context of cancer, there is strong evidence that suppression of antitumor immune responses in precancerous lesions and established cancers by tryptophan catabolism promotes tumor growth, which would make such catabolism an attractive target for therapeutic intervention (Dolušić E and Frederick R., Expert Opin Ther Pat., 2013, 23(10), 1367-81). Hence, a considerable effort is being made to identify selective and efficient inhibitors of tryptophan catabolism to enhance the efficacy of conventional chemotherapy, immune checkpoints (Holmgaard R B et al., J Exp Med., 2013, 210(7), 1389-402) or therapeutic vaccines.

In the context of neurological brain disorders, TDO2 expression has been demonstrated in neurons, brain vasculature and additionally in the case of schizophrenia in astroglial cells (Miller C et al., 2004, Neurobiology Dis, 15(3):618-29). The kynurenine pathway is now considered as a therapeutic target in cognitive diseases like bipolar disorder or Tourette syndrome and neurodegenerative disorders like Alzheimer, motor neuron disease like Amyotrophic lateral sclerosis, Multiple sclerosis, Huntington or Parkinson's disease (Stone T W, 2013, Br J of Pharmacol, 169(6): 1211-27; Wu et al, 2013, Plos One, 8(4):e59749; Füvesi et al, 2012, J Neural Transm, 119(2):225-34; Widner et al, 2002, J Neural Transm, 109(2):181-9; Comings et al, 1996, Pharmacogenetics, 6(4):307-18; Forrest 2010, J Neurochem, 112(1):112-22).

Cognitive changes related to Tryptophan catabolism have also been shown in patients infected with human immunodeficiency virus type-1 (HIV), called HIV-associated neurocognitive disorder (HAND) (Davies et al, 2010, Int J of Tryptophan Res, 3:121-40). In addition, T cell hyporesponsiveness has been recently associated with the Tryptophan catabolic pathway in HIV-infected patients with possibly extension to other chronic infectious diseases like e.g. Hepatitis C.

Some TDO2 inhibitors were proposed in WO2010/008427 and by Dolusic, E. et al. (Dolusic et al., J. Med. Chem., 2011, 54, 5320-5334), however either their affinity for the target is limited, or their pharmacokinetic properties are not suitable for development as a drug for human use.

Therefore, there is a need for new TDO2 inhibitors with improved efficacy for cancer treatment and/or prevention.

SUMMARY OF THE INVENTION

The present invention provides new TDO2 inhibitors which may be administered to a mammalian subject having a condition or disease where it is desirable to modulate, and in particular decrease, levels of TDO2, including, without limitation, patients diagnosed with cancer, or any subject being at risk of developing a cancer. Also provided are compositions containing these compounds and uses thereof.

In one aspect, compounds of Formula I are provided

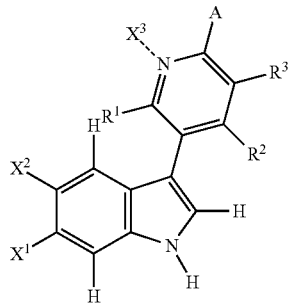

or pharmaceutically acceptable enantiomer, salts or solvates thereof, wherein: $X^1$, $X^2$, $X^3$, $R^1$, $R^2$ and $R^3$ are as defined herein. The compounds may be Formula I', I", Ia, Ia', Ib, Ib', Ic, Ic', Ic-1, Ic-2, Ic-3, Id, Id', Ie and/or If, or a pharmaceutically acceptable enantiomer, salt or solvate thereof. Preferably, the compounds are of Formula I, one of the subformula thereof, or a pharmaceutically acceptable salt thereof.

In another aspect, the invention provides a pharmaceutical composition containing a compound of Formula I, including, without limitation, Formula I', I", Ia, Ia', Ib, Ib', Ic, Ic', Ic-1, Ic-2, Ic-3, Id, Id', Ie and/or If, or a pharmaceutically acceptable enantiomer, salt or solvate thereof, and a pharmaceutically acceptable carrier.

In yet another aspect, the invention provides a medicament comprising a compound according to Formula I or any of Formula I', I", Ia, Ia', Ib, Ib', Ic, Ic', Ic-1, Ic-2, Ic-3, Id, Id', Ie and/or If, or a pharmaceutically acceptable enantiomer, salt or solvate thereof.

In still another aspect, the invention provides a method for treatment and/or prevention of cancer, neurodegenerative disorders such as Parkinson's disease, Alzheimer's disease and Huntington's disease, chronic viral infections such as HCV and HIV, depression, and obesity, which involves administering a compound of Formula I and/or of Formula I', I", Ia, Ia', Ib, Ib', Ic, Ic', Ic-1, Ic-2, Ic-3, Id, Id', Ie and/or If, or a pharmaceutically acceptable enantiomer, salt or solvate thereof. The cancer may be selected from, among others, bladder carcinoma, hepatocarcinoma, melanoma, mesothelioma, neuroblastoma, sarcoma, breast carcinoma, leukemia, renal cell carcinoma, colorectal carcinoma, head & neck carcinoma, lung carcinoma, brain tumor, glioblastoma, astrocytoma, myeloma, pancreatic carcinoma In a further aspect, the invention provides a method of treating a subject with a TDO2 inhibitor by administration of a compound of Formula I and/or of Formula I', I", Ia, Ia', Ib, Ib', Ic, Ic', Ic-1, Ic-2, Ic-3, Id, Id', Ie and/or If, or a pharmaceutically acceptable enantiomer, salt or solvate thereof.

In a further aspect, the invention provides a process for manufacturing a compound of Formula I or a pharmaceutically acceptable enantiomer, salt or solvate thereof, characterized in that it comprises (a1) reacting a compound of Formula II

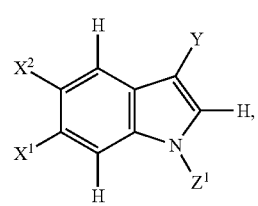

wherein $X^1$ and $X^2$ are as defined herein; $Z^1$ represents H or an amino protecting group such as for example an arylsulphonyl, a tert-butoxy carbonyl, a methoxymethyl, a paramethoxy benzyl, a benzyl or any other suitable protecting group known to those skilled in the art; Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art; with a compound of Formula III

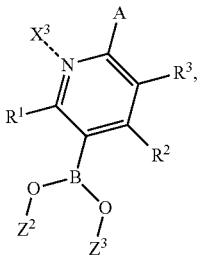

III wherein $R^1$, $R^2$, $R^3$, $X^3$ and A are defined herein; and $Z^2$ and $Z^3$ represent H or alkyl groups, with the possibility for $Z^2$ and $Z^3$ to form a ring; so as to obtain a compound of Formula IV,

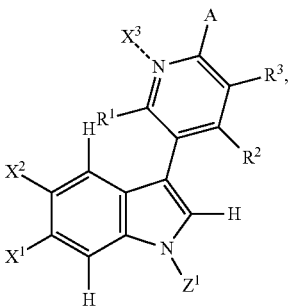

IV wherein $X^1$, $X^2$, $R^1$, $R^2$, $R^3$, $X^3$, A and $Z^1$ are above; and (b1) in the case wherein $Z^1$ is not H, deprotecting the indole amine of compound of Formula IV, to afford compound of Formula I.

Other aspects and advantages of the invention will be readily apparent from the following detailed description of the invention.

DETAILED DESCRIPTION OF THE INVENTION

The present invention provides new compounds useful for administration to a mammalian subject. These compounds and compositions are useful as TDO2 inhibitors and as such may be administered to a mammalian subject having a condition or disease associated with undesirable levels of TDO2, including, without limitation, patients diagnosed with cancer, or any subject being at risk of developing a cancer. Also provided are compositions containing these compounds and uses thereof.

Compounds

In one embodiment, compounds of Formula I are provided, having the structure:

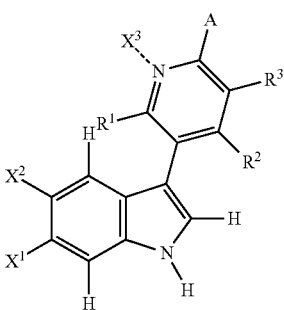

I and pharmaceutically acceptable enantiomers, salts and solvates thereof, wherein:

$X^1$ and $X^2$ represent each independently H, halogen, alkyl, haloalkyl, preferably H or F;

$X^3$ is absent or represents —O⁻, preferably $X^3$ is absent;

$R^1$, $R^2$ and $R^3$ represent each independently H, halogen, C1-C6 alkyl, alkoxy, haloalkyl, optionally substituted by one or more substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino; preferably $R^1$, $R^2$ and $R^3$ represent each independently H, halogen or methyl, preferably H or methyl, more preferably H;

A represents:
  a hydrogen atom;
  $CR^4R^5R^6$, $NR^4R^5$ or $OR^4$ wherein $R^4$, $R^5$ and $R^6$ represent each independently:
    a hydrogen atom;
    halogen, preferably F, Cl or I, more preferably F;
    hydroxyl;
    $OR^7$ or $NR^7R^8$ wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
    C1-C10 alkyl, linear or branched, preferably methyl, ethyl or propyl; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
    heterocyclyl, preferably selected from piperidine, pyrrolidine, piperazine; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
    —CO—$R^{10}$ or —$SO_2R^{10}$ wherein $R^{10}$ represents a group selected from alkyl, heterocyclyl (preferably piperidine, pyrrolidine, piperazine or tetrahydrothiopyrandioxide); optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

in CR⁴R⁵R⁶, R⁴, R⁵ and the carbon atom to which they are attached form together a ring, said ring being preferably selected from:
  cycloalkyl, optionally substituted with up to three substituents selected from the group comprising halogen, hydroxyl, OR⁷, COOR⁷, CONR⁷R⁸, NR⁷COR⁸, NR⁷R⁸, SO₂R⁷, SO₂NR⁷R⁸, NR⁷SO₂R⁸, SO₂R⁷, aryl, CO-alkyl, alkyl, the alkyl group being optionally substituted by one or more groups selected from halogen, hydroxyl, amino or COOH; wherein R⁷ and R⁸ represent each independently a hydrogen atom or a group, optionally substituted, selected from C1-C6 alkyl, aryl, arylalkyl, alkylaryl, heteroaryl, heteroarylalkyl, alkylheteroaryl, amino;
  heterocyclyl, preferably selected from morpholine, piperazine or piperidine; optionally substituted with up to three substituents selected from the group comprising halogen, hydroxyl, OR⁷, COOR⁷, CONR⁷R⁸, NR⁷COR⁸, NR⁷R⁸, SO₂R⁷, SO₂NR⁷R⁸, NR⁷SO₂R⁸, SO₂R⁷, aryl, CO-alkyl, alkyl, the alkyl group being optionally substituted by one or more groups selected from halogen, hydroxyl, amino or COOH; wherein R⁷ and R⁸ represent each independently a hydrogen atom or a group, optionally substituted, selected from C1-C6 alkyl, aryl, arylalkyl, alkylaryl, heteroaryl, heteroarylalkyl, alkylheteroaryl, amino;
in NR⁴R⁵, R⁴, R⁵ and the nitrogen atom to which they are attached form together a ring, said ring being preferably an heterocyclyl, preferably selected from morpholine, piperazine or piperidine; optionally substituted with up to three substituents selected from the group comprising halogen, hydroxyl, OR⁷, COOR⁷, CONR⁷R⁸, NR⁷COR⁸, NR⁷R⁸, SO₂R⁷, SO₂NR⁷R⁸, NR⁷SO₂R¹¹, SO₂R⁷, aryl, CO-alkyl, alkyl, the alkyl group being optionally substituted by one or more groups selected from halogen, hydroxyl, amino or COOH; wherein R⁷ and R⁸ represent each independently a hydrogen atom or a group, optionally substituted, selected from C1-C6 alkyl, aryl, arylalkyl, alkylaryl, heteroaryl, heteroarylalkyl, alkylheteroaryl, amino; and wherein R¹¹ represents a hydrogen atom or an optionally substituted group selected from aryl, arylalkyl, alkylaryl, heteroaryl, heteroarylalkyl, alkylheteroaryl, amino; or R¹¹ represents an alkyl group optionally substituted with up to three substituents selected from the group comprising halogen, hydroxyl, OR¹², COOR¹², CONR¹²R¹³, NR¹²COR¹³, NR¹²R¹³, SO₂R¹², SO₂NR¹²R¹³, NR¹²SO₂R¹³, SO₂R¹², aryl; wherein R¹² and R¹³ represent each independently a hydrogen atom or a group, optionally substituted, selected from C1-C6 alkyl, aryl, arylalkyl, alkylaryl, heteroaryl, heteroarylalkyl, alkylheteroaryl, amino;
under the condition that the compound of Formula I is not: 3-(pyridin-3-yl)-1H-indole; 3-((5-(1H-indol-3-yl)pyridin-2-yl)oxy)-2-methylquinuclidine; 5-methyl-3-(6-methylpyridin-3-yl)-1H-indole; or 3-methyl-5-(5-methyl-1H-indol-3-yl)pyridin-2-amine.

In one embodiment, a compound of Formula I as defined herein is an active pharmaceutical ingredient in free base form. In another embodiment, a compound of Formula I as defined herein is in a salt form of the compound. In still a further embodiment, a composition may contain a mixture or blend of a compound of Formula I as a free base and/or another form of the compound, e.g., a pharmaceutically acceptable salt.

In a further embodiment, when A is H, X¹, X², R¹, R² and R³ are not all H.

In still a further embodiment, compounds of Formula I are provided, having the structure:

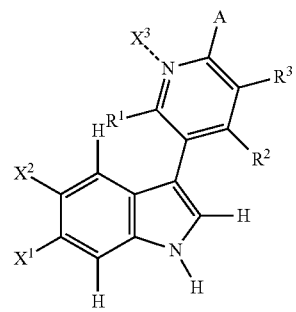

wherein:
  X¹ and X² represent each independently H, halogen, alkyl, haloalkyl, preferably H or F;
  X³ is absent or represents —O⁻, preferably X³ is absent;
  R¹, R² and R³ represent each independently H, halogen, C1-C6 alkyl, alkoxy, haloalkyl, optionally substituted by one or more substituents selected from halogen, hydroxyl, OR⁷, COOR⁷, CONR⁷R⁸, NR⁷COR⁸, NR⁷R⁸, SO₂R⁷, SO₂NR⁷R⁸, NR⁷SO₂R⁸, SO₂R⁷, aryl, CO-alkyl, or alkyl, the alkyl group being optionally substituted by one or more groups selected from halogen, hydroxyl, amino or COOH; wherein R⁷ and R⁸ represent each independently a hydrogen atom or a group, optionally substituted, selected from C1-C6 alkyl, aryl, arylalkyl, alkylaryl, heteroaryl, heteroarylalkyl, alkylheteroaryl, amino; preferably R¹, R² and R³ represent each independently H, halogen or methyl, preferably H or methyl, more preferably H;
  A represents:
    a hydrogen atom;
    CR⁴R⁵R⁶, NR⁴R⁵ or OR⁴ wherein R⁴, R⁵ and R⁶ represent each independently:
      a hydrogen atom;
      halogen, preferably F, Cl or I, more preferably F;
      hydroxyl;
      OR⁷ or NR⁷R⁸ wherein R⁷ and R⁸ represent each independently a hydrogen atom or a group, optionally substituted, selected from C1-C6 alkyl, aryl, arylalkyl, alkylaryl, heteroaryl, heteroarylalkyl, alkylheteroaryl, or amino;
      C1-C10 alkyl, linear or branched, preferably methyl, ethyl or propyl; optionally substituted with up to three substituents selected from halogen, hydroxyl, OR⁷, COOR⁷, CONR⁷R⁸, NR⁷COR⁸, NR⁷R⁸, SO₂R⁷, SO₂NR⁷R⁸, NR⁷SO₂R⁸, SOR⁷, aryl, or CO-alkyl, wherein R⁷ and R⁸ represent each independently a hydrogen atom or a group, optionally substituted, selected from C1-C6 alkyl, aryl, arylalkyl, alkylaryl, heteroaryl, heteroarylalkyl, alkylheteroaryl, or amino;
      heterocyclyl, preferably selected from piperidine, pyrrolidine, piperazine; optionally substituted with up to three substituents selected from halogen, hydroxyl, OR⁷, COOR⁷, CONR⁷R⁸, NR⁷COR⁸, NR⁷R⁸, SO₂R⁷, SO₂NR⁷R⁸, NR⁷SO₂R⁸, SO₂R⁷, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

—CO—$R^{10}$ or —$SO_2R^{10}$ wherein $R^{10}$ represents a group selected from alkyl, heterocyclyl (preferably piperidine, pyrrolidine, piperazine or tetrahydrothiopyrandioxide); optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

in $CR^4R^5R^6$, $R^4$, $R^5$ and the carbon atom to which they are attached form together a ring, said ring being preferably selected from:

cycloalkyl, optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

heterocyclyl, preferably selected from morpholine, piperazine or piperidine; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

in $NR^4R^5$, $R^4$, $R^5$ and the nitrogen atom to which they are attached form together a ring, said ring being preferably an heterocyclyl, preferably selected from morpholine, piperazine or piperidine; optionally substituted with up to three substituents selected halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^{11}$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino; and wherein $R^{11}$ represents a hydrogen atom or an optionally substituted group selected from aryl, arylalkyl, alkylaryl, heteroaryl, heteroarylalkyl, alkylheteroaryl, or amino; or $R^{11}$ represents an alkyl group optionally substituted with up to three substituents selected from halogen, hydroxyl, $OR^{12}$, $COOR^{12}$, $CONR^{12}R^{13}$, $NR^{12}COR^{13}$, $NR^{12}R^{13}$, $SO_2R^{12}$, $SO_2NR^{12}R^{13}$, $NR^{12}SO_2R^{13}$, $SO_2R^{12}$, or aryl; wherein $R^{12}$ and $R^{13}$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

or a pharmaceutically acceptable enantiomer, salt or solvate thereof.

under the condition that the compound of Formula I is not: 3-(pyridin-3-yl)-1H-indole; 3-((5-(1H-indol-3-yl)pyridin-2-yl)oxy)-2-methylquinuclidine; 5-methyl-3-(6-methylpyridin-3-yl)-1H-indole; or 3-methyl-5-(5-methyl-1H-indol-3-yl)pyridin-2-amine.

In another embodiment, a compound of Formula I is characterized by the formula in which: $X^1$ and $X^2$ represent each independently H, halogen, C1-C6 alkyl, cyano, or haloalkyl; $X^3$ is absent or represents H, —O,⁻ or C1-C4 alkyl;

$R^1$, $R^2$ and $R^3$ represent each independently H, halogen, optionally substituted C1-C6 alkyl, optionally substituted C1-C6 alkoxy, or optionally substituted C1-C6 haloalkyl, wherein the optionally substituted groups independently have one or more substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO—(C1-C6) alkyl, or C1-C6 alkyl, the alkyl group being optionally substituted by one or more of halogen, hydroxyl, amino or COOH; wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, or amino; and A represents:

(a) a hydrogen atom;

(b) oxo;

(c) $SO_2R^a$; wherein $R^a$ is amino, piperazine, piperazine substituted with $SO_2(C_1-C_4$ alkyl), or $NR^bR^{b''}$ wherein $R^b$ is H or $C_1-C_4$ alkyl and $R^{b''}$ is $CH_2CH_2CONH_2$, CH2-CH$_2$—N(H)(R$^c$)—$R^d$, wherein $R^c$ is $SO_2$ or CO, and $R^d$ is $C_1-C_4$ alkyl or amino;

(d) $CR^4R^5R^6$, (e) $NR^4R^6$, (f) $OR^4$, wherein $R^4$, $R^5$ and $R^6$ represent each independently:

(i) a hydrogen atom;

(ii) halogen;

(iii) hydroxyl;

(iv) $OR^7$ or $NR^7R^8$ wherein $R^7$ and $R^8$ represent each independently a hydrogen atom or a group, optionally substituted with C1-C6 alkyl, aryl, arylalkyl, alkylaryl, heteroaryl, heteroarylalkyl, alkylheteroaryl, or amino;

(v) C1-C10 alkyl, linear or branched, preferably methyl, ethyl or propyl; optionally substituted with 1, 2 or 3 independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, or CO—(C1-C6)alkyl, wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, C1-C4 alkylamino, or amino;

(vi) heterocyclyl, preferably selected from piperidine, pyrrolidine, piperazine, tetrahydropyran; optionally substituted with 1, 2, or 3 independently selected substituents consisting of halogen, hydroxyl, $OR^7$, COOR⁷, CONR⁷R⁸, NR⁷COR⁸, NR⁷R⁸, SO₂R⁷, SO₂NR⁷R⁸, NR⁷SO₂R⁸, SO₂R⁷, aryl, CO— (C1-C6) alkyl, or C1-C6 alkyl, the alkyl group being optionally substituted by one or more independently selected groups consisting of halogen, hydroxyl, amino or COOH; wherein R⁷ and R⁸ represent each independently a hydrogen atom or a group, optionally substituted, consisting of C1-C6 alkyl, aryl, arylalkyl, alkylaryl, heteroaryl, heteroarylalkyl, alkylheteroaryl, or amino;

(vii) —CO—R¹⁰ or —SO₂R¹⁰ wherein R¹⁰ represents a group consisting of C1-C6 alkyl, amino, C3 cycloalkyl, C1-C6 alkyl-heterocycl, or heterocyclyl; each optionally substituted with 1, 2 or 3 independently selected substituents consisting of halogen, hydroxyl, OR⁷, COOR⁷, CONR⁷R⁸, NR⁷COR⁸, NR⁷R⁸, SO₂R⁷, SO₂NR⁷R⁸, NR⁷SO₂R⁸, SOR⁷, aryl, CO—(C1-C6) alkyl, or C1-C6 alkyl, the alkyl group being optionally substituted by one or more independently selected groups consisting of halogen, hydroxyl, amino or COOH; wherein R⁷ and R⁸ represent each independently a hydrogen atom or a group, optionally substituted, consisting of C1-C6 alkyl, aryl, arylalkyl, alkylaryl, heteroaryl, heteroarylalkyl, alkylheteroaryl, or amino;

(viii) wherein when A is CR⁴R⁵R⁶, optionally R⁴, R⁵ and the carbon atom to which they are attached form together a ring, said ring consisting of: cycloalkyl, optionally substituted with 1, 2, or 3 independently selected substituents consisting of halogen, hydroxyl, OR⁷, COOR⁷, CONR⁷R⁸, NR⁷COR⁸, NR⁷R⁸, SO₂R⁷, SO₂NR⁷R⁸, NR⁷SO₂R⁸, SO₂R⁷, aryl, CO—(C1-C6) alkyl, or C1-C6 alkyl, the alkyl group being optionally substituted by one or more independently selected groups consisting of halogen, hydroxyl, amino or COOH; wherein R⁷ and R⁸ represent each independently a hydrogen atom or a group, optionally substituted, consisting of C1-C6 alkyl, aryl, arylalkyl, alkylaryl, heteroaryl, heteroarylalkyl, alkylheteroaryl, or amino; or heterocyclyl optionally substituted with 1, 2 or 3 independently selected substituents consisting of halogen, oxo, hydroxyl, OR⁷, COOR⁷, CONR⁷R⁸, NR⁷COR⁸, NR⁷R⁸, SO₂R⁷, SO₂NR⁷R⁸, NR⁷SO₂R⁸, SO₂R⁷, aryl, CO-alkyl, or C1-C6 alkyl, the alkyl group being optionally substituted by one or more independently selected groups consisting of halogen, hydroxyl, amino or COOH; wherein R⁷ and R⁸ represent each independently a hydrogen atom or a group, optionally substituted, consisting of C1-C6 alkyl, aryl, arylalkyl, alkylaryl, heteroaryl, heteroarylalkyl, alkylheteroaryl, or amino; or (ix) when A is NR⁴R⁵, optionally R⁴, R⁵ and the nitrogen atom to which they are attached form together a ring, said ring being optionally substituted with 1, 2 or 3 independently selected substituents consisting of oxo, halogen, hydroxyl, OR⁷, COOR⁷, CONR⁷R⁸, NR⁷COR⁸, NR⁷R⁸, SO₂R⁷, SO₂NR⁷R⁸, NR⁷SO₂R¹¹, SO₂R⁷, aryl, CO—(C1-C6) alkyl, or C1-C6 alkyl, the alkyl group being optionally substituted by one or more independently selected groups consisting of halogen, hydroxyl, amino or COOH; wherein R⁷ and R⁸ represent each independently a hydrogen atom or a group, optionally substituted, consisting of C1-C6 alkyl, aryl, arylalkyl, alkylaryl, heteroaryl, heteroarylalkyl, alkylheteroaryl, or amino; and wherein R¹¹ represents a hydrogen atom or an optionally substituted group selected from aryl, arylalkyl, alkylaryl, heteroaryl, heteroarylalkyl, alkylheteroaryl, or amino; or R¹¹ represents an C1-C6 alkyl group optionally substituted with a heterocycyl, or 1, 2 or 3 independently selected substituents consisting of halogen, hydroxyl, OR¹², COOR¹², CONR¹²R¹³, NR¹²COR¹³, NR¹²R¹³, SO₂R¹², SO₂NR¹²R¹³, NR¹²SO₂R¹³, SO₂R¹², or aryl; wherein R¹² and R¹³ represent each independently a hydrogen atom or a group, optionally substituted, consisting of C1-C6 alkyl, aryl, arylalkyl, alkylaryl, heteroaryl, heteroarylalkyl, alkylheteroaryl, or amino;

(g) benzimidazol, optionally substituted with a halogen, amino, or C1-C4 alkyl, or optionally A and R³ together form a 5-membered optionally saturated or partially saturated heterocylic ring fused to the piperidine ring to which A and R³ are bound, said 5-membered heterocyclic ring having at least one N in the ring and optionally further having a second N or an O in the ring, said ring optionally further having an -oxo or methyl substitution, said first or second N being optionally substituted with a CH₂(CO)NH₂, CH₂(COOH, CH₂(C00) (CH₂)ₙCH₃, wherein n is 1 or 2, or a pharmaceutically acceptable salt, enantiomer, or solvate thereof, under the condition that the compound of Formula I is not: 3-(pyridin-3-yl)-1H-indole; -((5-(1H-indol-3-yl)pyridin-2-yl)oxy)-2-methylquinuclidine; 5-methyl-3-(6-methylpyridin-3-yl)-1H-indole; or 3-methyl-5-(5-methyl-1H-indol-3-yl)pyridin-2-amine.

As used herein, unless otherwise specified, reference throughout the specification to compounds of Formula I as defined above, including the subformula I', I", Ia, Ia, Ia', Ib, Ib', Ic, Ic' Ic-1, Ic-2, Ic-3, Id, Id', Ie, and/or If, including pharmaceutically acceptable enantiomers, salts, solvates, polymorphs and crystal habits thereof, prodrugs and predrugs thereof and isotopically-labeled compounds of Formula I. Compositions of the invention may contain mixtures thereof.

In one embodiment, preferred compounds of Formula I are those of Formula I':

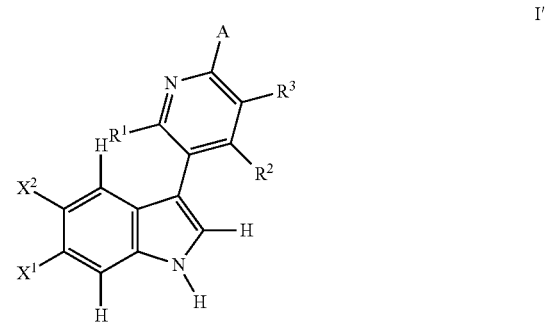

and pharmaceutically acceptable enantiomers, salts and solvates thereof, wherein X¹, X², R¹, R², R³ and A are as defined in Formula I. In one embodiment, the compound of Formula I' is a base or pharmaceutically acceptable salt thereof.

In one embodiment, preferred compounds of Formula I are those of Formula I":

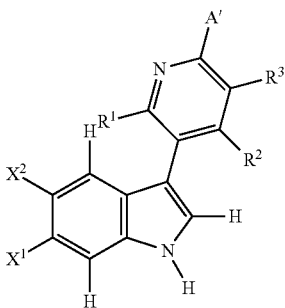

I″ and pharmaceutically acceptable enantiomers, salts and solvates thereof, wherein $X^1$, $X^2$, $R^1$, $R^2$ and $R^3$ are as defined in Formula I and A' represents $CR^4R^5R^6$, $NR^4R^5$ or $OR^4$, wherein $R^4$, $R^5$ and $R^6$ are as defined in Formula I. In one embodiment, the compound of Formula I″ is a base or pharmaceutically acceptable salt thereof.

In one embodiment, preferred compounds of Formula I are those of Formula Ia:

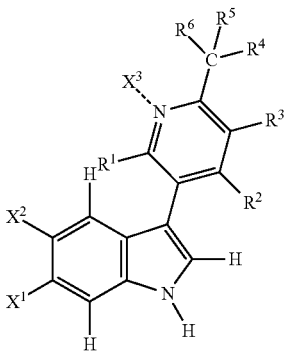

Ia and pharmaceutically acceptable enantiomers, salts and solvates thereof, wherein the substitutents are as defined in Formula Ia. In a further embodiment:

$X^1$ and $X^2$ represent each independently H, halogen, alkyl, haloalkyl, preferably H or F, more preferably $X^1$ represents F and $X^2$ represents H;

$X^3$ is absent or represents $—O^-$, preferably $X^3$ is absent;

$R^1$, $R^2$ and $R^3$ represent each independently H, halogen, C1-C6 alkyl, alkoxy, haloalkyl, optionally substituted by one or more substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino; preferably $R^1$, $R^2$ and $R^3$ represent each independently H, halogen or methyl, preferably H or methyl, more preferably $R^1$, $R^2$ and $R^3$ represent H;

$R^4$, $R^5$ and $R^6$ represent each independently:
a hydrogen atom;
halogen, preferably F, Cl or I, more preferably F;
hydroxyl;

$OR^7$ or $NR^7R^8$ wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

C1-C10 alkyl, linear or branched, preferably methyl, ethyl or propyl; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

heterocyclyl, preferably selected from piperidine, pyrrolidine, piperazine; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

$—CO—R^{10}$ or $—SO_2R^{10}$ wherein $R^{10}$ represents a group selected from alkyl, heterocyclyl (preferably piperidine, pyrrolidine, piperazine or tetrahydrothiopyrandioxide); optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

$R^4$, $R^5$ and the carbon atom to which they are attached form together a ring, said ring being preferably selected from:

cycloalkyl, optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

heterocyclyl, preferably selected from morpholine, piperazine or piperidine; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino.

In a further embodiment, in Formula Ia or Ia', or a pharmaceutically acceptable salt thereof:

$X^1$ and $X^2$ represent each independently H, halogen, alkyl, haloalkyl, preferably H or F, more preferably $X^1$ represents F and $X^2$ represents H;

$X^3$ is absent or represents —O⁻, preferably $X^3$ is absent;

$R^1$, $R^2$ and $R^3$ represent each independently H, halogen, C1-C6 alkyl, alkoxy, haloalkyl, optionally substituted by one or more substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more of halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino; preferably $R^1$, $R^2$ and $R^3$ represent each independently H, halogen or methyl, preferably H or methyl, more preferably $R^1$, $R^2$ and $R^3$ represent H;

$R^4$, $R^5$ and $R^6$ represent each independently:
- a hydrogen atom;
- halogen, preferably F, Cl or I, more preferably F;
- hydroxyl;
- $OR^7$ or $NR^7R^8$ wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
- C1-C10 alkyl, linear or branched, preferably methyl, ethyl or propyl; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, or CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
- heterocyclyl, preferably selected from piperidine, pyrrolidine, piperazine; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
- —CO—$R^{10}$ or —$SO_2R^{10}$ wherein $R^{10}$ represents a group selected from alkyl, heterocyclyl (preferably piperidine, pyrrolidine, piperazine or tetrahydrothiopyrandioxide); optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, or alkyl, the alkyl group being optionally substituted by one or more of halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
- $R^4$, $R^5$ and the carbon atom to which they are attached form together a ring, said ring being preferably selected from:
  - cycloalkyl, optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more of halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
  - heterocyclyl, preferably selected from morpholine, piperazine or piperidine; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

In one embodiment, preferred compounds of Formula Ia are those of Formula Ia':

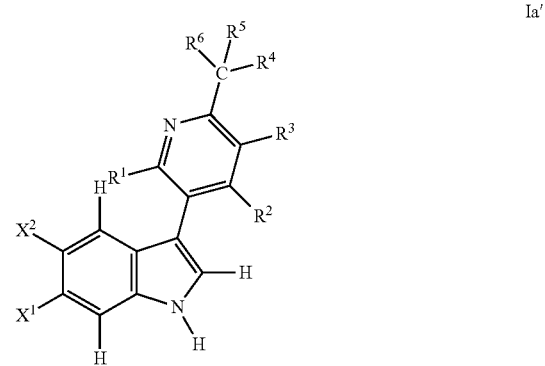

Ia' and pharmaceutically acceptable enantiomers, salts and solvates thereof, wherein $X^1$, $X^2$, $R^1$, $R^2$, $R^3$, $R^4$, $R^5$ and $R^6$ are as defined in Formula Ia. Other preferred compounds include those of Formula Ia' or a pharmaceutically acceptable salt thereof.

According to a specific embodiment, in Formula Ia or Ia', $X^1$ represents F and $X^2$ represents H. According to a specific embodiment, in Formula Ia or Ia', $R^1$, $R^2$ and $R^3$ represent hydrogen atoms. According to a specific embodiment, in Formula Ia or Ia', $X^1$ represents F, $X^2$ represents H and $R^1$, $R^2$ and $R^3$ represent hydrogen atoms. According to a specific embodiment, in Formula Ia or Ia', $R^5$ and $R^6$ represent hydrogen atoms. According to a specific embodiment, in Formula Ia or Ia', $X^1$ represents F, $X^2$ represents H, $R^1$, $R^2$ and $R^3$ represent hydrogen atoms and $R^5$ and $R^6$ represent hydrogen atoms. According to a specific embodiment, in Formula Ia or Ia', $R^4$ represents an alkyl, preferably methyl.

In one embodiment, preferred compounds of Formula I are those of Formula Ib:

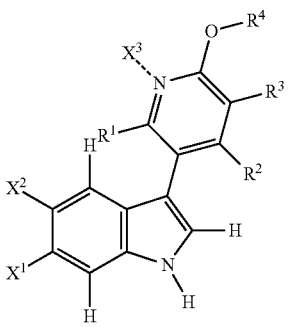

and pharmaceutically acceptable enantiomers, salts and solvates thereof, wherein:

$X^1$ and $X^2$ represent each independently H, halogen, alkyl, haloalkyl, preferably H or F, more preferably $X^1$ represents F and $X^2$ represents H;

$X^3$ is absent or represents —O⁻, preferably $X^3$ is absent;

$R^1$, $R^2$ and $R^3$ represent each independently H, halogen, C1-C6 alkyl, alkoxy, haloalkyl, optionally substituted by one or more substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

preferably $R^1$, $R^2$ and $R^3$ represent each independently H, halogen or methyl, preferably H or methyl, more preferably $R^1$, $R^2$ and $R^3$ represent H;

$R^4$ represents:
a hydrogen atom;
C1-C10 alkyl, linear or branched, preferably methyl, ethyl or propyl; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
heterocyclyl, preferably selected from piperidine, pyrrolidine, piperazine; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino.

In another embodiment, in Formula Ib, or a pharmaceutically acceptable salt thereof, $X^1$ and $X^2$ represent each independently H, halogen, alkyl, haloalkyl, preferably H or F, more preferably $X^1$ represents F and $X^2$ represents H;

$X^3$ is absent or represents —O⁻, preferably $X^3$ is absent;

$R^1$, $R^2$ and $R^3$ represent each independently H, halogen, C1-C6 alkyl, alkoxy, haloalkyl, optionally substituted by one or more substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino; preferably $R^1$, $R^2$ and $R^3$ represent each independently H, halogen or methyl, preferably H or methyl, more preferably $R^1$, $R^2$ and $R^3$ represent H;

$R^4$ represents:
a hydrogen atom;
C1-C10 alkyl, linear or branched, preferably methyl, ethyl or propyl; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, or CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
heterocyclyl, preferably selected from piperidine, pyrrolidine, piperazine; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

In one embodiment, preferred compounds of Formula Ib are those of Formula Ib':

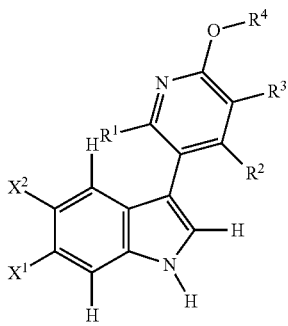

and pharmaceutically acceptable enantiomers, salts and solvates thereof, wherein $X^1$, $X^2$, $R^1$, $R^2$, $R^3$ and $R^4$ are as defined in Formula Ib. In a further embodiment, the compound is a pharmaceutically acceptable salt of Formula Ib or Ib'.

According to a specific embodiment, in Formula Ib or Ib', $X^1$ represents F and $X^2$ represents H. According to a specific embodiment, in Formula Ib or Ib', $R^1$, $R^2$ and $R^3$ represent hydrogen atoms. According to a specific embodiment, in Formula Ib or Ib', $X^1$ represents F, $X^2$ represents H and $R^1$, $R^2$ and $R^3$ represent hydrogen atoms.

According to another embodiment in Formula Ib or Ib', or a pharmaceutically acceptable salt thereof, $R^4$ is a hydrogen atom; or $R^4$ is C1-C10 alkyl, linear or branched, preferably methyl, ethyl or propyl; optionally substituted with 1, 2 or 3 independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, or CO—(C1-C6)alkyl, wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, C1-C4 alkylamino, or amino; or $R^4$ is a heterocyclyl, preferably piperidine, tetrahydropyran, pyrrolidine, or piperazine; optionally substituted with 1, 2 or 3 independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more independently selected groups consisting of halogen, hydroxyl, amino or COOH; wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, or amino.

According to a specific embodiment, in Formula Ib or Ib', $R^4$ represents an alkyl, optionally substituted, preferably methyl or optionally substituted ethyl, more preferably methyl or —$CH_2$—$CH_2$—$NR^7R^8$ wherein $R^7$ and $R^8$ are as defined in Formula Ib, preferably $R^7$ and $R^8$ represent alkyl groups, more preferably methyl groups.

According to another specific embodiment, in Formula Ib or Ib', $R^4$ represents an optionally substituted heterocyclyl, preferably an optionally substituted piperidine. According to one embodiment, the piperidine is substituted by an alkyl group, preferably methyl, or by $SO_2R^7$, wherein $R^7$ is as defined in Formula Ib and $R^7$ is preferably an alkyl, more preferably methyl.

In one embodiment, preferred compounds of Formula I are those of Formula Ic:

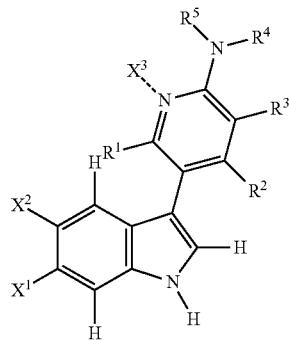

Ic and pharmaceutically acceptable enantiomers, salts and solvates thereof, wherein:

$X^1$ and $X^2$ represent each independently H, halogen, alkyl, haloalkyl, preferably H or F, more preferably $X^1$ represents F and $X^2$ represents H;

$X^3$ is absent or represents —$O^-$, preferably $X^3$ is absent;

$R^1$, $R^2$ and $R^3$ represent each independently H, halogen, C1-C6 alkyl, alkoxy, haloalkyl, optionally substituted by one or more substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino; preferably $R^1$, $R^2$ and $R^3$ represent each independently H, halogen or methyl, preferably H or methyl, more preferably H;

$R^4$, $R^5$ and $R^6$ represent each independently:

a hydrogen atom;

C1-C10 alkyl, linear or branched, preferably methyl, ethyl or propyl; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

heterocyclyl, preferably selected from piperidine, pyrrolidine, piperazine; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

—CO—$R^{10}$ or —$SO_2R^{10}$ wherein $R^{10}$ represents a group selected from alkyl, heterocyclyl (preferably piperidine, pyrrolidine, piperazine or tetrahydrothiopyrandioxide); optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

$R^4$, $R^5$ and the nitrogen atom to which they are attached form together a ring, said ring being preferably an heterocyclyl, preferably selected from morpholine, piperazine or piperidine; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^{11}$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino; and wherein $R^{11}$ represents a hydrogen atom or an optionally substituted group selected from aryl, arylalkyl, alkylaryl, heteroaryl, heteroarylalkyl, alkylheteroaryl, amino; or $R^{11}$ represents an alkyl group optionally substituted with up to three substituents selected from the group comprising halogen, hydroxyl, $OR^{12}$, $COOR^{12}$, $CONR^{12}R^{13}$, $NR^{12}COR^{13}$, $NR^{12}R^{13}$, $SO_2R^{12}$, $SO_2NR^{12}R^{13}$, $NR^{12}SO_2R^{13}$, $SO_2R^{12}$, aryl; wherein $R^{12}$ and $R^{13}$ represent each independently a hydrogen atom or a group, optionally substituted, selected from C1-C6 alkyl, aryl, arylalkyl, alkylaryl, heteroaryl, heteroarylalkyl, alkylheteroaryl, amino.

In another embodiment, in Formula Ic, or a pharmaceutically acceptable salt thereof, $X^1$ and $X^2$ represent each independently H, halogen, alkyl, haloalkyl, preferably H or F, more preferably $X^1$ represents F and $X^2$ represents H;

$X^3$ is absent or represents —O⁻, preferably $X^3$ is absent;

$R^1$, $R^2$ and $R^3$ represent each independently H, halogen, C1-C6 alkyl, alkoxy, haloalkyl, optionally substituted by one or more substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino; preferably $R^1$, $R^2$ and $R^3$ represent each independently H, halogen or methyl, preferably H or methyl, more preferably H;

$R^4$, $R^5$ and $R^6$ represent each independently:
a hydrogen atom;
C1-C10 alkyl, linear or branched, preferably methyl, ethyl or propyl; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, or CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
heterocyclyl, preferably selected from piperidine, pyrrolidine, piperazine; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
—CO—$R^{10}$ or —$SO_2R^{10}$ wherein $R^{10}$ represents a group selected from alkyl, heterocyclyl (preferably piperidine, pyrrolidine, piperazine or tetrahydrothiopyrandioxide); optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

$R^4$, $R^5$ and the nitrogen atom to which they are attached form together a ring, said ring being preferably an heterocyclyl, preferably selected from morpholine, piperazine or piperidine; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^{11}$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino; and wherein $R^{11}$ represents a hydrogen atom or an optionally substituted group selected from aryl, arylalkyl, alkylaryl, heteroaryl, heteroarylalkyl, alkylheteroaryl, or amino; or $R^{11}$ represents an alkyl group optionally substituted with up to three substituents selected from halogen, hydroxyl, $OR^{12}$, $COOR^{12}$, $CONR^{12}R^{13}$, $NR^{12}COR^{13}$, $NR^{12}R^{13}$, $SO_2R^{12}$, $SO_2NR^{12}R^{13}$, $NR^{12}SO_2R^{13}$, $SO_2R^{12}$, or aryl; wherein $R^{12}$ and $R^{13}$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

In a further embodiment of Formula Ic, $X^1$, $X^2$, $R^1$, $R^2$ and $R^3$ are as defined in Formula I; and $R^4$ is:
a hydrogen atom;
C1-C10 alkyl, linear or branched, methyl, ethyl or propyl; optionally substituted with 1, 2 or 3 independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, or CO—(C1-C6) alkyl, wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, C1-C4 alkylamino, or amino; or
heterocyclyl which is piperidine, tetrahydropyran, pyrrolidine, or piperazine; optionally substituted with 1, 2 or 3 independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more independently selected groups consisting of halogen, hydroxyl, amino or COOH; wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, or amino.

In one embodiment, preferred compounds of Formula Ic are those of Formula Ic':

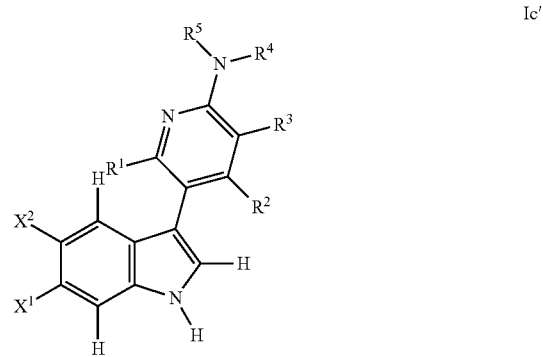

and pharmaceutically acceptable enantiomers, salts and solvates thereof, wherein $X^1$, $X^2$, $R^1$, $R^2$, $R^3$, $R^4$ and $R^5$ are as defined in Formula Ic. In one embodiment, the compound is a pharmaceutically acceptable salt of Formula Ic and Formula Ic'.

In one embodiment, in Formula Ic and/or Formula Ic': $R^4$, $R^5$ and $R^6$ represent each independently: a hydrogen atom; or a C1-C10 alkyl, linear or branched consisting of methyl, ethyl or propyl; any of which is optionally substituted with 1, 2 or 3 independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, or CO-alkyl, wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, C1-C4 alkylamino, or amino; or $R^4$, $R^5$ and $R^6$ represent each independently a heterocyclyl, preferably, piperidine, pyrrolidine, or piperazine; any of which is optionally substituted with 1, 2 or 3 independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, or C1-C4 alkyl amino; or $R^4$, $R^5$ and $R^6$ may also each independently —CO—$R^{10}$ or —$SO_2R^{10}$ wherein $R^{10}$ represents alkyl, amino, C3-cycloalkyl which is morpholine, or a heterocyclyl selected from piperidine, pyrrolidine, piperazine or tetrahydrothiopyrandioxide; wherein the C3-cycloakyl or the heterocycle is optionally substituted with 1, 2 or 3 independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, or alkyl, the alkyl group being optionally substituted by one or more of halogen, hydroxyl, amino or COOH; wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, or amino; or optionally $R^4$, $R^5$ and the nitrogen atom to which they are attached form together a ring, said ring being optionally substituted with 1, 2 or 3 independently selected substituents consisting of oxo, halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^{11}$, $SO_2R^7$, aryl, CO—(C1-C6)alkyl, or C1-C6 alkyl, the alkyl group being optionally substituted by one or more of halogen, hydroxyl, amino or COOH; wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, or amino; and wherein $R^{11}$ represents a hydrogen atom or an optionally substituted group consisting of aryl, arylalkyl, alkylaryl, heteroaryl, heteroarylalkyl, alkylheteroaryl, or amino; or $R^{11}$ represents an C1-C6 alkyl group optionally substituted with a heterocycyl, or 1, 2 or 3 independently selected substituents consisting of halogen, hydroxyl, $OR^{12}$, $COOR^{12}$, $CONR^{12}R^{13}$, $NR^{12}COR^{13}$, $NR^{12}R^{13}$, $SO_2R^{12}$, $SO_2NR^{12}R^{13}$, $NR^{12}SO_2R^{13}$, $SO_2R^{12}$, or aryl; wherein $R^{12}$ and $R^{13}$ represent each independently a hydrogen atom or a group, optionally substituted, consisting of C1-C6 alkyl, aryl, arylalkyl, alkylaryl, heteroaryl, heteroarylalkyl, alkylheteroaryl, or amino.

According to a specific embodiment, in Formula Ic or Ic', $X^1$ represents F and $X^2$ represents H. According to another specific embodiment, in Formula Ic or Ic', $X^1$ represents F and $X^2$ represents F. According to a specific embodiment, in Formula Ic or Ic', $R^1$, $R^2$ and $R^3$ represent hydrogen atoms. According to a specific embodiment, in Formula Ic or Ic', $X^1$ represents F, $X^2$ represents H and $R^1$, $R^2$ and $R^3$ represent hydrogen atoms. According to another specific embodiment, in Formula Ic or Ic', $X^1$ represents F, $X^2$ represents F and $R^1$, $R^2$ and $R^3$ represent hydrogen atoms.

According to a specific embodiment, in Formula Ic or Ic', $R^5$ represents an hydrogen atom. According to a specific embodiment, in Formula Ic or Ic', $R^4$ and $R^5$ represents hydrogen atoms.

According to a specific embodiment, in Formula Ic or Ic', $X^1$ represents F, $X^2$ represents H, $R^1$, $R^2$ and $R^3$ represent hydrogen atoms and $R^5$ represents an hydrogen atom. According to another specific embodiment, in Formula Ic or Ic', $X^1$ represents F, $X^2$ represents F, $R^1$, $R^2$ and $R^3$ represent hydrogen atoms and $R^5$ represents an hydrogen atom.

According to a specific embodiment, in Formula Ic or Ic', $R^5$ represents an alkyl, preferably methyl. According to a specific embodiment, in Formula Ic or Ic', $R^4$ and $R^5$ represents alkyl groups.

According to a specific embodiment, in Formula Ic or Ic', $R^4$ represents an alkyl optionally substituted, preferably optionally substituted methyl, optionally substituted ethyl or optionally substituted propyl. In this embodiment, the alkyl group is preferably substituted by hydroxyl, $COOR^7$, $CONR^7R^8$, $NR^7COR^8$, $NR^7R^8$, $SO_2R^7$, $NR^7SO_2R^8$, wherein $R^7$ and $R^8$ preferably represent each independently a hydrogen atom or an alkyl group; more preferably the alkyl group is substituted by NHCOMe, $NHSO_2Me$, $SO_2Me$, $SO_2NH_2$, $CONH_2$, $NMe_2$, OH or COOH.

According to another specific embodiment, in Formula Ic or Ic', $R^4$ represents an optionally substituted heterocyclyl, preferably an optionally substituted piperidine. According to one embodiment, the piperidine is substituted by an alkyl group, preferably methyl or ethyl, or by $SO_2R^7$, wherein $R^7$ is as defined in Formula Ic and $R^7$ is preferably an alkyl, more preferably methyl.

According to a specific embodiment, in Formula Ic or Ic', $R^4$, $R^5$ and the nitrogen atom to which they are attached form together a ring, said ring being preferably an heterocyclyl, preferably selected from optionally substituted morpholine, piperazine or piperidine. In this embodiment, the heterocyclyl group is preferably substituted by $NR^7COR^8$, $SO_2R^7$, $NR^7SO_2R^{11}$, CO-alkyl, alkyl, the alkyl group being optionally substituted by one or more groups selected from halogen, hydroxyl, amino or COOH; wherein $R^7$ and $R^8$ represent each independently a hydrogen atom or a optionally substituted alkyl; and wherein $R^{11}$ represents an alkyl group optionally substituted with up to three substituents selected from the group comprising halogen, hydroxyl, $OR^{12}$, $COOR^{12}$, $CONR^{12}R^{13}$, $NR^{12}COR^{13}$, $NR^{12}R^{13}$, $SO_2R^{12}$, $SO_2NR^{12}R^{13}$, $NR^{12}SO_2R^{13}$, $SO_2R^{12}$, aryl; wherein $R^{12}$ and $R^{13}$ represent each independently a hydrogen atom or a group, optionally substituted, selected from C1-C6 alkyl, aryl, arylalkyl, alkylaryl, heteroaryl, heteroarylalkyl, alkylheteroaryl, amino. According to a specific embodiment, the heterocyclyl group is substituted by Me, $COCH_2NH_2$, $SO_2Me$, $NHCOCH_2NH_2$ or $NHSO_2Me$ According to a preferred embodiment, $R^4$, $R^5$ and the nitrogen atom to which they are attached form together a morpholine, a piperazine or a piperidine, optionally substituted, more preferably morpholine, 4-methyl-piperazin-1-yl, 4-(2-aminoethanone)-piperazin-1-yl, 4-methylsulfonyl-piperazin-1-yl, 4-(2-amino-N-acetamide)-piperidin-1-yl or 4-N-methanesulfonamide-piperidin-1-yl.

According to another specific embodiment, in Formula Ic or Ic', $R^4$ represents —CO—$R^{10}$ wherein $R^{10}$ represents a group selected from alkyl or heterocyclyl, preferably methyl, ethyl, propyl, n-butyl, i-butyl, t-butyl, piperidine, piperazine or tetrahydrothiopyrandioxide. In this embodiment, the alkyl group or the heterocyclyl group may be substituted, preferably by $NH_2$, aryl or CO-alkyl; more preferably by $NH_2$, phenyl or COMe.

In one embodiment, preferred compounds of Formula Ic are those of Formula Ic-1:

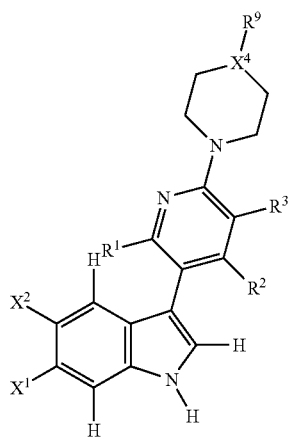

Ic-1 and pharmaceutically acceptable enantiomers, salts and solvates thereof, wherein:

$X^1$, $X^2$, $R^1$, $R^2$ and $R^3$ are as defined in Formula Ic;

$X^4$ represents CH, N or O;

$R^9$ is absent or represents H, halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^{11}$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino; and wherein $R^{11}$ represents a hydrogen atom or an optionally substituted group selected from aryl, arylalkyl, alkylaryl, heteroaryl, heteroarylalkyl, alkylheteroaryl, amino; or $R^{11}$ represents an alkyl group optionally substituted with up to three substituents selected from the group comprising halogen, hydroxyl, $OR^{12}$, $COOR^{12}$, $CONR^{12}R^{13}$, $NR^{12}COR^{13}$, $NR^{12}R^{13}$, $SO_2R^{12}$, $SO_2NR^{12}R^{13}$, $NR^{12}SO_2R^{13}$, $SO_2R^{12}$, aryl; wherein $R^{12}$ and $R^{13}$ represent each independently a hydrogen atom or a group, optionally substituted, selected from C1-C6 alkyl, aryl, arylalkyl, alkylaryl, heteroaryl, heteroarylalkyl, alkylheteroaryl, amino.

In one embodiment, in a compound of Formula Ic-I or a pharmaceutically acceptable salt thereof, X1, X2, R1, R2 and R3 are as defined in Formula Ic;

X4 represents CH, N or O;

R9 is absent or represents H, halogen, hydroxyl, OR7, COOR7, CONR7R8, NR7COR8, NR7R8, SO2R7, SO2NR7R8, NR7SO2R11, SO2R7, aryl, CO-alkyl, or alkyl, the alkyl group being optionally substituted by one or more groups selected from halogen, hydroxyl, amino or COOH; wherein R7 and R8 represent each independently a hydrogen atom or a group, optionally substituted, selected from C1-C6 alkyl, aryl, arylalkyl, alkylaryl, heteroaryl, heteroarylalkyl, alkylheteroaryl, or amino; and wherein R11 represents a hydrogen atom or an optionally substituted group selected from aryl, arylalkyl, alkylaryl, heteroaryl, heteroarylalkyl, alkylheteroaryl, or amino; or R11 represents an alkyl group optionally substituted with up to three substituents selected from halogen, hydroxyl, OR12, COOR12, CONR12R13, NR12COR13, NR12R13, SO2R12, SO2NR12R13, NR12SO2R13, SO2R12, or aryl; wherein R12 and R13 represent each independently a hydrogen atom or a group, optionally substituted, selected from C1-C6 alkyl, aryl, arylalkyl, alkylaryl, heteroaryl, heteroarylalkyl, alkylheteroaryl, or amino.

In one embodiment, preferred compounds of Formula Ic are those of Formula Ic-2:

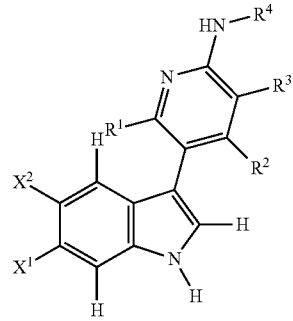

Ic-2 and pharmaceutically acceptable enantiomers, salts and solvates thereof, wherein:

$X^1$, $X^2$, $R^1$, $R^2$ and $R^3$ are as defined in Formula Ic; and $R^4$ represents:
- a hydrogen atom;
- C1-C10 alkyl, linear or branched, preferably methyl, ethyl or propyl; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
- heterocyclyl, preferably selected from piperidine, pyrrolidine, piperazine; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
- —CO—$R^{10}$ or —$SO_2R^{10}$ wherein $R^{10}$ represents a group selected from alkyl, heterocyclyl (preferably piperidine, pyrrolidine, piperazine or tetrahydrothiopyrandioxide); optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, alkyl, the alkyl group being optionally substituted by one or more groups selected from halogen, hydroxyl, amino or COOH;

wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino.

In an embodiment of the formula of Ic and Ic-2, or a pharmaceutically acceptable salt thereof, $X^1$, $X^2$, $R^1$, $R^2$ and $R^3$ are as defined in Formula Ic; and $R^4$ represents:
  a hydrogen atom;
  C1-C10 alkyl, linear or branched, preferably methyl, ethyl or propyl; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, or CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
  heterocyclyl, preferably selected from piperidine, pyrrolidine, piperazine; optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, or alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;
  —CO—$R^{10}$ or —$SO_2R^{10}$ wherein $R^{10}$ represents a group selected from alkyl, heterocyclyl (preferably piperidine, pyrrolidine, piperazine or tetrahydrothiopyrandioxide); optionally substituted with up to three substituents selected from halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

In one embodiment, in the formula of Ic and Ic-2, or a pharmaceutically acceptable salt thereof, $X^4$ represents CH, N or O; and $R^9$ is absent or represents H, halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^{11}$, $SO_2R^7$, aryl, CO-alkyl, alkyl, the alkyl group being optionally substituted by one or more independently selected groups consisting of halogen, hydroxyl, amino or COOH; wherein $R^7$ and $R^8$ represent each independently a hydrogen atom or a group, optionally substituted, consisting of C1-C6 alkyl, aryl, arylalkyl, alkylaryl, heteroaryl, heteroarylalkyl, alkylheteroaryl, amino; and wherein $R^{11}$ represents a hydrogen atom or an optionally substituted group selected from aryl, arylalkyl, alkylaryl, heteroaryl, heteroarylalkyl, alkylheteroaryl, amino; or $R^{11}$ represents an alkyl group optionally substituted with 1, 2 or 3 independently selected substituents consisting of halogen, hydroxyl, $OR^{12}$, $COOR^{12}$, $CONR^{12}R^{13}$, $NR^{12}COR^{13}$, $NR^{12}R^{13}$, $SO_2R^{12}$, $SO_2NR^{12}R^{13}$, $NR^{12}SO_2R^{13}$, $SO_2R^{12}$, or aryl; wherein $R^{12}$ and $R^{13}$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

In one embodiment, preferred compounds of Formula Ic are those of Formula Ic-3:

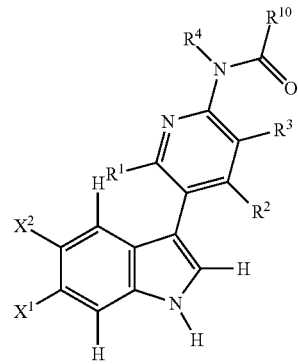

Ic-3 and pharmaceutically acceptable enantiomers, salts and solvates thereof, wherein:
  $X^1$, $X^2$, $R^1$, $R^2$, $R^3$ as defined in Formula Ic;
  $R^4$ represents
    a hydrogen atom;
    C1-C10 alkyl, linear or branched, preferably methyl, ethyl or propyl; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
    heterocyclyl, preferably selected from piperidine, pyrrolidine, piperazine; optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;
    —CO—$R^{10}$ or —$SO_2R^{10}$;
  $R^{10}$ represents a group selected from alkyl, heterocyclyl (preferably piperidine, pyrrolidine, piperazine or tetrahydrothiopyrandioxide); optionally substituted with up to three substituents selected from the group comprising halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SOR^7$, aryl, CO-alkyl, alkyl, the alkyl group being optionally substituted by one or more groups selected from halogen, hydroxyl, amino or COOH; wherein $R^7$ and $R^8$ represent each independently a hydrogen atom or a group, optionally substituted, selected from C1-C6 alkyl, aryl, arylalkyl, alkylaryl, heteroaryl, heteroarylalkyl, alkylheteroaryl, amino.

In another embodiment of Formula Ic-3, or a pharmaceutically acceptable salt thereof, $X^1$, $X^2$, $R^1$, $R^2$, $R^3$ are as defined in Formula Ic;
  $R^4$ represents
    a hydrogen atom;
    C1-C10 alkyl, linear or branched, preferably methyl, ethyl or propyl; optionally substituted with up to three substituents selected from halogen, hydroxyl, OR$^7$, COOR$^7$, CONR$^7$R$^8$, NR$^7$COR$^8$, NR$^7$R$^8$, SO$_2$R$^7$, SO$_2$NR$^7$R$^8$, NR$^7$SO$_2$R$^8$, SOR$^7$, aryl, or CO-alkyl, wherein R$^7$ and R$^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

heterocyclyl, preferably selected from piperidine, pyrrolidine, piperazine; optionally substituted with up to three substituents selected from halogen, hydroxyl, OR$^7$, COOR$^7$, CONR$^7$R$^8$, NR$^7$COR$^8$, NR$^7$R$^8$, SO$_2$R$^7$, SO$_2$NR$^7$R$^8$, NR$^7$SO$_2$R$^8$, SO$_2$R$^7$, aryl, CO-alkyl, or alkyl, the alkyl group being optionally substituted by one or more groups selected from halogen, hydroxyl, amino or COOH; wherein R$^7$ and R$^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino;

—CO—R$^{10}$ or —SO$_2$R$^{10}$;

R$^{10}$ represents a group selected from alkyl, heterocyclyl (preferably piperidine, pyrrolidine, piperazine or tetrahydrothiopyrandioxide); optionally substituted with up to three substituents selected from halogen, hydroxyl, OR$^7$, COOR$^7$, CONR$^7$R$^8$, NR$^7$COR$^8$, NR$^7$R$^8$, SO$_2$R$^7$, SO$_2$NR$^7$R$^8$, NR$^7$SO$_2$R$^8$, SOR$^7$, aryl, CO-alkyl, or alkyl, the alkyl group being optionally substituted by one or more of halogen, hydroxyl, amino or COOH; wherein R$^7$ and R$^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

In one embodiment, in formula Ic-3, R$^4$ represents a hydrogen atom; or C1-C10 alkyl, linear or branched, selected from methyl, ethyl or propyl; any of which is optionally substituted with 1, 2 or 3 independently selected substituents consisting of halogen, hydroxyl, OR$^7$, COOR$^7$, CONR$^7$R$^8$, NR$^7$COR$^8$, NR$^7$R$^8$, SO$_2$R$^7$, SO$_2$NR$^7$R$^8$, NR$^7$SO$_2$R$^8$, SOR$^7$, aryl, or CO-(c1-C6)alkyl, wherein R$^7$ and R$^8$ represent each independently a hydrogen atom or a group, optionally substituted, consisting of C1-C6 alkyl, aryl, arylalkyl, alkylaryl, heteroaryl, heteroarylalkyl, alkylheteroaryl, or amino;

(vi) heterocyclyl selected from piperidine, pyrrolidine, piperazine, or tetrahydropyran; any of which is optionally substituted with 1, 2 or 3 independently selected substituents consisting of halogen, hydroxyl, OR$^7$, COOR$^7$, CONR$^7$R$^8$, NR$^7$COR$^8$, NR$^7$R$^8$, SO$_2$R$^7$, SO$_2$NR$^7$R$^8$, NR$^7$SO$_2$R$^8$, SO$_2$R$^7$, aryl, CO—(C1-C6)alkyl, or C1-C6 alkyl, the alkyl group being optionally substituted by one or more independently selected groups consisting of halogen, hydroxyl, amino or COOH; wherein R$^7$ and R$^8$ represent each independently a hydrogen atom or a group, optionally substituted, selected from C1-C6 alkyl, aryl, arylalkyl, alkylaryl, heteroaryl, heteroarylalkyl, alkylheteroaryl, amino; or (viii) —CO—R$^{10}$ or —SO$_2$R$^{10}$; wherein R$^{10}$ represents a group, optionally substituted, consisting of C1-C6 alkyl, amino, C3 cycloalkyl, morpholine, or heterocyclyl selected from piperidine, pyrrolidine, piperazine or tetrahydrothiopyrandioxide; wherein the optionally substituted group has with 1, 2 or 3 independently selected substituents consisting of halogen, hydroxyl, OR$^7$, COOR$^7$, CONR$^7$R$^8$, NR$^7$COR$^8$, NR$^7$R$^8$, SO$_2$R$^7$, SO$_2$NR$^7$R$^8$, NR$^7$SO$_2$R$^8$, SOR$^7$, aryl, CO—(C1-C6)alkyl, or alkyl, the alkyl group being optionally substituted by one or more groups independently consisting of halogen, hydroxyl, amino or COOH; wherein R$^7$ and R$^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino.

According to a specific embodiment, in Formula Ic-3, R$^4$ is H.

In one embodiment, preferred compounds of Formula I are those of Formula Id:

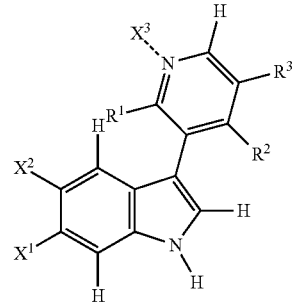

Id and pharmaceutically acceptable enantiomers, salts and solvates thereof, wherein:

X$^1$ and X$^2$ represent each independently H, halogen, alkyl, haloalkyl, preferably H or F, more preferably X$^1$ represents F and X$^2$ represents H or F;

X$^3$ is absent or represents —O$^-$, preferably X$^3$ is absent;

R$^1$, R$^2$ and R$^3$ represent each independently H, halogen, C1-C6 alkyl, alkoxy, haloalkyl, optionally substituted by one or more substituents selected from the group comprising halogen, hydroxyl, OR$^7$, COOR$^7$, CONR$^7$R$^8$, NR$^7$COR$^8$, NR$^7$R$^8$, SO$_2$R$^7$, SO$_2$NR$^7$R$^8$, NR$^7$SO$_2$R$^8$, SO$_2$R$^7$, aryl, CO-alkyl, alkyl, the alkyl group being optionally substituted by one or more groups selected from halogen, hydroxyl, amino or COOH; wherein R$^7$ and R$^8$ represent each independently a hydrogen atom or a group, optionally substituted, selected from C1-C6 alkyl, aryl, arylalkyl, alkylaryl, heteroaryl, heteroarylalkyl, alkylheteroaryl, amino;

preferably R$^1$, R$^2$ and R$^3$ represent each independently H, halogen or methyl, preferably H or methyl, more preferably H.

In one embodiment, in Formula Id, or a pharmaceutically acceptable salt thereof, X$^1$ and X$^2$ represent each independently H, halogen, alkyl, haloalkyl, preferably H or F, more preferably X$^1$ represents F and X$^2$ represents H or F;

X$^3$ is absent or represents —O$^-$, preferably X$^3$ is absent;

R$^1$, R$^2$ and R$^3$ represent each independently H, halogen, C1-C6 alkyl, alkoxy, haloalkyl, optionally substituted by one or more substituents selected halogen, hydroxyl, OR$^7$, COOR$^7$, CONR$^7$R$^8$, NR$^7$COR$^8$, NR$^7$R$^8$, SO$_2$R$^7$, SO$_2$NR$^7$R$^8$, NR$^7$SO$_2$R$^8$, SO$_2$R$^7$, aryl, CO-alkyl, or alkyl, the alkyl group being optionally substituted by one or more groups selected from halogen, hydroxyl, amino or COOH; wherein R$^7$ and R$^8$ represent each independently a hydrogen atom or a group, optionally substituted, selected from C1-C6 alkyl, aryl, arylalkyl, alkylaryl, heteroaryl, heteroarylalkyl, alkylheteroaryl, or amino; preferably R$^1$, R$^2$ and R$^3$ represent each independently H, halogen or methyl, preferably H or methyl, more preferably H.

In one embodiment, in Formula Id', X$^1$, X$^2$, R$^1$, R$^2$ and R$^3$ are not all H. In a further embodiment, X1 or X2 are independently H or F. In still a further embodiment, R$^1$, R$^2$ and R$^3$ represent each independently H, halogen or methyl.

In one embodiment, preferred compounds of Formula Id are those of Formula Id':

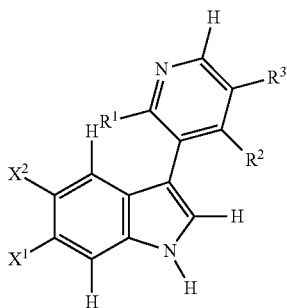

Id' and pharmaceutically acceptable enantiomers, salts and solvates thereof, wherein $X^1$, $X^2$, $R^1$, $R^2$ and $R^3$ are as defined in Formula Id.

According to a specific embodiment, in Formula Id or Id', $X^1$ represents F and $X^2$ represents H. According to another specific embodiment, in Formula Id or Id', $X^1$ represents F and $X^2$ represents F. According to a specific embodiment, in Formula Id or Id', $R^1$, $R^2$ and $R^3$ all represent hydrogen atoms. According to a specific embodiment, in Formula Id or Id', one of $R^1$, $R^2$ and $R^3$ represents an alkyl group, preferably a methyl, the others representing hydrogen atoms.

The compound may have Formula Ie:

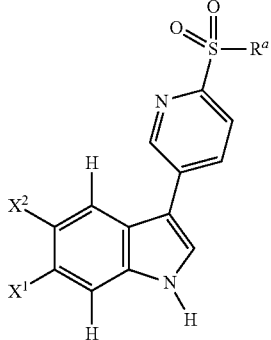

Ie or a pharmaceutically acceptable enantiomer, salt or solvate thereof, wherein $X^1$ and $X^2$ are each independently X1 and X2 are each independently H, halogen, cyano, or C1-C4 alkyl and wherein $R^a$ is amino, piperazine, piperazine substituted with $SO_2(C_1\text{-}C_4$ alkyl), or $NR^b R^{b''}$ wherein $R^b$ is H or $C_1\text{-}C_4$ alkyl and $R^{b''}$ is $CH_2CH_2CONH_2$ or $CH_2\text{—}CH_2\text{—}N(H)(R^c)\text{—}R^d$, wherein $R^c$ is $SO_2$ or CO, and $R^d$ is $C_1\text{-}C_4$ alkyl or amino. In one embodiment, $R^a$ is piperazine, optionally substituted with C1 alkyl. In another embodiment, $R^a$ is $NR^b R^{b''}$ wherein $R^b$ is H or $C_1\text{-}C_4$ alkyl and $R^{b''}$ is $CH_2\text{-}CH_2\text{—}N(H)(R^c)\text{—}R^d$, wherein $R^c$ is $SO_2$ or CO, and $R^d$ is $C_1\text{-}C_4$ alkyl or amino. In still another embodiment, $R^b$ is C1 alkyl. In a further embodiment, $R^d$ is C1 alkyl or amino.

The compound may have Formula If:

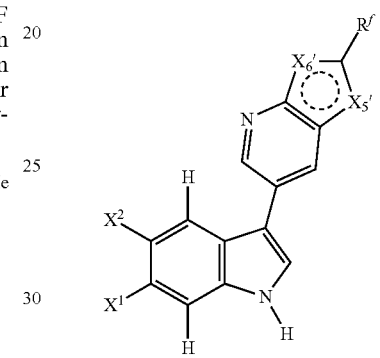

wherein one of X6' or X5' is N, and the other is selected from O, $CH_2$, $NR^{16}$, wherein $R^{16}$ is H or C1-C4 alkyl, and $R^f$ is H, C1-C4 alkyl, hydroxy, or oxo.

Illustrative compounds of Formula I are listed in Table 1 hereafter.

TABLE 1

| Cpd no | Structure | Chemical name | MW (calc'd) |
|---|---|---|---|
| 1 | 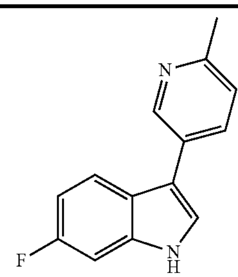 | 6-fluoro-3-(6-methylpyridin-3-yl)-1H-indole | 226.25 |
| 2 | 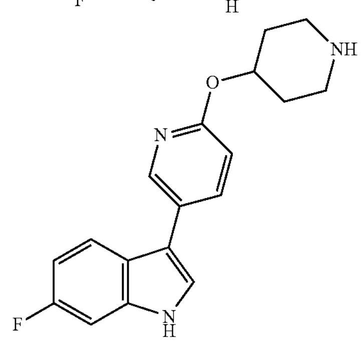 | 6-fluoro-3-(6-(piperidin-4-yloxy)pyridin-3-yl)-1H-indole | 311.36 |

TABLE 1-continued

| Cpd no | Structure | Chemical name | MW (calc'd) |
|---|---|---|---|
| 3 | 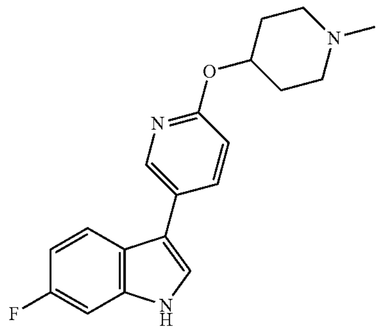 [SMILES: CN1CCC(Oc2ccc(-c3c[nH]c4cc(F)ccc34)cn2)CC1] | 6-fluoro-3-(6-((1-methylpiperidin-4-yl)oxy)pyridin-3-yl)-1H-indole | 325.39 |
| 4 | 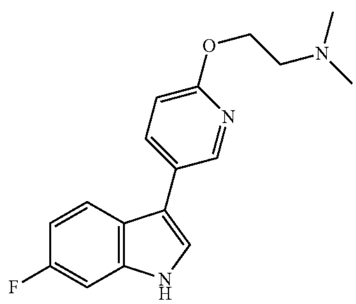 [SMILES: CN(C)CCOc1ccc(-c2c[nH]c3cc(F)ccc23)cn1] | 2-((5-(6-fluoro-1H-indol-3-yl)pyridin-2-yl)oxy)-N,N-dimethylethanamine | 299.35 |
| 5 | 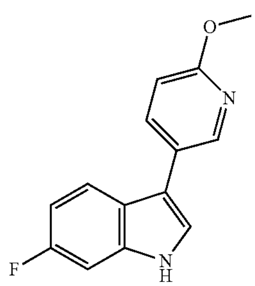 [SMILES: COc1ccc(-c2c[nH]c3cc(F)ccc23)cn1] | 6-fluoro-3-(6-methoxypyridin-3-yl)-1H-indole | 242.25 |
| 6 | 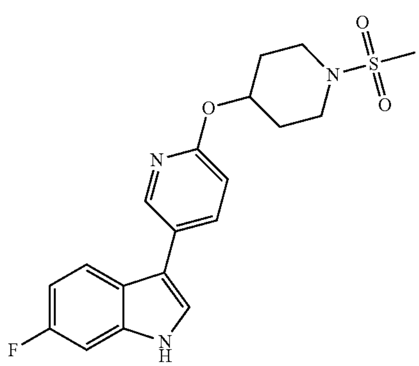 [SMILES: CS(=O)(=O)N1CCC(Oc2ccc(-c3c[nH]c4cc(F)ccc34)cn2)CC1] | 5-(6-fluoro-1H-indol-3-yl)-N-(1-(methylsulfonyl)piperidin-4-yl)pyridin-2-amine | 389.45 |
| 7 | 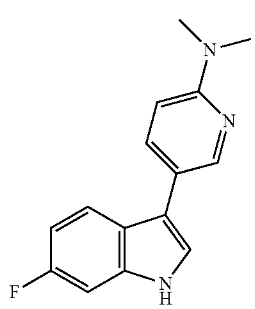 [SMILES: CN(C)c1ccc(-c2c[nH]c3cc(F)ccc23)cn1] | 5-(6-fluoro-1H-indol-3-yl)-N,N-dimethylpyridin-2-amine | 255.30 |

TABLE 1-continued
| Cpd no | Structure | Chemical name | MW (calc'd) |
|---|---|---|---|
| 8 | 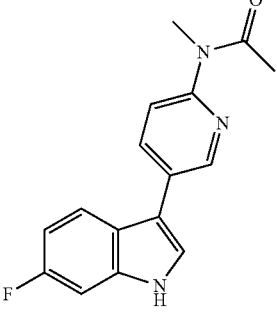 | N-(5-(6-fluoro-1H-indol-3-yl)pyridin-2-yl)-N-methylacetamide | 283.30 |
| 9 | 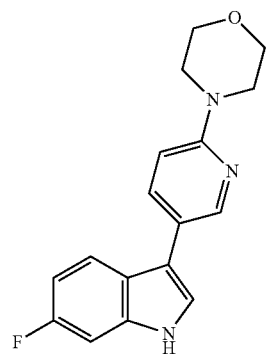 [SMILES: Fc1ccc2c(-c3ccc(N4CCOCC4)nc3)c[nH]c2c1] | 4-(5-(6-fluoro-1H-indol-3-yl)pyridin-2-yl)morpholine | 297.33 |
| 10 | 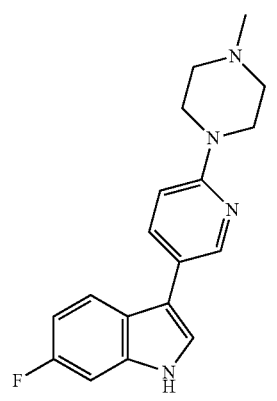 [SMILES: CN1CCN(c2ccc(-c3c[nH]c4cc(F)ccc34)cn2)CC1] | 6-fluoro-3-(6-(4-methylpiperazin-1-yl)pyridin-3-yl)-1H-indole | 310.38 |
| 11 | 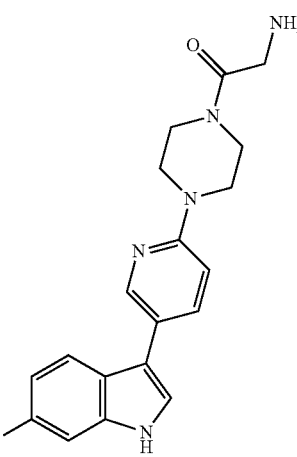 | 2-amino-1-(4-(5-(6-fluoro-1H-indol-3-yl)pyridin-2-yl)piperazin-1-yl)ethanone | 353.39 |

TABLE 1-continued

| Cpd no | Structure | Chemical name | MW (calc'd) |
|---|---|---|---|
| 12 | 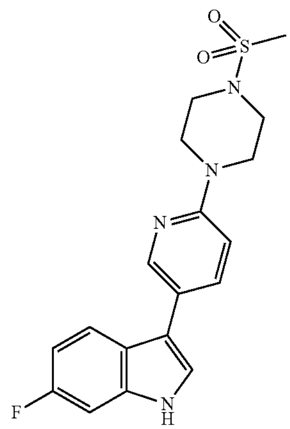 [SMILES: CS(=O)(=O)N1CCN(c2ccc(-c3c[nH]c4cc(F)ccc34)cn2)CC1] | 6-fluoro-3-(6-(4-(methylsulfonyl)piperazin-1-yl)pyridin-3-yl)-1H-indole | 374.43 |
| 13 | 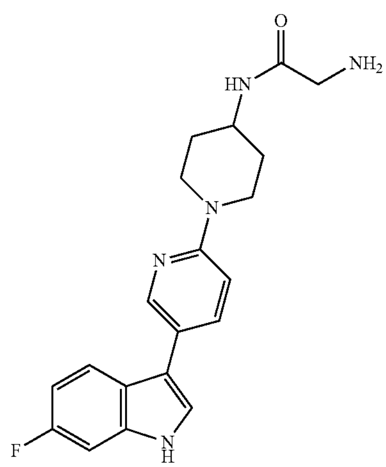 [SMILES: NCC(=O)NC1CCN(c2ccc(-c3c[nH]c4cc(F)ccc34)cn2)CC1] | 2-amino-N-(1-(5-(6-fluoro-1H-indol-3-yl)pyridin-2-yl)piperidin-4-yl)acetamide | 367.42 |
| 14 | 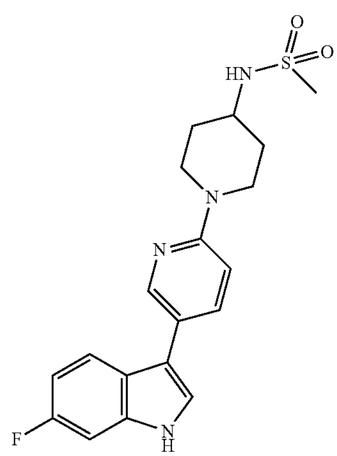 [SMILES: CS(=O)(=O)NC1CCN(c2ccc(-c3c[nH]c4cc(F)ccc34)cn2)CC1] | N-(1-(5-(6-fluoro-1H-indol-3-yl)pyridin-2-yl)piperidin-4-yl)methanesulfonamide | 388.46 |
| 15 | 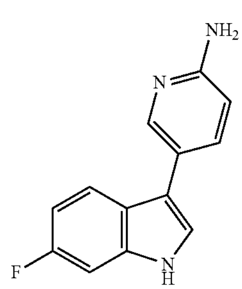 [SMILES: Nc1ccc(-c2c[nH]c3cc(F)ccc23)cn1] | 5-(6-fluoro-1H-indol-3-yl)pyridin-2-amine | 227.24 |

TABLE 1-continued

| Cpd no | Structure | Chemical name | MW (calc'd) |
|---|---|---|---|
| 16 | 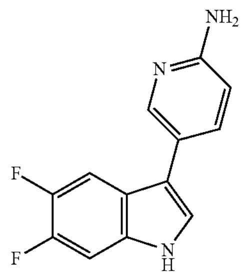 [SMILES: Nc1ccc(-c2c[nH]c3cc(F)c(F)cc23)cn1] | 5-(5,6-difluoro-1H-indol-3-yl)pyridin-2-amine | 245.23 |
| 17 | 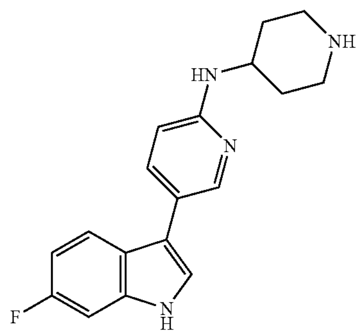 [SMILES: Fc1ccc2c(-c3ccc(NC4CCNCC4)nc3)c[nH]c2c1] | 5-(6-fluoro-1H-indol-3-yl)-N-(piperidin-4-yl)pyridin-2-amine | 310.37 |
| 18 | 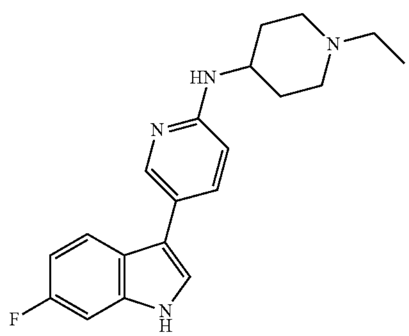 [SMILES: CCN1CCC(Nc2ccc(-c3c[nH]c4cc(F)ccc34)cn2)CC1] | N-(1-ethylpiperidin-4-yl)-5-(6-fluoro-1H-indol-3-yl)pyridin-2-amine | 338.43 |
| 19 | 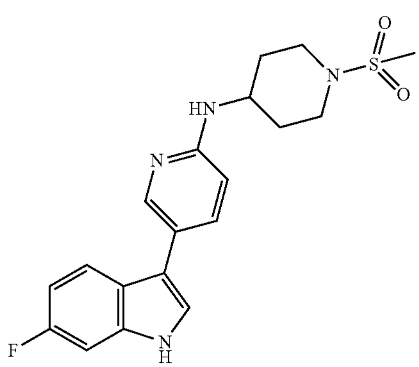 [SMILES: CS(=O)(=O)N1CCC(Nc2ccc(-c3c[nH]c4cc(F)ccc34)cn2)CC1] | 5-(6-fluoro-1H-indol-3-yl)-N-(1-(methylsulfonyl)piperidin-4-yl)pyridin-2-amine | 388.46 |
| 20 | 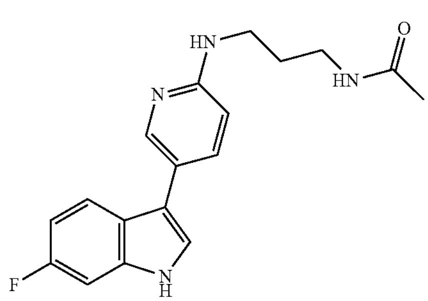 [SMILES: CC(=O)NCCCNc1ccc(-c2c[nH]c3cc(F)ccc23)cn1] | N-(3-((5-(6-fluoro-1H-indol-3-yl)pyridin-2-yl)amino)propyl)acetamide | 326.38 |

TABLE 1-continued
| Cpd no | Structure | Chemical name | MW (calc'd) |
|---|---|---|---|
| 21 | 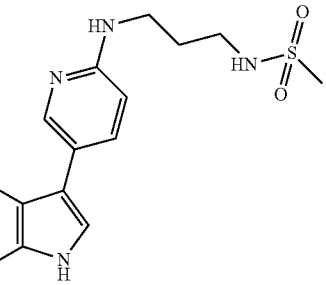 | N-(3-((5-(6-fluoro-1H-indol-3-yl)pyridin-2-yl)amino)propyl)methanesulfonamide | 362.42 |
| 22 | 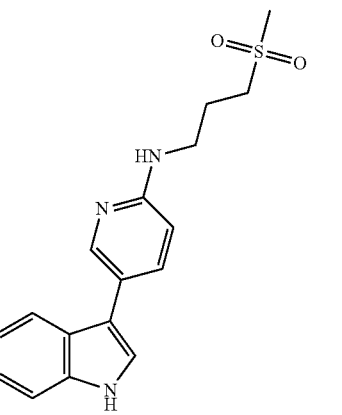 | 5-(6-fluoro-1H-indol-3-yl)-N-(3-(methylsulfonyl)propyl)pyridin-2-amine | 347.41 |
| 23 | 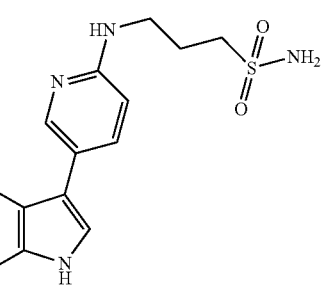 | 3-((5-(6-fluoro-1H-indol-3-yl)pyridin-2-yl)amino)propane-1-sulfonamide | 348.40 |
| 24 | 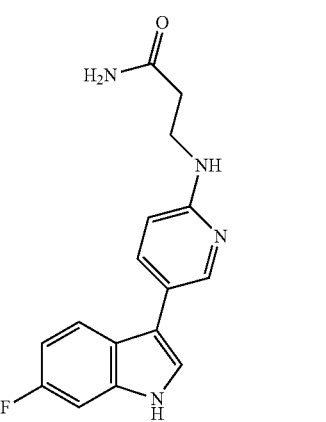 [SMILES: NC(=O)CCNc1ccc(-c2c[nH]c3cc(F)ccc23)cn1] | 3-((5-(6-fluoro-1H-indol-3-yl)pyridin-2-yl)amino)propanamide | 298.32 |

TABLE 1-continued
| Cpd no | Structure | Chemical name | MW (calc'd) |
|---|---|---|---|
| 25 | 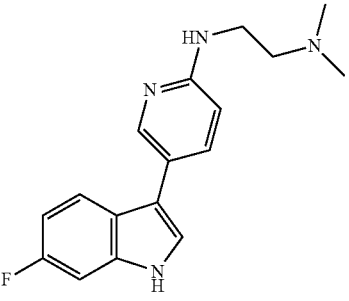 [SMILES: CN(C)CCNc1ccc(-c2c[nH]c3cc(F)ccc23)cn1] | $N^1$-(5-(6-fluoro-1H-indol-3-yl)pyridin-2-yl)-$N^2$,$N^2$-dimethylethane-1,2-diamine | 298.37 |
| 26 | 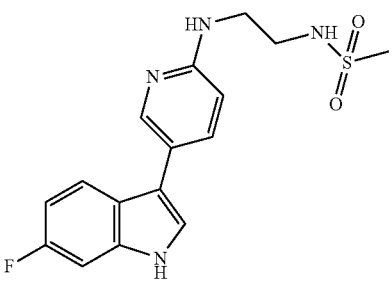 [SMILES: CS(=O)(=O)NCCNc1ccc(-c2c[nH]c3cc(F)ccc23)cn1] | N-(2-((5-(6-fluoro-1H-indol-3-yl)pyridin-2-yl)amino)ethyl)methanesulfonamide | 348.40 |
| 27 | 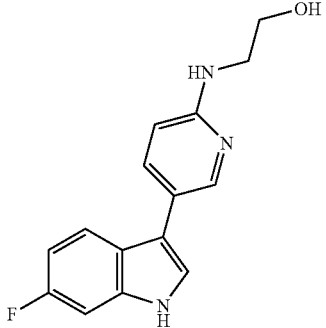 [SMILES: OCCNc1ccc(-c2c[nH]c3cc(F)ccc23)cn1] | 2-((5-(6-fluoro-1H-indol-3-yl)pyridin-2-yl)amino)ethanol | 271.30 |
| 28 | 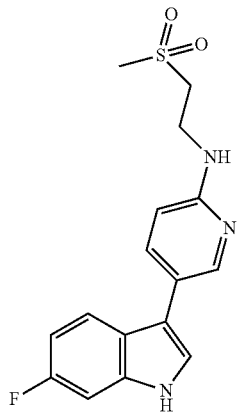 [SMILES: CS(=O)(=O)CCNc1ccc(-c2c[nH]c3cc(F)ccc23)cn1] | 5-(6-fluoro-1H-indol-3-yl)-N-(2-(methylsulfonyl)ethyl)pyridin-2-amine | 333.38 |

TABLE 1-continued

| Cpd no | Structure | Chemical name | MW (calc'd) |
|---|---|---|---|
| 29 | 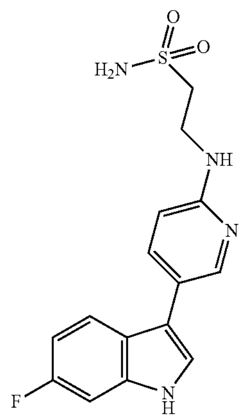 [SMILES: NS(=O)(=O)CCNc1ccc(-c2c[nH]c3cc(F)ccc23)cn1] | 2-((5-(6-fluoro-1H-indol-3-yl)pyridin-2-yl)amino)ethanesulfonamide | 334.37 |
| 30 | 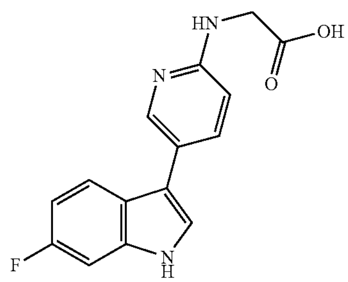 [SMILES: O=C(O)CNc1ccc(-c2c[nH]c3cc(F)ccc23)cn1] | 2-((5-(6-fluoro-1H-indol-3-yl)pyridin-2-yl)amino)acetic acid | 285.28 |
| 31 | 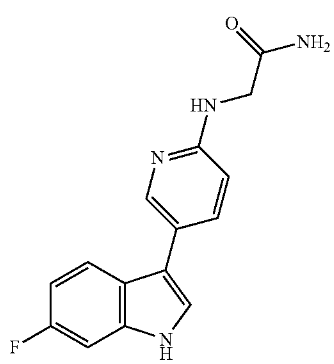 [SMILES: NC(=O)CNc1ccc(-c2c[nH]c3cc(F)ccc23)cn1] | 2-((5-(6-fluoro-1H-indol-3-yl)pyridin-2-yl)amino)acetamide | 284.29 |
| 32 | 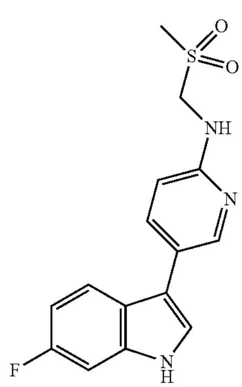 [SMILES: CS(=O)(=O)CNc1ccc(-c2c[nH]c3cc(F)ccc23)cn1] | ((5-(6-fluoro-1H-indol-3-yl)pyridin-2-yl)amino)methanesulfonamide | 320.34 |

TABLE 1-continued

| Cpd no | Structure | Chemical name | MW (calc'd) |
|---|---|---|---|
| 33 | 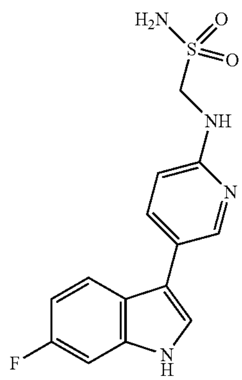 [SMILES: NS(=O)(=O)CNc1ccc(-c2c[nH]c3cc(F)ccc23)cn1] | 5-(6-fluoro-1H-indol-3-yl)-N-methylpyridin-2-amine | 241.26 |
| 34 | 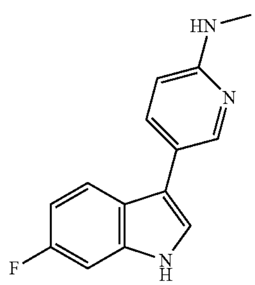 [SMILES: CNc1ccc(-c2c[nH]c3cc(F)ccc23)cn1] | 5-(6-fluoro-1H-indol-3-yl)-N-methylpyridin-2-amine | 241.27 |
| 35 | 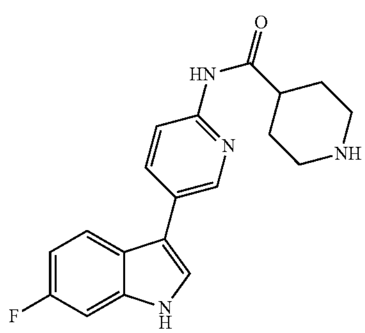 [SMILES: O=C(Nc1ccc(-c2c[nH]c3cc(F)ccc23)cn1)C1CCNCC1] | N-(5-(6-fluoro-1H-indol-3-yl)pyridin-2-yl)piperidine-4-carboxamide | 338.38 |
| 36 | 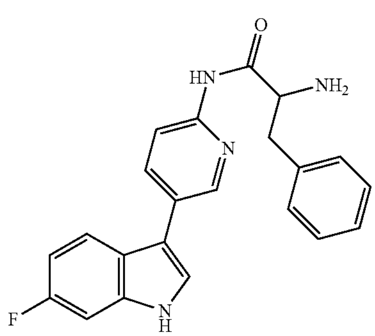 [SMILES: NC(Cc1ccccc1)C(=O)Nc1ccc(-c2c[nH]c3cc(F)ccc23)cn1] | 2-amino-N-(5-(6-fluoro-1H-indol-3-yl)pyridin-2-yl)-3-phenylpropanamide | 374.41 |

TABLE 1-continued

| Cpd no | Structure | Chemical name | MW (calc'd) |
|---|---|---|---|
| 37 | 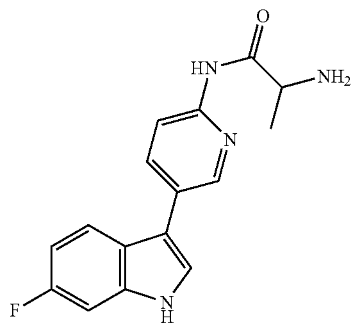 [SMILES: CC(N)C(=O)Nc1ccc(-c2c[nH]c3cc(F)ccc23)cn1] | 2-amino-N-(5-(6-fluoro-1H-indol-3-yl)pyridin-2-yl)propanamide | 298.32 |
| 38 | 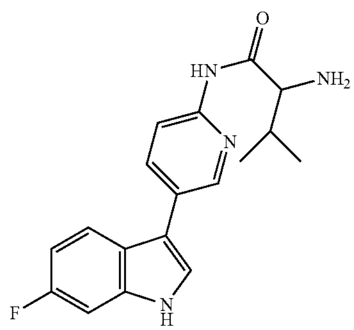 [SMILES: CC(C)C(N)C(=O)Nc1ccc(-c2c[nH]c3cc(F)ccc23)cn1] | 2-amino-N-(5-(6-fluoro-1H-indol-3-yl)pyridin-2-yl)-3-methylbutanamide | 326.37 |
| 39 | 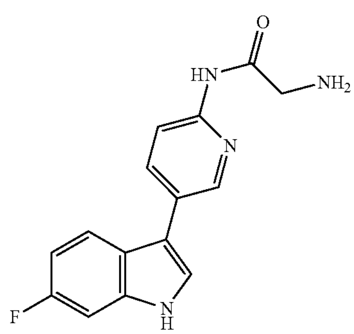 [SMILES: NCC(=O)Nc1ccc(-c2c[nH]c3cc(F)ccc23)cn1] | 2-amino-N-(5-(6-fluoro-1H-indol-3-yl)pyridin-2-yl)acetamide | 284.29 |
| 40 | 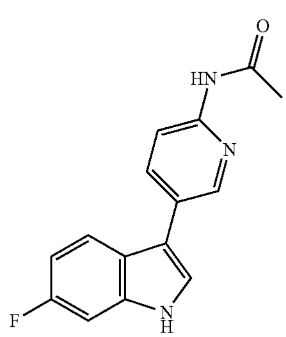 [SMILES: CC(=O)Nc1ccc(-c2c[nH]c3cc(F)ccc23)cn1] | N-(5-(6-fluoro-1H-indol-3-yl)pyridin-2-yl)acetamide | 269.27 |

TABLE 1-continued
| Cpd no | Structure | Chemical name | MW (calc'd) |
|---|---|---|---|
| 41 | 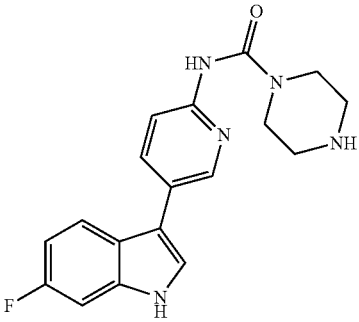 [SMILES: O=C(Nc1ccc(-c2c[nH]c3cc(F)ccc23)cn1)N1CCNCC1] | N-(5-(6-fluoro-1H-indol-3-yl)pyridin-2-yl)piperazine-1-carboxamide | 339.37 |
| 42 | 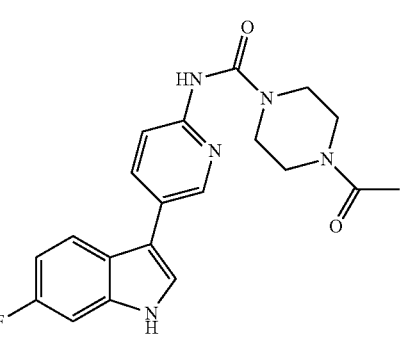 | 4-acetyl-N-(5-(6-fluoro-1H-indol-3-yl)pyridin-2-yl)piperazine-1-carboxamide | 381.40 |
| 43 | 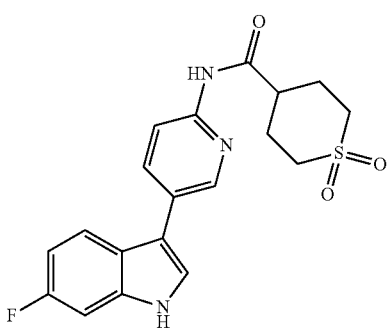 [SMILES: O=C(Nc1ccc(-c2c[nH]c3cc(F)ccc23)cn1)C1CCS(=O)(=O)CC1] | N-(5-(6-fluoro-1H-indol-3-yl)pyridin-2-yl)tetrahydro-2H-thiopyran-4-carboxamide 1,1-dioxide | 387.43 |
| 44 | 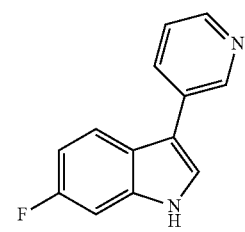 [SMILES: Fc1ccc2c(-c3cccnc3)c[nH]c2c1] | 6-fluoro-3-(pyridin-3-yl)-1H-indole | 212.23 |
| 45 | 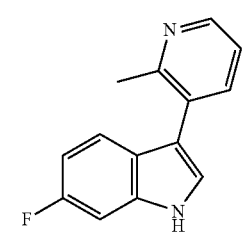 [SMILES: Cc1ncccc1-c1c[nH]c2cc(F)ccc12] | 6-fluoro-3-(2-methylpyridin-3-yl)-1H-indole | 226.25 |

TABLE 1-continued

| Cpd no | Structure | Chemical name | MW (calc'd) |
| --- | --- | --- | --- |
| 46 | 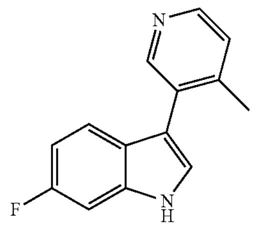 [SMILES: Cc1ccncc1-c1c[nH]c2cc(F)ccc12] | 6-fluoro-3-(4-methylpyridin-3-yl)-1H-indole | 226.25 |
| 47 | 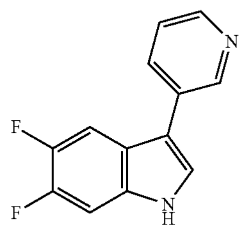 [SMILES: Fc1cc2[nH]cc(-c3cccnc3)c2cc1F] | 5,6-difluoro-3-(pyridin-3-yl)-1H-indole | 230.22 |
| 48 | 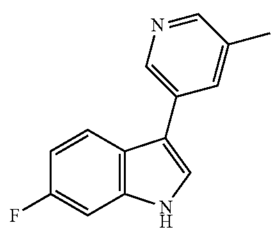 [SMILES: Cc1cncc(-c2c[nH]c3cc(F)ccc23)c1] | 6-fluoro-3-(5-methylpyridin-3-yl)-1H-indole | 226.25 |
| 49 | 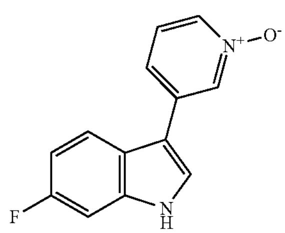 [SMILES: [O-][n+]1cccc(-c2c[nH]c3cc(F)ccc23)c1] | 3-(6-fluoro-1H-indol-3-yl)pyridine 1-oxide | 228.23 |
| 50 | 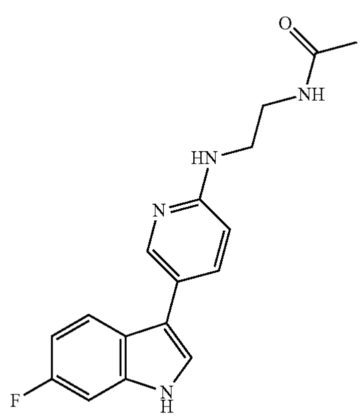 [SMILES: CC(=O)NCCNc1ccc(-c2c[nH]c3cc(F)ccc23)cn1] | N-(2-((5-(6-fluoro-1H-indol-3-yl)pyridin-2-yl)amino)ethyl)acetamide | 312.34 |

TABLE 1-continued
| Cpd no | Structure | Chemical name | MW (calc'd) |
|---|---|---|---|
| 51 | 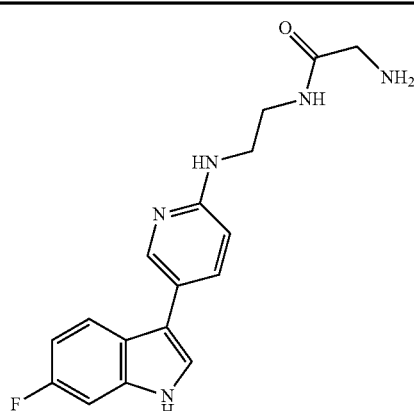 | 2-amino-N-(2-((5-(6-fluoro-1H-indol-3-yl)pyridin-2-yl)amino)ethyl)acetamide | 327.36 |
| 52 | 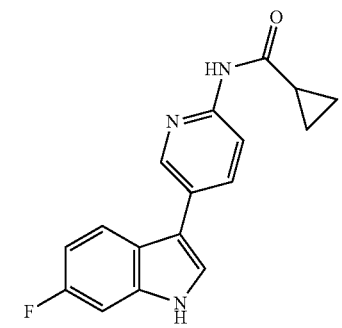 [SMILES: O=C(Nc1ccc(-c2c[nH]c3cc(F)ccc23)cn1)C1CC1] | N-(5-(6-fluoro-1H-indol-3-yl)pyridin-2-yl)cyclopropanecarboxamide | 295.31 |
| 53 | 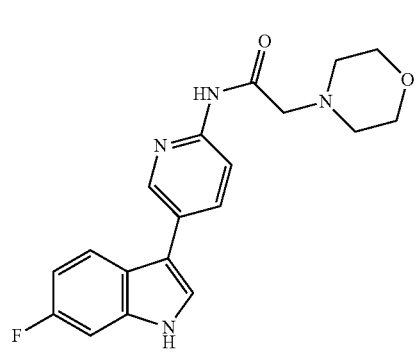 [SMILES: O=C(CN1CCOCC1)Nc1ccc(-c2c[nH]c3cc(F)ccc23)cn1] | N-(5-(6-fluoro-1H-indol-3-yl)pyridin-2-yl)-2-morpholinoacetamide | 354.38 |
| 54 | 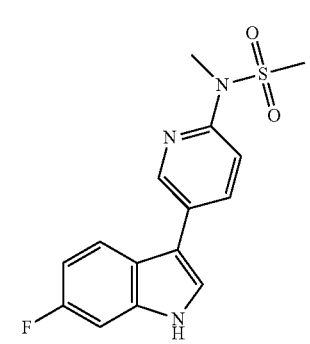 [SMILES: CN(c1ccc(-c2c[nH]c3cc(F)ccc23)cn1)S(C)(=O)=O] | N-(5-(6-fluoro-1H-indol-3-yl)pyridin-2-yl)-N-methylmethanesulfonamide | 319.35 |

TABLE 1-continued
| Cpd no | Structure | Chemical name | MW (calc'd) |
|---|---|---|---|
| 55 | 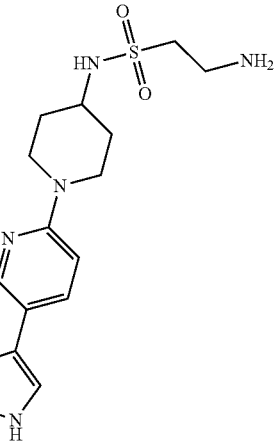 | 2-amino-N-(1-(5-(6-fluoro-1H-indol-3-yl)pyridin-2-yl)piperidin-4-yl)ethanesulfonamide | 417.50 |
| 56 | 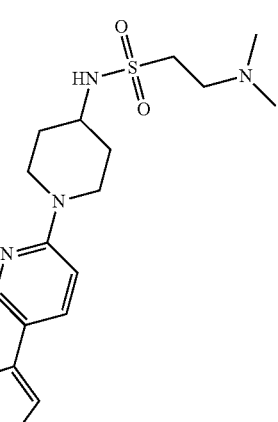 | 2-(dimethylamino)-N-(1-(5-(6-fluoro-1H-indol-3-yl)pyridin-2-yl)piperidin-4-yl)ethanesulfonamide | 445.55 |
| 57 | 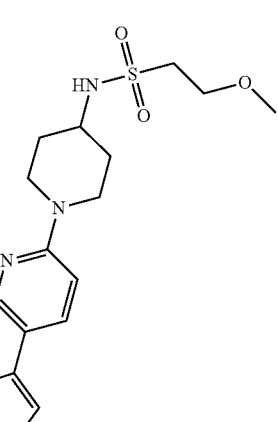 | N-(1-(5-(6-fluoro-1H-indol-3-yl)pyridin-2-yl)piperidin-4-yl)-2-methoxyethanesulfonamide | 432.51 |

TABLE 1-continued
| Cpd no | Structure | Chemical name | MW (calc'd) |
|---|---|---|---|
| 58 | 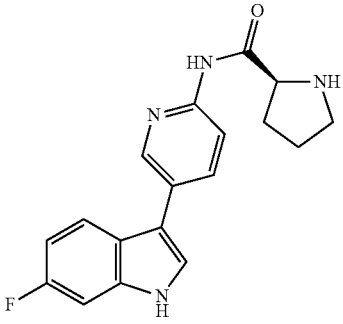 [SMILES: O=C(Nc1ccc(-c2c[nH]c3cc(F)ccc23)cn1)[C@@H]1CCCN1] | (S)-N-(5-(6-fluoro-1H-indol-3-yl)pyridin-2-yl)pyrrolidine-2-carboxamide | 324.35 |
| 59 | 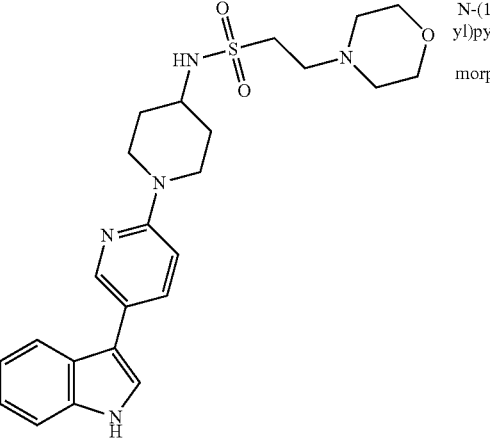 | N-(1-(5-(6-fluoro-1H-indol-3-yl)pyridin-2-yl)piperidin-4-yl)-2-morpholinoethanesulfonamide | 487.59 |
| 60 | 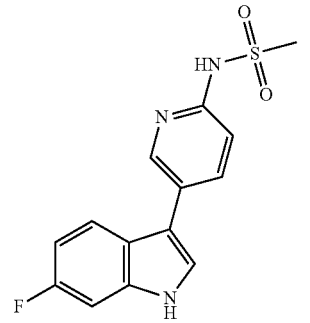 [SMILES: CS(=O)(=O)Nc1ccc(-c2c[nH]c3cc(F)ccc23)cn1] | N-(5-(6-fluoro-1H-indol-3-yl)pyridin-2-yl)methanesulfonamide | 305.33 |
| 61 | 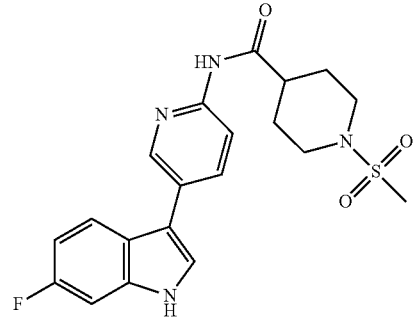 [SMILES: CS(=O)(=O)N1CCC(C(=O)Nc2ccc(-c3c[nH]c4cc(F)ccc34)cn2)CC1] | N-(5-(6-fluoro-1H-indol-3-yl)pyridin-2-yl)-1-(methylsulfonyl)piperidine-4-carboxamide | 416.47 |

TABLE 1-continued
| Cpd no | Structure | Chemical name | MW (calc'd) |
|---|---|---|---|
| 62 | 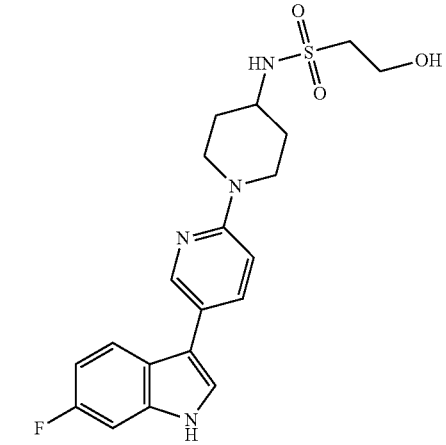 [SMILES: O=S(=O)(CCO)NC1CCN(c2ccc(-c3c[nH]c4cc(F)ccc34)cn2)CC1] | N-(1-(5-(6-fluoro-1H-indol-3-yl)pyridin-2-yl)piperidin-4-yl)-2-hydroxyethanesulfonamide | 418.49 |
| 63 | 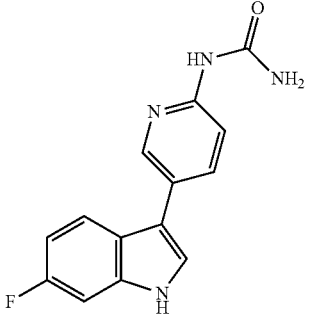 [SMILES: NC(=O)Nc1ccc(-c2c[nH]c3cc(F)ccc23)cn1] | 1-(5-(6-fluoro-1H-indol-3-yl)pyridin-2-yl)urea | 270.26 |
| 64 | 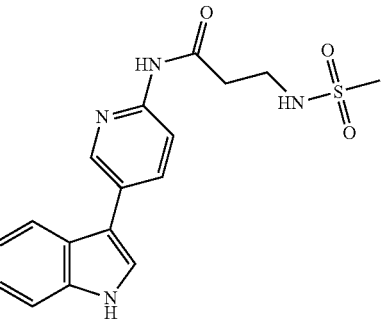 | N-(5-(6-fluoro-1H-indol-3-yl)pyridin-2-yl)-3-(methylsulfonamido)propanamide | 376.41 |
| 65 | 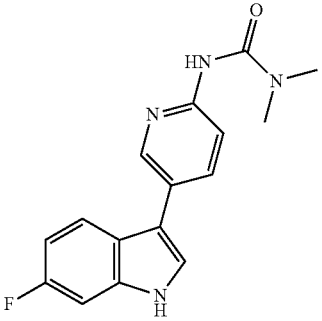 [SMILES: CN(C)C(=O)Nc1ccc(-c2c[nH]c3cc(F)ccc23)cn1] | 3-(5-(6-fluoro-1H-indol-3-yl)pyridin-2-yl)-1,1-dimethylurea | 298.31 |

TABLE 1-continued

| Cpd no | Structure | Chemical name | MW (calc'd) |
|---|---|---|---|
| 66 | 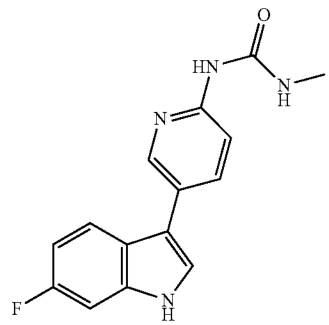 [SMILES: CNC(=O)Nc1ccc(-c2c[nH]c3cc(F)ccc23)cn1] | 1-(5-(6-fluoro-1H-indol-3-yl)pyridin-2-yl)-3-methylurea | 284.29 |
| 67 | 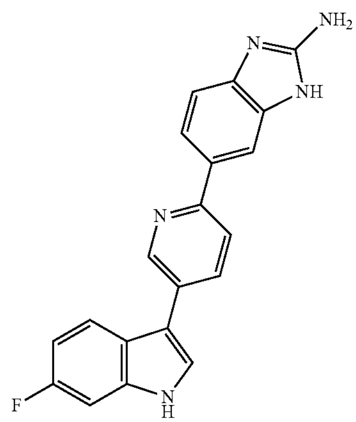 [SMILES: Nc1nc2ccc(-c3ccc(-c4c[nH]c5cc(F)ccc45)cn3)cc2[nH]1] | 6-(5-(6-fluoro-1H-indol-3-yl)pyridin-2-yl)-1H-benzo[d]imidazol-2-amine | 343.36 |
| 68 | 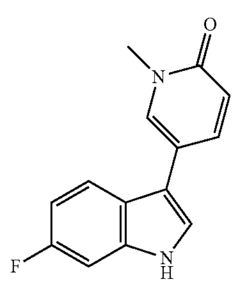 [SMILES: Cn1cc(-c2c[nH]c3cc(F)ccc23)ccc1=O] | 5-(6-fluoro-1H-indol-3-yl)-1-methylpyridin-2(1H)-one | 242.25 |
| 69 | 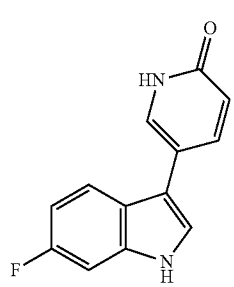 [SMILES: O=c1ccc(-c2c[nH]c3cc(F)ccc23)c[nH]1] | 5-(6-fluoro-1H-indol-3-yl)pyridin-2(1H)-one | 228.22 |

TABLE 1-continued

| Cpd no | Structure | Chemical name | MW (calc'd) |
|---|---|---|---|
| 70 | 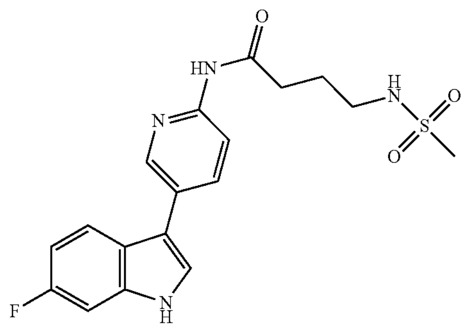 [SMILES: CS(=O)(=O)NCCCC(=O)Nc1ccc(-c2c[nH]c3cc(F)ccc23)cn1] | N-(5-(6-fluoro-1H-indol-3-yl)pyridin-2-yl)-4-(methylsulfonamido)butanamide | 390.43 |
| 71 | 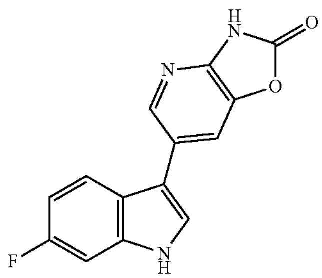 [SMILES: O=c1[nH]c2ncc(-c3c[nH]c4cc(F)ccc34)cc2o1] | 6-(6-fluoro-1H-indol-3-yl)oxazolo[4,5-b]pyridin-2(3H)-one | 269.23 |
| 72 | 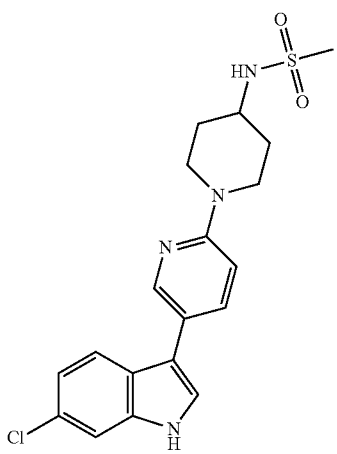 [SMILES: CS(=O)(=O)NC1CCN(c2ccc(-c3c[nH]c4cc(Cl)ccc34)cn2)CC1] | N-(1-(5-(6-chloro-1H-indol-3-yl)pyridin-2-yl)piperidin-4-yl)methanesulfonamide | 404.91 |
| 73 | 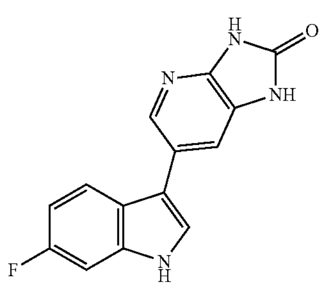 [SMILES: O=c1[nH]c2cc(-c3c[nH]c4cc(F)ccc34)cnc2[nH]1] | 6-(6-fluoro-1H-indol-3-yl)-1H-imidazo[4,5-b]pyridin-2(3H)-one | 268.25 |
| 74 | 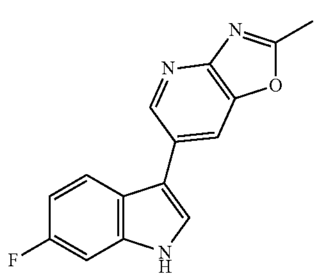 [SMILES: Cc1nc2ncc(-c3c[nH]c4cc(F)ccc34)cc2o1] | 6-(6-fluoro-1H-indol-3-yl)-2-methyloxazolo[4,5-b]pyridine | 267.26 |

TABLE 1-continued

| Cpd no | Structure | Chemical name | MW (calc'd) |
|---|---|---|---|
| 75 | 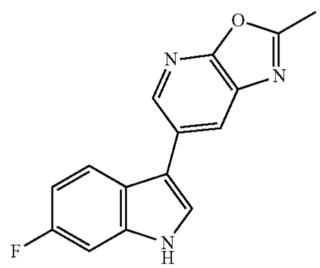 [SMILES: Cc1nc2cc(-c3c[nH]c4cc(F)ccc34)cnc2o1] | 6-(6-fluoro-1H-indol-3-yl)-2-methyloxazolo[5,4-b]pyridine | 267.26 |
| 76 | 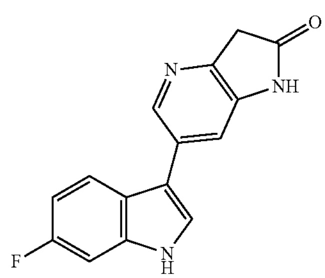 [SMILES: O=C1Cc2ncc(-c3c[nH]c4cc(F)ccc34)cc2N1] | 6-(6-fluoro-1H-indol-3-yl)-1H-pyrrolo[3,2-b]pyridin-2(3H)-one | 267.26 |
| 77 | 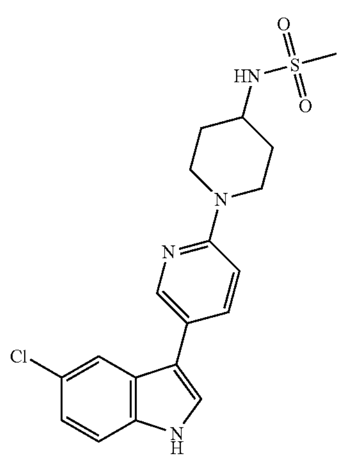 [SMILES: CS(=O)(=O)NC1CCN(c2ccc(-c3c[nH]c4ccc(Cl)cc34)cn2)CC1] | N-(1-(5-(5-chloro-1H-indol-3-yl)pyridin-2-yl)piperidin-4-yl)methanesulfonamide | 404.91 |
| 78 | 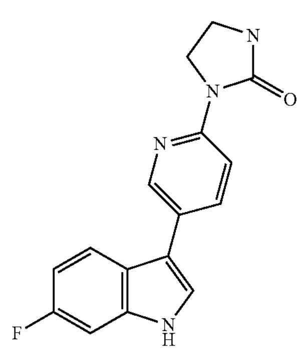 [SMILES: O=C1NCCN1c1ccc(-c2c[nH]c3cc(F)ccc23)cn1] | 1-(5-(6-fluoro-1H-indol-3-yl)pyridin-2-yl)imidazolidin-2-one | 296.30 |

TABLE 1-continued
| Cpd no | Structure | Chemical name | MW (calc'd) |
|---|---|---|---|
| 79 | 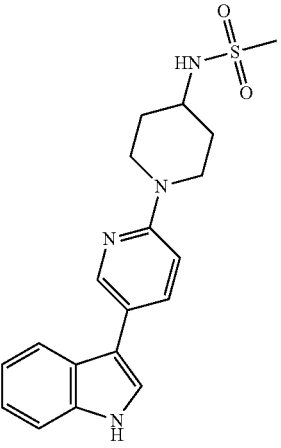 [SMILES: CS(=O)(=O)NC1CCN(c2ccc(-c3c[nH]c4ccccc34)cn2)CC1] | N-(1-(5-(1H-indol-3-yl)pyridin-2-yl)piperidin-4-yl)methanesulfonamide | 370.47 |
| 80 | 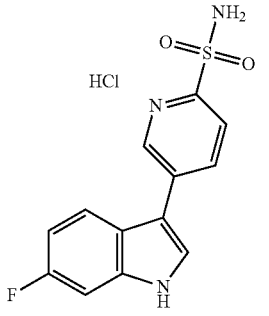 [SMILES: NS(=O)(=O)c1ccc(-c2c[nH]c3cc(F)ccc23)cn1 ; Cl] | 5-(6-fluoro-1H-indol-3-yl)pyridine-2-sulfonamide hydrochloride | 327.76 |
| 81 | 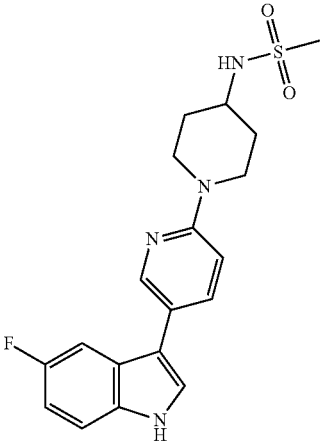 [SMILES: CS(=O)(=O)NC1CCN(c2ccc(-c3c[nH]c4ccc(F)cc34)cn2)CC1] | N-(1-(5-(5-fluoro-1H-indol-3-yl)pyridin-2-yl)piperidin-4-yl)methanesulfonamide | 388.46 |
| 82 | 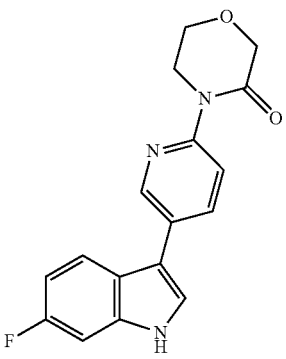 [SMILES: O=C1COCCN1c1ccc(-c2c[nH]c3cc(F)ccc23)cn1] | 4-(5-(6-fluoro-1H-indol-3-yl)pyridin-2-yl)morpholin-3-one | 311.31 |

TABLE 1-continued

| Cpd no | Structure | Chemical name | MW (calc'd) |
|---|---|---|---|
| 83 | 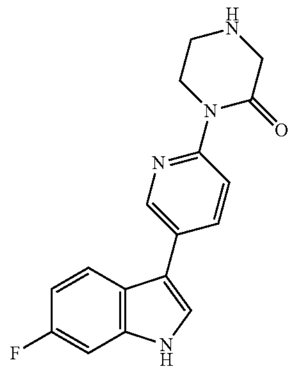 [SMILES: O=C1CNCCN1c1ccc(-c2c[nH]c3cc(F)ccc23)cn1] | 1-(5-(6-fluoro-1H-indol-3-yl)pyridin-2-yl)piperazin-2-one | 310.33 |
| 84 | 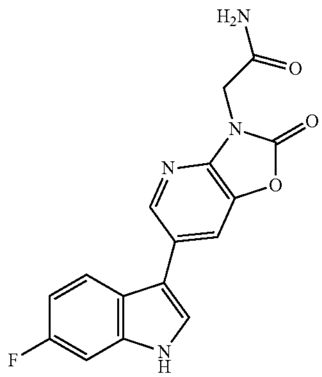 [SMILES: NC(=O)Cn1c(=O)oc2cc(-c3c[nH]c4cc(F)ccc34)cnc21] | 2-(6-(6-fluoro-1H-indol-3-yl)-2-oxooxazolo[4,5-b]pyridin-3(2H)-yl)acetamide | 326.28 |
| 85 | 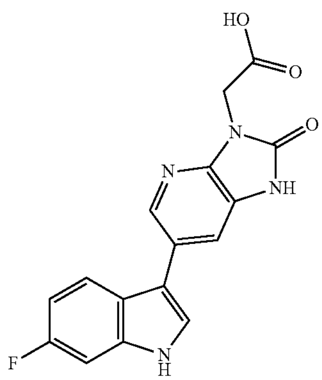 [SMILES: O=C(O)Cn1c(=O)[nH]c2cc(-c3c[nH]c4cc(F)ccc34)cnc21] | 2-(6-(6-fluoro-1H-indol-3-yl)-2-oxo-1H-imidazo[4,5-b]pyridin-3(2H)-yl)acetic acid | 326.28 |
| 86 | 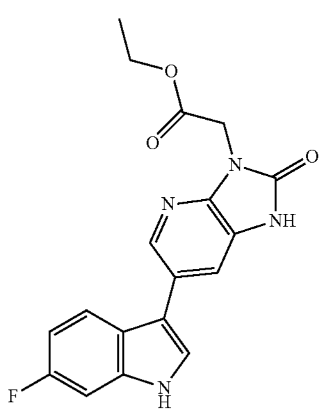 [SMILES: CCOC(=O)Cn1c(=O)[nH]c2cc(-c3c[nH]c4cc(F)ccc34)cnc21] | ethyl 2-(6-(6-fluoro-1H-indol-3-yl)-2-oxo-1H-imidazo[4,5-b]pyridin-3(2H)-yl)acetate | 354.34 |

TABLE 1-continued

| Cpd no | Structure | Chemical name | MW (calc'd) |
|---|---|---|---|
| 87 | 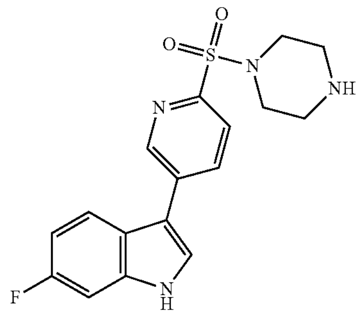 [SMILES: O=S(=O)(c1ccc(-c2c[nH]c3cc(F)ccc23)cn1)N1CCNCC1] | 6-fluoro-3-(6-(piperazin-1-ylsulfonyl)pyridin-3-yl)-1H-indole | 360.41 |
| 88 | 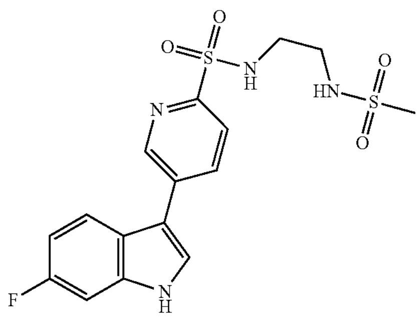 [SMILES: CS(=O)(=O)NCCNS(=O)(=O)c1ccc(-c2c[nH]c3cc(F)ccc23)cn1] | 5-(6-fluoro-1H-indol-3-yl)-N-(2-(methylsulfonamido)ethyl)pyridine-2-sulfonamide | 412.46 |
| 89 | 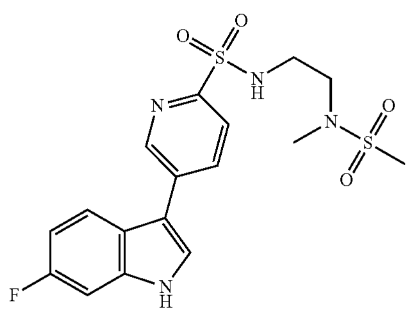 [SMILES: CN(CCNS(=O)(=O)c1ccc(-c2c[nH]c3cc(F)ccc23)cn1)S(C)(=O)=O] | 5-(6-fluoro-1H-indol-3-yl)-N-(2-(N-methylmethylsulfonamido)ethyl)pyridine-2-sulfonamide | 426.49 |
| 90 | 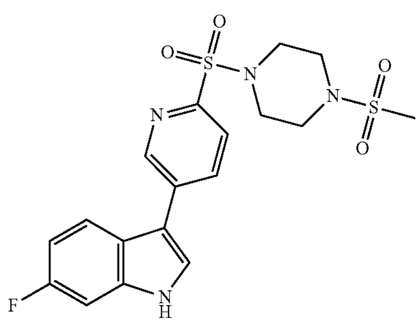 [SMILES: CS(=O)(=O)N1CCN(S(=O)(=O)c2ccc(-c3c[nH]c4cc(F)ccc34)cn2)CC1] | : 6-fluoro-3-(6-((4-(methylsulfonyl)piperazin-1-yl)sulfonyl)pyridin-3-yl)-1H-indole | 438.50 |
| 91 | 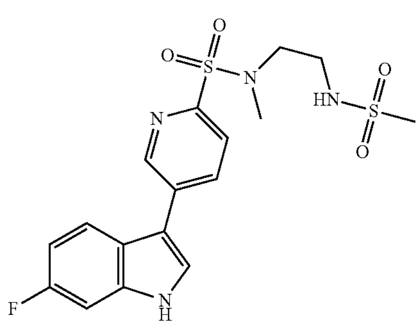 [SMILES: CN(CCNS(C)(=O)=O)S(=O)(=O)c1ccc(-c2c[nH]c3cc(F)ccc23)cn1] | 5-(6-fluoro-1H-indol-3-yl)-N-methyl-N-(2-(methylsulfonamido)ethyl)pyridine-2-sulfonamide | 426.49 |

TABLE 1-continued

| Cpd no | Structure | Chemical name | MW (calc'd) |
|---|---|---|---|
| 92 | 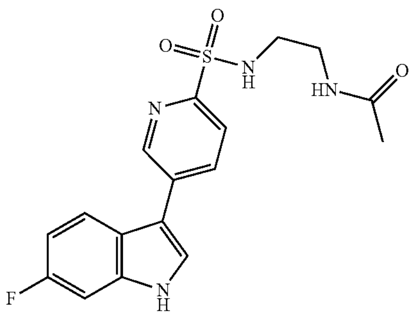 [SMILES: CC(=O)NCCNS(=O)(=O)c1ccc(-c2c[nH]c3cc(F)ccc23)cn1] | N-(2-(5-(6-fluoro-1H-indol-3-yl)pyridine-2-sulfonamido)ethyl)acetamide | 376.41 |
| 93 | 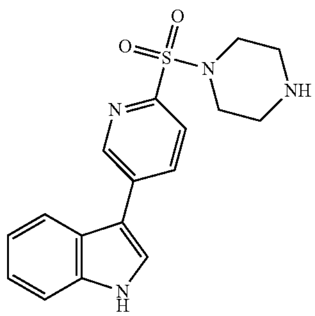 [SMILES: O=S(=O)(c1ccc(-c2c[nH]c3ccccc23)cn1)N1CCNCC1] | 3-(6-(piperazin-1-ylsulfonyl)pyridin-3-yl)-1H-indole | 342.42 |
| 94 | 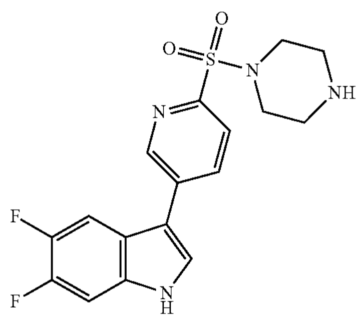 [SMILES: O=S(=O)(c1ccc(-c2c[nH]c3cc(F)c(F)cc23)cn1)N1CCNCC1] | 5,6-difluoro-3-(6-(piperazin-1-ylsulfonyl)pyridin-3-yl)-1H-indole | 378.40 |
| 95 | 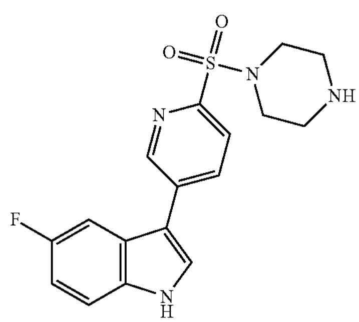 [SMILES: O=S(=O)(c1ccc(-c2c[nH]c3ccc(F)cc23)cn1)N1CCNCC1] | 5-fluoro-3-(6-(piperazin-1-ylsulfonyl)pyridin-3-yl)-1H-indole | 360.41 |
| 96 | 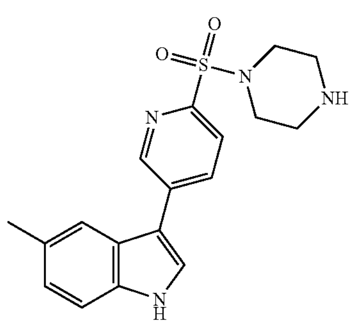 [SMILES: Cc1ccc2[nH]cc(-c3ccc(S(=O)(=O)N4CCNCC4)nc3)c2c1] | 5-methyl-3-(6-(piperazin-1-ylsulfonyl)pyridin-3-yl)-1H-indole | 356.44 |

TABLE 1-continued

| Cpd no | Structure | Chemical name | MW (calc'd) |
|---|---|---|---|
| 97 | 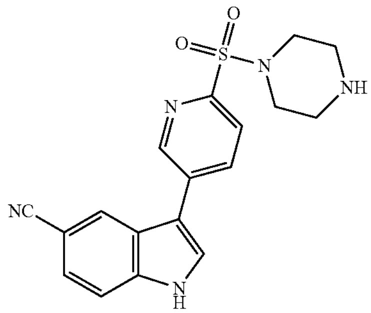 [SMILES: N#Cc1ccc2[nH]cc(-c3ccc(S(=O)(=O)N4CCNCC4)nc3)c2c1] | 3-(6-(piperazin-1-ylsulfonyl)pyridin-3-yl)-1H-indole-5-carbonitrile | 367.43 |
| 98 | 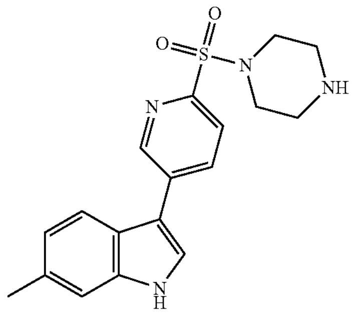 [SMILES: Cc1ccc2c(-c3ccc(S(=O)(=O)N4CCNCC4)nc3)c[nH]c2c1] | 6-methyl-3-(6-(piperazin-1-ylsulfonyl)pyridin-3-yl)-1H-indole | 356.44 |
| 99 | 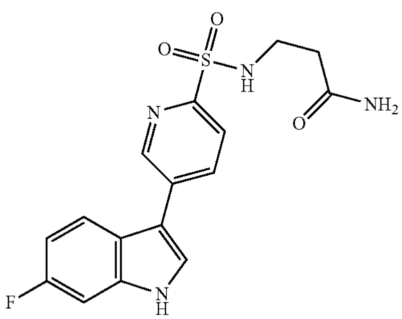 [SMILES: NC(=O)CCNS(=O)(=O)c1ccc(-c2c[nH]c3cc(F)ccc23)cn1] | 3-(5-(6-fluoro-1H-indol-3-yl)pyridine-2-sulfonamido)propanamide | 362.38 |
| 100 | 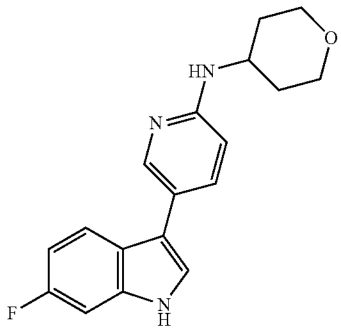 [SMILES: Fc1ccc2c(-c3ccc(NC4CCOCC4)nc3)c[nH]c2c1] | 5-(6-fluoro-1H-indol-3-yl)-N-(tetrahydro-2H-pyran-4-yl)pyridin-2-amine | 311.35 |
| 101 | | 3-(5-(6-fluoro-1H-indol-3-yl)-N-methylpyridine-2-sulfonamido)propanamide | 376.41 | or pharmaceutically acceptable enantiomers, salts and solvates thereof.

In Table 1, the term "Cpd" means compound.

The compounds of Table 1 were named using ChemBioDraw® Ultra version 12.0 (PerkinElmer).

The compounds of Formula I and subformulae thereof may contain an asymmetric (chiral) center and thus may exist as different stereoisomeric forms. Accordingly, the present invention includes all possible stereoisomers and includes not only racemic compounds but the individual enantiomers and their non-racemic mixtures as well. Where multiple chiral centers exist in compounds of the present invention, the invention includes each possible combination of chiral centers within a compound, as well as all possible enantiomeric and diastereomeric mixtures thereof. All chiral, diastereomeric, and racemic forms of a structure are intended, unless the specific stereochemistry or isomeric form is specifically indicated. When a compound is desired as a single enantiomer, such may be obtained by stereospecific synthesis, by resolution of the final product or any convenient intermediate, or by chiral chromatographic methods as each are known in the art. Resolution of the final product, an intermediate, or a starting material may be performed by any suitable method known in the art.

The compounds of Formula I may be in the form of pharmaceutically acceptable salts and may be administered in as "a pharmaceutically acceptable salt" form alone, or in a mixture with another compound of Formula I as defined herein, whether in base, salt or another form. Pharmaceutically acceptable salts of the compounds of Formula I include the acid addition and base salts thereof. Suitable acid addition salts are formed from acids which form non-toxic salts. Examples include the acetate, adipate, aspartate, benzoate, benzenesulfonate, besylate, borate, bicarbonate/carbonate, bisulphate/sulphate, borate, bromide, hydrobromide, hydrochloride, methylbromide, camsylate, chloride, citrate, clavulanate, cyclamate, edetate, edisylate, esylate, estolate, formate, fumarate, gluceptate, gluconate, glucuronate, glutamate, glycollylarsanilate, hexafluorophosphate, hibenzate, hydrochloride/chloride, dihydrochloride, hydrobromide/bromide, hydroiodide/iodide, hydrabamine, hydroxynaphthoate, isethionate, iodide, isothionate, lactate, lactobionate, laurate, malate, maleate, mandelate, malonate, mesylate, methylsulphate, mucate, naphthylate, napsylate/2-napsylate, nicotinate, nitrate, methylnitrate, N-methylglucamine, oleate, orotate, oxalate, palmitate, pamoate (embonate), pantothenate, phosphate/diphosphate (e.g., hydrogen phosphate or dihydrogen phosphate), pyroglutamate, saccharate, salicylate, stearate, succinate, sulfate, subacetate, tannate, tartrate, bitartrate, tosylate, trifluoroacetate and xinofoate salts, polygalacturonate, hexylresorcinate, teoclate, triethiodide, panoate, and valerate. These salts may be used as a dosage form for modifying the solubility or hydrolysis characteristics of the free base of Formula I or can be used in sustained release or pro-drug formulations.

Suitable base salts are formed from bases which form non-toxic salts. Examples include the aluminium, arginine, benzathine, calcium, calcium edetate, carbonate, choline, diethylamine (ethylenediamine), diolamine, glycine, lysine, magnesium, meglumine, olamine, potassium, sodium, tromethamine, 2-(diethylamino)ethanol, ethanolamine, morpholine, 4-(2-hydroxyethyl)morpholine, ornithine, ammonia, N-methyl-glutamine, N,N'-dibenzylethylene-diamine, chloroprocaine, diethanolamine, procaine, N-benzylphenethyl-amine, diethylamine, piperazine, tris(hydroxymethyl)aminomethane, and tetramethylammonium hydroxide, and zinc salts. Hemisalts of acids and bases may also be formed, for example, hemisulphate and hemicalcium salts. Preferred, pharmaceutically acceptable salts include hydrochloride/chloride, hydrobromide/bromide, bisulphate/sulphate, nitrate, citrate, and acetate. Optionally, a composition of the invention may contain both a pharmaceutically acceptable salt and the base form of a compound of Formula I.

These salts may be prepared by standard procedures, e.g. by reacting a free acid with a suitable organic or inorganic base. For example, pharmaceutically acceptable salts of compounds of Formula I, or a subformula thereof, may be prepared by one or more of these methods, or by another method known to the skilled artisan: (i) by reacting the compound of Formula II with the desired acid; (ii) by reacting the compound of Formula III with the desired base; (iii) by removing an acid- or base-labile protecting group from a suitable precursor of the compound of Formula IV or by ring-opening a suitable cyclic precursor, for example, a lactone or lactam, using the desired acid; or (iv) by converting one salt of the compound of Formula IV to another by reaction with an appropriate acid or by means of a suitable ion exchange column. All these reactions are typically carried out in solution. The salt, may precipitate from solution and be collected by filtration or may be recovered by evaporation of the solvent. The degree of ionization in the salt may vary from completely ionized to almost non-ionized.

When the compounds contain an acidic group as well as a basic group, the compounds may also form internal salts, and such compounds are within the scope of the invention. When the compounds of Formula I contain a hydrogen-donating heteroatom (e.g., NH), the invention also covers salts and/or isomers formed by transfer of said hydrogen atom to a basic group or atom within the molecule. Where a basic group is present, such as amino, an acidic salt, i.e., hydrochloride, hydrobromide, acetate, palmoate, and the like, can be used as the dosage form.

Also, in the case of an alcohol group being present, pharmaceutically acceptable esters can be employed, e.g., acetate, maleate, pivaloyloxymethyl, and the like, and those esters known in the art for modifying solubility or hydrolysis characteristics for use as sustained release or prodrug formulations.

All references to compounds of Formula I in the specification include references to its subformula (I', I", Ia, Ia', Ib, Ib', Ic, Ic', Ic-1, Ic-2, Ic-3, Id, Id', Ie and If), including enantiomers, salts, solvates, polymorphs and crystal habits thereof, multi-component complexes, liquid crystals, prodrugs and isomers thereof (including optical, geometric and tautomeric isomers) and isotopically-labeled compounds of Formula I, and mixtures thereof.

In addition, although generally, with respect to the salts of the compounds of Formula I, pharmaceutically acceptable salts are preferred, it should be noted that the invention in its broadest sense also included non-pharmaceutically acceptable salts, which may for example be used in the isolation and/or purification of the compounds of the invention. For example, salts formed with optically active acids or bases may be used to form diastereoisomeric salts that can facilitate the separation of optically active isomers of the compounds of Formula I above.

The invention also generally covers all pharmaceutically acceptable predrugs and prodrugs of the compounds of Formula I.

Process for Manufacturing

The compounds of Formula I can be prepared by different ways with reactions known to a person skilled in the art.

The invention further relates to a first process for manufacturing of compounds of Formula I:

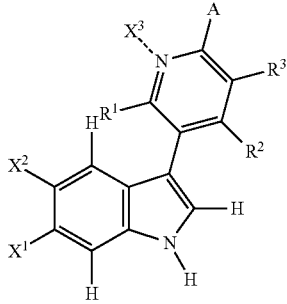

I and pharmaceutically acceptable enantiomers, salts and solvates thereof, wherein $X^1$, $X^2$, $R^1$, $R^2$, $R^3$ and A are as defined in Formula I;
comprising:
(a1)) reacting a compound of Formula II

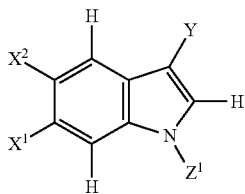

II wherein
$X^1$ and $X^2$ are as defined in Formula I;
$Z^1$ represents H or an amino protecting group such as for example an arylsulphonyl, a tert-butoxy carbonyl, a methoxymethyl, a para-methoxy benzyl, a benzyl or any other suitable protecting group known to those skilled in the art;
Y represents an halogen (preferably iodine, bromine or chlorine), an alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any leaving group known to those skilled in the art;
with a compound of Formula III

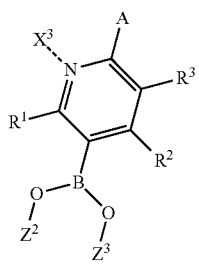

III wherein
$R^1$, $R^2$, $R^3$, $X^3$ and A are as defined in Formula I;
$Z^2$ and $Z^3$ represent H or alkyl groups, with the possibility for $Z^2$ and $Z^3$ to form a ring;

so as to obtain a compound of Formula IV,

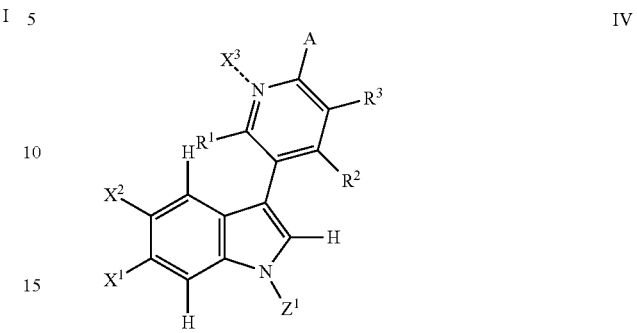

IV wherein $X^1$, $X^2$, $R^1$, $R^2$, $R^3$, $X^3$, A and $Z^1$ are as defined above;
and
(b1) in the case wherein $Z^1$ is not H, deprotecting the indole amine of compound of Formula IV, to afford compound of Formula I.

According to one embodiment, step (a1) of the process of the invention may be performed with or without a catalyst such as but not limited to $Pd_2(dba)_3$, $Pd(PPh_3)_4$, dichlorobis (triphenylphosphine)palladium(II) or 1,1'-bis(diphenylphosphino)ferrocene-dichloro palladium(II), $Pd(OAc)_2$, or Pd/C in the presence or absence of an additional ligand, such as but not limited to X-Phos, S-Phos, $P(oTol)_3$, $PPh_3$, BINAP, $P(tBu)_3$ or any other suitable phosphine ligand known to those skilled in the art.

According to one embodiment, step (a1)) of the process of the invention may be performed in the presence of bases such as but not limited to $K_3PO_4$, $K_2CO_3$, $Na_2CO_3$.

According to one embodiment, step (a1) of the process of the invention may be performed in the presence of a suitable solvent such as but not limited to dioxane, THF, DMF, water or mixtures thereof, preferably in a mixture of dioxane or THF and water.

According to one embodiment, step (a1) of the process of the invention may be performed at a temperature ranging from 20° C. to about 180° C., with or without microwave irradiation, for a period ranging from 10 minutes to a few hours, e.g. 10 minutes to 24 h.

According to one embodiment, the deprotection (b1) may be performed, depending on the nature of the group $Z^1$, by treatment with bases, such as but not limited to sodium hydroxide, potassium hydroxide, potassium carbonate. According to one embodiment, the deprotection may be performed in the presence or absence of a suitable solvent such as but not limited to methanol, ethanol, isopropanol, tert-butanol, THF, DMF, Dioxane, water or a mixture thereof. According to one embodiment, the deprotection may be performed at a temperature ranging from 20° C. to 100° C., preferably at about 85° C., for a few hours, e.g. one hour to 24 h.

According to an alternative embodiment, the deprotection (b1) may be performed, depending on the nature of the group $Z^1$ in the presence of strong acids, such as but not limited to HCl, TFA, HF, HBr. According to one embodiment, the deprotection may be performed in the presence or absence of a suitable solvent such as methanol, ethanol, isopropanol, tert-butanol, THF, DMF, Dioxane, water or a mixture thereof. According to one embodiment, the deprotection may be performed at a temperature between about 20° C. to about 100° C., for a period comprised between 10 minutes and a few hours, e.g. 10 minutes to 24 h.

The invention further relates to a second process of manufacturing of compounds of Formula Ic'

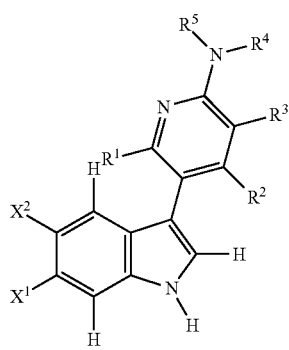

and pharmaceutically acceptable enantiomers, salts and solvates thereof, wherein $X^1, X^2, R^1, R^2, R^3, R^4$ and $R^5$ are as defined in Formula Ic;
comprising:
(a2) reacting a compound of Formula V

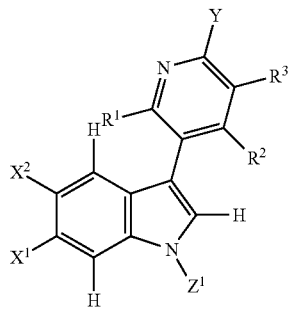

wherein $X^1, X^2, R^1, R^2$ and $R^3$ are as defined in Formula Ic; and
$Z^1$ represents H or an amino protecting group such as for example an arylsulphonyl, a tert-butoxy carbonyl, a methoxymethyl, a para-methoxy benzyl, a benzyl or any other suitable protecting group known to those skilled in the art;
Y represents an halogen (preferably iodine, bromine or chlorine), alkylsulfonyloxy having 1-6 carbon atoms (preferably methylsulfonyloxy or trifluoromethyl-sulfonyloxy) or arylsulfonyloxy having 6-10 carbon atoms (preferably phenyl- or p-tolylsulfonyloxy), or any other leaving group known to those skilled in the art;

with a compound of Formula VI

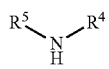

wherein $R^4$ and $R^5$ are as defined in Formula Ic;
so as to obtain a compound of Formula VII

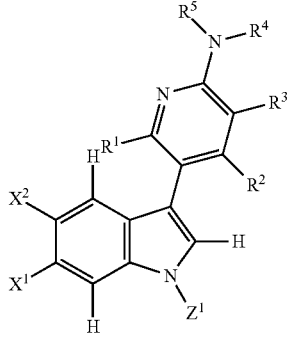

wherein $X^1, X^2, R^1, R^2, R^3, R^4, R^5$ and $Z^1$ are as defined above;
and
(b2) in the case wherein $Z^1$ is not H, deprotecting the indole amine of compound of Formula VII, to afford compound of Formula Ic'.

According to one embodiment, step (a2) of the process of the invention may be performed in the absence or presence of bases such as but not limited to triethylamine, diisopropyl ethyl amine, DBU, cesium carbonate, sodium carbonate, potassium carbonate, sodium hydroxide, potassium hydroxide According to one embodiment, step (a2) of the process of the invention may be performed in the presence of a suitable solvent such as but not limited to DMSO, DMF, methanol, ethanol, isopropanol, tert-butanol, THF, dioxane, dichloromethane, water.

According to one embodiment, step (a2) of the process of the invention may be performed at a temperature ranging from 20° C. to about 180° C., with or without microwave irradiation.

According to one embodiment, step (a2) of the process of the invention may be performed for a period ranging from 10 minutes to a few hours, e.g. 10 minutes to 24 h.

According to one embodiment, the deprotection step (b2) may be performed in conditions described above for deprotection (b1).

The invention further relates to a third process of manufacturing of compounds of Formula Ic-2

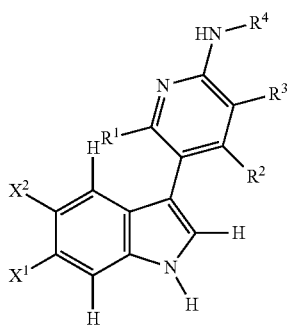

and pharmaceutically acceptable enantiomers, salts and solvates thereof, wherein $X^1$, $X^2$, $R^1$, $R^2$, $R^3$ and $R^4$ are as defined in Formula Ic-2;

comprising:

(a3) reacting a compound of Formula VIII

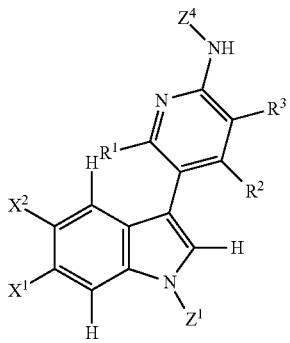

VIII wherein $X^1$, $X^2$, $R^1$, $R^2$, $R^3$ are as defined in Formula Ic-2;

$Z^1$ represents H or an amino protecting group such as for example an arylsulphonyl, a tert-butoxy carbonyl, a methoxymethyl, a para-methoxy benzyl, a benzyl or any other suitable protecting group known to those skilled in the art;

$Z^4$ represents an alkyloxycarbonyl group, such as for example Boc or Cbz;

with a compound of Formula IX $$Y—R^4 \quad \text{IX}$$

wherein $R^4$ is as defined in Formula Ic-2; and

Y represents an halogen (preferably iodine, bromine or chlorine), alkylsulfonyloxy having 1-6 carbon atoms (preferably methylsulfonyloxy or trifluoromethylsulfonyloxy) or arylsulfonyloxy having 6-10 carbon atoms (preferably phenyl- or p-tolylsulfonyloxy), or any other leaving group known to those skilled in the art;

so as to obtain a compound of Formula X

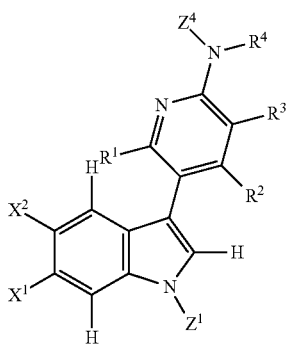

X wherein $X^1$, $X^2$, $R^1$, $R^2$, $R^3$, $R^4$, $Z^1$ and $Z^4$ are as defined above;

(a4) reacting compound of Formula X to afford compound of Formula XI

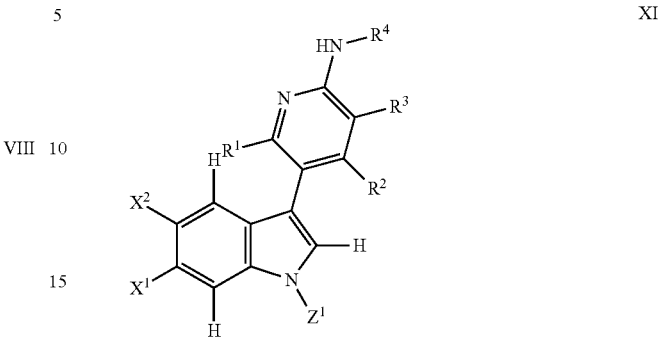

XI wherein $X^1$, $X^2$, $R^1$, $R^2$, $R^3$, $R^4$ and $Z^1$ are as defined above;

and (b3) in the case wherein $Z^1$ is not H, deprotecting the indole amine of compound of Formula XI, to afford compound of Formula Ic-2.

According to one embodiment, step (a3) of the process of the invention may be performed in the presence of bases such as but not limited to sodium hydride, lithium diisopropyl amide, buthyl lithium, sodium hydroxide, potassium hydroxide, cesium carbonate, sodium carbonate, potassium carbonate.

According to one embodiment, step (a3) of the process of the invention may be performed in the presence of a suitable solvent such as but not limited to DMF, methanol, ethanol, isopropanol, tert-butanol, THF, dioxane, dichloromethane, water.

According to one embodiment, step (a3) of the process of the invention may be performed in the presence or absence of catalytic amounts of appropriate iodide salts, such as but not limited to tetrabutylammonium iodide.

According to one embodiment, step (a3) of the process of the invention may be performed at a temperature ranging from 20° C. to about 180° C., with or without microwave irradiation.

According to one embodiment, step (a3) of the process of the invention may be performed for a period ranging from 10 minutes and a few hours, e.g. 10 minutes to 24 h.

According to one embodiment, step (a4) of the process of the invention may be performed by treatment with acids, such as but not limited to hydrogen chloride, trifluoroacetic acid, hydrogen bromide or hydrogen fluoride.

According to one embodiment, step (a4) of the process of the invention may be performed in the presence of a suitable solvent such as but not limited to THF, dioxane, DCM, DMF, methanol, ethanol, isopropanol, tert-butanol, water or a mixture thereof.

According to one embodiment, step (a4) of the process of the invention may be performed at a temperature between about 20° C. to about 100° C., in the presence or absence of microwave irradiation.

According to one embodiment, step (a4) of the process of the invention may be performed for a few hours, e.g. one hour to 24 h.

According to one embodiment, the deprotection step (b3) may be performed in conditions described above for deprotection (b1).

In general, the synthesis pathways for any individual compound of Formula (I) will depend on the specific substituents of each molecule and upon the ready availability of intermediates necessary; again such factors being appreciated by those of ordinary skill in the art.

According to a further general process, compounds of Formula I can be converted to alternative compounds of Formula I, employing suitable interconversion techniques well known by a person skilled in the art.

Compounds of the Formula I and related formulae can furthermore be obtained by liberating compounds of the Formula I from one of their functional derivatives by treatment with a solvolysing or hydrogenolysing agent.

Preferred starting materials for the solvolysis or hydrogenolysis are those which conform to the Formula I and related formulae, but contain corresponding protected amino and/or hydroxyl groups instead of one or more free amino and/or hydroxyl groups, preferably those which carry an amino-protecting group instead of an H atom bonded to an N atom, in particular those which carry an R*—N group, in which R* denotes an amino-protecting group, instead of an HN group, and/or those which carry a hydroxyl-protecting group instead of the H atom of a hydroxyl group, for example those which conform to the Formula I, but carry a —COOR group, in which R denotes a hydroxyl-protecting group, instead of a —COOH group.

It is also possible for a plurality of—identical or different—protected amino and/or hydroxyl groups to be present in the molecule of the starting material. If the protecting groups present are different from one another, they can in many cases be cleaved off selectively.

The term "amino-protecting group" is known in general terms and relates to groups which are suitable for protecting (blocking) an amino group against chemical reactions, but which are easy to remove after the desired chemical reaction has been carried out elsewhere in the molecule. Typical of such groups are, in particular, unsubstituted or substituted acyl, aryl, aralkoxymethyl or aralkyl groups. Since the amino-protecting groups are removed after the desired reaction (or reaction sequence), their type and size are furthermore not crucial; however, preference is given to those having 1-20, in particular 1-8, carbon atoms. The term "acyl group" is to be understood in the broadest sense in connection with the present process. It includes acyl groups derived from aliphatic, araliphatic, aromatic or heterocyclic carboxylic acids or sulfonic acids, and, in particular, alkoxy¬carbonyl, aryloxycarbonyl and especially aralkoxycarbonyl groups. Examples of such acyl groups are alkanoyl, such as acetyl, propionyl and butyryl; aralkanoyl, such as phenylacetyl; aroyl, such as benzoyl and tolyl; aryloxyalkanoyl, such as POA; alkoxycarbonyl, such as methoxy¬carbonyl, ethoxycarbonyl, 2,2,2-trichloroethoxycarbonyl, BOO (tert-butoxycarbonyl) and 2-iodoethoxycarbonyl; aralkoxycarbonyl, such as CBZ ("carbobenzoxy"), 4-methoxybenzyloxycarbonyl and FMOC; and arylsulfonyl, such as Mtr. Preferred amino-protecting groups are BOO and Mtr, further¬more CBZ, Fmoc, benzyl and acetyl.

The term "hydroxyl-protecting group" is likewise known in general terms and relates to groups which are suitable for protecting a hydroxyl group against chemical reactions, but are easy to remove after the desired chemical reaction has been carried out elsewhere in the molecule. Typical of such groups are the above-mentioned unsubstituted or substituted aryl, aralkyl or acyl groups, furthermore also alkyl groups. The nature and size of the hydroxyl-protecting groups are not crucial since they are removed again after the desired chemical reaction or reaction sequence; preference is given to groups having 1-20, in particular 1-10, carbon atoms. Examples of hydroxyl-protecting groups are, inter alia, benzyl, 4-methoxybenzyl, p-nitrobenzoyl, p-toluenesulfonyl, tert-butyl and acetyl, where benzyl and tert-butyl are particularly preferred.

The compounds of the Formula I and related formulae are liberated from their functional derivatives—depending on the protecting group used—by using for example strong inorganic acids, such as hydrochloric acid, perchloric acid or sulfuric acid, strong organic carboxylic acids, such as trichloroacetic acid, TFA or sulfonic acids, such as benzene- or p-toluenesulfonic acid. The presence of an additional inert solvent is possible, but is not always necessary. Suitable inert solvents are preferably organic, for example carboxylic acids, such as acetic acid, ethers, such as tetrahydrofuran or dioxane, amides, such as DMF, halogenated hydrocarbons, such as dichloromethane, furthermore also alcohols, such as methanol, ethanol or isopropanol, and water. Mixtures of the above-mentioned solvents are furthermore suitable. TFA is preferably used in excess without addition of a further solvent, and perchloric acid is preferably used in the form of a mixture of acetic acid and 70% perchloric acid in the ratio 9:1. The reaction temperatures for the cleavage are advantageously between about 0 and about 50° C., preferably between 15 and 30° C. (room temperature).

The BOC, OtBu and Mtr groups can, for example, preferably be cleaved off using TFA in dichloromethane or using approximately 3 to 5N HCl in dioxane at 15-30° C., and the FMOC group can be cleaved off using an approximately 5 to 50% solution of dimethylamine, diethylamine or piperidine in DMF at 15-30° C.

Protecting groups which can be removed hydrogenolytically (for example CBZ, benzyl or the liberation of the amidino group from the oxadiazole derivative thereof) can be cleaved off, for example, by treatment with hydrogen in the presence of a catalyst (for example a noble-metal catalyst, such as palladium, advantageously on a support, such as carbon). Suitable solvents here are those indicated above, in particular, for example, alcohols, such as methanol or ethanol, or amides, such as DMF. The hydrogenolysis is generally carried out at temperatures between about 0 and 100° C. and pressures between about 1 and 200 bar, preferably at 20-30° C. and 1-10 bar. Hydrogenolysis of the CBZ group succeeds well, for example, on 5 to 10% Pd/C in methanol or using ammonium formate (instead of hydrogen) on Pd/C in methanol/DMF at 20-30° C.

Examples of suitable inert solvents are hydrocarbons, such as hexane, petroleum ether, benzene, toluene or xylene; chlorinated hydrocarbons, such as trichloroethylene, 1,2-dichloroethane, tetrachloromethane, trifluoromethylbenzene, chloroform or dichloromethane; alcohols, such as methanol, ethanol, isopropanol, n-propanol, n-butanol or tert-butanol; ethers, such as diethyl ether, diisopropyl ether, tetrahydrofuran (THF) or dioxane; glycol ethers, such as ethylene glycol monomethyl or monoethyl ether or ethylene glycol dimethyl ether (diglyme); ketones, such as acetone or butanone; amides, such as acetamide, dimethylacetamide, N-methylpyrrolidone (NMP) or dimethylformamide (DMF); nitriles, such as acetonitrile; sulfoxides, such as dimethyl sulfoxide (DMSO); carbon disulfide; carboxylic acids, such as formic acid or acetic acid; nitro compounds, such as nitromethane or nitrobenzene; esters, such as ethyl acetate, or mixtures of the said solvents.

Esters can be hydrolysed, for example, using HCl, $H_2SO_4$, or using LiOH, NaOH or KOH in water, water/THF, water/THF/ethanol or water/dioxane, at temperatures between 0 and 100° C.

Free amino groups can furthermore be acylated in a conventional manner using an acyl chloride or anhydride or alkylated using an unsubstituted or substituted alkyl halide, advantageously in an inert solvent, such as dichloromethane or THF and/or in the presence of a base, such as triethylamine or pyridine, at temperatures between −60° C. and +30° C.

For all the protection and deprotection methods, see Philip J. Kocienski, in "Protecting Groups", Georg Thieme Verlag Stuttgart, New York, 1994 and, Theodora W. Greene and Peter G. M. Wuts in "Protective Groups in Organic Synthesis", Wiley Interscience, 3rd Edition 1999.

Reaction schemes as described in the example section are illustrative only and should not be construed as limiting the invention in any way.

Applications

The invention is further directed to the use of the compounds of the invention or pharmaceutically acceptable enantiomers, salts and solvates thereof as TDO2 inhibitors.

Accordingly, in a particularly preferred embodiment, the invention relates to the use of compounds of Formula I and subformulae, including Formula Ia', Formula Ib', Formula Ic', Formula Ic-1, Formula Ic-2, Formula Ic-3, and/or Formula Id', Formula Ie and Formula If in particular those of Table 1 above, and/or pharmaceutically acceptable enantiomers, salts and solvates thereof, as TDO2 inhibitors.

Accordingly, in another aspect, the invention relates to the use of these compounds or enantiomers, salts and solvates thereof for the synthesis of pharmaceutical active ingredients, such as TDO2 inhibitors.

In one embodiment, the invention relates to the use of compounds of Formula I and subformulae, including Formula Ia', Formula Ib', Formula Ic', Formula Ic-1, Formula Ic-2, Formula Ic-3, Formula Id', Formula Ie, and/or Formula If, in particular those of Table 1 above, or pharmaceutically acceptable enantiomers, salts and solvates thereof, for increasing immune recognition and destruction of the cancer cells.

The compounds of the invention are therefore useful as medicaments, in particular in the prevention and/or treatment of cancer.

In one embodiment, compounds of Formula I, including subformula as defined herein, are useful in the treatment and/or prevention of cancer, neurodegenerative disorders such as Parkinson's disease, Alzheimer's disease and Huntington's disease, chronic viral infections such as HCV and HIV, depression, and obesity. Thus, these compounds may be formulated for administration to a mammalian species in need thereof in a therapeutically effective amount.

Various cancers are known in the art. The cancer may be metastatic or non-metastatic. The cancer may be may be familial or sporadic. In some embodiments, the cancer is selected from the group consisting of: leukemia and multiple myeloma. Additional cancers that can be treated using the methods of the invention include, for example, benign and malignant solid tumours and benign and malignant non-solid tumours.

Examples of solid tumours include, but are not limited to: biliary tract cancer, brain cancer (including glioblastomas and medulloblastomas), breast cancer, cervical cancer, choriocarcinoma, colon cancer, endometrial cancer, esophageal cancer, gastric cancer, intraepithelial neoplasms (including Bowen's disease and Paget's disease), liver cancer, lung cancer, neuroblastomas, oral cancer (including squamous cell carcinoma), ovarian cancer (including those arising from epithelial cells, stromal cells, germ cells and mesenchymal cells), pancreatic cancer, prostate cancer, rectal cancer, renal cancer (including adenocarcinoma and Wilms tumour), sarcomas (including leiomyosarcoma, rhabdomyosarcoma, liposarcoma, fibrosarcoma and osteosarcoma), skin cancer (including melanoma, Kaposi's sarcoma, basocellular cancer and squamous cell cancer), testicular cancer including germinal tumours (seminomas, and non-seminomas such as teratomas and choriocarcinomas), stromal tumours, germ cell tumours, and thyroid cancer (including thyroid adenocarcinoma and medullary carcinoma).

Examples of non-solid tumours include but are not limited to hematological neoplasms. As used herein, a hematologic neoplasm is a term of art which includes lymphoid disorders, myeloid disorders, and AIDS associated leukemias.

Lymphoid disorders include but are not limited to acute lymphocytic leukemia and chronic lymphoproliferative disorders (e.g., lymphomas, myelomas, and chronic lymphoid leukemias). Lymphomas include, for example, Hodgkin's disease, non-Hodgkin's lymphoma lymphomas, and lymphocytic lymphomas). Chronic lymphoid leukemias include, for example, T cell chronic lymphoid leukemias and B cell chronic lymphoid leukemias.

In one embodiment, compounds of Formula I and its subformula as defined herein or pharmaceutically acceptable enantiomers, salts or solvates thereof are for use in the treatment and/or prevention of a cancer selected from bladder carcinoma, hepatocarcinoma, melanoma, mesothelioma, neuroblastoma, sarcoma, breast carcinoma, leukemia, renal cell carcinoma, colorectal carcinoma, head & neck carcinoma, lung carcinoma, brain tumor, glioblastoma, astrocytoma, myeloma, pancreatic carcinoma, gynaecological cancers (ovarian carcinoma, cervical cancer, endometrial cancer).

In one embodiment, compounds of Formula I and its subformula as defined herein or pharmaceutically acceptable enantiomers, salts or solvates thereof are for use in the treatment and/or prevention of a cancer selected from bladder carcinoma, hepatocarcinoma, melanoma, mesothelioma, neuroblastoma, sarcoma, breast carcinoma, leukemia, renal cell carcinoma, colorectal carcinoma, head & neck carcinoma, lung carcinoma, brain tumor, glioblastoma, astrocytoma, myeloma, pancreatic carcinoma.

In one embodiment, compounds of Formula I and its subformula as defined herein or pharmaceutically acceptable enantiomers, salts or solvates thereof are for use in the treatment and/or prevention of a cancer selected gynaecological cancers such as for example ovarian carcinoma, cervical cancer, endometrial cancer.

In a specific embodiment, compounds of Formula I and its subformula as defined herein or pharmaceutically acceptable enantiomers, salts or solvates thereof are for use in the treatment and/or prevention of a cancer selected from hepatocarcinoma and glioblastoma.

The invention further relates to a method for treatment or prevention of a cancer selected from bladder carcinoma, hepatocarcinoma, melanoma, mesothelioma, neuroblastoma, sarcoma, breast carcinoma, leukemia, renal cell carcinoma, colorectal carcinoma, head & neck carcinoma, lung carcinoma, brain tumor, glioblastoma, astrocytoma, myeloma, pancreatic carcinoma, gynaecological cancers (ovarian carcinoma, cervical cancer, endometrial cancer), which comprises administering to a mammalian species in need thereof a therapeutically effective amount of the compound according to the invention or a pharmaceutically acceptable enantiomers, salts or solvates thereof.

The invention further relates to a method for treatment or prevention of a cancer selected from bladder carcinoma, hepatocarcinoma, melanoma, mesothelioma, neuroblastoma, sarcoma, breast carcinoma, leukemia, renal cell carcinoma, colorectal carcinoma, head & neck carcinoma, lung carcinoma, brain tumor, glioblastoma, astrocytoma, myeloma, pancreatic carcinoma, which comprises administering to a mammalian species in need thereof a therapeutically effective amount of the compound according to the invention or a pharmaceutically acceptable enantiomers, salts or solvates thereof.

The invention further relates to a method for treatment or prevention of a cancer selected from gynaecological cancers such as for example ovarian carcinoma, cervical cancer, endometrial cancer; which comprises administering to a mammalian species in need thereof a therapeutically effective amount of the compound according to the invention or a pharmaceutically acceptable enantiomers, salts or solvates thereof.

In a specific embodiment, the method for treatment or prevention is a method for treatment or prevention of a cancer selected from hepatocarcinoma and glioblastoma, which comprises administering to a mammalian species in need thereof a therapeutically effective amount of the compound according to the invention or a pharmaceutically acceptable enantiomers, salts or solvates thereof.

In another embodiment, a method is provided for delaying in patient the onset of cancer comprising the administration of a pharmaceutically effective amount of a compound of Formula I or the subformula provided herein, including, Formula Ia', Formula Ib', Formula Ic', Formula Ic-1, Formula Ic-2, Formula Ic-3, Formula Id', and/or Formula Ie and/or Formula If or pharmaceutically acceptable enantiomer, salt and solvate thereof to a patient in need thereof.

Preferably, the patient is a warm-blooded animal, more preferably a mammal, more preferably, a human. In some instances, the mammal may be a companion animal such as a dog or cat. However, other non-human mammalian (veterinary) subjects may be treated using the compounds of Formula I and its subformula as defined herein.

The compounds of Formula I and its subformula as defined herein are especially useful in the treatment and/or prevention of cancer.

In a specific embodiment, the compounds of Formula I and its subformula as defined herein are especially useful in the treatment and/or prevention of cancer.

The invention further provides the use of a compound of Formula I or the subformula provided herein, including, Formula Ia', Formula Ib', Formula Ic', Formula Ic-1, Formula Ic-2, Formula Ic-3, Formula Id', and/or Formula Ie and/or Formula If, or a pharmaceutically acceptable enantiomer, salt and solvate thereof for the manufacture of a medicament for treating and/or preventing cancer.

According to a further feature of the present invention there is provided a method for modulating TDO2 activity, in a patient, preferably a warm blooded animal (e.g., mammal), and even more preferably a human, in need of such treatment, which comprises administering to said patient an effective amount of compound of the present invention, or a pharmaceutically acceptable enantiomer, salt and solvate thereof.

Formulations

The invention also provides pharmaceutical compositions comprising a compound of Formula I or a pharmaceutically acceptable enantiomer, salt and solvate thereof and at least one pharmaceutically acceptable carrier, diluent, excipient and/or adjuvant. As indicated above, the invention also covers pharmaceutical compositions which contain, in addition to a compound of the present invention, a pharmaceutically acceptable enantiomer, salt and solvate thereof as active ingredient, additional therapeutic agents and/or active ingredients.

Another object of this invention is a medicament comprising at least one compound of Formula I, or a pharmaceutically acceptable enantiomer, salt and solvate thereof, as active ingredient.

According to a further feature there is provided the use of a compound of Formula I or a pharmaceutically acceptable enantiomer, salt and solvate thereof for the manufacture of a medicament for modulating TDO2 activity in a patient, in need of such treatment, which comprises administering to said patient an effective amount of compound of the present invention, or a pharmaceutically acceptable enantiomer, salt and solvate thereof.

Generally, for pharmaceutical use, the compounds of Formula I and its subformula as defined herein may be formulated as a pharmaceutical preparation comprising at least one compound of Formula I and at least one pharmaceutically acceptable carrier, diluent, excipient and/or adjuvant, and optionally one or more further pharmaceutically active compounds.

By means of non-limiting examples, such a formulation may be in a form suitable for oral administration, for parenteral administration (such as by intravenous, intramuscular or subcutaneous injection or intravenous infusion), for topical administration (including ocular), for administration by inhalation, by a skin patch, by an implant, by a suppository, etc. Such suitable administration forms—which may be solid, semi-solid or liquid, depending on the manner of administration—as well as methods and carriers, diluents and excipients for use in the preparation thereof, will be clear to the skilled person; reference is made to the latest edition of Remington's Pharmaceutical Sciences.

Some preferred, but non-limiting examples of such preparations include tablets, pills, powders, lozenges, sachets, cachets, elixirs, suspensions, emulsions, solutions, syrups, aerosols, ointments, cremes, lotions, soft and hard gelatin capsules, suppositories, drops, sterile injectable solutions and sterile packaged powders (which are usually reconstituted prior to use) for administration as a bolus and/or for continuous administration, which may be formulated with carriers, excipients, and diluents that are suitable per se for such formulations, such as lactose, dextrose, sucrose, sorbitol, mannitol, starches, gum acacia, calcium phosphate, alginates, tragacanth, gelatin, calcium silicate, microcrystalline cellulose, polyvinylpyrrolidone, polyethylene glycol, cellulose, (sterile) water, methylcellulose, methyl- and propylhydroxybenzoates, talc, magnesium stearate, edible oils, vegetable oils and mineral oils or suitable mixtures thereof. The formulations can optionally contain other substances that are commonly used in pharmaceutical formulations, such as lubricating agents, wetting agents, emulsifying and suspending agents, dispersing agents, desintegrants, bulking agents, fillers, preserving agents, sweetening agents, flavoring agents, flow regulators, release agents, etc. The compositions may also be formulated so as to provide rapid, sustained or delayed release of the active compound(s) contained therein.

The pharmaceutical preparations described herein are preferably in a unit dosage form, and may be suitably packaged, for example in a box, blister, vial, bottle, sachet, ampoule or in any other suitable single-dose or multi-dose holder or container (which may be properly labeled); optionally with one or more leaflets containing product information and/or instructions for use.

Depending on the condition to be prevented or treated and the route of administration, the active compound of the invention may be administered as a single daily dose, divided over one or more daily doses, or essentially continuously, e.g. using a drip infusion.

Definitions

In the present invention, the following terms have the following meanings:

Where groups may be substituted, such groups may be substituted with one or more substituents, and preferably with one, two or three substituents. Substituents may be selected from but not limited to, for example, the group comprising halogen, hydroxyl, oxo, nitro, amido, carboxy, amino, cyano, haloalkoxy, and haloalkyl.

The term "halogen" means fluoro (F), chloro (Cl), bromo (B), or iodo (I). Preferred halo groups are fluoro and chloro.

The following definitions are used in connection with the compounds described herein. In general, the number of carbon atoms present in a given group is designated "$C_x$ to $C_y$", where x and y are the lower and upper limits, respectively. The carbon number as used in the definitions herein refers to carbon backbone and carbon branching, but does not include carbon atoms of the substituents, such as alkoxy substitutions and the like. Unless indicated otherwise, the nomenclature of substituents that are not explicitly defined herein are determined by naming from left to right the terminal portion of the functionality followed by the adjacent functionality toward the point of attachment. As used herein, "optionally substituted" means that at least 1 hydrogen atom of the optionally substituted group has been replaced.

The term "alkyl" by itself or as part of another substituent refers to a hydrocarbyl radical of Formula $C_nH_{2n+1}$ wherein n is a number greater than or equal to 1. Alkyl groups may contain 1 to 10 carbons (inclusive), i.e., C1, C2, C3, C4, C5, C6, C7, C8, C9 or C10, i.e., C1-C10 alkyl. In certain embodiments, alkyl groups of this invention comprise from 1 to 6 carbon atoms, preferably from 1 to 4 carbon atoms, more preferably from 1 to 3 carbon atoms. Alkyl groups may be linear or branched and may be substituted as indicated herein. Suitable alkyl groups include methyl, ethyl, n-propyl, i-propyl, n-butyl, i-butyl, s-butyl and t-butyl, pentyl and its isomers (e.g., n-pentyl, iso-pentyl), and hexyl and its isomers (e.g., n-hexyl, iso-hexyl). In one embodiment, the first carbon in a substituted alkyl chain as defined herein is unsubstituted. In another embodiment, a substituted alkyl as defined herein only has 1 or 2 substitutions. In one embodiment, a substituted alkyl is substituted with one or more groups selected from a halogen, hydroxyl, amino or COOH; in one embodiment, the substitution is not at the C1 position.

The term "haloalkyl" alone or in combination, refers to an alkyl radical having the meaning as defined above wherein one or more hydrogens are replaced with a halogen as defined above in a substituted alkyl. Non-limiting examples of such haloalkyl radicals include fluoromethyl, difluoromethyl, trifluoro methyl and the like. In one example, the haloalkyl is a C1 to C6 alkyl group substituted with at least one halogen. In another example, the haloalkyl is a C1 to C4 alkyl group substituted with at least one halogen. Each halogen substitution may be independently selected.

The term "cycloalkyl" as used herein is a cyclic alkyl group, that is to say, a monovalent, saturated, or unsaturated hydrocarbyl group having 1 or 2 cyclic structures. Cycloalkyl includes monocyclic or bicyclic hydrocarbyl groups. Cycloalkyl groups may comprise 3 or more carbon atoms in the ring and generally, according to this invention comprise from 3 to 10, more preferably from 3 to 8 carbon atoms still more preferably from 3 to 6 carbon atoms. Examples of cycloalkyl groups include but are not limited to cyclopropyl, cyclobutyl, cyclopentyl, cyclohexyl, with cyclopropyl being particularly preferred.

Where at least one carbon atom in a cycloalkyl group is replaced with a heteroatom, the resultant ring is referred to herein as "heterocyclyl".

The term "heteroatom" refers to a sulfur, nitrogen or oxygen atom.

The terms "heterocyclyl" or "heterocycle" as used herein by itself or as part of another group refer to non-aromatic, fully saturated or partially unsaturated cyclic groups (for example, 3 to 7 member monocyclic, 7 to 11 member bicyclic, or containing a total of 3 to 10 ring atoms) which have at least one heteroatom in at least one carbon atom-containing ring. Each ring of the heterocyclic group containing a heteroatom may have 1, 2, 3 or 4 heteroatoms selected from nitrogen, oxygen and/or sulfur atoms, where the nitrogen and sulfur heteroatoms may optionally be oxidized and the nitrogen heteroatoms may optionally be quaternized. The heterocycle may contain 3 to 7 carbon atoms (inclusive), or an integer therebetween. Any of the carbon atoms of the heterocyclic group may be substituted by oxo (for example piperidone, pyrrolidinone). The heterocyclic group may be attached at any heteroatom or carbon atom of the ring or ring system, where valence allows. The rings of multi-ring heterocycles may be fused, bridged and/or joined through one or more spiro atoms. Non limiting exemplary heterocyclic groups include piperidinyl, azetidinyl, tetrahydropyranyl, piperazinyl, imidazolinyl, morpholinyl, oxetanyl, pyrazolidinyl imidazolidinyl, isoxazolinyl, oxazolidinyl, isoxazolidinyl, thiazolidinyl, isothiazolidinyl, indolyl, indolinyl, isoindolinyl, tetrahydrofuranyl, tetrahydroquinolinyl, thiomorpholinyl, thiomorpholinylsulfoxide, thiomorpholinylsulfone, pyrrolizinyl.

The term "aryl" as used herein refers to a polyunsaturated, aromatic hydrocarbyl group having a single ring (i.e. phenyl) or multiple aromatic rings fused together (e.g. naphtyl) or linked covalently, typically containing 5 to 12 atoms; preferably 6 to 10, wherein at least one ring is aromatic. The aromatic ring may optionally include one to two additional rings (either cycloalkyl, heterocyclyl or heteroaryl) fused thereto. Aryl is also intended to include the partially hydrogenated derivatives of the carbocyclic (carbon-containing ring) systems enumerated herein. Non-limiting examples of aryl comprise phenyl, biphenylyl, biphenylenylnaphthalenyl, indenyl.

The term "heteroaryl" as used herein by itself or as part of another group refers but is not limited to 5 to 12 carbon-atom aromatic rings or ring systems containing 1 to 2 rings which are fused together or linked covalently, typically containing 5 to 6 atoms; at least one of which is aromatic, in which one or more carbon atoms in one or more of these rings is replaced by oxygen, nitrogen and/or sulfur atoms where the nitrogen and sulfur heteroatoms may optionally be oxidized and the nitrogen heteroatoms may optionally be quaternized. Such rings may be fused to an aryl, cycloalkyl, heteroaryl or heterocyclyl ring. Non-limiting examples of such heteroaryl, include: pyridazinyl, pyridinyl, furanyl, thiophenyl, pyrazolyl, imidazolyl, oxazolyl, isoxazolyl, thiazolyl, isothiazolyl, triazolyl, oxadiazolyl, thiadiazolyl, tetrazolyl, oxatriazolyl, thiatriazolyl, pyrimidyl, pyrazinyl, oxazinyl, dioxinyl, thiazinyl, triazinyl, indolyl, indolizinyl, isoindolyl, benzofuranyl, isobenzofuranyl, benzothiophenyl, isobenzothiophenyl, indazolyl, benzimidazolyl, quinolinyl, isoquinolinyl, cinnolinyl, quinazolinyl, quinoxalinyl.

The term "arylalkyl" refers to any group -alkyl-aryl. The term "alkylaryl" refers to any group -aryl-alkyl.

The term "heteroarylalkyl" refers to any group -alkyl-heteroaryl. The term "alkylheteroaryl" refers to any group -heteroaryl-alkyl.

The term "alkoxy" refers to any group O-alkyl. The term "haloalkoxy" refers to any group O-haloalkyl, wherein haloalkyl is as defined above, and wherein the halogen group is a substituent in a substituted alkyl as defined above.

The term "oxo" refers to a =O moiety.

The term "amino" refers to a $-NH_2$ group or any group derived thereof by substitution of one nor two hydrogen atom by an organic aliphatic or aromatic group. Preferably, groups derived from $-NH_2$ are "alkylamino" groups, i.e. N-alkyl groups, comprising monoalkylamino and dialkylamino. Non-limited examples of the term "amino" include $NH_2$, NHMe or $NMe_2$.

The term "amino-protecting group" refers to a protecting group for an amine function. According to a preferred embodiment, the amino-protecting group is selected in the groups comprising: arylsulphonyl, tert-butoxy carbonyl, methoxymethyl, para-methoxy benzyl or benzyl.

The term "leaving group" refers to a molecular fragment that departs with a pair of electrons in heterolytic bond cleavage. According to a preferred embodiment, the leaving group is selected in the groups comprising: halogen, preferably iodine, bromine or chlorine; alkylsulfonyloxy having 1-6 carbon atoms, preferably methylsulfonyloxy or trifluoromethylsulfonyloxy; or arylsulfonyloxy having 6-10 carbon atoms, preferably phenyl- or p-tolylsulfonyloxy.

The term "solvate" is used herein to describe a compound in this invention that contains stoichiometric or sub-stoichiometric amounts of one or more pharmaceutically acceptable solvent molecule, e.g., ethanol. Typically, a solvate does not significantly alter the physiological activity or toxicity of the compounds, and as such may function as pharmacological equivalents to non-solvate compounds of Formula I and its subformula as defined herein. The term "solvate" as used herein is a combination, physical association and/or solvation of a compound of the present invention with a solvent molecule. This physical association involves varying degrees of ionic and covalent bonding, including hydrogen bonding. In certain instances, the solvate can be isolated, such as when one or more solvent molecules are incorporated into the crystal lattice of a crystalline solid. Thus, "solvate" encompasses both solution-phase and isolatable solvates. "Solvate" may encompass solvates of salts of the compounds of Formula I.

The term "hydrate" refers to when the solvent molecule is water and may be an inorganic salt containing $nH_2O$, wherein n is the number of water molecules per formula unit of the salt. N may be ½, 1½, or an integer from 1 to 10. A hydrate which has lost water is termed an anhydride.

The term "prodrug" as used herein means the pharmacologically acceptable derivatives of compounds of Formula I as defined herein, such as for example esters, whose in vivo biotransformation product generates the biologically active drug. Prodrugs are generally characterized by increased bio-availability and are readily metabolized into biologically active compounds in vivo.

The term "predrug", as used herein, means any compound that will be modified to form a drug species of Formula I as defined herein, wherein the modification may take place either inside or outside of the body, and either before or after the predrug reaches the area of the body where administration of the drug is indicated.

The term "patient" or "subject" refers to a warm-blooded animal, more preferably a mammal, and most preferably a human, who/which is awaiting the receipt of, or is receiving medical care or is/will be the object of a medical procedure.

The term "human" refers to a subject of both genders and at any stage of development (i.e. neonate, infant, juvenile, adolescent, adult).

The terms "treat", "treating" and "treatment", as used herein, are meant to include alleviating, attenuating or abrogating a condition or disease and/or its attendant symptoms.

The terms "prevent", "preventing" and "prevention", as used herein, refer to a method of delaying or precluding the onset of a condition or disease and/or its attendant symptoms, barring a patient from acquiring a condition or disease, or reducing a patient's risk of acquiring a condition or disease.

The term "therapeutically effective amount" (or more simply an "effective amount") as used herein means the amount of active agent or active ingredient that is sufficient to achieve the desired therapeutic or prophylactic effect in the patient to which/whom it is administered.

The term "administration", or a variant thereof (e.g. "administering"), means providing the active agent or active ingredient, alone or as part of a pharmaceutically acceptable composition, to the patient in whom/which the condition, symptom, or disease is to be treated or prevented.

By "pharmaceutically acceptable" is meant that the ingredients of a pharmaceutical composition are compatible with each other and not deleterious to the patient thereof.

The term "pharmaceutical vehicle" as used herein means a carrier or inert medium used as solvent or diluent in which the pharmaceutically active agent is formulated and/or administered. Non-limiting examples of pharmaceutical vehicles include creams, gels, lotions, solutions, and liposomes.

The words "comprise", "comprises", and "comprising" are to be interpreted inclusively rather than exclusively. The works "consist", "consisting", and its variants, are to be interpreted exclusively, rather than inclusively.

As used herein, the term "about" means a variability of 10% from the reference given, unless otherwise specified.

EXAMPLES

The present invention will be better understood with reference to the following examples. These examples are intended to representative of specific embodiments of the invention, and are not intended as limiting the scope of the invention.

I. Chemistry Examples

The mass spectrometry (MS) data provided in the examples described below were obtained as followed: Mass spectrum: LC/MS Agilent 6110 (electron spray ionization (ESI)) or a Waters Acquity SQD (ESI)

The NMR data provided in the examples described below were obtained as followed: Bruker Ultrashield™ 400 PLUS and Bruker Fourier 300 MHz and TMS was used as an internal standard.

The microwave chemistry was performed on a single mode microwave reactor Initiator Microwave System EU from Biotage.

Preparative high performance liquid chromatography (HPLC) purifications were performed with a mass directed autopurification Fractionlynx from Waters equipped with a Xbridge™ Prep C18 OBD column 19×150 mm 5 μm, unless otherwise reported. All HPLC purifications were performed with a gradient of $CH_3CN/H_2O/NH_4HCO_3$ (5 mM), $CH_3CN/H_2O/TFA$ (0.1%), or $CH_3CN/H_2O/NH_3H_2O$ (0.1%).

The following abbreviations are used herein and have the indicated definitions: ACN is acetonitrile; DMSO is dimethylsulfoxide; DCM is dichloromethane; DIPEA is diisopropylethylamine; DMF is N,N-dimethylformamide; dppf is 1,1'-bis(diphenylphosphino)ferrocene; EtOH is ethanol; HATU is 2-(1H-7-azabenzotriazol-1-yl)-1,1,3,3-tetramethyl uronium hexafluorophosphate methanaminium; Hz is hertz; KOAc is potassium acetate; MeOH is methanol; MHz is megahertz; mM is millimolar; mL is milliliter; min is minutes; mol is moles; $M^+$ is molecular ion; $[M+H]^+$ is protonated molecular ion; N is normality; NMR is nuclear magnetic resonance; $PPh_3$ is triphenylphosphine; psi is pound per square inch; PPM is parts per million; qd po means daily by mouth; rt is room temperature; RT is retention time; TLC is thin layer chromatography; TFA is trifluoroacetic acid; TEA is triethylamine.

I.1. Synthesis of Intermediate Compounds

Intermediate 1:
3-bromo-6-fluoro-1-(phenylsulfonyl)-1H-indole

To a solution of 6-fluoro-1-(phenylsulfonyl)-1H-indole (prepared as described in Bioorg. Med. Chem. 2011, 19, 4782-4795; 1.0 g; 3.6 mmol) in DCM (20 mL) at 0° C. was added a solution of bromine (0.64 g; 4.0 mmol) in DCM (20 mL) dropwise. The mixture was stirred at 0° C. for 30 minutes, then added saturated aqueous $Na_2S_2O_3$ (10 mL), and stirred at r.t. for 10 minute. The organic layer was separated and the aqueous layer was extracted with DCM (10 mL×2). The combined organic layers were washed with saturated aqueous $NaHCO_3$ (20 mL×2), water (20 mL×2), brine (20 mL), dried over anhydrous $Na_2SO_4$, filtered, and concentrated to afford 1.26 g (99%) of the title compound as a pink solid. $^1H$ NMR (400 MHz, DMSO-$d_6$) δ [ppm]: 8.21 (s, 1H), 8.13-8.11 (m, 2H), 7.83-7.73 (m, 2H), 7.66-7.62 (m, 2H), 7.52-7.49 (m, 1H), 7.30-7.26 (m, 1H).

Intermediate 2: 3-(6-chloropyridin-3-yl)-6-fluoro-1-(phenylsulfonyl)-1H-indole

To a solution of 3-bromo-6-fluoro-1-(phenylsulfonyl)-1H-indole (Intermediate 1; 1.00 g; 2.82 mmol), 6-chloropyridin-3-ylboronic acid (889 mg; 5.65 mmol), $K_3PO_4$ (1.80 g; 8.48 mmol) in dioxane (40 mL) and water (4 mL) was added Pd(dppf)$Cl_2$.DCM (231 mg; 0.28 mmol) under nitrogen. The mixture was heated at 100° C. for 6 hours. The mixture was filtered through Celite, diluted with EtOAc (100 mL) and water (100 mL). The aqueous layer was extracted with EtOAc (50 mL×2). The combined organic layers were washed with brine, dried over anhydrous $Na_2SO_4$, filtered, concentrated, and purified by a silica gel chromatography (petroleum ether/EtOAc=1/1) to afford 0.61 g (56%) of the title compound as a yellow solid. LC-MS: m/z 387.0 $[M+H]^+$. $^1H$ NMR (400 MHz, DMSO-$d_6$) δ [ppm]: 8.79 (d, J=2.4 Hz, 1H), 8.37 (s, 1H), 8.23 (dd, J=8.4, 2.4 Hz, 1H), 8.17-8.13 (m, 2H), 7.87 (dd, J=8.8, 5.2 Hz, 1H), 7.82 (dd, J=9.7, 2.2 Hz, 1H), 7.76-7.71 (m, 1H), 7.67-7.63 (m, 2H), 7.62 (d, J=8.4 Hz, 1H), 7.25 (ddd, J=9.2, 8.8, 2.2 Hz, 1H).

Intermediate 3: tert-butyl 5-(6-fluoro-1-(phenylsulfonyl)-1H-indol-3-yl)pyridin-2-ylcarbamate To a solution of 6-fluoro-3-iodo-1-(phenylsulfonyl)-1H-indole (prepared as described in WO2010/136491; 535 mg; 1.33 mmol), tert-butyl 5-(4,4,5,5-tetramethyl-1,3,2-dioxaborolan-2-yl)pyridin-2-ylcarbamate (640 mg; 2.0 mmol), $K_3PO_4$ (848 mg; 3.99 mmol) in dioxane (20 mL) and water (2 mL) was added Pd(dppf)$Cl_2$.DCM (110 mg; 0.133 mmol) under nitrogen. The mixture was stirred at 90° C. overnight. The mixture was filtered through Celite, diluted with EtOAc (100 mL) and water (100 mL). The aqueous layer was extracted with EtOAc (50 mL×2). The combined organic layers were washed with brine, dried over anhydrous $Na_2SO_4$, filtered, concentrated, and purified by a silica gel chromatography (petroleum ether/EtOAc=10/1-2/1) to afford 400 mg (64%) of the title compound as a yellow solid. LC-MS: m/z 468.1 $[M+H]^+$.

Intermediate 4: tert-butyl 4-(5-(4,4,5,5-tetramethyl-1,3,2-dioxaborolan-2-yl)pyridin-2-yloxy)piperidine-1-carboxylate A mixture of tert-butyl 4-(5-bromopyridin-2-yloxy)piperidine-1-carboxylate (prepared as described in WO2007/146759A1; 1.30 g; 3.64 mmol), 4,4,4',4',5,5,5',5'-octamethyl-2,2'-bi(1,3,2-dioxaborolane (1.38 g; 5.44 mmol), Pd(dppf)$Cl_2$.DCM (297 mg; 0.36 mmol), KOAc (1.07 g; 10.9 mmol) in DMF (30 mL) was stirred at 80° C. for 6 hours under nitrogen. The mixture was concentrated in vacuo, suspended in EtOAc (50 mL), filtered through Celite, and concentrated to afford the title compound as a brown semi-solid, which was used directly without further purification. LC-MS: m/z 405.2 $[M+H]^+$.

Intermediate 5: 5,6-difluoro-3-iodo-1H-indole

To a mixture of 5,6-difluoro-1H-indole (500 mg; 3.27 mmol) and KOH (458 mg; 8.18 mmol) in DMF (6.2 mL) was added a solution of iodine (837.5 mg; 3.3 mmol) in DMF (6.3 mL). The mixture was stirred at r.t. for 12 hours. It was poured into an ice-water mixture (60 mL) and extracted with EtOAc (20 mL×3). The combined organic layers was washed with brine (100 mL) and dried over anhydrous $Na_2SO_4$, filtered, concentrated to afford 930 mg (100%) of the title compound as a red solid. It was used to next step without further purification. $^1H$ NMR (400 MHz, DMSO-$d_6$) δ [ppm]: 11.68 (s, 1H), 7.61 (d, J=2.5 Hz, 1H), 7.47 (dd, J=11.0, 6.9 Hz, 1H), 7.21 (dd, J=10.8, 7.9 Hz, 1H).

Intermediate 6:
5,6-difluoro-3-iodo-1-(phenylsulfonyl)-1H-indole

To a solution of 5,6-difluoro-3-iodo-1H-indole (Intermediate 5; 930 mg; 3.33 mmol) in THF (20 mL) at 0° C. was added NaH (266.4 mg; 60%; 6.66 mmol) under nitrogen. The mixture was stirred at r.t. for 15 minutes before a solution of benzenesulfonyl chloride (763.4 mg; 4.32 mmol) in THF (2 mL) was added dropwise. The reaction was stirred at r.t. for 12 hours, quenched with an ice-water mixture (60 mL) and extracted with EtOAc (30 mL×3). The combined organic layers were washed with brine (100 mL), dried over anhydrous $Na_2SO_4$, filtered, concentrated, and purified by a silica gel chromatography (petroleum ether/EtOAc=10/1-3/1) to afford 1.01 g (72%) of the title compound as a yellow solid. $^1$H NMR (400 MHz, DMSO-d$_6$) δ [ppm]: 8.19 (s, 1H), 8.14-8.10 (m, 2H), 8.07-8.00 (m, 1H), 7.78-7.72 (m, 1H), 7.66-7.61 (m, 2H), 7.41 (dd, J=10.2, 7.8 Hz, 1H).

Intermediate 7: 1-(methylsulfonyl)piperidin-4-amine

To a solution of tert-butyl (1-(methylsulfonyl)piperidin-4-yl)carbamate (2.72 g; 9.77 mmol) in DCM (30 mL) was added TFA (10.6 mL; 143 mmol). The mixture was stirred at r.t. for 1.5 hours and concentrated in vacuo. The residue was triturated with diethyl ether (30 mL), filtered, and washed with diethyl ether (30 mL). The solid was dissolved in H$_2$O (60 mL), basified with aqueous NaOH to pH=11, and extracted with DCM/i-PrOH (10/1, 60 mL×10). The combined organic layers were dried over anhydrous Na$_2$SO$_4$, filtered, and concentrated to afford 1.4 g (80%) of the title compound as a yellow oil. LC-MS: m/z 179.0 [M+H]$^+$. $^1$H NMR (300 MHz, CDCl$_3$) δ [ppm]: 3.50-3.38 (m, 2H), 2.82 (s, 3H), 2.80-2.61 (m, 3H), 1.80-1.70 (m, 2H), 1.33-1.23 (m, 2H).

Intermediate 8: N$^1$-(5-(6-fluoro-1-(phenylsulfonyl)-1H-indol-3-yl)pyridin-2-yl)propane-1,3-diamine A solution of 3-(6-chloropyridin-3-yl)-6-fluoro-1-(phenylsulfonyl)-1H-indole (Intermediate 2; 600 mg; 1.55 mmol) in propane-1,3-diamine (1.5 mL) was heated at 180° C. for 2 hours in a microwave reactor. The mixture was cooled to r.t., poured into H$_2$O (30 mL) and filtered. The solid was dissolved in EtOAc (30 mL), dried over anhydrous Na$_2$SO$_4$, filtered, and concentrated to afford 600 mg (91%) of the title compound as a yellow semi-solid, which was used directly without further purification. LC-MS: m/z 424.9 [M+H]$^+$.

Intermediate 9: N$^1$-(5-(6-fluoro-1H-indol-3-yl)pyridin-2-yl)propane-1,3-diamine To a solution of N$^1$-(5-(6-fluoro-1-(phenylsulfonyl)-1H-indol-3-yl)pyridin-2-yl)propane-1,3-diamine (Intermediate 8; 219 mg; 0.52 mmol) in MeOH (15 mL) was added a solution of NaOH (102 mg; 2.55 mmol) in water (1 mL). The mixture was stirred at 80° C. for 1 hour, concentrated, and purified by reversed phase flash chromatography to afford 145 mg (100%) of the title compound as a white solid. LC-MS: m/z 285.0 [M+H]$^+$.

Intermediate 10: 1-(5-(6-fluoro-1H-indol-3-yl)pyridin-2-yl)piperidin-4-amine

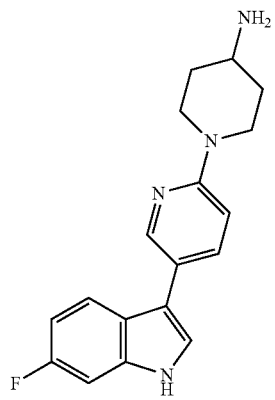 [SMILES: NC1CCN(c2ccc(-c3c[nH]c4cc(F)ccc34)cn2)CC1]

Step 1: 1-(5-(6-fluoro-1-(phenylsulfonyl)-1H-indol-3-yl)pyridin-2-yl)piperidin-4-amine A solution of 3-(6-chloropyridin-3-yl)-6-fluoro-1-(phenylsulfonyl)-1H-indole (Intermediate 2; 250 mg; 0.65 mmol) and tert-butyl 4-aminopiperidine-1-carboxylate (648 mg; 3.23 mmol) in NMP (0.1 mL) was heated at 180° C. for 2 hours in a microwave reactor. The mixture was purified by preparative TLC (EtOAc) and preparative TLC (DCM/MeOH=10/1, v/v) to afford 291 mg (100%) of the title compound as a yellow solid. $^1$H NMR (300 MHz, DMSO-d$_6$) δ [ppm]: 8.46 (d, J=2.2 Hz, 1H), 8.14-8.03 (m, 3H), 7.88 (dd, J=8.8, 2.2 Hz, 1H), 7.69-7.81 (m, 3H), 7.71-7.69 (m, 2H), 7.26-7.15 (m, 1H), 6.99 (d, J=9.1 Hz, 1H), 4.47-4.31 (m, 2H), 4.16-4.04 (m, 1H), 2.99-2.91 (m, 2H), 2.06-1.94 (m, 2H), 1.63-1.47 (m, 2H).

Step 2

To a solution of 1-(5-(6-fluoro-1-(phenylsulfonyl)-1H-indol-3-yl)pyridin-2-yl)piperidin-4-amine (346 mg; 0.77 mmol) in MeOH (20 mL) was added a solution of NaOH (154 mg; 3.85 mmol) in water (2 mL). The mixture was stirred at 85° C. for 1 hour, concentrated, and purified by preparative TLC (DCM/MeOH=10/1, v/v) to afford 249 mg (>100%) of the title compound as a white solid. LC-MS: m/z 311.0 [M+H]$^+$. $^1$H NMR (400 MHz, DMSO-d$_6$) δ [ppm]: 11.37 (br s, 1H), 8.43 (d, J=2.4 Hz, 1H), 7.81 (dd, J=8.6, 2.4 Hz, 1H), 7.73 (dd, J=8.7, 5.3 Hz, 1H), 7.59 (d, J=2.0 Hz, 1H), 7.20 (dd, J=10.1, 2.2 Hz, 1H), 6.94 (d, J=8.6 Hz, 1H), 6.92 (ddd, J=9.6, 8.7, 2.2 Hz, 1H), 5.22 (br s, 2H), 4.33-4.21 (m, 2H), 3.03 (tt, J=10.7, 4.1 Hz, 1H), 2.96-2.85 (m, 2H), 1.90-1.80 (m, 2H), 1.43-1.29 (m, 2H).

Intermediate 11: 3-(6-bromopyridin-3-yl)-6-fluoro-1-(phenylsulfonyl)-1H-indole

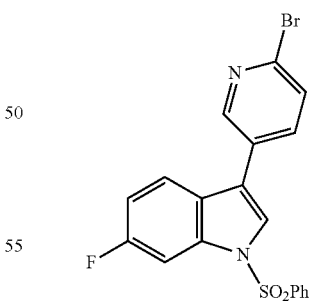

Following the general method as outlined in Intermediate 2, starting from 6-fluoro-3-iodo-1-(phenylsulfonyl)-1H-indole (prepared as described in WO2010/136491; 4.98 g; 12.4 mmol), 2-bromopyridine-5-boronic acid (3.00 g; 14.8 mmol), 3.03 g (57%) of the title compound was obtained as a brown solid after purification by a silica gel chromatography (petroleum ether/DCM=1/1, v/v). LC-MS: m/z 431.2 [M+H]$^+$. $^1$H NMR (300 MHz, DMSO-d$_6$) δ [ppm]: 8.77 (d, J=2.4 Hz, 1H), 8.39 (s, 1H), 8.21-8.08 (m, 3H), 7.87 (dd, J=8.8, 5.3 Hz, 1H), 7.82 (dd, J=9.9, 2.2 Hz, 1H), 7.78-7.70 (m, 2H), 7.68-7.59 (m, 2H), 7.25 (ddd, J=9.5, 8.8, 2.2 Hz, 1H).

Intermediate 12: 6-fluoro-1-(phenylsulfonyl)-3-(6-(piperazin-1-yl)pyridin-3-yl)-1H-indole

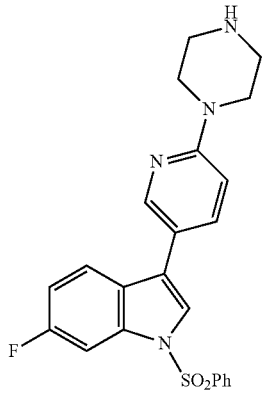

Following the general method as outlined in Intermediate 8, starting from 3-(6-chloropyridin-3-yl)-6-fluoro-1-(phenylsulfonyl)-1H-indole (Intermediate 2; 600 mg; 1.55 mmol) and piperazine (1.00 g; 11.6 mmol), 675 mg (100%) of the crude title compound was obtained as a yellow oil, which was used directly without further purification. LC-MS: m/z 436.9 [M+H]$^+$.

Intermediate 13: 6-fluoro-3-(6-(piperazin-1-yl)pyridin-3-yl)-1H-indole

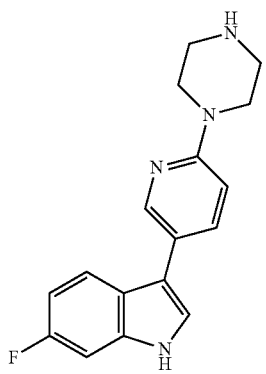 [SMILES: Fc1ccc2c(-c3ccc(N4CCNCC4)nc3)c[nH]c2c1]

Following the general method as outlined in Intermediate 9, starting from 6-fluoro-1-(phenylsulfonyl)-3-(6-(piperazin-1-yl)pyridin-3-yl)-1H-indole (Intermediate 12; 675 mg crude; 1.55 mmol), 440 mg (95%) of the title compound was obtained as a yellow solid after purification by preparative TLC (DCM/MeOH=10/1). LC-MS: m/z 297.0 [M+H]$^+$.

Intermediate 14: N$^1$-(5-(6-fluoro-1-(phenylsulfonyl)-1H-indol-3-yl)pyridin-2-yl)ethane-1,2-diamine

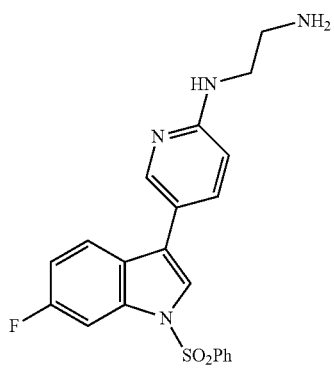

Following the general method as outlined in Intermediate 8, starting from 3-(6-chloropyridin-3-yl)-6-fluoro-1-(phenylsulfonyl)-1H-indole (Intermediate 2; 700 mg; 1.81 mmol) and ethylenediamine (3.00 mL; 44.9 mmol), 704 mg (95%) of the crude title compound was obtained as a yellow oil, which was used directly without further purification. LC-MS: m/z 410.9 [M+H]$^+$.

Intermediate 15: N$^1$-(5-(6-fluoro-1H-indol-3-yl)pyridin-2-yl)ethane-1,2-diamine

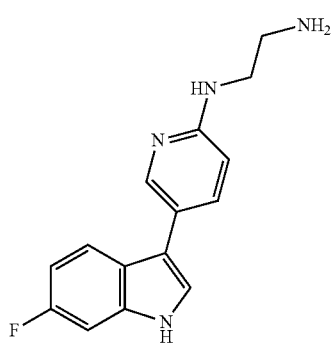 [SMILES: NCCNc1ccc(-c2c[nH]c3cc(F)ccc23)cn1]

Following the general method as outlined in Intermediate 9, starting from N'-(5-(6-fluoro-1-(phenylsulfonyl)-1H-indol-3-yl)pyridin-2-yl)ethane-1,2-diamine (Intermediate 14; 704 mg crude; 1.72 mmol), 450 mg (97%) of the crude title compound was obtained as a yellow solid, which was used directly without further purification. LC-MS: m/z 271.0 [M+H]$^+$.

Intermediate 16: N-(1-(5-(6-fluoro-1H-indol-3-yl)pyridin-2-yl)piperidin-4-yl)ethenesulfonamide

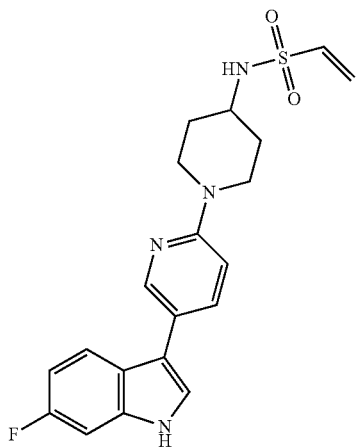 [SMILES: C=CS(=O)(=O)NC1CCN(c2ccc(-c3c[nH]c4cc(F)ccc34)cn2)CC1]

To a solution of 1-(5-(6-fluoro-1H-indol-3-yl)pyridin-2-yl)piperidin-4-amine (Intermediate 10; 200 mg; 0.64 mmol) and Et₃N (228 mg; 2.25 mmol) in DCM (50 mL) and DMF (5 mL) was added 2-chloroethanesulfonyl chloride (126 mg; 0.77 mmol) dropwise at 0° C. The reaction mixture was stirred at room temperature for 2 hours, concentrated, and purified by preparative TLC (EtOAc) to afford 200 mg (78%) of the title compound as a brown semi-solid. LC-MS: m/z 400.9 [M+H]$^+$. $^1$H NMR (400 MHz, DMSO-d$_6$) δ [ppm]: 11.34 (br s, 1H), 8.42 (d, J=2.4 Hz, 1H), 7.80 (dd, J=8.8, 2.4 Hz, 1H), 7.74 (dd, J=8.7, 5.5 Hz, 1H), 7.58 (d, J=2.4 Hz, 1H), 7.41 (d, J=7.2 Hz, 1H), 7.20 (dd, J=10.1, 2.4 Hz, 1H), 6.93 (d, J=8.8 Hz, 1H), 6.92 (ddd, J=9.7, 8.7, 2.2 Hz, 1H), 6.79 (dd, J=16.5, 9.9 Hz, 1H), 6.06 (d, J=16.5 Hz, 1H), 5.95 (d, J=9.9 Hz, 1H), 4.25-4.16 (m, 2H), 3.36-3.24 (m, 1H), 3.01-2.90 (m, 2H), 1.90-1.81 (m, 2H), 1.54-1.38 (m, 2H).

Intermediate 17: phenyl (5-(6-fluoro-1-(phenylsulfonyl)-1H-indol-3-yl)pyridin-2-yl)carbamate

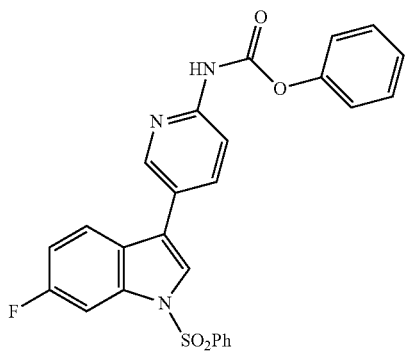

To a solution of 5-(6-fluoro-1-(phenylsulfonyl)-1H-indol-3-yl)pyridin-2-amine hydrochloride (Example 15 Step 1; 403 mg; 1.00 mmol) in pyridine (4 mL) was added phenyl chloroformate (359 mg; 2.29 mmol). The reaction mixture was stirred at room temperature overnight, concentrated and triturated with EtOAc to afford 160 mg (33%) of the crude title compound as a yellow solid, which was used directly without further purification. LC-MS: m/z 487.8 [M+H]$^+$. $^1$H NMR (400 MHz, DMSO-d$_6$) δ [ppm]: 10.93 (s, 1H), 8.70 (d, J=2.2 Hz, 1H), 8.28 (s, 1H), 8.18 (dd, J=8.6, 2.2 Hz, 1H), 8.17-8.12 (m, 2H), 7.93 (d, J=8.6 Hz, 1H), 7.87 (dd, J=8.7, 5.3 Hz, 1H), 7.82 (dd, J=9.9, 2.2 Hz, 1H), 7.77-7.71 (m, 1H), 7.68-7.60 (m, 2H), 7.50-7.42 (m, 2H), 7.33-7.21 (m, 4H).

Intermediate 18: tert-butyl 6-fluoro-3-(2-oxo-2,3-dihydrooxazolo[4,5-b]pyridin-6-yl)-1H-indole-1-carboxylate

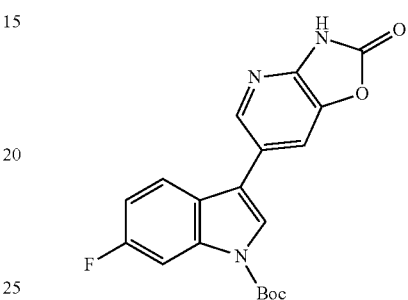

A mixture of 6-fluoro-3-(4,4,5,5-tetramethyl-1,3,2-dioxaborolan-2-yl)-1H-indole-1-carboxylate (1.10 g; 3.05 mmol), 6-bromooxazolo[4,5-b]pyridin-2(3H)-one (918 mg; 4.27 mmol; prepared as described in *J. Med. Chem.* 1993, 36, 497.), Pd(dppf)Cl$_2$ (219 mg; 0.30 mmol), and K$_2$CO$_3$ (1.26 g; 9.12 mmol) in dioxane (15 mL) and water (3 mL) was stirred at 95° C. for 16 hours under nitrogen. The reaction mixture was cooled to room temperature, diluted with EtOAc (100 mL) and water (30 mL) and filtered. The aqueous layer was extracted with EtOAc (100 mL). The combined organic layers were washed with brine (30 mL×2), dried over anhydrous Na$_2$SO$_4$, filtered, concentrated, and purified by a silica gel chromatography (petroleum ether/EtOAc=5/1-3/1, v/v) to afford 320 mg (28%) of the title compound as a white solid. LC-MS: m/z 368.5 [M+H]$^+$. $^1$H NMR (400 MHz, DMSO-d$_6$) δ [ppm]: 12.56 (br s, 1H), 8.39 (d, J=2.0 Hz, 1H), 8.02 (s, 1H), 8.01 (d, J=2.0 Hz, 1H), 7.92-7.83 (m, 2H), 7.21 (ddd, J=9.7, 8.7, 2.4 Hz, 1H), 1.66 (s, 9H).

I.2. Synthesis of Final Compounds

Example 1: 6-fluoro-3-(6-methylpyridin-3-yl)-1H-indole

Step 1: 6-fluoro-3-(6-methylpyridin-3-yl)-1-(phenylsulfonyl)-1H-indole

To a solution of 3-bromo-6-fluoro-1-(phenylsulfonyl)-1H-indole (Intermediate 1; 308 mg; 0.87 mmol), 2-methyl-5-(4,4,5,5-tetramethyl-[1,3,2]dioxaborolan-2-yl)pyridine (381 mg; 1.74 mmol), K$_3$PO$_4$ (922 mg; 4.34 mmol) in dioxane (5 mL) and water (1 mL) was added Pd$_2$dba$_3$ (40 mg; 0.044 mmol) and S-Phos (40 mg; 0.097 mmol) under nitrogen. The mixture was heated at 125° C. for 30 minutes in a microwave reactor. The mixture was diluted with EtOAc (20 mL) and water (10 mL). The organic layer was separated, washed with brine (5 mL), dried over anhydrous Na$_2$SO$_4$, filtered, concentrated, and purified by a silica gel chromatography (petroleum ether/EtOAc=10/1-2/1) to afford 160 mg (50%) of the title compound as a red solid. LC-MS: m/z 367.1 [M+H]$^+$.

Step 2

To a solution of 6-fluoro-3-(6-methylpyridin-3-yl)-1-(phenylsulfonyl)-1H-indole (Step 1; 160 mg; 0.44 mmol) in MeOH (10 mL) was added a solution of NaOH (105 mg; 2.62 mmol) in water (0.5 mL). The reaction mixture was stirred at 85° C. for 30 minutes, concentrated, diluted with H$_2$O (5 mL), and extracted with Et$_2$O (10 mL×3). The combined organic layers were washed with water (10 mL×2), brine (10 mL), dried over anhydrous Na$_2$SO$_4$, filtered, concentrated, and purified by preparative HPLC to afford 33.3 mg (34%) of the title compound as a white solid. LC-MS: m/z 227.1 [M+H]$^+$. $^1$H NMR (400 MHz, DMSO-d$_6$) δ [ppm]: 11.53 (s, 1H), 8.77 (d, J=2.3 Hz, 1H), 7.96 (dd, J=8.0, 2.3 Hz, 1H), 7.82 (dd, J=8.8, 5.4 Hz, 1H), 7.77 (d, J=2.5 Hz, 1H), 7.31 (d, J=8.0 Hz, 1H), 7.24 (dd, J=9.9, 2.4 Hz, 1H), 6.96 (ddd, J=9.6, 8.8, 2.4 Hz, 1H), 2.50 (s, 3H).

Example 2: 6-fluoro-3-(6-(piperidin-4-yloxy)pyridin-3-yl)-1H-indole

Step 1: tert-butyl 4-(5-(6-fluoro-1-(phenylsulfonyl)-1H-indol-3-yl)pyridin-2-yloxy)piperidine-1-carboxylate To a solution of 6-fluoro-3-iodo-1-(phenylsulfonyl)-1H-indole (prepared as in WO2010/136491A; 730 mg; 1.82 mmol), tert-butyl 4-(5-(4,4,5,5-tetramethyl-1,3,2-dioxaborolan-2-yl)pyridin-2-yloxy)piperidine-1-carboxylate (Intermediate 4; 1.47 g; 3.64 mmol), K$_3$PO$_4$ (1.16 g; 5.46 mmol) in dioxane (20 mL) and water (2 mL) was added Pd(dppf)Cl$_2$.DCM (149 mg; 0.18 mmol) under nitrogen. The mixture was stirred at 90° C. overnight. The mixture was filtered through Celite, diluted with EtOAc (100 mL) and water (100 mL). The aqueous layer was extracted with EtOAc (50 mL×2). The combined organic layers were washed with brine, dried over anhydrous Na$_2$SO$_4$, filtered, concentrated, and purified by a silica gel chromatography (petroleum ether/EtOAc=10/1-5/1) to afford 580 mg (58%) of the title compound as a yellow solid. LC-MS: m/z 552.1 [M+H]$^+$. $^1$H NMR (400 MHz, CDCl$_3$) δ [ppm]: 8.33 (d, J=2.3 Hz, 1H), 7.97-7.89 (m, 2H), 7.79 (dd, J=9.6, 2.3 Hz, 1H), 7.75 (dd, J=8.5, 2.4 Hz, 1H), 7.62 (s, 1H), 7.61-7.55 (m, 2H), 7.49 (dd, J=9.9, 5.6 Hz, 2H), 7.05 (td, J=8.9, 2.3 Hz, 1H), 6.82 (d, J=8.5 Hz, 1H), 5.33-5.18 (m, 1H), 3.85-3.74 (m, 2H), 3.36-3.23 (m, 2H), 2.04-1.92 (m, 2H), 1.71-1.80 (m, 2H), 1.48 (s, 9H).

Step 2: 6-fluoro-1-(phenylsulfonyl)-3-(6-(piperidin-4-yloxy)pyridin-3-yl)-1H-indole To a solution of tert-butyl 4-(5-(6-fluoro-1-(phenylsulfonyl)-1H-indol-3-yl)pyridin-2-yloxy)piperidine-1-carboxylate (Step 1; 580 mg; 1.05 mmol) in MeOH (10 mL) was added HCl in Et$_2$O (4 M; 10 mL). The resulting mixture was stirred for 30 minutes. The reaction was concentrated in vacuo, diluted with water (10 mL), neutralized with saturated aqueous NaHCO$_3$, and extracted with EtOAc (30 mL×2). The combined organic layers were washed with brine (30 mL), dried over anhydrous Na$_2$SO$_4$, filtered, and concentrated to afford 473 mg (100%) of the title compound as a yellow solid, which was used directly without further purification. LC-MS: m/z 452.1 [M+H]$^+$. $^1$H NMR (300 MHz, DMSO-d$_6$) δ [ppm]: 8.48 (d, J=2.4 Hz, 1H), 8.17-8.07 (m, 3H), 8.02 (dd, J=8.6, 2.5 Hz, 1H), 7.84-7.77 (m, 2H), 7.75-7.71 (m, 1H), 7.65-7.58 (m, 2H), 7.21 (td, J=9.2, 2.3 Hz, 1H), 6.88 (d, J=8.6 Hz, 1H), 5.16-4.97 (m, 1H), 3.00-2.93 (m, 2H), 2.61-2.53 (m, 2H), 1.98-1.94 (m, 2H), 1.56-1.44 (m, 2H).

Step 3

Following the general method as outlined in Example 1 Step 2, starting from 6-fluoro-1-(phenylsulfonyl)-3-(6-(piperidin-4-yloxy)pyridin-3-yl)-1H-indole (Step 2; 240 mg; 0.53 mmol), 57 mg (34%) of the title compound was obtained as a yellow solid after purification by preparative HPLC. LC-MS: m/z 312.1 [M+H]$^+$. $^1$H NMR (400 MHz, DMSO-d$_6$) δ [ppm]: 11.42 (s, 1H), 8.43 (d, J=2.4 Hz, 1H), 7.96 (dd, J=8.6, 2.4 Hz, 1H), 7.77 (dd, J=8.7, 5.3 Hz, 1H), 7.66 (d, J=2.1 Hz, 1H), 7.22 (dd, J=10.0, 2.3 Hz, 1H), 6.93 (ddd, J=9.5, 8.7, 2.3 Hz, 1H), 6.84 (d, J=8.6 Hz, 1H), 5.13-4.98 (m, 1H), 3.03-2.88 (m, 2H), 2.61-2.55 (m, 2H), 2.04-1.90 (m, 2H), 1.54-1.45 (m 2H).

Example 3: 6-fluoro-3-(6-(1-methylpiperidin-4-yloxy)pyridin-3-yl)-1H-indole

The title compound was obtained (5 mg, 3%) as a yellow solid after purification by preparative HPLC in Step 3 of Example 2. LC-MS: m/z 326.1 [M+H]$^+$. $^1$H NMR (300 MHz, DMSO-d$_6$) δ [ppm]: 11.58 (br s, 1H), 8.45 (d, J=2.4 Hz, 1H), 8.01 (dd, J=8.5, 2.4 Hz, 1H), 7.77 (dd, J=8.8, 5.3 Hz, 1H), 7.68 (d, J=2.4 Hz, 1H), 7.23 (dd, J=10.0, 2.3 Hz, 1H), 7.02-6.81 (m, 2H), 5.32-5.11 (m, 1H), 3.31-3.01 (m, 4H), 2.69 (s, 3H), 2.31-2.16 (m, 2H), 2.12-1.95 (m, 2H).

Example 4: 2-(5-(6-fluoro-1H-indol-3-yl)pyridin-2-yloxy)-N,N-dimethylethanamine

Following the general method as outlined in Example 27, starting from 3-(6-chloropyridin-3-yl)-6-fluoro-1-(phenylsulfonyl)-1H-indole (Intermediate 2; 250 mg; 0.65 mmol), 2-(dimethylamino)ethanol (3.0 mL), and NaH (518 mg; 12.9 mmol; 60% in mineral oil), 113 mg (58%) of the title compound was obtained as a white solid after purification by silica gel chromatography (DCM/MeOH=10/1). LC-MS: m/z 300.1 [M+H]$^+$. $^1$H NMR (400 MHz, DMSO-d$_6$) δ [ppm]: 11.43 (s, 1H), 8.45 (d, J=2.4 Hz, 1H), 7.98 (dd, J=8.5, 2.4 Hz, 1H), 7.77 (dd, J=8.7, 5.4 Hz, 1H), 7.67 (d, J=2.5 Hz, 1H), 7.22 (dd, J=10.0, 2.4 Hz, 1H), 6.94 (ddd, J=9.6, 8.7, 2.4 Hz, 1H), 6.88 (d, J=8.5 Hz, 1H), 4.37 (t, J=5.9 Hz, 2H), 2.64 (t, J=5.9 Hz, 2H), 2.23 (s, 6H).

Example 5: 6-fluoro-3-(6-methoxypyridin-3-yl)-1H-indole

Step 1: 6-fluoro-3-(6-methoxypyridin-3-yl)-1-(phenylsulfonyl)-1H-indole

Following the general method as outlined in Example 1 Step 1, starting from 3-bromo-6-fluoro-1-(phenylsulfonyl)-1H-indole (Intermediate 1; 300 mg; 0.85 mmol), 6-methoxypyridin-3-ylboronic acid (195 mg; 1.28 mmol), $K_3PO_4$ (451 mg; 2.12 mmol), $Pd_2dba_3$ (76 mg; 0.083 mmol), and S-phos (81 mg; 0.20 mmol), 319 mg (98%) of the title compound was obtained as a white solid after purification by a silica gel chromatography (petroleum ether/EtOAc=50/1-10/1). LC-MS: m/z 383.1 $[M+H]^+$. $^1$H NMR (300 MHz, DMSO-$d_6$) δ [ppm]: 8.52 (d, J=2.0 Hz, 1H), 8.18 (s, 1H), 8.16-8.09 (m, 2H), 8.05 (dd, J=8.6, 2.5 Hz, 1H), 7.85-7.77 (m, 2H), 7.73-7.69 (m, 1H), 7.65-7.59 (m, 2H), 7.22 (td, J=9.2, 2.3 Hz, 1H), 6.94 (d, J=8.6 Hz, 1H), 3.90 (s, 3H).

Step 2

Following the general method as outlined in Example 1 step 2, starting from 6-fluoro-3-(6-methoxypyridin-3-yl)-1-(phenylsulfonyl)-1H-indole (Step 1; 315 mg; 0.82 mmol), 170 mg (85%) of the title compound was obtained as a white solid. LC-MS: m/z 243.1 $[M+H]^+$. $^1$H NMR (400 MHz, DMSO-$d_6$) δ [ppm]: 11.45 (s, 1H), 8.47 (d, J=2.4 Hz, 1H), 7.99 (dd, J=8.5, 2.4 Hz, 1H), 7.78 (dd, J=8.8, 5.3 Hz, 1H), 7.68 (d, J=2.5 Hz, 1H), 7.22 (dd, J=10.0, 2.4 Hz, 1H), 6.94 (ddd, J=9.6, 8.8, 2.4 Hz, 1H), 6.90 (d, J=8.5 Hz, 1H), 3.89 (s, 3H).

Example 6: 6-fluoro-3-(6-(1-(methylsulfonyl)piperidin-4-yloxy)pyridin-3-yl)-1H-indole

Step 1: 6-fluoro-3-(6-((1-(methylsulfonyl)piperidin-4-yl)oxy)pyridin-3-yl)-1-(phenylsulfonyl)-1H-indole Following the general method as outlined in Example 14 Step 2, starting from 6-fluoro-1-(phenylsulfonyl)-3-(6-(piperidin-4-yloxy)pyridin-3-yl)-1H-indole (Example 2 Step 2; 240 mg; 0.53 mmol), 280 mg (100%) of the title compound was obtained as a yellow solid, which was used directly without further purification. LC-MS: m/z 530.1 $[M+H]^+$. $^1$H NMR (400 MHz, DMSO-$d_6$) δ [ppm]: 8.51 (d, J=2.3 Hz, 1H), 8.17 (s, 1H), 8.15-8.11 (m, 2H), 8.06 (dd, J=8.5, 2.5 Hz, 1H), 7.84-7.77 (m, 2H), 7.76-7.71 (m, 1H), 7.65-7.60 (m, 2H), 7.22 (td, J=9.1, 2.2 Hz, 1H), 6.94 (d, J=8.6 Hz, 1H), 5.25-5.16 (m, 1H), 3.45-3.37 (m, 2H), 3.18-3.12 (m, 2H), 2.92 (s, 3H), 2.15-2.03 (m, 2H), 1.88-1.75 (m, 2H).

Step 2

Following the general method as outlined in Example 1 Step 2, starting from 6-fluoro-3-(6-((1-(methylsulfonyl)piperidin-4-yl)oxy)pyridin-3-yl)-1-(phenylsulfonyl)-1H-indole (Step 1; 280 mg; 0.52 mmol), 51 mg (25%) of the title compound was obtained as a white solid after purification by preparative HPLC. LC-MS: m/z 390.0 $[M+H]^+$. $^1$H NMR (400 MHz, DMSO-$d_6$) δ [ppm]: 11.46 (br s, 1H), 8.45 (d, J=2.4 Hz, 1H), 8.00 (dd, J=8.5, 2.4 Hz, 1H), 7.77 (dd, J=8.8, 5.4 Hz, 1H), 7.68 (d, J=2.4 Hz, 1H), 7.23 (dd, J=10.0, 2.3 Hz, 1H), 6.94 (ddd, J=9.4, 8.8, 2.3 Hz, 1H), 6.89 (d, J=8.5 Hz, 1H), 5.18 (tt, J=4.0, 4.0 Hz, 1H), 3.45-3.37 (m, 2H), 3.18-3.09 (m, 2H), 2.92 (s, 3H), 2.14-2.05 (m, 2H), 1.82-1.78 (m, 2H).

Example 7: 5-(6-fluoro-1H-indol-3-yl)-N,N-dimethylpyridin-2-amine

Step 1: 5-(6-fluoro-1-(phenylsulfonyl)-1H-indol-3-yl)-N,N-dimethylpyridin-2-amine Following the general method as outlined in Example 34 Step 1, starting from 3-(6-chloropyridin-3-yl)-6-fluoro-1-(phenylsulfonyl)-1H-indole (Intermediate 2; 200 mg; 0.52 mmol) and dimethylamine (8.0 mL; 16 mmol; 2 M in THF), 180 mg (88%) of the title compound was obtained as a brown solid after purification by a silica gel chromatography (petroleum ether/EtOAc=10/1-5/1). LC-MS: m/z 396.1 $[M+H]^+$.

Step 2

Following the general method as outlined in Example 1 Step 2, starting from 5-(6-fluoro-1-(phenylsulfonyl)-1H-indol-3-yl)-N,N-dimethylpyridin-2-amine (Step 1; 180 mg; 0.46 mmol), 35 mg (30%) of the title compound was obtained as a yellow solid after purification by preparative HPLC. LC-MS: m/z 256.1 $[M+H]^+$. $^1$H NMR (400 MHz, DMSO-$d_6$) δ [ppm]: 11.31 (s, 1H), 8.40 (d, J=2.3 Hz, 1H), 7.79 (dd, J=8.6, 2.3 Hz, 1H), 7.73 (dd, J=8.8, 5.4 Hz, 1H), 7.55 (d, J=2.4 Hz, 1H), 7.19 (dd, J=10.0, 2.4 Hz, 1H), 6.91 (ddd, J=9.6, 8.8, 2.4 Hz, 1H), 6.73 (d, J=8.6 Hz, 1H), 3.05 (s, 6H).

Example 8: N-(5-(6-fluoro-1H-indol-3-yl)pyridin-2-yl)-N-methylacetamide

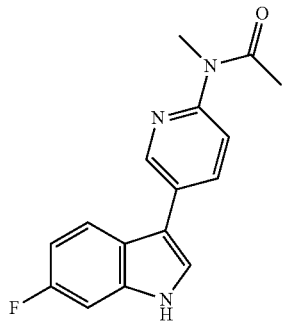 [SMILES: CC(=O)N(C)c1ccc(-c2c[nH]c3cc(F)ccc23)cn1]

To a stirred solution of 5-(6-fluoro-1H-indol-3-yl)-N-methylpyridin-2-amine (Example 34; 52 mg; 0.22 mmol) in pyridine (8 mL) was added AcCl (50 mg; 0.64 mmol) at 0° C. The mixture was stirred at room temperature for 1 hour, concentrated, and purified by a silica gel chromatography (DCM/MeOH=200/1-20/1, v/v) and then preparative TLC (DCM/MeOH=15/1, v/v) to afford 55 mg (90%) of the title compound as an off-white solid. LC-MS: m/z 284.1 $[M+H]^+$. $^1$H NMR (400 MHz, DMSO-$d_6$) δ [ppm]: 11.61 (br s, 1H), 8.80 (d, J=2.4 Hz, 1H), 8.16 (dd, J=8.4, 2.4 Hz, 1H), 7.88 (dd, J=8.7, 5.3 Hz, 1H), 7.87 (d, J=2.2 Hz, 1H), 7.55 (d, J=8.4 Hz, 1H), 7.26 (dd, J=9.9, 2.4 Hz, 1H), 6.98 (ddd, J=9.6, 8.7, 2.4 Hz, 1H), 3.30 (s, 3H), 2.05 (s, 3H).

Example 9: 4-(5-(6-fluoro-1H-indol-3-yl)pyridin-2-yl)morpholine

Step 1: 4-(5-(6-fluoro-1-(phenylsulfonyl)-1H-indol-3-yl)pyridin-2-yl)morpholine A solution of 3-(6-chloropyridin-3-yl)-6-fluoro-1-(phenylsulfonyl)-1H-indole (Intermediate 2; 250 mg; 0.65 mmol) in morpholine (6.5 mL) was heated at 180° C. for 3 hours in a microwave reactor. The mixture was concentrated in vacuo to afford 283 mg (100%) of the title compound as a yellow semi-solid, which was used directly without further purification. LC-MS: m/z 438.1 [M+H]$^+$. $^1$H NMR (400 MHz, DMSO-d$_6$) δ [ppm]: 8.48 (d, J=2.4 Hz, 1H), 8.15-8.05 (m, 3H), 7.90 (dd, J=8.8, 2.4 Hz, 1H), 7.83-7.76 (m, 2H), 7.74-7.70 (m, 1H), 7.65-7.59 (m, 2H), 7.21 (td, J=9.1, 2.3 Hz, 1H), 6.94 (d, J=8.8 Hz, 1H), 3.75-3.68 (m, 4H), 3.52-3.47 (m, 4H).

Step 2

Following the general method as outlined in Example 1 Step 2, starting from 4-(5-(6-fluoro-1-(phenylsulfonyl)-1H-indol-3-yl)pyridin-2-yl)morpholine (Step 1; 283 mg; 0.65 mmol), 60 mg (31%) of the title compound was obtained as a white solid after purification by preparative TLC (petroleum ether/EtOAc=1/1). LC-MS: m/z 298.1 [M+H]$^+$. $^1$H NMR (400 MHz, DMSO-d$_6$) δ [ppm]: 11.34 (s, 1H), 8.46 (s, 1H), 7.85 (dd, J=8.7, 1.7 Hz, 1H), 7.75 (dd, J=8.7, 5.4 Hz, 1H), 7.60 (d, J=1.9 Hz, 1H), 7.20 (dd, J=9.8, 1.8 Hz, 1H), 6.94 (ddd, J=9.5, 8.7, 1.8 Hz, 1H), 6.91 (d, J=8.7 Hz, 1H), 3.86-3.65 (m, 4H), 3.56-3.37 (m, 4H).

Example 10: 6-fluoro-3-(6-(4-methylpiperazin-1-yl)pyridin-3-yl)-1H-indole

Step 1: 6-fluoro-3-(6-(4-methylpiperazin-1-yl)pyridin-3-yl)-1-(phenylsulfonyl)-1H-indole Following the general method as outlined in Example 9 Step 1, starting from 3-(6-chloropyridin-3-yl)-6-fluoro-1-(phenylsulfonyl)-1H-indole (Intermediate 2; 250 mg; 0.65 mmol) and 1-methyl-piperazine (7.0 mL), 308 mg (100%) of the title compound was obtained as a yellow semi-solid, which was used directly without further purification. LC-MS: m/z 451.1 [M+H]$^+$. $^1$H NMR (300 MHz, DMSO-d$_6$) δ [ppm]: 8.45 (d, J=2.1 Hz, 1H), 8.14-8.08 (m, 2H), 8.06 (s, 1H), 7.86 (dd, J=9.0, 5.4 Hz, 1H), 7.82-7.74 (m, 2H), 7.72-7.67 (m, 1H), 7.65-7.57 (m, 2H), 7.25-7.15 (m, 1H), 6.93 (d, J=8.9 Hz, 1H), 3.57-3.47 (m, 4H), 2.73-2.43 (m, 4H), 2.22 (s, 3H).

Step 2

Following the general method as outlined in Example 1 Step 2, starting from 6-fluoro-3-(6-(4-methylpiperazin-1-yl)pyridin-3-yl)-1-(phenylsulfonyl)-1H-indole (Step 1; 308 mg; 0.65 mmol), 130 mg (64%) of the title compound was obtained as a white solid after purification by preparative HPLC. LC-MS: m/z 311.1 [M+H]$^+$. $^1$H NMR (400 MHz, DMSO-d$_6$) δ [ppm]: 11.33 (s, 1H), 8.44 (d, J=2.0 Hz, 1H), 7.82 (dd, J=8.9, 2.0 Hz, 1H), 7.74 (dd, J=8.7, 5.4 Hz, 1H), 7.58 (s, 1H), 7.20 (dd, J=9.9, 1.9 Hz, 1H), 6.88 (ddd, J=9.5, 8.7, 1.9 Hz, 1H), 6.90 (d, J=8.9 Hz, 1H), 3.53-3.45 (m, 4H), 2.44-2.39 (m, 4H), 2.23 (s, 3H).

Example 11: 2-amino-1-(4-(5-(6-fluoro-1H-indol-3-yl)pyridin-2-yl)piperazin-1-yl)ethanone

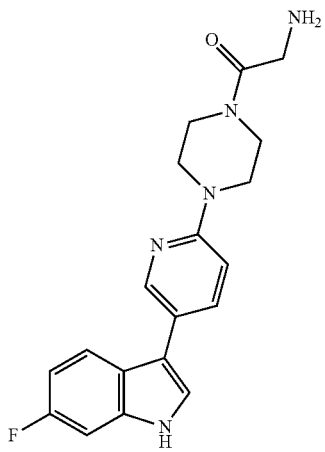 [SMILES: NCC(=O)N1CCN(c2ccc(-c3c[nH]c4cc(F)ccc34)cn2)CC1]

Step 1: tert-butyl (2-(4-(5-(6-fluoro-1H-indol-3-yl)pyridin-2-yl)piperazin-1-yl)-2-oxoethyl)carbamate

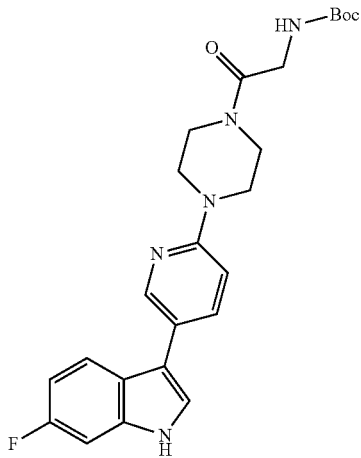 [SMILES: CC(C)(C)OC(=O)NCC(=O)N1CCN(c2ccc(-c3c[nH]c4cc(F)ccc34)cn2)CC1]

A mixture of Boc-Glycine (190 mg; 1.08 mmol), HATU (410 mg; 1.08 mmol) and DIPEA (279 mg; 2.16 mmol) in DMF (15 mL) was stirred at room temperature for 0.5 hour and then added 6-fluoro-3-(6-(piperazin-1-yl)pyridin-3-yl)-1H-indole (Intermediate 13; 214 mg; 0.72 mmol). The reaction mixture was stirred at room temperature for 0.5 h, poured into water (50 mL) and filtered. The precipitate was dissolved in EtOAc (30 mL), dried over anhydrous Na$_2$SO$_4$, filtered, and concentrated to afford 398 mg (>100%) of the crude title compound as a yellow solid, which was used directly without further purification. LC-MS: m/z 453.9 [M+H]$^+$. $^1$H NMR (400 MHz, DMSO-d$_6$) δ [ppm]: 11.57 (br s, 1H), 8.35 (s, 1H), 8.08 (s, 1H), 7.79-7.69 (m, 2H), 7.24 (dd, J=9.9, 2.0 Hz, 1H), 7.19 (s, 1H), 6.97 (ddd, J=9.7, 8.7, 2.2 Hz, 1H), 6.84 (br t, J=5.2 Hz, 1H), 3.86 (d, J=5.2 Hz, 2H), 3.75-3.51 (m, 8H), 1.39 (s, 9H).

Step 2

Following the general method as outlined in Intermediate 10 Step 2, starting from tert-butyl (2-(4-(5-(6-fluoro-1H- indol-3-yl)pyridin-2-yl)piperazin-1-yl)-2-oxoethyl)carbamate (Step 1; 398 mg crude; 0.72 mmol), 75 mg (29%) of the title compound was obtained as a white solid after purification by preparative HPLC. LC-MS: m/z 354.2 [M+H]$^+$. $^1$H NMR (400 MHz, DMSO-d$_6$) δ [ppm]: 11.38 (br s, 1H), 8.46 (s, 1H), 7.86 (d, J=8.4 Hz, 1H), 7.75 (dd, J=8.7, 5.4 Hz, 1H), 7.62 (s, 1H), 7.21 (dd, J=10.0, 2.4 Hz, 1H), 7.01-6.88 (m, 2H), 3.68-3.40 (m, 10H), 2.80 (br s, 2H).

Example 12: 6-fluoro-3-(6-(4-(methylsulfonyl)piperazin-1-yl)pyridin-3-yl)-1H-indole

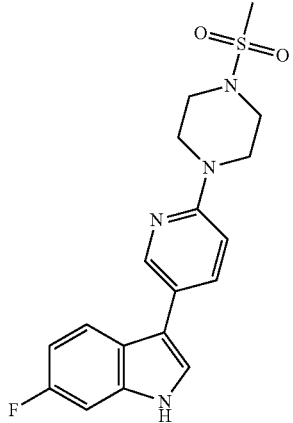 [SMILES: CS(=O)(=O)N1CCN(c2ccc(-c3c[nH]c4cc(F)ccc34)cn2)CC1]

To a solution of 6-fluoro-3-(6-(piperazin-1-yl)pyridin-3-yl)-1H-indole (Intermediate 13; 150 mg; 0.51 mmol), Et$_3$N (153 mg; 1.51 mmol) in DCM (20 mL) was added methanesulfonyl chloride (87 mg; 0.76 mmol) dropwise at 0° C. The reaction mixture was stirred at room temperature for 1 hour, concentrated, and purified by preparative HPLC to afford 100 mg (53%) of the title compound as a white solid. LC-MS: m/z 374.9 [M+H]$^+$. $^1$H NMR (400 MHz, DMSO-d$_6$) δ [ppm]: 11.38 (br s, 1H), 8.47 (d, J=2.4 Hz, 1H), 7.87 (dd, J=8.6, 2.4 Hz, 1H), 7.75 (dd, J=8.8, 5.3 Hz, 1H), 7.62 (d, J=2.2 Hz, 1H), 7.21 (dd, J=9.9, 2.4 Hz, 1H), 6.99 (d, J=8.6 Hz, 1H), 6.93 (ddd, J=9.6, 8.8, 2.4 Hz, 1H), 3.69-3.61 (m, 4H), 3.26-3.19 (m, 4H), 2.92 (s, 3H).

Example 13: 2-amino-N-(1-(5-(6-fluoro-1H-indol-3-yl)pyridin-2-yl)piperidin-4-yl)acetamide

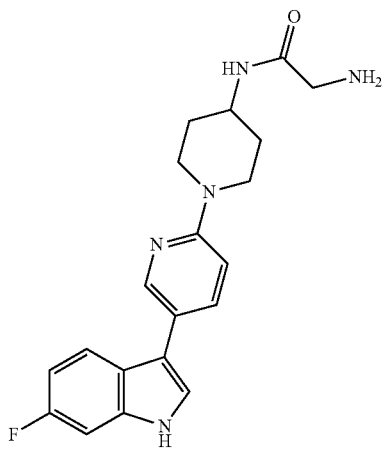 [SMILES: NCC(=O)NC1CCN(c2ccc(-c3c[nH]c4cc(F)ccc34)cn2)CC1]

Step 1: tert-butyl (2-((1-(5-(6-fluoro-1H-indol-3-yl)pyridin-2-yl)piperidin-4-yl)amino)-2-oxoethyl)carbamate Following the general method as outlined in Example 11 Step 1, starting from 1-(5-(6-fluoro-1H-indol-3-yl)pyridin-2-yl)piperidin-4-amine (Intermediate 10; 150 mg; 0.48 mmol), 225 mg (100%) of the crude title compound was obtained as a yellow solid, which was used directly without further purification. LC-MS: m/z 468.0 [M+H]$^+$. $^1$H NMR (400 MHz, DMSO-d$_6$) δ [ppm]: 11.61 (br s, 1H), 8.31 (s, 1H), 8.06 (br s, 1H), 7.88 (d, J=7.2 Hz, 1H), 7.77-7.69 (m, 2H), 7.30-7.15 (m, 2H), 7.02-6.93 (m, 1H), 6.91 (br t, J=5.6 Hz, 1H), 4.34-4.20 (m, 2H), 3.99-3.82 (m, 1H), 3.56-3.48 (m, 2H), 3.26-3.10 (m, 2H), 1.89-1.76 (m, 2H), 1.51-1.39 (m, 2H), 1.38 (s, 9H).

Step 2

Following the general method as outlined in Intermediate 10, starting from tert-butyl (2-((1-(5-(6-fluoro-1H-indol-3-yl)pyridin-2-yl)piperidin-4-yl)amino)-2-oxoethyl)carbamate (Step 1; 225 mg crude; 0.48 mmol), 55 mg (31%) of the title compound was obtained as a white solid after purification by preparative HPLC. LC-MS: m/z 368.2 [M+H]$^+$. $^1$H NMR (400 MHz, DMSO-d$_6$) δ [ppm]: 11.36 (s, 1H), 8.43 (d, J=2.2 Hz, 1H), 7.84-7.78 (m, 2H), 7.74 (dd, J=8.8, 5.3 Hz, 1H), 7.59 (d, J=2.2 Hz, 1H), 7.20 (dd, J=10.1, 2.2 Hz, 1H), 6.94 (d, J=8.6 Hz, 1H), 6.92 (ddd, J=9.5, 8.8, 2.2 Hz, 1H), 4.28-4.18 (m, 2H), 3.93-3.80 (m, 1H), 3.09 (s, 2H), 3.94-2.93 (m, 2H), 2.54 (br s, 2H), 1.85-1.75 (m, 2H), 1.50-1.37 (m, 2H).

Example 14: N-(1-(5-(6-fluoro-1H-indol-3-yl)pyridin-2-yl)piperidin-4-yl)methanesulfonamide Step 1: 1-(5-(6-fluoro-1-(phenylsulfonyl)-1H-indol-3-yl)pyridin-2-yl)piperidin-4-amine Following the general method as outlined in Example 9 Step 1, starting from 3-(6-chloropyridin-3-yl)-6-fluoro-1-(phenylsulfonyl)-1H-indole (Intermediate 2; 250 mg; 0.65 mmol) and tert-butyl 4-aminopiperidine-1-carboxylate (648 mg; 3.24 mmol), 291 mg (100%) of the title compound was obtained as a yellow solid after purification by preparative TLC (DCM/MeOH=10/1). LC-MS: m/z 451.1 [M+H]$^+$. $^1$H NMR (300 MHz, DMSO-d$_6$) δ [ppm]: 8.46 (d, J=2.2 Hz, 1H), 8.14-8.03 (m, 3H), 7.88 (dd, J=8.8, 2.2 Hz, 1H), 7.69-7.81 (m, 3H), 7.71-7.69 (m, 2H), 7.26-7.15 (m, 1H), 6.99 (d, J=9.1 Hz, 1H), 4.47-4.31 (m, 2H), 4.16-4.04 (m, 1H), 2.99-2.91 (m, 2H), 2.06-1.94 (m, 2H), 1.63-1.47 (m, 2H).

Step 2: N-(1-(5-(6-fluoro-1-(phenylsulfonyl)-1H-indol-3-yl)pyridin-2-yl)piperidin-4-yl)methanesulfonamide To a solution of 1-(5-(6-fluoro-1-(phenylsulfonyl)-1H-indol-3-yl)pyridin-2-yl)piperidin-4-amine (Step 1; 290 mg; 0.64 mmol) and Et$_3$N (0.23 mL; 1.64 mmol) in DCM (20 mL) was added MsCl (109 mg; 0.96 mmol) was added dropwise at 0° C. The mixture was stirred at r.t. for 30 minutes. The mixture was diluted with DCM (50 mL), washed with saturated aqueous NaHCO$_3$ (50 mL×3), brine (50 mL), and concentrated to afford 338 mg (100%) of the title compound as a yellow solid, which was used directly without further purification. LC-MS: m/z 529.1 [M+H]$^+$.

Step 3

Following the general method as outlined in Example 1 Step 2, starting from N-(1-(5-(6-fluoro-1-(phenylsulfonyl)-1H-indol-3-yl)pyridin-2-yl)piperidin-4-yl)methanesulfonamide (Step 2; 200 mg; 0.38 mmol), 27 mg (18%) of the title compound was obtained as a white solid after purification by preparative HPLC. LC-MS: m/z 389.1 [M+H]$^+$. $^1$H NMR (400 MHz, DMSO-d$_6$) δ [ppm]: 11.33 (s, 1H), 8.42 (d, J=2.3 Hz, 1H), 7.81 (dd, J=8.9, 2.3 Hz, 1H), 7.74 (dd, J=8.8, 5.5 Hz, 1H), 7.58 (d, J=2.4 Hz, 1H), 7.20 (dd, J=9.9, 2.4 Hz, 1H), 7.11 (d, J=7.4 Hz, 1H), 7.00-6.84 (m, 2H), 4.27-4.16 (m, 2H), 3.47-3.37 (m, 1H), 3.05-2.97 (m, 2H), 2.95 (s, 3H), 1.96-1.85 (m, 2H), 1.48-1.41 (m, 2H).

Example 15:
5-(6-fluoro-1H-indol-3-yl)pyridin-2-amine

Step 1: 5-(6-fluoro-1-(phenylsulfonyl)-1H-indol-3-yl)pyridin-2-amine hydrochloride Following the general method as outlined in Example 2 Step 1, starting from tert-butyl 5-(6-fluoro-1-(phenylsulfonyl)-1H-indol-3-yl)pyridin-2-ylcarbamate (Intermediate 3; 310 mg; 0.66 mmol), 290 mg (100%) of the title compound was obtained as a brown solid, which was used directly without further purification. LC-MS: m/z 368.1 [M+H]$^+$.

Step 2

Following the general method as outlined in Example 1 Step 2, starting from 5-(6-fluoro-1-(phenylsulfonyl)-1H-indol-3-yl)pyridin-2-amine hydrochloride (Step 1; 290 mg; 0.66 mmol), 75 mg (50%) of the title compound was obtained as a yellow solid after purification by preparative HPLC. LC-MS: m/z 228.1 [M+H]$^+$. $^1$H NMR (400 MHz, DMSO-d$_6$) δ [ppm]: 11.26 (s, 1H), 8.21 (d, J=2.2 Hz, 1H), 7.70 (dd, J=8.7, 5.5 Hz, 1H), 7.66 (dd, J=8.5, 2.2 Hz, 1H), 7.51 (d, J=2.2 Hz, 1H), 7.18 (dd, J=10.0, 2.2 Hz, 1H), 6.90 (ddd, J=9.5, 8.7, 2.2 Hz, 1H), 6.54 (d, J=8.5 Hz, 1H), 5.85 (s, 2H).

Example 16:
5-(5,6-difluoro-1H-indol-3-yl)pyridin-2-amine

Step 1: tert-butyl (5-(5,6-difluoro-1-(phenylsulfonyl)-1H-indol-3-yl)pyridin-2-yl)carbamate Following the general method as outlined in Intermediate 3, starting from 5,6-difluoro-3-iodo-1-(phenylsulfonyl)-1H-indole (Intermediate 6; 300 mg; 0.72 mmol), 320 mg (92%) of the title compound was obtained as a yellow solid after purification by a silica gel chromatography (petroleum ether/EtOAc=1/1). LC-MS: m/z 486.1 [M+H]$^+$.

Step 2: 5-(5,6-difluoro-1-(phenylsulfonyl)-1H-indol-3-yl)pyridin-2-amine hydrochloride Following the general method as outlined in Example 2 Step 2, starting from tert-butyl (5-(5,6-difluoro-1-(phenylsulfonyl)-1H-indol-3-yl)pyridin-2-yl)carbamate (Step 1; 320 mg; 0.66 mmol), 300 mg (>100%) of the title compound was obtained as a yellow solid, which was used directly without further purification. LC-MS: m/z 386.1 [M+H]$^+$.

Step 3

Following the general method as outlined in Example 1 Step 2, starting from 5-(5,6-difluoro-1-(phenylsulfonyl)-1H-indol-3-yl)pyridin-2-amine hydrochloride (Step 2; 300 mg), 26 mg (16%) of the title compound was obtained as a white solid after purification by preparative HPLC. LC-MS: m/z 246.1 [M+H]$^+$. $^1$H NMR (400 MHz, DMSO-d$_6$) δ [ppm]: 11.37 (br s, 1H), 8.20 (d, J=2.1 Hz, 1H), 7.69-7.61 (m, 2H), 7.59 (s, 1H), 7.42 (dd, J=11.2, 7.1 Hz, 1H), 6.55 (d, J=8.5 Hz, 1H), 5.86 (s, 2H).

Example 17: 5-(6-fluoro-1H-indol-3-yl)-N-(piperidin-4-yl)pyridin-2-amine

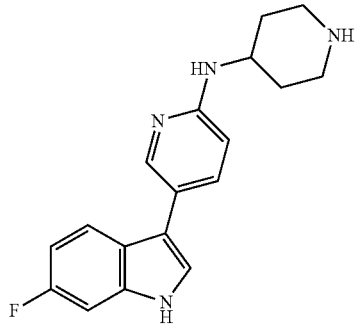 [SMILES: Fc1ccc2c(-c3ccc(NC4CCNCC4)nc3)c[nH]c2c1]

Step 1: 5-(6-fluoro-1-(phenylsulfonyl)-1H-indol-3-yl)-N-(1-(4-methoxybenzyl)piperidin-4-yl)pyridin-2-amine

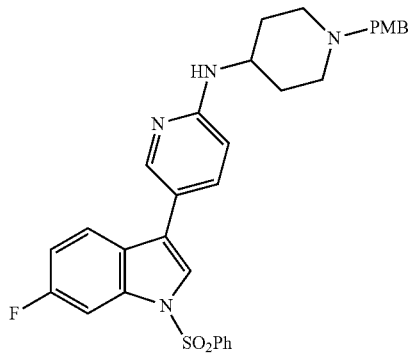

Following the general method as outlined in Example 2 Step 2, starting from 3-(6-chloropyridin-3-yl)-6-fluoro-1-(phenylsulfonyl)-1H-indole (Intermediate 2; 600 mg; 1.55 mmol) and 1-(4-methoxybenzyl)piperidin-4-amine (1.00 g; 4.55 mmol), 800 mg (90%) of the title compound was obtained as a black oil after purification by reverse phase flash chromatography (45-95% MeCN/H$_2$O). LC-MS: m/z 570.9 [M+H]$^+$.

Step 2: 1-chloroethyl 4-(((1-chloroethoxy)carbonyl)(5-(6-fluoro-1-(phenylsulfonyl)-1H-indol-3-yl)pyridin-2-yl)amino)piperidine-1-carboxylate

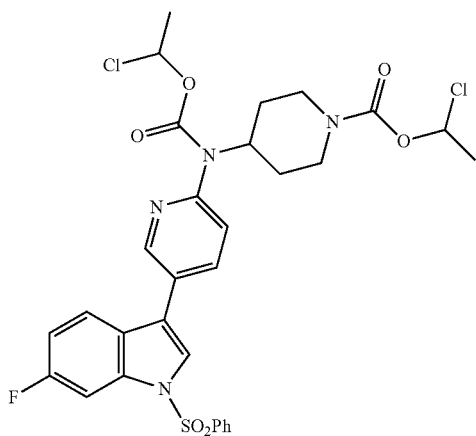

A mixture of 5-(6-fluoro-1-(phenylsulfonyl)-1H-indol-3-yl)-N-(1-(4-methoxybenzyl)piperidin-4-yl)pyridin-2-amine (Step 1; 800 mg; 1.40 mmol) and 1-chloroethyl chloroformate (2 mL; 18.5 mmol) in 1,2-dichloroethane (10 mL) was stirred at 75° C. for 12 hours. The reaction mixture was concentrated to afford 130 mg (14%) of the crude title compound as a yellow oil, which was used for next step without further purification. LC-MS 663.1 [M+H]$^+$.

Step 3

Following the general method as outlined in Example 1, starting from 1-chloroethyl 4-(((1-chloroethoxy)carbonyl)(5-(6-fluoro-1-(phenylsulfonyl)-1H-indol-3-yl)pyridin-2-yl)amino)piperidine-1-carboxylate (Step 2; 130 mg crude; 0.20 mmol), 10 mg (16%) of the title compound was obtained as a white solid after purification by preparative HPLC. LC-MS: m/z 311.1 [M+H]$^+$. $^1$H NMR (400 MHz, MeOH-d$_4$) δ [ppm]: 8.21 (d, J=2.4 Hz, 1H), 7.72 (dd, J=8.6, 2.4 Hz, 1H), 7.67 (dd, J=8.8, 5.3 Hz, 1H), 7.35 (s, 1H), 7.10 (dd, J=9.9, 2.2 Hz, 1H), 6.86 (ddd, J=9.6, 8.8, 2.2 Hz, 1H), 6.65 (d, J=8.6 Hz, 1H), 3.90 (tt, J=10.3, 4.0 Hz, 1H), 3.32-3.23 (m, 2H), 2.99-2.86 (m, 2H), 2.21-2.11 (m, 2H), 1.65-1.52 (m, 2H).

Example 18: N-(1-ethylpiperidin-4-yl)-5-(6-fluoro-1H-indol-3-yl)pyridin-2-amine

Step 1: N-(1-benzylpiperidin-4-yl)-5-(6-fluoro-1H-indol-3-yl)pyridin-2-amine

Following the general method as outlined in Example 9 Step 1, starting from 3-(6-chloropyridin-3-yl)-6-fluoro-1-(phenylsulfonyl)-1H-indole (Intermediate 2; 600 mg; 1.55 mmol), 1-benzylpiperidin-4-amine (1.0 mL), and NMP (1.0 mL), 60 mg (10%) of the title compound was obtained as a yellow solid after purification by preparative TLC (DCM/MeOH=10/1). LC-MS: m/z 401.1 [M+H]$^+$.

Step 2

A mixture of N-(1-benzylpiperidin-4-yl)-5-(6-fluoro-1H-indol-3-yl)pyridin-2-amine (Step 1; 60 mg; 0.15 mmol) 10% Pd/C (10 mg) and in EtOH (20 mL) was hydrogenated at 60° C. and 50 psi. The mixture was filtered through Celite, concentrated, and purified by preparative HPLC to afford 3 mg (6%) of the title compound as a white solid. LC-MS: m/z 339.1 [M+H]$^+$. $^1$H NMR (300 MHz, DMSO-d$_6$) δ [ppm]: 11.25 (s, 1H), 8.25 (d, J=2.4 Hz, 1H), 7.71 (dd, J=8.7, 5.4 Hz, 1H), 7.63 (dd, J=8.6, 2.4 Hz, 1H), 7.49 (d, J=2.1 Hz, 1H), 7.18 (dd, J=10.1, 2.3 Hz, 1H), 6.89 (ddd, J=9.0, 8.7, 2.3 Hz, 1H), 6.55 (d, J=8.6 Hz, 1H), 6.34 (d, J=7.6 Hz, 1H), 3.80-3.56 (m, 1H), 2.86-2.80 (m, 2H), 2.32 (q, J=7.2 Hz, 2H), 2.07-1.79 (m, 4H), 1.53-1.33 (m, 2H), 1.00 (t, J=7.2 Hz, 3H).

Example 19: 5-(6-fluoro-1H-indol-3-yl)-N-(1-(methylsulfonyl)piperidin-4-yl)pyridin-2-amine Following the general method as outlined in Example 27, starting from 3-(6-chloropyridin-3-yl)-6-fluoro-1-(phenylsulfonyl)-1H-indole (Intermediate 2; 252 mg; 0.65 mmol) and 1-(methylsulfonyl)piperidin-4-amine (Intermediate 7; 1.21 g; 6.78 mmol), 31 mg (12%) of the title compound was obtained as a white solid. LC-MS: m/z 389.1 [M+H]$^+$. $^1$H NMR (300 MHz, DMSO-d$_6$) δ [ppm]: 11.25 (s, 1H), 8.25 (d, J=2.1 Hz, 1H), 7.70 (dd, J=8.5, 5.3 Hz, 1H), 7.65 (dd, J=8.5, 2.1 Hz, 1H), 7.49 (d, J=2.2 Hz, 1H), 7.16 (dd, J=10.2, 2.0 Hz, 1H), 6.88 (ddd, J=9.5, 8.5, 2.0 Hz, 1H), 6.56 (d, J=8.7 Hz, 1H), 6.49 (d, J=7.4 Hz, 1H), 3.94-3.79 (m, 1H), 3.55-3.49 (m, 2H), 2.94-2.87 (m, 2H), 2.87 (s, 3H), 2.07-1.97 (m, 2H), 1.56-1.39 (m, 2H).

Example 20: N-(3-(5-(6-fluoro-1H-indol-3-yl)pyridin-2-ylamino)propyl)acetamide

To a mixture of N$^1$-(5-(6-fluoro-1H-indol-3-yl)pyridin-2-yl)propane-1,3-diamine (Intermediate 9; 240 mg; 0.84 mmol) and Et$_3$N (248 mg; 2.45 mmol) in DCM (30 mL) was added AcCl (96 mg; 1.22 mmol) at 0° C. The mixture was stirred at r.t. for 1 hour. The mixture was diluted with DCM (50 mL), washed with saturated aqueous NaHCO$_3$ (50 mL×3), brine (50 mL), dried over anhydrous Na$_2$SO$_4$, filtered, concentrated, and purified by preparative HPLC to afford 81 mg (29%) of the title compound as a white solid. LC-MS: m/z 327.1 [M+H]+. $^1$H NMR (300 MHz, DMSO-d$_6$) δ [ppm]: 11.27 (s, 1H), 8.27 (d, J=2.2 Hz, 1H), 7.88 (t, J=5.7 Hz, 1H), 7.71 (dd, J=8.8, 5.5 Hz, 1H), 7.65 (dd, J=8.6, 2.2 Hz, 1H), 7.50 (d, J=2.3 Hz, 1H), 7.18 (dd, J=10.0, 2.4 Hz, 1H), 6.90 (ddd, J=9.5, 8.8, 2.4 Hz, 1H), 6.55 (d, J=8.6 Hz, 1H), 6.47 (t, J=5.6 Hz, 1H), 3.34 (dt, J=12.6, 7.1 Hz, 2H), 3.11 (dt, J=12.7, 6.7 Hz, 2H), 1.80 (s, 3H), 1.66 (tt, J=7.1, 6.7 Hz, 2H).

Example 21: N-(3-(5-(6-fluoro-1H-indol-3-yl)pyridin-2-ylamino)propyl)methanesulfonamide To a mixture of N$^1$-(5-(6-fluoro-1H-indol-3-yl)pyridin-2-yl)propane-1,3-diamine (Intermediate 9; 220 mg; 0.77 mmol) and Et$_3$N (234 mg; 2.31 mmol) in DCM (60 mL) was added MsCl (132 mg; 1.15 mmol) at 0° C. The mixture was stirred at r.t. for 1 hour. The mixture was diluted with DCM (50 mL), washed with saturated aqueous NaHCO₃ (50 mL×3), brine (50 mL), dried over anhydrous Na₂SO₄, filtered, concentrated, and purified by preparative HPLC to afford 80 mg (29%) of the title compound as a yellow solid. LC-MS: m/z 363.1 [M+H]+. ¹H NMR (300 MHz, DMSO-d₆) δ [ppm]: 11.27 (s, 1H), 8.27 (d, J=2.4 Hz, 1H), 7.71 (dd, J=8.9, 5.4 Hz, 1H), 7.67 (dd, J=8.7, 2.4 Hz, 1H), 7.51 (d, J=2.1 Hz, 1H), 7.18 (dd, J=10.1, 2.2 Hz, 1H), 7.03 (t, J=5.9 Hz, 1H), 6.90 (ddd, J=9.6, 8.9, 2.2 Hz, 1H), 6.57 (d, J=8.7 Hz, 1H), 6.48 (t, J=5.4 Hz, 1H), 3.39-3.22 (m, 2H), 3.08-2.98 (m, 2H), 2.89 (s, 3H), 1.84-1.59 (m, 2H).

Example 22: 5-(6-fluoro-1H-indol-3-yl)-N-(3-(methylsulfonyl)propyl)pyridin-2-amine

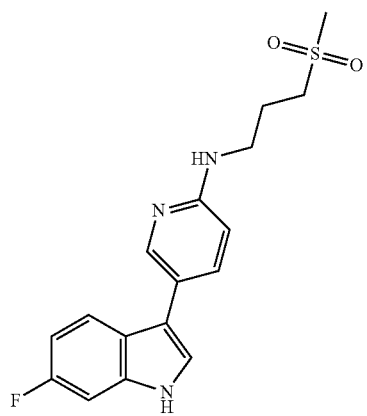 [SMILES: CS(=O)(=O)CCCNc1ccc(-c2c[nH]c3cc(F)ccc23)cn1]

Step 1: 5-(6-fluoro-1-(phenylsulfonyl)-1H-indol-3-yl)-N-(3-(methylsulfonyl)propyl)pyridin-2-amine

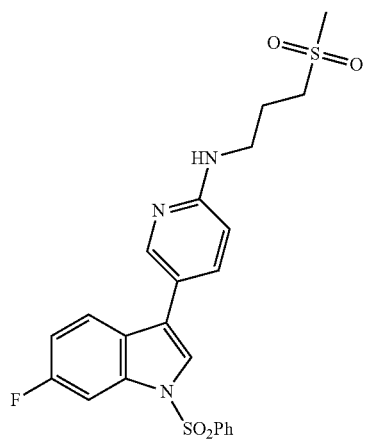

Following the general method as outlined in Example 2 Step 2, starting from 3-(6-chloropyridin-3-yl)-6-fluoro-1-(phenylsulfonyl)-1H-indole (Intermediate 2; 100 mg; 0.26 mmol) and 3-(methylsulfonyl)propan-1-amine (146 mg; 1.06 mmol; prepared as described in *J. Am. Chem. Soc.* 1994, 116, 4660.), 160 mg (>100%) of the crude title compound was obtained as a brown oil, which was used directly without further purification. LC-MS: m/z 487.8 [M+H]⁺.

Step 2

Following the general method as outlined in Example 1, starting from 5-(6-fluoro-1-(phenylsulfonyl)-1H-indol-3-yl)-N-(3-(methylsulfonyl)propyl)pyridin-2-amine (Step 1; 160 mg crude; 0.36 mmol), 26 mg (29%) of the title compound was obtained as a white solid after purification by preparative HPLC (NH₄OAc as additive). LC-MS: m/z 348.1 [M+H]⁺. ¹H NMR (400 MHz, CDCl₃) δ [ppm]: 8.35 (d, J=2.2 Hz, 1H), 8.28 (br s, 1H), 7.75-7.67 (m, 2H), 7.25 (d, J=2.2 Hz, 1H), 7.11 (dd, J=9.8, 2.2 Hz, 1H), 6.93 (ddd, J=9.6, 8.7, 2.2 Hz, 1H), 6.53 (d, J=8.6 Hz, 1H), 4.84 (br s, 1H), 3.60 (td, J=6.5, 5.0 Hz, 2H), 3.18 (t, J=7.6 Hz, 2H), 2.95 (s, 3H), 2.24 (tt, J=7.6, 6.5 Hz, 2H).

Example 23: 3-((5-(6-fluoro-1H-indol-3-yl)pyridin-2-yl)amino)propane-1-sulfonamide

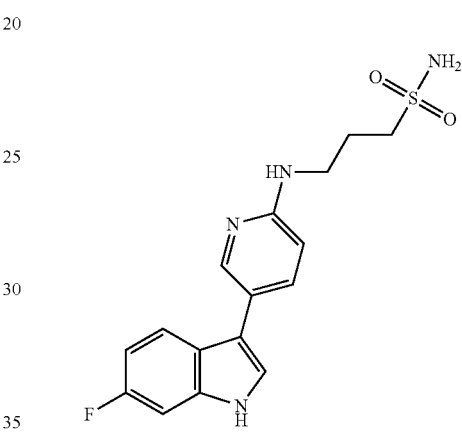

Step 1: 3-((5-(6-fluoro-1-(phenylsulfonyl)-1H-indol-3-yl)pyridin-2-yl)amino)propane-1-sulfonamide

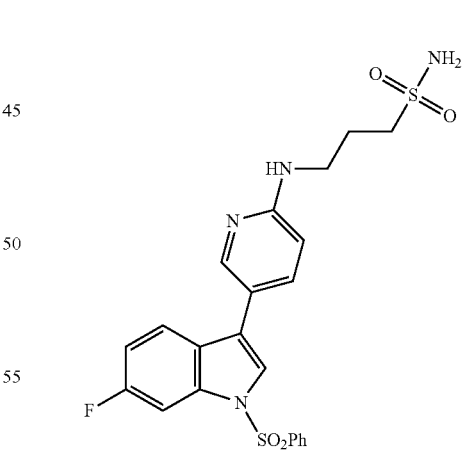

A mixture of 3-(6-bromopyridin-3-yl)-6-fluoro-1-(phenylsulfonyl)-1H-indole (Intermediate 11; 100 mg; 0.23 mmol), 3-aminopropane-1-sulfonamide (100 mg; 0.72 mmol), DIPEA (60 mg; 0.46 mmol) in NMP (0.6 mL) was stirred at 200° C. for 4 hours in a microwave reactor. The mixture was diluted with EtOAc (30 mL), washed with water (10 mL), brine (10 mL), dried over anhydrous Na₂SO₄, filtered, concentrated, and purified by preparative TLC (DCM/MeOH=10/1, v/v) to afford 50 mg (44%) of the title compound as a yellow solid. LC-MS: m/z 486.8 [M+H]⁺.

Step 2

Following the general method as outlined in Example 1, starting from 3-((5-(6-fluoro-1-(phenylsulfonyl)-1H-indol-3-yl)pyridin-2-yl)amino)propane-1-sulfonamide (Step 1; 80 mg; 0.16 mmol), 40 mg (70%) of the title compound was obtained as a yellow solid after purification by preparative TLC (DCM/MeOH=10/1, v/v). LC-MS: m/z 349.1 [M+H]⁺. ¹H NMR (400 MHz, DMSO-d₆) δ [ppm]: 11.30 (br s, 1H), 8.27 (d, J=2.2 Hz, 1H), 7.71 (dd, J=8.8, 5.4 Hz, 1H), 7.70 (dd, J=8.6, 2.2 Hz, 1H), 7.53 (d, J=2.2 Hz, 1H), 7.19 (dd, J=10.1, 2.2 Hz, 1H), 6.91 (ddd, J=9.6, 8.8, 2.2 Hz, 1H), 6.81 (br s, 2H), 6.72 (br s, 1H), 6.59 (d, J=8.6 Hz, 1H), 3.40 (td, J=6.7, 5.6 Hz, 2H), 3.06 (t, J=7.8 Hz, 2H), 1.97 (tt, J=7.8, 6.7 Hz, 2H).

Example 25: N¹-(5-(6-fluoro-1H-indol-3-yl)pyridin-2-yl)-N²,N²-dimethylethane-1,2-diamine Step 1: N¹-(5-(6-fluoro-1-(phenylsulfonyl)-1H-indol-3-yl)pyridin-2-yl)-N²,N²-dimethylethane-1,2-diamine Following the general method as outlined in Example 9 Step 1, starting from 3-(6-chloropyridin-3-yl)-6-fluoro-1-(phenylsulfonyl)-1H-indole (Intermediate 2; 250 mg; 0.65 mmol) and N,N-dimethylethylenediamine (4.0 mL), 283 mg (100%) of the title compound was obtained as a yellow semi-solid, which was used directly without further purification. LC-MS: m/z 439.1 [M+H]⁺.

Step 2

Following the general method as outlined in Example 1 Step 2, starting from N¹-(5-(6-fluoro-1-(phenylsulfonyl)-1H-indol-3-yl)pyridin-2-yl)-N²,N²-dimethylethane-1,2-diamine (Step 1; 283 mg; 0.65 mmol), 30 mg (15%) of the title compound was obtained as a white solid after purification by preparative HPLC. LC-MS: m/z 299.2 [M+H]⁺. ¹H NMR (400 MHz, MeOH-d₄) δ [ppm]: 8.38 (d, J=2.3 Hz, 1H), 7.83 (dd, J=8.6, 2.3 Hz, 1H), 7.72 (dd, J=8.8, 5.2 Hz, 1H), 7.41 (s, 1H), 7.14 (dd, J=9.8, 2.3 Hz, 1H), 6.89 (ddd, J=9.6, 8.8, 2.3 Hz, 1H), 6.78 (d, J=8.6, 1 H), 3.73-3.69 (m, 2H), 3.34-3.32 (m, 2H), 2.98 (s, 6H).

Example 26: N-(2-(5-(6-fluoro-1H-indol-3-yl)pyridin-2-ylamino)ethyl)methanesulfonamide hydrochloride Following the general method as outlined in Example 21, starting from N¹-(5-(6-fluoro-1H-indol-3-yl)pyridin-2-yl)ethane-1,2-diamine (Intermediate 15; 220 mg), 72 mg (26%) of the title compound was obtained as a yellow solid after purification by preparative HPLC (0.1% HCl in H₂O/MeCN). LC-MS: m/z 349.1 [M+H]⁺. ¹H NMR (300 MHz, DMSO-d₆) δ [ppm]: 13.89 (br s, 1H), 11.66 (s, 1H), 8.77 (br s, 1H), 8.28 (dd, J=9.0, 1.6 Hz, 1H), 8.10 (s, 1H), 7.82 (d, J=2.5 Hz, 1H), 7.74 (dd, J=8.8, 5.3 Hz, 1H), 7.32 (t, J=6.0 Hz, 1H), 7.26 (dd, J=9.9, 2.3 Hz, 1H), 7.21 (d, J=9.2 Hz, 1H), 7.00 (ddd, J=9.3, 8.8, 2.3 Hz, 1H), 3.62-3.53 (m, 2H), 3.28-3.16 (m, 2H), 2.96 (s, 3H).

Example 27: 2-(5-(6-fluoro-1H-indol-3-yl)pyridin-2-ylamino)ethanol

A mixture of 3-(6-chloropyridin-3-yl)-6-fluoro-1-(phenylsulfonyl)-1H-indole (Intermediate 2; 250 mg; 0.65 mmol) and 2-aminoethanol (4 mL) in DMSO (3 mL) was heated at 180° C. for 3 hours in a microwave reactor. The mixture was diluted with H₂O (20 mL) and extracted with EtOAc (20 mL×3). The combined organic layers were washed with water (10 mL×3), brine (10 mL), dried over anhydrous Na₂SO₄, filtered, concentrated, and purified by preparative TLC (DCM/MeOH=10/1) to afford 48 mg (27%) of the title compound as a yellow solid. LC-MS: m/z 272.1 [M+H]⁺. ¹H NMR (400 MHz, MeOH-d₄) δ [ppm]: 8.23 (d, J=2.2 Hz, 1H), 7.76 (dd, J=8.7, 2.2 Hz, 1H), 7.69 (dd, J=8.7, 5.3 Hz, 1H), 7.37 (s, 1H), 7.12 (dd, J=9.8, 2.2 Hz, 1H), 6.88 (ddd, J=9.2, 8.7, 2.2 Hz, 1H), 6.69 (d, J=8.7 Hz, 1H), 3.77 (t, J=5.5 Hz, 2H), 3.48 (t, J=5.5 Hz, 2H).

Example 28: 5-(6-fluoro-1H-indol-3-yl)-N-(2-(methylsulfonyl)ethyl)pyridin-2-amine

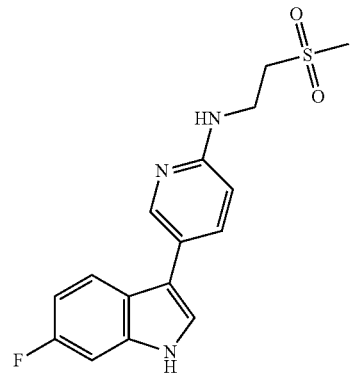 [SMILES: CS(=O)(=O)CCNc1ccc(-c2c[nH]c3cc(F)ccc23)cn1]

Step 1: tert-butyl (5-(6-fluoro-1-(phenylsulfonyl)-1H-indol-3-yl)pyridin-2-yl)(2-(methylsulfonyl)ethyl)carbamate

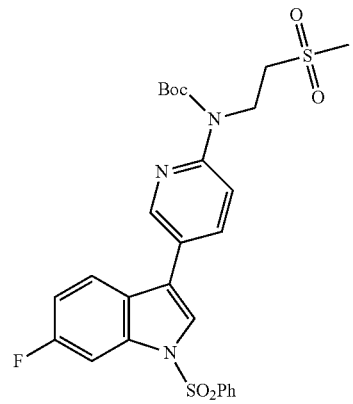

To a solution of tert-butyl (5-(6-fluoro-1-(phenylsulfonyl)-1H-indol-3-yl)pyridin-2-yl)carbamate (Intermediate 3; 500 mg; 1.07 mmol) in anhydrous DMF (5 mL) was added NaH (47 mg; 1.2 mmol; 60% in mineral oil, w/w). The reaction mixture was stirred for 10 minutes and added methyl vinyl sulfone (170 mg; 1.60 mmol). The reaction mixture was stirred for 2 hours, diluted with aqueous NH₄Cl (20 mL) and extracted with EtOAc (20 mL×3). The combined organic layers were concentrated and purified by reverse phase flash chromatography (30-95% ACN/H$_2$O) to afford 113 mg (18%) of the title compound as a yellow oil. LC-MS: m/z 573.8 [M+H]$^+$.

Step 2: tert-butyl (5-(6-fluoro-1H-indol-3-yl)pyridin-2-yl)(2-(methylsulfonyl)ethyl)carbamate

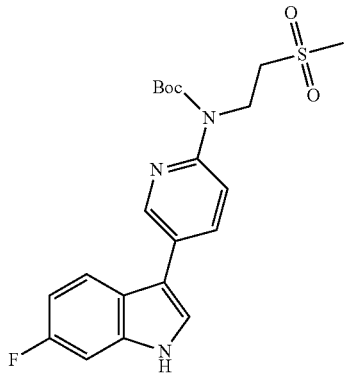 [SMILES: CC(C)(C)OC(=O)N(CCS(C)(=O)=O)c1ccc(-c2c[nH]c3cc(F)ccc23)cn1]

Following the general method as outlined in Example 1, starting from tert-butyl (5-(6-fluoro-1-(phenylsulfonyl)-1H-indol-3-yl)pyridin-2-yl)(2-(methylsulfonyl)ethyl)carbamate (Step 1; 113 mg; 0.20 mmol), 100 mg (>100%) of the crude title compound was obtained as a yellow oil, which was used directly without further purification. LC-MS: m/z 433.9 [M+H]$^+$.

Step 3

Following the general method as outlined in Intermediate 10 Step 2, starting from tert-butyl (5-(6-fluoro-1H-indol-3-yl)pyridin-2-yl)(2-(methylsulfonyl)ethyl)carbamate (Step 2; 100 mg crude; 0.20 mmol), 14.1 mg (21%) of the title compound was obtained as a white solid after purification by preparative HPLC. LC-MS: m/z 334.0 [M+H]$^+$. $^1$H NMR (400 MHz, CDCl$_3$) δ [ppm]: 8.40 (br s, 1H), 8.38 (d, J=1.8 Hz, 1H), 7.74-7.65 (m, 2H), 7.26-7.23 (m, 1H), 7.14-7.08 (m, 1H), 6.98-6.90 (m, 1H), 6.56 (d, J=8.6 Hz, 1H), 5.03 (br t, J=5.8 Hz, 1H), 3.98 (td, J=5.9, 5.8 Hz, 2H), 3.43 (t, J=5.9 Hz, 2H), 2.98 (s, 3H).

Example 29: 2-((5-(6-fluoro-1H-indol-3-yl)pyridin-2-yl)amino)ethanesulfonamide

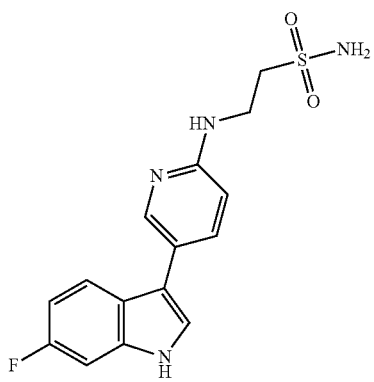 [SMILES: NS(=O)(=O)CCNc1ccc(-c2c[nH]c3cc(F)ccc23)cn1]

Step 1: 2-((5-(6-fluoro-1-(phenylsulfonyl)-1H-indol-3-yl)pyridin-2-yl)amino)ethanesulfonamide

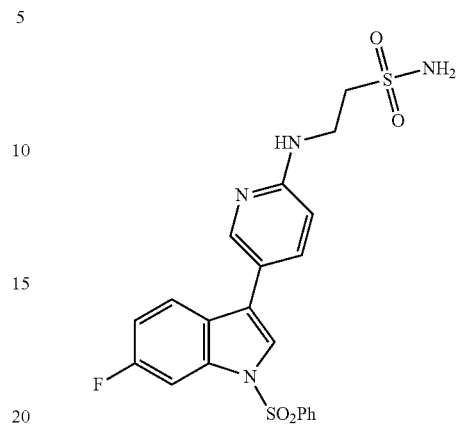

Following the general method as outlined in Example 23 Step 1, starting from 3-(6-bromopyridin-3-yl)-6-fluoro-1-(phenylsulfonyl)-1H-indole (Intermediate 11; 150 mg; 0.35 mmol) and 2-aminoethanesulfonamide (100 mg; 0.81 mmol), 65 mg (39%) of the title compound was obtained as a yellow solid after purification by preparative TLC (DCM/MeOH=10/1, v/v).
LC-MS: m/z 474.7 [M+H]$^+$.

Step 2

Following the general method as outlined in Example 1, starting from 2-((5-(6-fluoro-1-(phenylsulfonyl)-1H-indol-3-yl)pyridin-2-yl)amino)ethanesulfonamide (Step 1; 65 mg; 0.14 mmol), 16 mg (35%) of the title compound was obtained as a yellow solid after purification by preparative TLC (DCM/MeOH=10/1, v/v). LC-MS: m/z 335.1 [M+H]$^+$. $^1$H NMR (400 MHz, MeOH-d$_4$) δ [ppm]: 8.26 (d, J=2.2 Hz, 1H), 7.77 (dd, J=8.6, 2.2 Hz, 1H), 7.68 (dd, J=8.8, 5.3 Hz, 1H), 7.37 (s, 1H), 7.11 (dd, J=9.9, 2.4 Hz, 1H), 6.87 (ddd, J=9.6, 8.8, 2.4 Hz, 1H), 6.69 (d, J=8.6 Hz, 1H), 3.84 (t, J=6.6 Hz, 2H), 3.40 (t, J=6.6 Hz, 2H).

Example 30: 2-(5-(6-fluoro-1H-indol-3-yl)pyridin-2-ylamino)acetic acid

Step 1: ethyl 2-((tert-butoxycarbonyl)(5-(6-fluoro-1-(phenylsulfonyl)-1H-indol-3-yl)pyridin-2-yl)amino)acetate To a solution of tert-butyl 5-(6-fluoro-1-(phenylsulfonyl)-1H-indol-3-yl)pyridin-2-ylcarbamate (Intermediate 3; 240 mg; 0.51 mmol) in DMF (20 mL) was added NaH (25 mg; 0.62 mmol; 60% in mineral oil) at 0° C. under nitrogen. The mixture was stirred at r.t. for 30 minutes and cooled to 0° C. BrCH$_2$CO$_2$Et (103 mg; 0.62 mmol) was added and the mixture was further stirred at r.t. for 2 hours. The mixture was poured into H$_2$O (40 mL) and the aqueous layer was extracted with EtOAc (50 mL×2). The combined organic layers were washed with brine (40 mL), dried over anhydrous Na$_2$SO$_4$, filtered, and concentrated to afford 284 mg (100%) of the title compound as a brown oil, which was used directly without further purification. LC-MS: m/z 554.1 [M+H]⁺.

Step 2: ethyl 2-((5-(6-fluoro-1-(phenylsulfonyl)-1H-indol-3-yl)pyridin-2-yl)amino)acetate hydrochloride To a solution of ethyl 2-((tert-butoxycarbonyl)(5-(6-fluoro-1-(phenylsulfonyl)-1H-indol-3-yl)pyridin-2-yl)amino)acetate (Step 1; 284 mg; 0.51 mmol) in dioxane (2 mL) was added concentrated aqueous HCl (2 mL). The mixture was stirred at r.t. for 1 hour and concentrated to afford 268 mg (100%) of the title compound as a yellow oil, which was used directly without further purification. LC-MS: m/z 454.1 [M+H]⁺.

Step 3

Following the general method as outlined in Example 1 Step 2, starting from ethyl ethyl 2-((5-(6-fluoro-1-(phenylsulfonyl)-1H-indol-3-yl)pyridin-2-yl)amino)acetate hydrochloride (Step 2; 268 mg; 0.51 mmol), 20 mg (13%) of the title compound was obtained as a yellow solid after purification by preparative HPLC. LC-MS: m/z 284.2 [M–H]⁻. $^1$H NMR (400 MHz, DMSO-$d_6$) δ [ppm]: 13.35 (br s, 1H), 11.61 (s, 1H), 8.45 (br s, 1H), 8.22 (d, J=9.3 Hz, 1H), 8.16 (s, 1H), 7.78 (d, J=2.6 Hz, 1H), 7.75 (dd, J=8.7, 5.3 Hz, 1H), 7.26 (dd, J=9.9, 2.4 Hz, 1H), 7.18 (d, J=9.3 Hz, 1H), 6.98 (ddd, J=9.5, 8.7, 2.4 Hz, 1H), 4.25 (s, 2H).

Example 31: 2-(5-(6-fluoro-1H-indol-3-yl)pyridin-2-ylamino)acetamide

Step 1: tert-butyl (2-amino-2-oxoethyl)(5-(6-fluoro-1-(phenylsulfonyl)-1H-indol-3-yl)pyridin-2-yl)carbamate Following the general method as outlined in Example 30 Step 1, starting from tert-butyl 5-(6-fluoro-1-(phenylsulfonyl)-1H-indol-3-yl)pyridin-2-ylcarbamate (Intermediate 3; 240 mg; 0.51 mmol), NaH (25 mg; 0.62 mmol; 60% in mineral oil), 2-bromo-acetamide (159 mg; 1.15 mmol), and KI (190 mg; 1.15 mmol), 180 mg (44%) of the title compound was obtained as a yellow solid after purification by preparative HPLC. LC-MS: m/z 525.1 [M+H]⁺. $^1$H NMR (400 MHz, DMSO-$d_6$) δ [ppm]: 8.66 (d, J=2.4 Hz, 1H), 8.25 (s, 1H), 8.17-8.08 (m, 3H), 7.90 (d, J=8.6 Hz, 1H), 7.88-7.84 (m, 1H), 7.81 (dd, J=9.8, 2.3 Hz, 1H), 7.76-7.69 (m, 1H), 7.65-7.60 (m, 2H), 7.41 (s, 1H), 7.24 (td, J=9.1, 2.4 Hz, 1H), 6.97 (s, 1H), 4.53 (s, 2H), 1.47 (s, 9H).

Step 2: 2-((5-(6-fluoro-1-(phenylsulfonyl)-1H-indol-3-yl)pyridin-2-yl)amino)acetamide Following the general method as outlined in Example 30 Step 2, starting from tert-butyl (2-amino-2-oxoethyl)(5-(6-fluoro-1-(phenylsulfonyl)-1H-indol-3-yl)pyridin-2-yl)carbamate (Step 1; 142 mg; 0.27 mmol), 114 mg (100%) of the title compound was obtained as a green oil, which was used directly without further purification. LC-MS: m/z 425.1 [M+H]⁺.

Step 3

Following the general method as outlined in Example 1 Step 2, starting from 2-((5-(6-fluoro-1-(phenylsulfonyl)-1H-indol-3-yl)pyridin-2-yl)amino)acetamide (Step 2; 100 mg; 0.24 mmol), 13 mg (19%) of the title compound was obtained as a yellow solid after purification by preparative HPLC. LC-MS: m/z 285.1 [M+H]⁺. $^1$H NMR (400 MHz, DMSO-$d_6$) δ [ppm]: 11.48 (s, 1H), 8.21 (s, 1H), 8.04 (d, J=7.3 Hz, 1H), 7.74 (dd, J=8.6, 5.6 Hz, 1H), 7.68 (s, 1H), 7.52 (s, 1H), 7.32-7.10 (m, 3H), 6.94-7.00 (m, 2H), 3.97 (s, 2H).

Example 34: 5-(6-fluoro-1H-indol-3-yl)-N-methyl-pyridin-2-amine

Step 1: 5-(6-fluoro-1-(phenylsulfonyl)-1H-indol-3-yl)-N-methylpyridin-2-amine

A solution of 3-(6-chloropyridin-3-yl)-6-fluoro-1-(phenylsulfonyl)-1H-indole (Intermediate 2; 300 mg; 0.78 mmol) and methylamine (15.0 mL; 30 mmol; 2.0 M in THF) in DMSO (2 mL) was stirred at 130° C. for 48 h in a autoclave. The mixture was cooled to r.t. and concentrated to in vacuo. The residual was purified by a silica gel chromatography (petroleum ether/EtOAc=10/1-5/1) to afford 70 mg (23%) of the title compound as a yellow solid. LC-MS: m/z 382.1 [M+H]⁺.

Step 2

Following the general method as outlined in Example 1 Step 2, starting from 5-(6-fluoro-1-(phenylsulfonyl)-1H-indol-3-yl)-N-methylpyridin-2-amine (Step 1; 70 mg; 0.18 mmol), 28 mg (63%) of the title compound was obtained as a yellow solid after purification by preparative TLC (petroleum ether/EtOAc=1/1). LC-MS: m/z 242.1 [M+H]⁺. $^1$H NMR (400 MHz, MeOH-$d_4$) δ [ppm]: 8.10 (d, J=2.2 Hz, 1H), 7.65 (dd, J=8.7, 2.2 Hz, 1H), 7.57 (dd, J=8.7, 5.3 Hz, 1H), 7.25 (s, 1H), 7.00 (dd, J=9.6, 2.2 Hz, 1H), 6.76 (ddd, J=9.3, 8.7, 2.2 Hz, 1H), 6.54 (d, J=8.7 Hz, 1H), 2.81 (s, 3H).

Example 35: N-(5-(6-fluoro-1H-indol-3-yl)pyridin-2-yl)piperidine-4-carboxamide

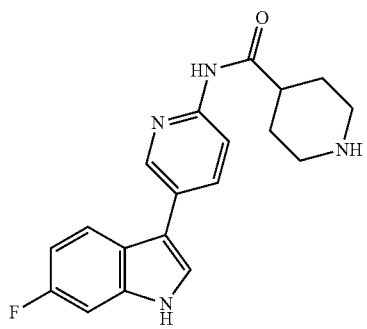 [SMILES: O=C(Nc1ccc(-c2c[nH]c3cc(F)ccc23)cn1)C1CCNCC1]

125

Step 1: tert-butyl 4-((5-(6-fluoro-1H-indol-3-yl)pyridin-2-yl)carbamoyl)piperidine-1-carboxylate

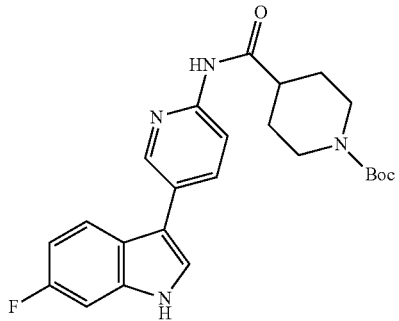 [SMILES: CC(C)(C)OC(=O)N1CCC(C(=O)Nc2ccc(-c3c[nH]c4cc(F)ccc34)cn2)CC1]

Following the general method as outlined in Example 11 Step 1, starting from 5-(6-fluoro-1H-indol-3-yl)pyridin-2-amine (Example 15; 800 mg; 3.52 mmol) and 1-(tert-butoxycarbonyl)piperidine-4-carboxylic acid (888 mg; 3.87 mmol), 700 mg (45%) of the title compound was obtained as a yellow solid after purification by silica gel chromatograph (petroleum ether/EtOAc=1/4, v/v). LC-MS: m/z 438.9 [M+H]$^+$.

Step 2

Following the general method as outlined in Intermediate 10 Step 2, starting from tert-butyl 4-((5-(6-fluoro-1H-indol-3-yl)pyridin-2-yl)carbamoyl)piperidine-1-carboxylate (Step 1; 700 mg; 1.60 mmol), 440 mg (81%) of the title compound was obtained as a white solid after purification by preparative HPLC. LC-MS: m/z 339.1 [M+H]$^+$. $^1$H NMR (400 MHz, DMSO-d$_6$) δ [ppm]: 11.51 (br s, 1H), 10.38 (br s, 1H), 8.62 (d, J=2.2 Hz, 1H), 8.16 (d, J=8.6 Hz, 1H), 8.05 (dd, J=8.6, 2.2 Hz, 1H), 7.82 (dd, J=8.8, 5.3 Hz, 1H), 7.76 (d, J=2.2 Hz, 1H), 7.23 (dd, J=9.9, 2.4 Hz, 1H), 6.96 (ddd, J=9.5, 8.8, 2.4 Hz, 1H), 3.03-2.91 (m, 2H), 2.82-2.50 (m, 2H), 2.50-2.40 (m, 2H), 1.74-1.63 (m, 2H), 1.58-1.43 (m, 2H)

Example 36: (S)-2-amino-N-(5-(6-fluoro-1H-indol-3-yl)pyridin-2-yl)-3-phenylpropanamide

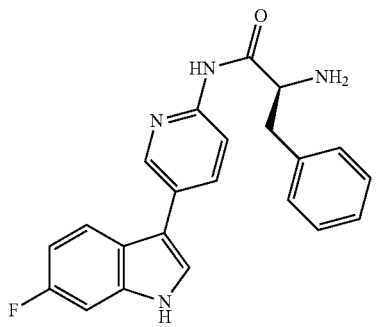 [SMILES: N[C@@H](Cc1ccccc1)C(=O)Nc1ccc(-c2c[nH]c3cc(F)ccc23)cn1]

126

Step 1: (S)-tert-butyl (1-((5-(6-fluoro-1H-indol-3-yl)pyridin-2-yl)amino)-1-oxo-3-phenylpropan-2-yl)carbamate

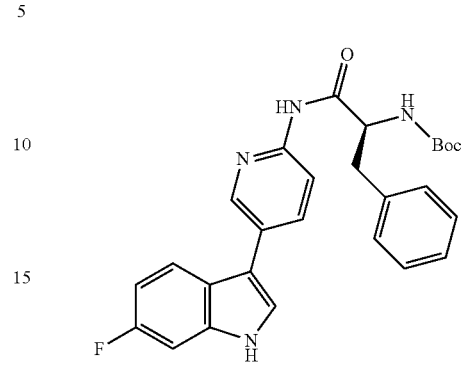

Following the general method as outlined in Example 11 Step 1, starting from 5-(6-fluoro-1H-indol-3-yl)pyridin-2-amine (Example 15; 200 mg; 0.88 mmol) and Boc-Phe-OH (194 mg; 0.73 mmol), 145 mg (42%) of the title compound was obtained as a yellow solid after purification by a silica gel chromatograph (petroleum ether/EtOAc=3/1, v/v). LC-MS: m/z 475.5 [M+H]$^+$.

Step 2

Following the general method as outlined in Intermediate 10 Step 2, starting from (S)-tert-butyl (1-((5-(6-fluoro-1H-indol-3-yl)pyridin-2-yl)amino)-1-oxo-3-phenylpropan-2-yl)carbamate (Step 1; 145 mg; 0.31 mmol), 42 mg (37%) of the title compound was obtained as a yellow solid after purification by preparative TLC (DCM/MeOH=20/1, v/v). LC-MS: m/z 375.2 [M+H]$^+$. $^1$H NMR (400 MHz, DMSO-d$_6$) δ [ppm]: 11.54 (br s, 1H), 10.49 (br s, 1H), 8.63 (d, J=2.2 Hz, 1H), 8.21 (d, J=8.4 Hz, 1H), 8.11 (dd, J=8.4, 2.2 Hz, 1H), 7.84 (dd, J=8.7, 5.3 Hz, 1H), 7.79 (d, J=2.0 Hz, 1H), 7.34-7.17 (m, 6H), 6.97 (ddd, J=9.6, 8.7, 2.4 Hz, 1H), 3.70 (dd, J=8.4, 4.4 Hz, 1H), 3.08 (dd, J=13.4, 4.4 Hz, 1H), 2.74 (dd, J=13.4, 8.4 Hz, 1H), 2.30 (br s, 2H).

The general methods described in the specification may be used to generate the racemate of this compound, 2-amino-N-(5-(6-fluoro-1H-indol-3-yl)pyridin-2-yl)phenylpropanamide or the R-enantiomer of the compound generated in this example,

Example 37: (S)-2-amino-N-(5-(6-fluoro-1H-indol-3-yl)pyridin-2-yl)propanamide

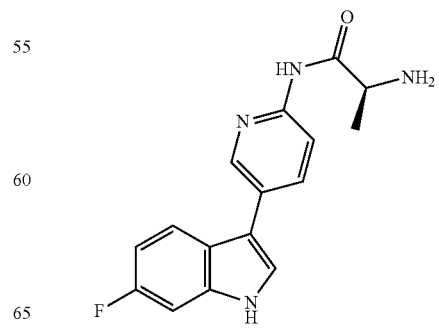

127

Step 1: (S)-tert-butyl (1-((5-(6-fluoro-1H-indol-3-yl)pyridin-2-yl)amino)-1-oxopropan-2-yl)carbamate

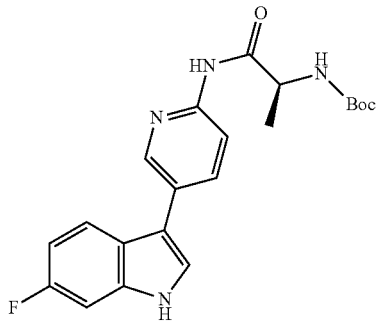 [SMILES: C[C@H](NC(=O)OC(C)(C)C)C(=O)Nc1ccc(-c2c[nH]c3cc(F)ccc23)cn1]

Following the general method as outlined in Example 11 Step 1, starting from 5-(6-fluoro-1H-indol-3-yl)pyridin-2-amine (Example 15; 200 mg; 0.88 mmol) and Boc-Ala-OH (183 mg; 0.97 mmol), 376 mg (>100%) of the crude title compound was obtained as a yellow oil, which was used directly without further purification. LC-MS: m/z 398.9 [M+H]$^+$.

Step 2

Following the general method as outlined in Intermediate 10 Step 2, starting from (S)-tert-butyl (1-((5-(6-fluoro-1H-indol-3-yl)pyridin-2-yl)amino)-1-oxopropan-2-yl)carbamate (Step 1; 376 mg crude; 0.88 mmol), 17 mg (6%) of the title compound was obtained as a white solid after purification by preparative HPLC. LC-MS: m/z 299.1 [M+H]$^+$. $^1$H NMR (400 MHz, MeOH-d$_4$) δ [ppm]: 8.58 (d, J=2.4 Hz, 1H), 8.19 (d, J=8.6 Hz, 1H), 8.05 (dd, J=8.6, 2.4 Hz, 1H), 7.76 (dd, J=8.8, 5.3 Hz, 1H), 7.53 (s, 1H), 7.14 (dd, J=9.8, 2.4 Hz, 1H), 6.90 (ddd, J=9.6, 8.8, 2.4 Hz, 1H), 3.65 (q, J=7.0 Hz, 1H), 1.40 (d, J=7.0 Hz, 3H).

The general methods described in the specification may be used to generate the racemate of this compound, 2-amino-N-(5-(6-fluoro-1H-indol-3-yl)pyridin-2-yl)propamide or the R-enantiomer of the compound generated in this example, Example 38: (S)-2-amino-N-(5-(6-fluoro-1H-indol-3-yl)pyridin-2-yl)-3-methylbutanamide

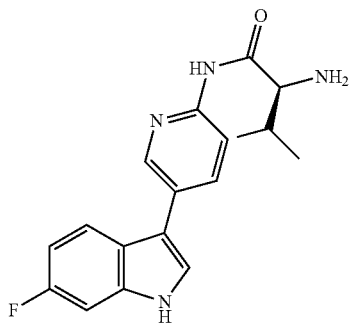 [SMILES: CC(C)[C@H](N)C(=O)Nc1ccc(-c2c[nH]c3cc(F)ccc23)cn1]

128

Step 1: (S)-tert-butyl (1-((5-(6-fluoro-1H-indol-3-yl)pyridin-2-yl)amino)-3-methyl-1-oxobutan-2-yl)carbamate

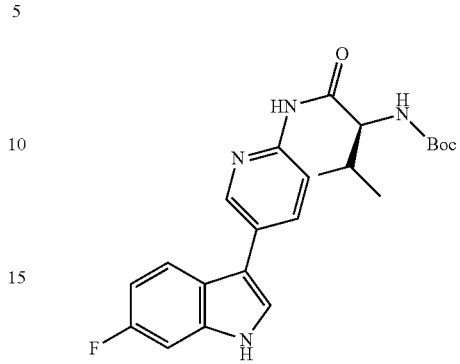

Following the general method as outlined in Example 11 Step 1, starting from 5-(6-fluoro-1H-indol-3-yl)pyridin-2-amine (Example 15; 200 mg; 0.88 mmol) and Boc-Val-OH (200 mg; 0.92 mmol), 450 mg (>100%) of the crude title compound was obtained as a black oil, which was used directly without further purification. LC-MS: m/z 426.9 [M+H]$^+$.

Step 2

Following the general method as outlined in Intermediate 10 Step 2, starting from (S)-tert-butyl (1-((5-(6-fluoro-1H-indol-3-yl)pyridin-2-yl)amino)-3-methyl-1-oxobutan-2-yl)carbamate (Step 1; 450 mg crude; 0.88 mmol), 33 mg (11%) of the title compound was obtained as a white solid after purification by preparative HPLC. LC-MS: m/z 327.1 [M+H]$^+$. $^1$H NMR (400 MHz, DMSO-d$_6$) δ [ppm]: 11.52 (s, 1H), 10.39 (br s, 1H), 8.63 (d, J=2.2 Hz, 1H), 8.21 (d, J=8.6 Hz, 1H), 8.09 (dd, J=8.6, 2.2 Hz, 1H), 7.84 (dd, J=8.7, 5.3 Hz, 1H), 7.77 (d, J=2.4 Hz, 1H), 7.24 (dd, J=9.9, 2.3 Hz, 1H), 6.97 (ddd, J=9.6, 8.7, 2.3 Hz, 1H), 3.26 (d, J=4.8 Hz, 1H), 2.12-1.96 (m, 1H), 2.10 (br s, 2H), 0.95 (d, J=6.8 Hz, 3H), 0.85 (d, J=6.8 Hz, 3H).

The general methods described in the specification may be used to generate the racemate of this compound, 2-amino-N-(5-(6-fluoro-1H-indol-3-yl)pyridin-2-yl)methylbutamide or the R-enantiomer of the compound generated in this example.

Example 39: 2-amino-N-(5-(6-fluoro-1H-indol-3-yl)pyridin-2-yl)acetamide

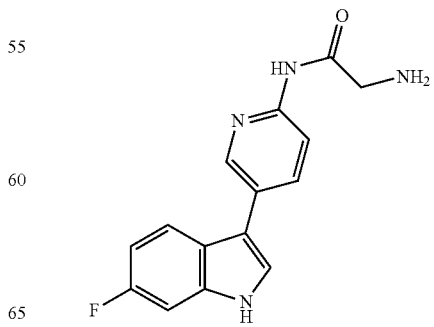

Step 1: tert-butyl (2-((5-(6-fluoro-1H-indol-3-yl)pyridin-2-yl)amino)-2-oxoethyl)carbamate

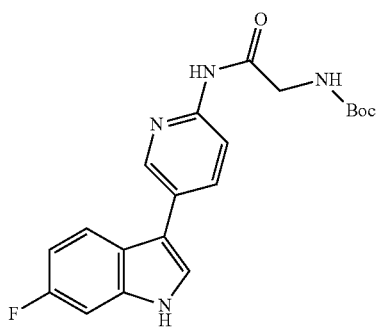 [SMILES: CC(C)(C)OC(=O)NCC(=O)Nc1ccc(-c2c[nH]c3cc(F)ccc23)cn1]

Following the general method as outlined in Example 11 Step 1, starting from 5-(6-fluoro-1H-indol-3-yl)pyridin-2-amine (Example 15; 370 mg; 1.63 mmol) and Boc-glycine (238 mg; 1.36 mmol), 550 mg (>100%) of the crude title compound was obtained as a yellow oil, which was used directly without further purification. LC-MS: m/z 384.9 [M+H]$^+$.

Step 2

Following the general method as outlined in Intermediate 10 Step 2, starting from tert-butyl (2-((5-(6-fluoro-1H-indol-3-yl)pyridin-2-yl)amino)-2-oxoethyl)carbamate (Step 1; 550 mg crude; 1.36 mmol), 25 mg (6%) of the title compound was obtained as a white solid after purification by preparative HPLC. LC-MS: m/z 285.1 [M+H]$^+$. $^1$H NMR (400 MHz, DMSO-d$_6$) δ [ppm]: 11.53 (s, 1H), 8.64 (d, J=2.4 Hz, 1H), 8.20 (d, J=8.6 Hz, 1H), 8.11 (dd, J=8.6, 2.4 Hz, 1H), 7.84 (dd, J=8.8, 5.3 Hz, 1H), 7.78 (d, J=2.0 Hz, 1H), 7.24 (dd, J=9.9, 2.2 Hz, 1H), 6.97 (ddd, J=9.6, 8.8, 2.2 Hz, 1H), 3.35 (s, 2H), 2.51 (br s, 2H).

Example 40: N-(5-(6-fluoro-1H-indol-3-yl)pyridin-2-yl)acetamide

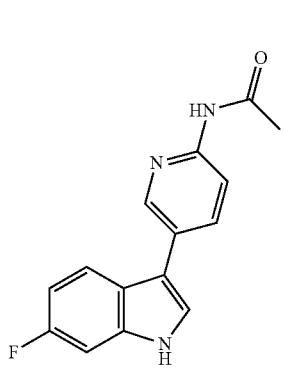

Step 1: N-(5-(6-fluoro-1-(phenylsulfonyl)-1H-indol-3-yl)pyridin-2-yl)acetamide

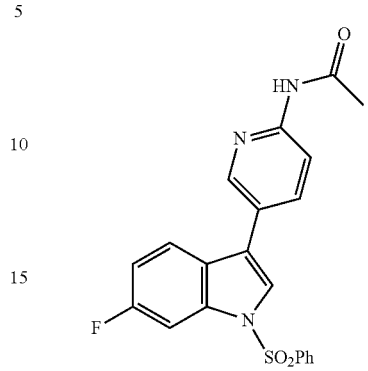

To a mixture of 5-(6-fluoro-1-(phenylsulfonyl)-1H-indol-3-yl)pyridin-2-amine (Example 15 Step 1; 400 mg; 1.09 mmol) and pyridine (1.6 mL; 19.9 mmol) in DMF (10 mL) was added Ac$_2$O (144 mg; 1.41 mmol). The reaction mixture was stirred at room temperature for 48 hours, poured into an ice-water mixture (100 mL) and extracted with EtOAc (30 mL×3). The combined organic layers were dried over anhydrous MgSO$_4$, filtered, and concentrated to afford 170 mg (38%) of the crude title compound as a yellow oil, which was used directly without further purification. LC-MS: m/z 410.1 [M+H]$^+$.

Step 2

Following the general method as outlined in Example 1, starting from N-(5-(6-fluoro-1-(phenylsulfonyl)-1H-indol-3-yl)pyridin-2-yl)acetamide (Step 1; 170 mg; 0.42 mmol), 41 mg (37%) of the title compound was obtained as a white solid after purification by preparative HPLC. LC-MS: m/z 270.1 [M+H]$^+$. $^1$H NMR (400 MHz, DMSO-d$_6$) δ [ppm]: 11.50 (br s, 1H), 10.50 (br s, 1H), 8.62 (d, J=2.4 Hz, 1H), 8.14 (d, J=8.4 Hz, 1H), 8.06 (dd, J=8.4, 2.4 Hz, 1H), 7.83 (dd, J=8.8, 5.3 Hz, 1H), 7.77 (d, J=2.2 Hz, 1H), 7.23 (dd, J=10.0, 2.2 Hz, 1H), 6.96 (ddd, J=9.6, 8.8, 2.2 Hz, 1H), 2.11 (s, 3H).

Example 42: 1-acetyl-N-(5-(6-fluoro-1H-indol-3-yl)pyridin-2-yl)piperidine-4-carboxamide

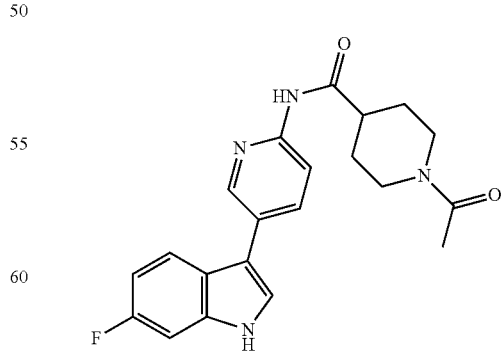

To a solution of N-(5-(6-fluoro-1H-indol-3-yl)pyridin-2-yl)piperidine-4-carboxamide (Example 35; 100 mg; 0.30 mmol) in THF (3 mL) and anhydrous DMF (3 mL) was added Ac$_2$O (39 mg; 0.38 mmol). The reaction mixture was stirred at room temperature for 1 hour, concentrated, and purified by preparative HPLC to afford 53 mg (47%) of the title product as a white solid. LC-MS: m/z 381.1 [M+H]$^+$. $^1$H NMR (400 MHz, DMSO-d$_6$) δ [ppm]: 11.51 (br s, 1H), 10.52 (br s, 1H), 8.63 (d, J=2.4 Hz, 1H), 8.15 (d, J=8.6 Hz, 1H), 8.07 (dd, J=8.6, 2.4 Hz, 1H), 7.83 (dd, J=8.7, 5.3 Hz, 1H), 7.77 (d, J=2.4 Hz, 1H), 7.23 (dd, J=10.0, 2.4 Hz, 1H), 6.96 (ddd, J=9.6, 8.7, 2.4 Hz, 1H), 4.47-3.37 (m, 1H), 3.94-3.83 (m, 1H), 3.13-2.99 (m, 1H), 2.83-2.70 (m, 1H), 2.63-2.51 (m, 1H), 2.10 (s, 3H), 1.89-1.75 (m, 2H), 1.67-1.53 (m, 1H), 1.51-1.37 (m, 1H).

Example 43: N-(5-(6-fluoro-1H-indol-3-yl)pyridin-2-yl)tetrahydro-2H-thiopyran-4-carboxamide 1,1-dioxide Example 44: 6-fluoro-3-(pyridin-3-yl)-1H-indole Step 1: 6-fluoro-1-(phenylsulfonyl)-3-(pyridin-3-yl)-1H-indole To a solution of 3-bromo-6-fluoro-1-(phenylsulfonyl)-1H-indole (Intermediate 1; 1.00 g; 2.82 mmol), pyridin-3-ylboronic acid (400 mg; 3.25 mmol), K$_3$PO$_4$ (1.41 g; 6.60 mmol) in dioxane (20 mL) and water (2 mL) was added Pd$_2$dba$_3$ (260 mg; 0.28 mmol) and S-Phos (260 mg; 0.63 mmol) under nitrogen. The mixture was heated at 125° C. for 30 minutes in a microwave reactor. The mixture was diluted with EtOAc (20 mL) and water (10 mL). The organic layer was separated, washed with brine (5 mL), dried over anhydrous Na$_2$SO$_4$, filtered, concentrated, and purified by a silica gel chromatography (petroleum ether/EtOAc=1/1) to afford 200 mg (20%) of the title compound as a white solid. LC-MS: m/z 353.0 [M+H]$^+$ Step 2

To a solution of 6-fluoro-1-(phenylsulfonyl)-3-(pyridin-3-yl)-1H-indole (Step 1; 150 mg; 0.43 mmol) in MeOH (5 mL) was added a solution of NaOH (68 mg; 1.7 mmol) in water (2 mL). The reaction mixture was stirred at 80° C. for 30 minutes, concentrated, diluted with H$_2$O (5 mL), and extracted with Et$_2$O (10 mL×3). The combined organic layers were washed with water (10 mL×2), brine (10 mL), dried over anhydrous Na$_2$SO$_4$, filtered, concentrated, and purified by preparative HPLC to afford 60 mg (66%) of the title compound as a white solid. LC-MS: m/z 213.2 [M+H]$^+$. $^1$H NMR (400 MHz, DMSO-d$_6$) δ [ppm]: 11.59 (br s, 1H), 8.91 (d, J=1.6 Hz, 1H), 8.44 (dd, J=4.7, 1.6 Hz, 1H), 8.08 (ddd, J=8.0, 2.4, 1.6 Hz, 1H), 7.37 (dd, J=8.8, 5.4 Hz, 1H), 7.84 (s, 1H), 7.44 (dd, J=8.0, 4.7 Hz, 1H), 7.25 (dd, J=9.9, 2.4 Hz, 1H), 6.98 (ddd, J=8.8, 7.2, 2.4 Hz, 1H).

Example 45: 6-fluoro-3-(2-methylpyridin-3-yl)-1H-indole

Step 1: 6-fluoro-3-(2-methylpyridin-3-yl)-1-(phenylsulfonyl)-1H-indole

Following the general method as outlined in Example 1 Step 1, starting from 3-bromo-6-fluoro-1-(phenylsulfonyl)-1H-indole (Intermediate 1; 120 mg; 0.34 mmol) and 2-methyl-3-(4,4,5,5-tetramethyl-[1,3,2]dioxaborolan-2-yl)pyridine (381 mg; 1.74 mmol), 100 mg (81%) of the title compound was obtained as a red solid after purification by a silica gel chromatography (petroleum ether/EtOAc=10/1-2/1). LC-MS: m/z 367 [M+H]$^+$.

Step 2

Following the general method as outlined in Example 1 Step 2, starting from 6-fluoro-3-(2-methylpyridin-3-yl)-1-(phenylsulfonyl)-1H-indole (Step 1; 100 mg; 0.27 mmol), 17.5 mg (28%) of the title compound was obtained as a white solid after purification by preparative HPLC. LC-MS: m/z 225.2 [M–H]$^-$. $^1$H NMR (400 MHz, DMSO-d$_6$) δ [ppm]: 11.55 (br s, 1H), 8.42 (dd, J=4.7, 1.6 Hz, 1H), 7.72 (dd, J=7.6, 1.6 Hz, 1H), 7.53 (s, 1H), 7.37 (dd, J=8.6, 5.7 Hz, 1H), 7.28 (dd, J=7.6, 4.7 Hz, 1H), 7.24 (dd, J=10.0, 2.2 Hz, 1H), 6.90 (ddd, J=9.6, 8.6, 2.2 Hz, 1H), 2.48 (s, 3H).

Example 46: 6-fluoro-3-(4-methylpyridin-3-yl)-1H-indole

Step 1: 6-fluoro-3-(4-methylpyridin-3-yl)-1-(phenylsulfonyl)-1H-indole

Following the general method as outlined in Example 1 Step 1, starting from 3-bromo-6-fluoro-1-(phenylsulfonyl)-1H-indole (Intermediate 1; 200 mg; 0.56 mmol) and (4-methylpyridin-3-yl)boronic acid (100 mg; 0.73 mmol), 50 mg (24%) of the title compound was obtained as a white solid after purification by a silica gel chromatography (petroleum ether/EtOAc=10/1-1/1). LC-MS: m/z 367.1 [M+H]$^+$.

Step 2

Following the general method as outlined in Example 1 Step 2, starting from 6-fluoro-3-(4-methylpyridin-3-yl)-1-(phenylsulfonyl)-1H-indole (Step 1; 50 mg; 0.14 mmol), 5 mg (16%) of the title compound was obtained as a white solid after purification by preparative HPLC. LC-MS: m/z 227.1 [M+H]$^+$. $^1$H NMR (400 MHz, CDCl$_3$) δ [ppm]: 8.66 (s, 1H), 8.58 (s, 1H), 8.45 (d, J=4.9 Hz, 1H), 7.37 (dd, J=8.6, 5.3 Hz, 1H), 7.25 (d, J=4.9 Hz, 1H), 7.22 (d, J=2.0 Hz, 1H), 7.14 (dd, J=9.4, 1.9 Hz, 1H), 6.93 (ddd, J=9.2, 8.6, 1.9 Hz, 1H), 2.32 (s, 3H).

Example 47: 5,6-difluoro-3-(pyridin-3-yl)-1H-indole

Step 1: 5,6-difluoro-1-(phenylsulfonyl)-3-(pyridin-3-yl)-1H-indole

Following the general method as outlined in Example 1 Step 1, starting from 5,6-difluoro-3-iodo-1-(phenylsulfonyl)-1H-indole (Intermediate 6; 250 mg; 0.60 mmol), 100 mg (45%) of the title compound was obtained as a yellow solid after purification by a silica gel chromatography (petroleum ether/EtOAc=1/1). LC-MS: m/z 371.1 [M+H]$^+$. $^1$H NMR (400 MHz, DMSO-d$_6$) δ [ppm]: 8.94 (d, J=1.7 Hz, 1H), 8.60 (dd, J=4.8, 1.6 Hz, 1H), 8.40 (s, 1H), 8.20-8.13 (m, 3H), 8.07 (dd, J=10.9, 6.9 Hz, 1H), 7.91 (dd, J=10.9, 7.7 Hz, 1H), 7.77-7.72 (m, 1H), 7.66-7.61 (m, 2H), 7.50 (dd, J=8.0, 4.7 Hz, 1H).

Step 2

Following the general method as outlined in Example 1 Step 2, starting from 5,6-difluoro-1-(phenylsulfonyl)-3-(pyridin-3-yl)-1H-indole (Step 1; 100 mg; 0.27 mmol), 36 mg (58%) of the title compound was obtained as a white solid after purification by preparative HPLC. LC-MS: m/z 231.1 [M+H]+. 1H NMR (400 MHz, DMSO-d6) δ [ppm]: 11.68 (s, 1H), 8.91 (d, J=2.0 Hz, 1H), 8.45 (d, J=4.7 Hz, 1H), 8.08 (d, J=7.9 Hz, 1H), 7.91 (s, 1H), 7.83 (dd, J=11.7, 7.9 Hz, 1H), 7.49 (dd, J=11.0, 7.2 Hz, 1H), 7.44 (dd, J=7.9, 4.8 Hz, 1H).

Example 48: 6-fluoro-3-(5-methylpyridin-3-yl)-1H-indole

Step 1: 6-fluoro-3-(5-methylpyridin-3-yl)-1-(phenylsulfonyl)-1H-indole

Following the general method as outlined in Example 1 Step 1, starting from 6-fluoro-3-iodo-1-(phenylsulfonyl)-1H-indole (prepared as described in WO2010/136491; 465 mg; 1.16 mmol) and 3-methyl-5-(4,4,5,5-tetramethyl-[1,3,2]dioxaborolan-2-yl)pyridine (762 mg; 3.48 mmol), 220 mg (52%) of the title compound was obtained as a yellow oil after purification by reverse phase chromatography. LC-MS: m/z 367.1 [M+H]+.

Step 2

Following the general method as outlined in Example 1 Step 2, starting from 6-fluoro-3-(5-methylpyridin-3-yl)-1-(phenylsulfonyl)-1H-indole (Step 1; 220 mg; 0.60 mmol), 44.9 mg (33%) of the title compound was obtained as a tan solid after purification by reverse phase chromatography. LC-MS: m/z 227.1 [M+H]+. 1H NMR (400 MHz, DMSO-d6) δ [ppm]: 11.54 (s, 1H), 8.71 (d, J=1.7 Hz, 1H), 8.28 (s, 1H), 7.88 (s, 1H), 7.86 (dd, J=8.8, 5.5 Hz, 1H), 7.80 (s, 1H), 7.24 (dd, J=9.8, 2.0 Hz, 1H), 6.97 (ddd, J=9.4, 8.8, 2.0 Hz, 1H), 2.37 (s, 3H).

Example 49: 3-(6-fluoro-1H-indol-3-yl)pyridine 1-oxide

Step 1: 3-(6-fluoro-1-(phenylsulfonyl)-1H-indol-3-yl)pyridine 1-oxide

To a solution of 6-fluoro-1-(phenylsulfonyl)-3-(pyridin-3-yl)-1H-indole (Example 1 Step 1; 200 mg; 0.57 mmol) in anhydrous DCM (5 mL) was added mCPBA (187 mg; 0.67 mmol; 80% in water) at 0° C. The mixture was stirred at r.t. for 16 hours and diluted with aqueous saturated NaHCO3 (10 mL). The aqueous layer was extracted with DCM (20 mL). The combined organic layers were washed with brine (10 mL), dried over anhydrous Na2SO4, filtered, concentrated, and purified by a silica gel chromatography (DCM/MeOH=20/1) to afford 175 mg (83%) of the title compound as a white solid. 1H NMR (400 MHz, CDCl3) δ [ppm]: 8.47 (s, 1H), 8.22 (d, J=5.6, 1.2 Hz, 1H), 7.99-7.89 (m, 2H), 7.81 (dd, J=9.4, 2.3 Hz, 1H), 7.77 (s, 1H), 7.67-7.60 (m, 2H), 7.56-7.50 (m, 2H), 7.49-7.44 (m, 1H), 7.42-7.36 (m, 1H), 7.10 (td, J=8.9, 2.2 Hz, 1H).

Step 2

Following the general method as outlined in Example 1 Step 2, starting from 3-(6-fluoro-1-(phenylsulfonyl)-1H-indol-3-yl)pyridine 1-oxide (Step 1; 170 mg; 0.46 mmol), 60 mg (57%) of the title compound was obtained as a white solid after purification by preparative HPLC. LC-MS: m/z 229.1 [M+H]+. 1H NMR (400 MHz, DMSO-d6) δ [ppm]: 11.74 (s, 1H), 8.55 (s, 1H), 8.10 (dd, J=6.5 Hz, 1H), 7.98 (d, J=2.7 Hz, 1H), 7.86 (dd, J=8.8, 5.2 Hz, 1H), 7.70 (d, J=8.0 Hz, 1H), 7.46 (dd, J=8.0, 6.5 Hz, 1H), 7.27 (dd, J=9.8, 2.4 Hz, 1H), 7.01 (ddd, J=9.5, 8.8, 2.4 Hz, 1H).

Example 50: N-(2-((5-(6-fluoro-1H-indol-3-yl)pyridin-2-yl)amino)ethyl)acetamide

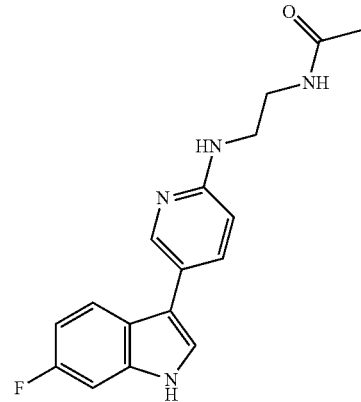 [SMILES: CC(=O)NCCNc1ccc(-c2c[nH]c3cc(F)ccc23)cn1]

Following the general method as outlined in Example 20, starting from N1-(5-(6-fluoro-1H-indol-3-yl)pyridin-2-yl)ethane-1,2-diamine (Intermediate 15; 150 mg crude; 0.55 mmol), 23 mg (13%) of the title compound was obtained as a yellow solid after purification by preparative TLC (DCM/MeOH=20/1, v/v). LC-MS: m/z 313.1 [M+H]+. 1H NMR (400 MHz, DMSO-d6) δ [ppm]: 11.28 (br s, 1H), 8.27 (d, J=2.2 Hz, 1H), 7.98 (br t, J=5.3 Hz, 1H), 7.71 (dd, J=8.8, 5.5 Hz, 1H), 7.67 (dd, J=8.6, 2.2 Hz, 1H), 7.52 (d, J=2.3 Hz, 1H), 7.18 (dd, J=10.0, 2.4 Hz, 1H), 6.90 (ddd, J=9.6, 8.8, 2.4 Hz, 1H), 6.56 (d, J=8.6 Hz, 1H), 6.55 (t, J=5.6 Hz, 1H), 3.32 (td, J=7.1, 5.3 Hz, 2H), 3.22 (td, J=7.1, 5.6 Hz, 2H), 1.82 (s, 3H).

Example 51: 2-amino-N-(2-((5-(6-fluoro-1H-indol-3-yl)pyridin-2-yl)amino)ethyl)acetamide

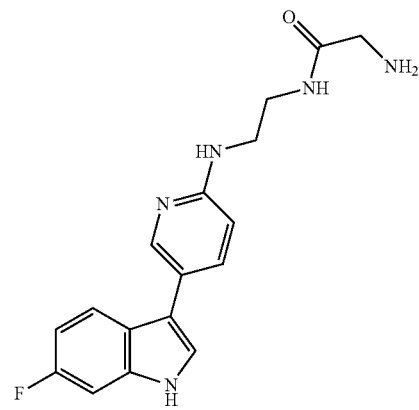 [SMILES: NCC(=O)NCCNc1ccc(-c2c[nH]c3cc(F)ccc23)cn1]

Step 1: tert-butyl (2-((2-((5-(6-fluoro-1H-indol-3-yl)pyridin-2-yl)amino)ethyl)amino)-2-oxoethyl)carbamate

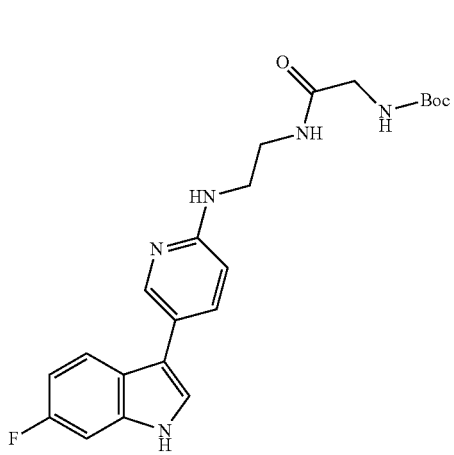 [SMILES: CC(C)(C)OC(=O)NCC(=O)NCCNc1ccc(-c2c[nH]c3cc(F)ccc23)cn1]

Following the general method as outlined in Example 11 Step 1, starting from $N^1$-(5-(6-fluoro-1H-indol-3-yl)pyridin-2-yl)ethane-1,2-diamine (Intermediate 15; 200 mg crude; 0.74 mmol) and Boc-glycine (259 mg; 1.48 mmol), 311 mg (98%) of the crude title compound was obtained as a brown solid, which was used directly without further purification. LC-MS: m/z 427.9 [M+H]$^+$.

Step 2

Following the general method as outlined in Intermediate 10 Step 2, starting from tert-butyl (2-((1-(5-(6-fluoro-1H-indol-3-yl)pyridin-2-yl)piperidin-4-yl)amino)-2-oxoethyl)carbamate (Step 1; 311 mg crude; 0.73 mmol), 47 mg (19%) of the title compound was obtained as a yellow solid after purification by preparative HPLC. LC-MS: m/z 328.1 [M+H]$^+$. $^1$H NMR (400 MHz, DMSO-d$_6$) δ [ppm]: 11.29 (br s, 1H), 8.28 (d, J=2.2 Hz, 1H), 8.06 (br t, 1H), 7.76-7.63 (m, 2H), 7.52 (d, J=2.2 Hz, 1H), 7.19 (dd, J=9.9, 2.4 Hz, 1H), 6.90 (ddd, J=9.6, 8.7, 2.4 Hz, 1H), 6.60 (br t, 1H), 6.57 (d, J=8.6 Hz, 1H), 3.37-3.24 (m, 4H), 3.08 (s, 2H), 1.93 (br s, 2H).

Example 52: N-(5-(6-fluoro-1H-indol-3-yl)pyridin-2-yl)cyclopropanecarboxamide

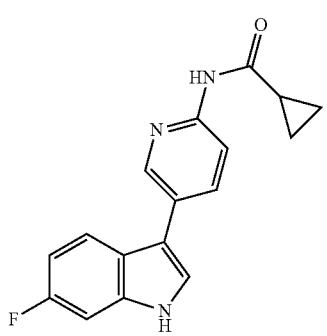

Step 1: N-(5-(6-fluoro-1-(phenylsulfonyl)-1H-indol-3-yl)pyridin-2-yl)cyclopropanecarboxamide

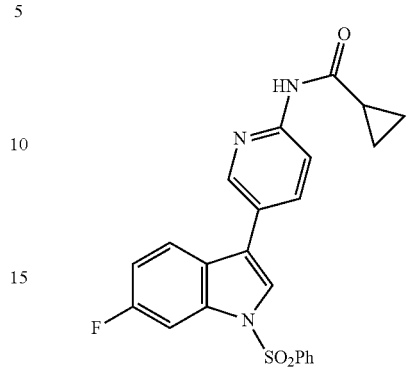

To a solution of 5-(6-fluoro-1-(phenylsulfonyl)-1H-indol-3-yl)pyridin-2-amine hydrochloride (Example 15 Step 1; 300 mg; 0.74 mmol) in pyridine (6 mL) was added cyclopropanecarbonyl chloride (117 mg; 1.12 mmol). The reaction mixture was stirred at room temperature for 2 hours, concentrated, dissolved in EtOAc (50 mL), washed with water (10 mL) and brine (10 mL), and concentrated to afford 345 mg (>100%) of the crude title compound as a black oil, which was used directly without further purification. LC-MS: m/z 435.8 [M+H]$^+$.

Step 2

Following the general method as outlined in Example 1, starting from N-(5-(6-fluoro-1-(phenylsulfonyl)-1H-indol-3-yl)pyridin-2-yl)cyclopropanecarboxamide (Step 1; 345 mg crude; 0.74 mmol), 80 mg (36%) of the title compound was obtained as a white solid after purification by preparative HPLC. LC-MS: m/z 296.1 [M+H]$^+$. $^1$H NMR (400 MHz, DMSO-d$_6$) δ [ppm]: 11.50 (br s, 1H), 10.80 (br s, 1H), 8.63 (d, J=2.4 Hz, 1H), 8.14 (d, J=8.6 Hz, 1H), 8.05 (dd, J=8.6, 2.4 Hz, 1H), 7.83 (dd, J=8.8, 5.3 Hz, 1H), 7.77 (d, J=2.4 Hz, 1H), 7.23 (dd, J=10.0, 2.2 Hz, 1H), 6.96 (ddd, J=9.6, 8.8, 2.2 Hz, 1H), 2.07-1.98 (m, 1H), 0.88-0.78 (m, 4H).

Example 53: N-(5-(6-fluoro-1H-indol-3-yl)pyridin-2-yl)-2-morpholinoacetamide

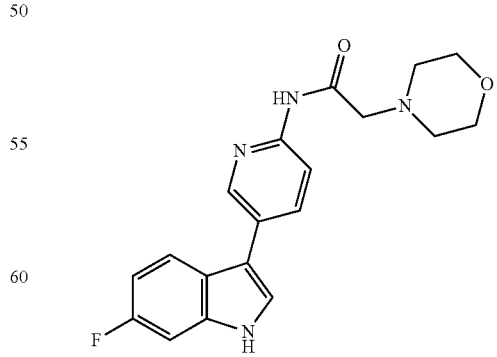

Following the general method as outlined in Example 11 Step 1, starting from 5-(6-fluoro-1H-indol-3-yl)pyridin-2-amine (Example 8; 200 mg; 0.88 mmol) and morpholin-4- yl-acetic acid (140 mg; 0.96 mmol), 60 mg (19%) of the title compound was obtained as a yellow solid after purification by preparative HPLC. LC-MS: m/z 353.2 [M+H]⁺. ¹H NMR (400 MHz, DMSO-d₆) δ [ppm]: 11.53 (br s, 1H), 9.99 (br s, 1H), 8.64 (d, J=2.4 Hz, 1H), 8.16 (d, J=8.6 Hz, 1H), 8.11 (dd, J=8.6, 2.4 Hz, 1H), 7.84 (dd, J=8.8, 5.4 Hz, 1H), 7.78 (s, 1H), 7.24 (dd, J=9.9, 2.4 Hz, 1H), 6.97 (ddd, J=9.6, 8.6, 2.4 Hz, 1H), 3.70-3.62 (m, 4H), 3.22 (s, 2H), 2.61-2.53 (m, 4H).

Example 54: N-(5-(6-fluoro-1H-indol-3-yl)pyridin-2-yl)-N-methylmethanesulfonamide

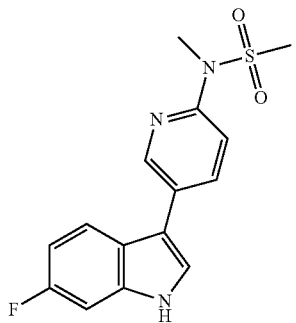 [SMILES: CN(c1ccc(-c2c[nH]c3cc(F)ccc23)cn1)S(C)(=O)=O]

To a stirred solution of 5-(6-fluoro-1H-indol-3-yl)-N-methylpyridin-2-amine (Example 34; 63 mg; 0.26 mmol) in pyridine (8 mL) was added MsCl (89 mg; 0.78 mmol) at 0° C. The mixture was stirred at room temperature for 1 hour, concentrated, diluted with water (30 mL), and extracted with EOAc (30 mL×2). The combined organic layers were washed with brine (30 mL×2), dried over anhydrous Na₂SO₄, filtered, concentrated, and purified by a silica gel chromatography (DCM/MeOH=20/1, v/v) to afford 40 mg (48%) of the title compound as a white solid. LC-MS: m/z 320.1 [M+H]⁺. ¹H NMR (400 MHz, DMSO-d₆) δ [ppm]: 11.60 (br s, 1H), 8.76 (d, J=2.4 Hz, 1H), 8.14 (dd, J=8.6, 2.4 Hz, 1H), 7.86 (dd, J=8.8, 5.3 Hz, 1H), 7.84 (d, J=2.4 Hz, 1H), 7.46 (d, J=8.6 Hz, 1H), 7.25 (dd, J=9.9, 2.4 Hz, 1H), 6.98 (ddd, J=9.6, 8.8, 2.4 Hz, 1H), 3.32 (s, 3H), 3.15 (s, 3H).

Example 55: 2-amino-N-(1-(5-(6-fluoro-1H-indol-3-yl)pyridin-2-yl)piperidin-4-yl)ethanesulfonamide

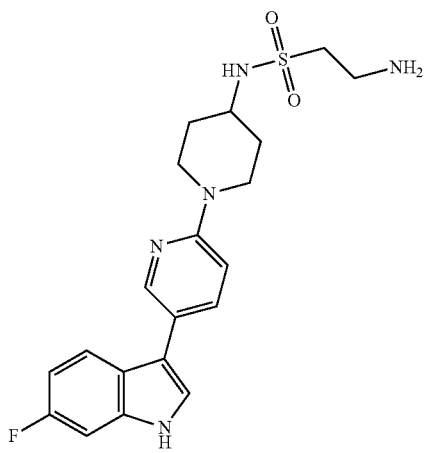 [SMILES: NCCS(=O)(=O)NC1CCN(c2ccc(-c3c[nH]c4cc(F)ccc34)cn2)CC1]

Step 1: 2-(1,3-dioxoisoindolin-2-yl)-N-(1-(5-(6-fluoro-1H-indol-3-yl)pyridin-2-yl)piperidin-4-yl)ethanesulfonamide

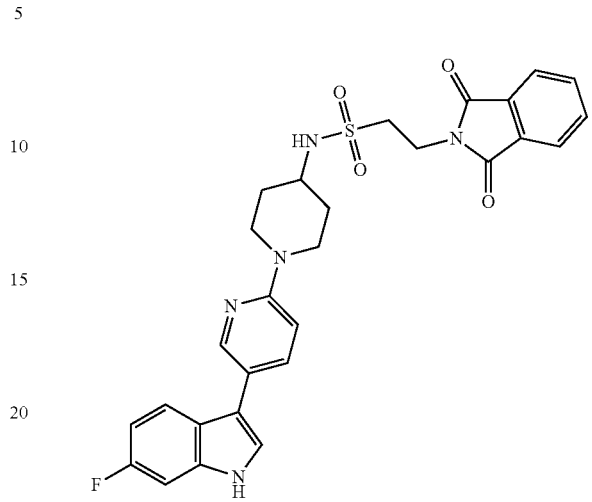

To the solution of 1-(5-(6-fluoro-1H-indol-3-yl)pyridin-2-yl)piperidin-4-amine (Intermediate 10; 310 mg; 1.00 mmol) in DCM (50 mL) and DMF (5 mL) was added Et₃N (354 mg; 3.50 mmol) and 2-(phthalimido)ethanesulfonyl chloride (328 mg; 1.20 mmol). The mixture was stirred at room temperature for 4 hours, diluted with DCM (50 mL), washed with water (20 mL), brine (20 mL), dried over anhydrous Na₂SO₄, and concentrated. The residue which contained some DMF was added to an ice-water mixture dropwise and the precipitate was collected by vacuum filtration and dried to afford 600 mg (>100%) of the crude title compound as a yellow solid, which was used directly without further purification. LC-MS: m/z 548.5 [M+H]⁺. ¹H NMR (400 MHz, DMSO-d₆) δ [ppm]: 11.34 (br s, 1H), 8.43 (d, J=2.4 Hz, 1H), 7.92-7.89 (m, 2H), 7.88-7.84 (m, 2H), 7.81 (dd, J=8.6, 2.4 Hz, 1H), 7.74 (dd, J=8.8, 5.3 Hz, 1H), 7.59 (d, J=2.4 Hz, 1H), 7.46 (br s, 1H), 7.20 (dd, J=10.1, 2.4 Hz, 1H), 6.95 (d, J=8.6 Hz, 1H), 6.92 (ddd, J=9.6, 8.8, 2.4 Hz, 1H), 4.32-4.19 (m, 2H), 4.01-3.91 (m, 2H), 3.47-3.36 (m, 3H), 3.03-2.92 (m, 2H), 1.98-1.87 (m, 2H), 1.55-1.41 (m, 2H).

Step 2

A mixture of 2-(1,3-dioxoisoindolin-2-yl)-N-(1-(5-(6-fluoro-1H-indol-3-yl)pyridin-2-yl)piperidin-4-yl)ethanesulfonamide (Step 1; 560 mg crude; 0.93 mmol) and hydrazine hydrate (88 mg; 1.50 mmol; 85% w/w) in EtOH (20 mL) was stirred at reflux for 2 hours. The reaction mixture was filtered, concentrated, and purified by preparative HPLC to afford 140 mg (36%) of the title compound as a white solid. LC-MS: m/z 418.2 [M+H]⁺. ¹H NMR (400 MHz, DMSO-d₆) δ [ppm]: 11.34 (br s, 1H), 8.42 (d, J=2.4 Hz, 1H), 7.81 (dd, J=8.6, 2.4 Hz, 1H), 7.74 (dd, J=8.8, 5.4 Hz, 1H), 7.59 (d, J=2.4 Hz, 1H), 7.20 (dd, J=10.1, 2.4 Hz, 1H), 6.94 (d, J=8.6 Hz, 1H), 6.92 (ddd, J=9.6, 8.8, 2.4 Hz, 1H), 4.28-4.19 (m, 2H), 3.38 (tt, J=10.8, 4.2 Hz, 1H), 3.11 (t, J=6.8 Hz, 2H), 3.02-2.91 (m, 2H), 2.89 (t, J=6.8 Hz, 2H), 2.57-2.51 (m, 2H), 1.94-1.84 (m, 2H), 1.52-1.38 (m, 2H).

Example 56: 2-(dimethylamino)-N-(1-(5-(6-fluoro-1H-indol-3-yl)pyridin-2-yl)piperidin-4-yl)ethanesulfonamide

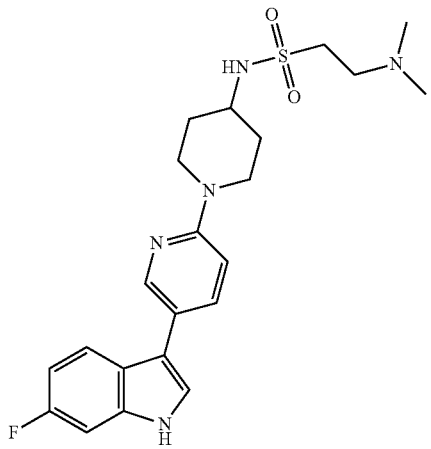 [SMILES: CN(C)CCS(=O)(=O)NC1CCN(c2ccc(-c3c[nH]c4cc(F)ccc34)cn2)CC1]

To a solution of N-(1-(5-(6-fluoro-1H-indol-3-yl)pyridin-2-yl)piperidin-4-yl)ethenesulfonamide (Intermediate 16; 200 mg; 0.50 mmol) in THF (10 mL) was added dimethylamine in THF (5.00 mmol; 2.50 mL; 2 M in THF). The reaction mixture was stirred for 30 minutes, concentrated, and purified by preparative HPLC to afford 40 mg (18%) of the title compound as a white solid. LC-MS: m/z 445.9 [M+H]+. 1H NMR (400 MHz, DMSO-d6) δ [ppm]: 11.34 (br s, 1H), 8.42 (d, J=2.2 Hz, 1H), 7.80 (dd, J=8.4, 2.2, Hz, 1H), 7.74 (dd, J=8.7, 5.3 Hz, 1H), 7.59 (d, J=2.2 Hz, 1H), 7.25-7.15 (m, 2H), 6.96-6.88 (m, 1H), 6.93 (d, J=8.4 Hz, 1H), 4.29-4.18 (m, 2H), 3.49-3.36 (m, 1H), 3.19 (t, J=7.2 Hz, 2H), 3.03-2.89 (m, 2H), 2.61 (t, J=7.2 Hz, 2H), 2.17 (s, 6H), 1.94-1.82 (m, 2H), 1.54-1.43 (m, 2H).

Example 57: N-(1-(5-(6-fluoro-1H-indol-3-yl)pyridin-2-yl)piperidin-4-yl)-2-methoxyethanesulfonamide

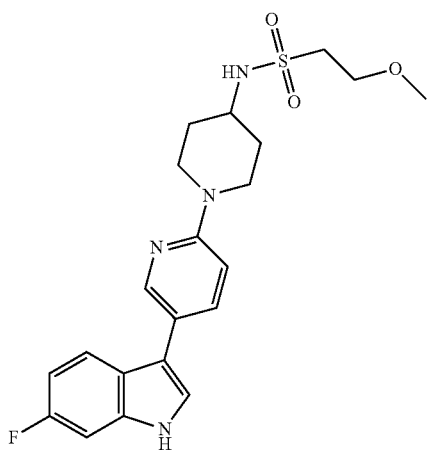 [SMILES: COCCS(=O)(=O)NC1CCN(c2ccc(-c3c[nH]c4cc(F)ccc34)cn2)CC1]

To the solution of 1-(5-(6-fluoro-1H-indol-3-yl)pyridin-2-yl)piperidin-4-amine (Intermediate 10; 200 mg; 0.64 mmol) and Et3N (197 mg; 1.95 mmol) in DCM (50 mL) and DMF (5 mL) was added 2-methoxyethanesulfonyl chloride (80 mg; 0.50 mmol). The mixture was stirred at room temperature for 4 hours, concentrated, and purification by preparative HPLC to afford 120 mg (55%) of the title compound as a white solid. LC-MS: m/z 433.1 [M+H]+. 1H NMR (400 MHz, MeOH-d4) δ [ppm]: 8.37 (d, J=2.2 Hz, 1H), 7.87-7.81 (m, 1H), 7.69 (dd, J=8.8, 5.3 Hz, 1H), 7.39 (d, J=2.2 Hz, 1H), 7.11 (dd, J=9.9, 2.3 Hz, 1H), 6.97-6.91 (m, 1H), 6.87 (ddd, J=9.6, 8.8, 2.3 Hz, 1H), 4.25-4.15 (m, 2H), 3.79 (t, J=6.1 Hz, 2H), 3.54-3.44 (m, 1H), 3.37 (s, 3H), 3.36 (t, J=6.1 Hz, 2H), 3.10-2.98 (m, 2H), 2.11-1.99 (m, 2H), 1.69-1.54 (m, 2H).

Example 58: (S)—N-(5-(6-fluoro-1H-indol-3-yl)pyridin-2-yl)pyrrolidine-2-carboxamide

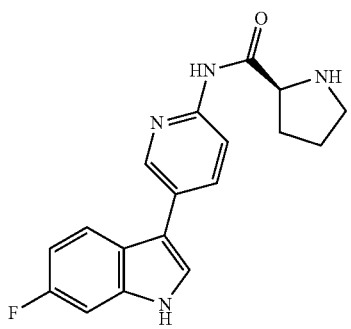 [SMILES: O=C(Nc1ccc(-c2c[nH]c3cc(F)ccc23)cn1)[C@@H]1CCCN1]

Step 1: (S)-tert-butyl 2-((5-(6-fluoro-1H-indol-3-yl)pyridin-2-yl)carbamoyl)pyrrolidine-1-carboxylate

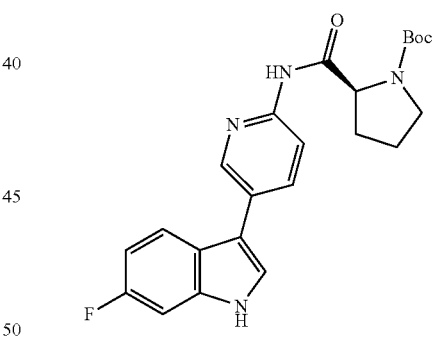

Following the general method as outlined in Example 11 Step 1, starting from 5-(6-fluoro-1H-indol-3-yl)pyridin-2-amine (Example 15; 200 mg; 0.88 mmol) and Boc-Pro-OH (377 mg; 1.75 mmol), 430 mg (>100%) of the crude title compound was obtained as a yellow solid, which was used directly without further purification.
LC-MS: m/z 424.9 [M+H]+.

Step 2

Following the general method as outlined in Intermediate 10 Step 2, starting from (S)-tert-butyl 2-((5-(6-fluoro-1H-indol-3-yl)pyridin-2-yl)carbamoyl)pyrrolidine-1-carboxylate (Step 1; 400 mg crude; 0.82 mmol), 60 mg (23%) of the title compound was obtained as a white solid after purification by preparative HPLC. LC-MS: m/z 325.1 [M+H]+.

¹H NMR (400 MHz, DMSO-d₆) δ [ppm]: 11.54 (br s, 1H), 10.34 (br s, 1H), 8.63 (d, J=2.2 Hz, 1H), 8.18 (d, J=8.4 Hz, 1H), 8.11 (dd, J=8.4, 2.2 Hz, 1H), 7.83 (dd, J=8.7, 5.3 Hz, 1H), 7.78 (d, J=2.0 Hz, 1H), 7.24 (dd, J=9.9, 2.4 Hz, 1H), 6.97 (ddd, J=9.6, 8.7, 2.4 Hz, 1H), 3.80 (dd, J=8.8, 5.5 Hz, 2H), 3.02-2.92 (m, 1H), 2.92-2.81 (m, 1H), 2.17-2.02 (m, 1H), 1.89-1.76 (m, 1H), 1.74-1.59 (m, 2H). [α]²⁰_D=−39.0 (c=0.20, MeOH).

Example 59: N-(1-(5-(6-fluoro-1H-indol-3-yl)pyridin-2-yl)piperidin-4-yl)-2-morpholinoethanesulfonamide

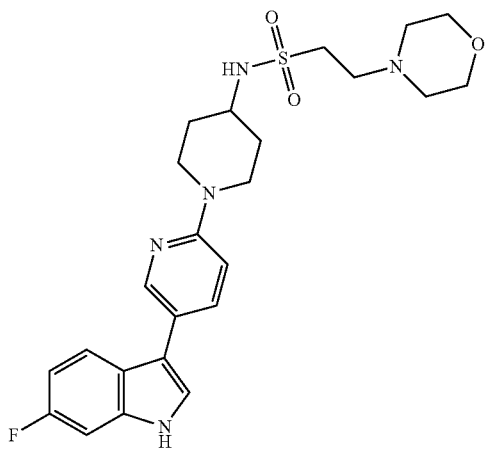 [SMILES: O=S(=O)(CCN1CCOCC1)NC1CCN(c2ccc(-c3c[nH]c4cc(F)ccc34)cn2)CC1]

Following the general method as outlined in Example 56, starting from N-(1-(5-(6-fluoro-1H-indol-3-yl)pyridin-2-yl)piperidin-4-yl)ethenesulfonamide (Intermediate 16; 258 mg; 0.64 mmol) and morpholine (280 mg; 3.21 mmol), 50 mg (16%) of the title compound was obtained as a white solid after purification by preparative HPLC. LC-MS: m/z 488.2 [M+H]⁺. ¹H NMR (400 MHz, DMSO-d₆) δ [ppm]: 11.34 (br s, 1H), 8.42 (d, J=2.2 Hz, 1H), 7.80 (dd, J=8.6, 2.2 Hz, 1H), 7.74 (dd, J=8.8, 5.3 Hz, 1H), 7.59 (d, J=2.2 Hz, 1H), 7.25-7.17 (m, 2H), 6.96-6.87 (m, 1H), 6.93 (d, J=8.6 Hz, 1H), 4.31-4.17 (m, 2H), 3.64-3.51 (m, 4H), 3.50-3.37 (m, 1H), 3.23 (t, J=7.2 Hz, 2H), 3.03-2.88 (m, 2H), 2.66 (t, J=7.2 Hz, 2H), 2.46-2.36 (m, 4H), 1.95-1.83 (m, 2H), 1.54-1.37 (m, 2H).

Example 60: N-(5-(6-fluoro-1H-indol-3-yl)pyridin-2-yl)methanesulfonamide

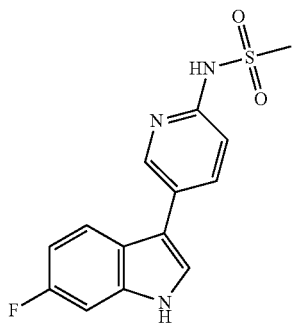

To a stirred solution of 5-(6-fluoro-1H-indol-3-yl)pyridin-2-amine (Example 15; 200 mg; 0.88 mmol) in pyridine (5 mL) was added MsCl (151 mg; 1.32 mmol) dropwise. The mixture was stirred at room temperature for 48 hours, concentrated, and purified by preparative HPLC to afford 106 mg (39%) of the title compound as a yellow solid. LC-MS: m/z 306.1 [M+H]⁺. ¹H NMR (400 MHz, DMSO-d₆) δ [ppm]: 11.51 (br s, 1H), 10.66 (br s, 1H), 8.56 (d, J=2.2 Hz, 1H), 8.04 (dd, J=8.4, 2.2 Hz, 1H), 7.80 (dd, J=8.7, 5.3 Hz, 1H), 7.73 (d, J=2.2 Hz, 1H), 7.24 (dd, J=9.9, 2.2 Hz, 1H), 7.06 (d, J=8.4 Hz, 1H), 6.96 (ddd, J=9.6, 8.7, 2.4 Hz, 1H), 3.31 (s, 3H).

Example 61: N-(5-(6-fluoro-1H-indol-3-yl)pyridin-2-yl)-1-(methylsulfonyl)piperidine-4-carboxamide

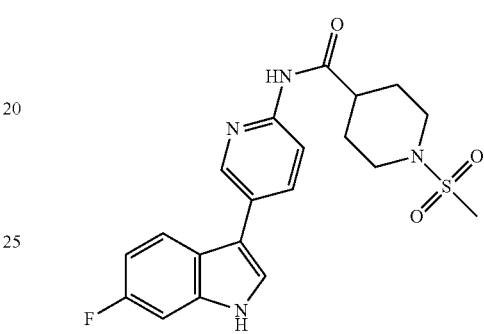

Following the general method as outlined in Example 11 Step 1, starting from 5-(6-fluoro-1H-indol-3-yl)pyridin-2-amine (Example 15; 200 mg; 0.88 mmol) and 1-(methylsulfonyl)piperidine-4-carboxylic acid (190 mg; 0.92 mmol), 90 mg (25%) of the title compound was obtained as a yellow solid after purification by preparative HPLC. LC-MS: m/z 417.1 [M+H]⁺. ¹H NMR (400 MHz, DMSO-d₆) δ [ppm]: 11.52 (br s, 1H), 10.58 (br s, 1H), 8.64 (d, J=2.4 Hz, 1H), 8.16 (d, J=8.6 Hz, 1H), 8.08 (dd, J=8.6, 2.4 Hz, 1H), 7.83 (dd, J=8.8, 5.3 Hz, 1H), 7.78 (d, J=2.4 Hz, 1H), 7.23 (dd, J=9.9, 2.2 Hz, 1H), 6.97 (ddd, J=9.5, 8.8, 2.2 Hz, 1H), 3.67-3.58 (m, 2H), 2.90 (s, 3H), 2.81-2.70 (m, 2H), 2.69-2.59 (m, 1H), 2.00-1.88 (m, 2H), 1.75-1.59 (m, 2H).

Example 62: N-(1-(5-(6-fluoro-1H-indol-3-yl)pyridin-2-yl)piperidin-4-yl)-2-hydroxyethanesulfonamide

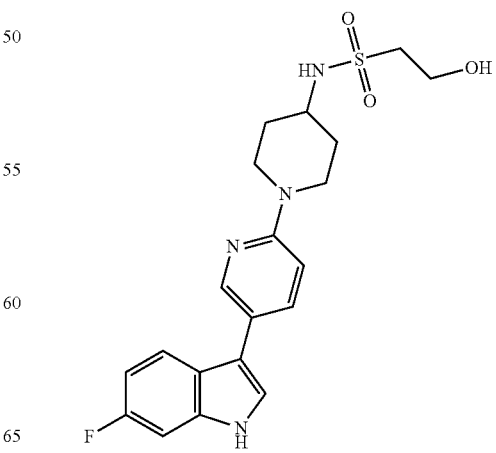

To the solution of N-(1-(5-(6-fluoro-1H-indol-3-yl)pyridin-2-yl)piperidin-4-yl)-2-methoxyethanesulfonamide (Example 57; 200 mg; 0.46 mmol) in DCM (50 mL) was added BBr₃ (0.11 mL; 1.1 mmol) dropwise at −50° C. under nitrogen. The reaction mixture was stirred at −50° C. for 30 minutes, quenched with saturated aqueous NaHCO₃ (40 mL), and extracted with EtOAc (80 mL×2). The combined organic layers were dried over anhydrous Na₂SO₄, filtered, concentrated, and purified by preparative TLC (DCM/MeOH=10/1, v/v) to afford 73 mg (38%) of the title compound as a yellow solid. LC-MS: m/z 419.1 [M+H]⁺. ¹H NMR (400 MHz, DMSO-d₆) δ [ppm]: 11.35 (br s, 1H), 8.42 (d, J=2.2 Hz, 1H), 7.81 (dd, J=8.4, 2.2 Hz, 1H), 7.74 (dd, J=8.7, 5.4 Hz, 1H), 7.58 (d, J=2.2 Hz, 1H), 7.20 (dd, J=9.9, 2.4 Hz, 1H), 7.12 (d, J=7.6 Hz, 1H), 6.94 (d, J=8.4 Hz, 1H), 6.92 (ddd, J=9.6, 8.7, 2.2 Hz, 1H), 4.91 (br s, 1H), 4.28-4.16 (m, 2H), 3.80-3.71 (m, 2H), 3.48-3.35 (m, 1H), 3.21 (t, J=6.8 Hz, 2H), 3.03-2.91 (m, 2H), 1.95-1.83 (m, 2H), 1.52-1.37 (m, 2H).

Example 63: 1-(5-(6-fluoro-1H-indol-3-yl)pyridin-2-yl)urea

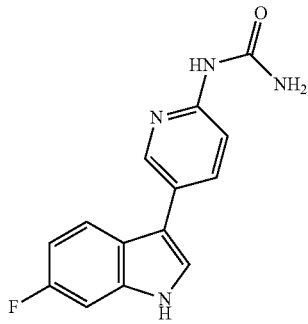 [SMILES: NC(=O)Nc1ccc(-c2c[nH]c3cc(F)ccc23)cn1]

Step 1: 2,2,2-trichloro-N-((5-(6-fluoro-1-(phenylsulfonyl)-1H-indol-3-yl)pyridin-2-yl)carbamoyl)acetamide and 1-(5-(6-fluoro-1-(phenylsulfonyl)-1H-indol-3-yl)pyridin-2-yl)urea

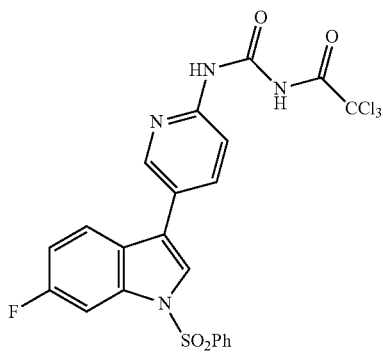

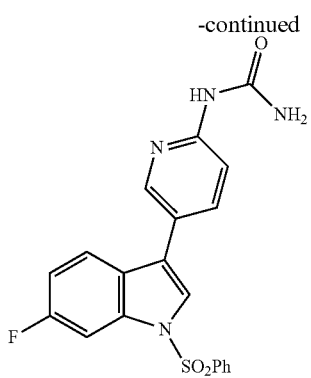

To a solution of 5-(6-fluoro-1-(phenylsulfonyl)-1H-indol-3-yl)pyridin-2-amine hydrochloride (Example 15 Step 1; 202 mg; 0.50 mmol) in THF (5 mL) was added NaH (80.0 mg; 2.00 mmol; 60% in mineral oil, w/w) at 0° C. The reaction mixture was stirred at 0° C. for 30 minutes before 2,2,2-trichloroacetyl isocyanate (141 mg; 0.75 mmol) was added. The reaction mixture was stirred at room temperature for 5 hours, quenched with water (20 mL) and extracted with EtOAc (20 mL×3). The combined organic layers were concentrated and purified by preparative TLC (petroleum ether/EtOAc=1/1, v/v) to afford 80 mg (29%) of 2,2,2-trichloro-N-((5-(6-fluoro-1-(phenylsulfonyl)-1H-indol-3-yl)pyridin-2-yl)carbamoyl)acetamide and 40 mg (19%) of 1-(5-(6-fluoro-1-(phenylsulfonyl)-1H-indol-3-yl)pyridin-2-yl)urea as white solids. LC-MS: m/z 555.4 [M+H]⁺. LC-MS: m/z 411.5 [M+H]⁺.

Step 2

Following the general method as outlined in Example 1, starting from a mixture of 2,2,2-trichloro-N-((5-(6-fluoro-1-(phenylsulfonyl)-1H-indol-3-yl)pyridin-2-yl)carbamoyl)acetamide and 1-(5-(6-fluoro-1-(phenylsulfonyl)-1H-indol-3-yl)pyridin-2-yl)urea (Step 1; 80 mg and 40 mg; 0.14 and 0.10 mmol), 15 mg (23%) of the title compound was obtained as a white solid after purification by preparative HPLC. LC-MS: m/z 271.1 [M+H]⁺. ¹H NMR (400 MHz, DMSO-d₆) δ [ppm]: 11.45 (br s, 1H), 9.14 (br s, 1H), 8.50 (br s, 1H), 7.97 (dd, J=8.4, 2.0 Hz, 1H), 7.80 (dd, J=8.7, 5.3 Hz, 1H), 7.69 (d, J=2.0 Hz, 1H), 7.49 (d, J=8.4 Hz, 1H), 7.21 (dd, J=9.8, 2.4 Hz, 1H), 7.01 (br s, 2H), 6.95 (ddd, J=9.7, 8.7, 2.4 Hz, 1H).

Example 64: N-(5-(6-fluoro-1H-indol-3-yl)pyridin-2-yl)-3-(methylsulfonamido)propanamide

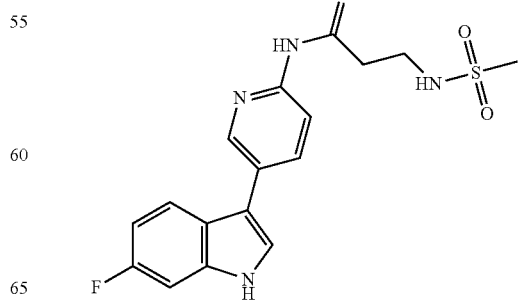

Following the general method as outlined in Example 11 Step 1, starting from 5-(6-fluoro-1H-indol-3-yl)pyridin-2-amine (Example 15; 800 mg; 3.52 mmol) and 3-(methylsulfonamido)propanoic acid (162 mg; 0.97 mmol; prepared as described in U.S. Pat. No. 4,623,715), 35 mg (11%) of the title compound was obtained as a white solid after purification by preparative HPLC. LC-MS: m/z 377.1 [M+H]$^+$. $^1$H NMR (400 MHz, DMSO-d$_6$) δ [ppm]: 11.51 (br s, 1H), 10.58 (br s, 1H), 8.63 (d, J=2.4 Hz, 1H), 8.16 (d, J=8.6 Hz, 1H), 8.08 (dd, J=8.6, 2.4 Hz, 1H), 7.83 (dd, J=8.7, 5.4 Hz, 1H), 7.77 (d, J=2.4 Hz, 1H), 7.23 (dd, J=9.9, 2.4 Hz, 1H), 7.09 (t, J=5.8 Hz, 1H), 6.96 (ddd, J=9.6, 8.7, 2.4 Hz, 1H), 3.27 (td, J=6.9, 5.8 Hz, 2H), 2.92 (s, 3H), 2.65 (t, J=6.9 Hz, 2H).

Example 65: 3-(5-(6-fluoro-1H-indol-3-yl)pyridin-2-yl)-1,1-dimethylurea

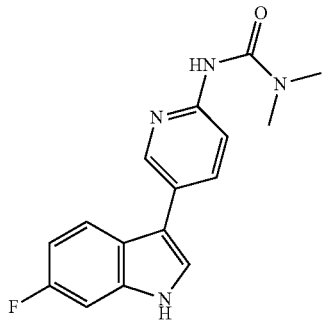 [SMILES: CN(C)C(=O)Nc1ccc(-c2c[nH]c3cc(F)ccc23)cn1]

Step 1: 3-(5-(6-fluoro-1-(phenylsulfonyl)-1H-indol-3-yl)pyridin-2-yl)-1,1-dimethylurea

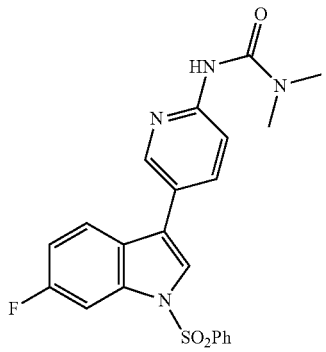

To the solution of phenyl (5-(6-fluoro-1-(phenylsulfonyl)-1H-indol-3-yl)pyridin-2-yl)carbamate (Intermediate 17; 120 mg crude; 0.25 mmol) in DMF (2 mL) was added dimethylamine (2.00 mL; 4.00 mmol; 2M in THF). The mixture was stirred at room temperature for 6 hours, concentrated in vacuo to remove THF, poured into water (20 mL), and extracted with EtOAc (40 mL). The organic layer was washed with water (20 mL×2), brine (20 mL), dried over anhydrous Na$_2$SO$_4$, filtered, and concentrated to afford 200 mg (>100%) of the crude title compound as a yellow solid, which was used directly without further purification. LC-MS: m/z 439.5 [M+H]$^+$.

Step 2

Following the general method as outlined in Example 1, starting from 3-(5-(6-fluoro-1-(phenylsulfonyl)-1H-indol-3-yl)pyridin-2-yl)-1,1-dimethylurea (Step 1; 200 mg crude; 0.25 mmol), 49 mg (67%) of the title compound was obtained as a yellow solid after purification by preparative TLC (DCM/MeOH=10/1, v/v). LC-MS: m/z 299.1 [M+H]$^+$. $^1$H NMR (400 MHz, DMSO-d$_6$) δ [ppm]: 11.46 (br s, 1H), 8.84 (br s, 1H), 8.53 (d, J=2.4 Hz, 1H), 7.98 (dd, J=8.6, 2.4 Hz, 1H), 7.88 (d, J=8.6 Hz, 1H), 7.80 (dd, J=8.8, 5.4 Hz, 1H), 7.72 (d, J=2.4 Hz, 1H), 7.22 (dd, J=9.9, 2.4 Hz, 1H), 6.95 (ddd, J=9.6, 8.8, 2.4 Hz, 1H), 2.96 (s, 6H).

Example 66: 1-(5-(6-fluoro-1H-indol-3-yl)pyridin-2-yl)-3-methylurea

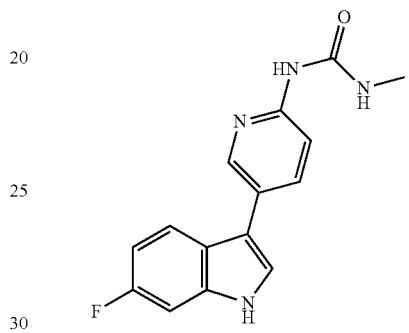

Step 1: 1-(5-(6-fluoro-1-(phenylsulfonyl)-1H-indol-3-yl)pyridin-2-yl)-3-methylurea

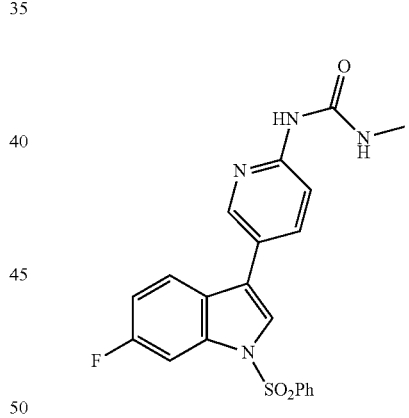

To the solution of phenyl (5-(6-fluoro-1-(phenylsulfonyl)-1H-indol-3-yl)pyridin-2-yl)carbamate (Intermediate 17; 500 mg crude; 1.03 mmol) in DMF (1.5 mL) was added methylamine (2.00 mL; 4.00 mmol; 2M in THF). The mixture was stirred at room temperature for 6 hours, concentrated to remove THF, poured into water (20 mL), and extracted with EtOAc (40 mL×2). The organic layer was washed with water (40 mL×2), brine (40 mL), dried over anhydrous Na$_2$SO$_4$, filtered, and concentrated to afford 234 mg (54%) of the crude title compound as a white solid, which was used directly without further purification. LC-MS: m/z 425.5 [M+H]$^+$.

Step 2

Following the general method as outlined in Example 1, starting from 1-(5-(6-fluoro-1-(phenylsulfonyl)-1H-indol-3- yl)pyridin-2-yl)-3-methylurea (Step 1; 230 mg crude; 0.54 mmol), 85 mg (55%) of the title compound was obtained as a white solid after purification by preparative TLC (DCM/MeOH=10/1, v/v). LC-MS: m/z 285.1 [M+H]+. 1H NMR (400 MHz, DMSO-$d_6$) δ [ppm]: 11.45 (br s, 1H), 8.84 (br s, 1H), 8.49 (d, J=2.4 Hz, 1H), 8.11 (br s, 1H), 7.98 (dd, J=8.6, 2.4 Hz, 1H), 7.80 (dd, J=8.8, 5.3 Hz, 1H), 7.69 (d, J=2.4 Hz, 1H), 7.39 (d, J=8.6 Hz, 1H), 7.22 (dd, J=9.9, 2.4 Hz, 1H), 6.94 (ddd, J=9.6, 8.8, 2.4 Hz, 1H), 2.75 (d, J=4.6 Hz, 3H).

Example 67: 6-(5-(6-fluoro-1H-indol-3-yl)pyridin-2-yl)-1H-benzo[d]imidazol-2-amine

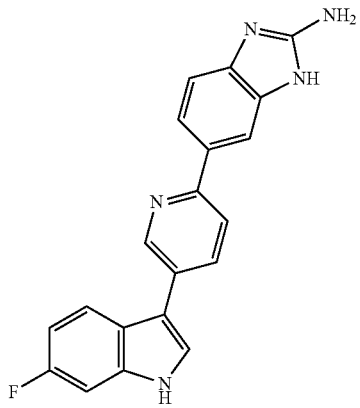 [SMILES: Nc1nc2ccc(-c3ccc(-c4c[nH]c5cc(F)ccc45)cn3)cc2[nH]1]

A mixture of 3-(6-bromopyridin-3-yl)-6-fluoro-1-(phenylsulfonyl)-1H-indole (Intermediate 11; 222 mg; 0.51 mmol), 6-(4,4,5,5-tetramethyl-1,3,2-dioxaborolan-2-yl)-1H-benzimidazol-2-amine (200 mg; 0.77 mmol; prepared as described in US2007117818), Pd(PPh$_3$)$_4$ (28 mg; 0.024 mmol) and K$_2$CO$_3$ (316 mg; 2.00 mmol; in 1 mL water) in DMF (5 mL) was stirred at 150° C. for 1 hour in a microwave reactor. The reaction mixture was diluted with EtOAc (50 mL), filtered through Celite, and diluted with saturated aquesou NH$_4$Cl (50 mL). The organic layer was separated and the aqueous layer was extracted with EtOAc (50 mL×3). The combined organic layers were washed with water (20 mL×2), brine (20 mL), dried over anhydrous Na$_2$SO$_4$, filtered, concentrated, and purified by preparative HPLC to afford 20 mg (11%) of the title compound as a white solid. LC-MS: m/z 344.1 [M+H]+. 1H NMR (300 MHz, DMSO-$d_6$) δ [ppm]: 11.57 (br s, 1H), 10.80 (br s, 1H), 8.94 (d, J=2.4 Hz, 1H), 8.08 (dd, J=8.4, 2.4 Hz, 1H), 7.93 (s, 1H), 7.92-7.88 (m, 2H), 7.85 (d, J=2.4 Hz, 1H), 7.72-7.66 (m, 1H), 7.26 (dd, J=9.9, 2.4 Hz, 1H), 7.17 (d, J=8.4 Hz, 1H), 7.04-6.95 (m, 1H), 6.27 (br s, 2H).

Example 68: 5-(6-fluoro-1H-indol-3-yl)-1-methyl-pyridin-2(1H)-one

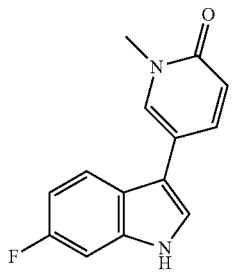 [SMILES: Cn1cc(-c2c[nH]c3cc(F)ccc23)ccc1=O]

10 mg (10%) of the title compound was isolated from the reaction mixture of Example 69 after purification by preparative HPLC. LC-MS: m/z 243.1 [M+H]+. 1H NMR (400 MHz, MeOH-$d_4$) δ [ppm]: 7.89 (d, J=2.4 Hz, 1H), 7.88 (dd, J=9.0, 2.4 Hz, 1H), 7.70 (dd, J=8.8, 5.3 Hz, 1H), 7.42 (s, 1H), 7.11 (dd, J=9.9, 2.4 Hz, 1H), 6.89 (ddd, J=9.6, 8.8, 2.4 Hz, 1H), 6.66 (d, J=9.0 Hz, 1H), 3.67 (s, 3H).

Example 69: 5-(6-fluoro-1H-indol-3-yl)pyridin-2(1H)-one

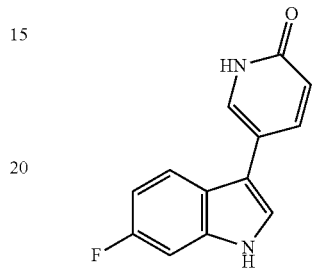

Step 1: 5-(6-fluoro-1-(phenylsulfonyl)-1H-indol-3-yl)pyridin-2(1H)-one

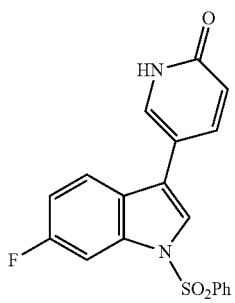

To a solution of 3-(6-bromopyridin-3-yl)-6-fluoro-1-(phenylsulfonyl)-1H-indole (Intermediate 11; 800 mg; 1.85 mmol) in water (4 mL) and dioxane (4 mL) was added concentrated aqueous HBr (8 mL). The reaction mixture was stirred at 150° C. for 4 hours in a microwave reactor. The reaction mixture was treated with aqueous Na$_2$CO$_3$ to adjust pH to 8 and extracted with EtOAc (50 mL×2). The combined organic layers were dried over anhydrous Na$_2$SO$_4$, filtered, concentrated, and reslurried with EtOAc (10 mL) to afford 160 mg (23%) of the crude title compound as a yellow solid, which was used directly without further purification. LC-MS: m/z 369.4 [M+H]+.

Step 2

Following the general method as outlined in Example 1, starting from 5-(6-fluoro-1-(phenylsulfonyl)-1H-indol-3-yl)pyridin-2(1H)-one (Step 1; 160 mg crude; 0.43 mmol), 40 mg (40%) of the title compound was obtained as a white solid after purification by preparative HPLC. LC-MS: m/z 229.0 [M+H]+. 1H NMR (300 MHz, DMSO-$d_6$) δ [ppm]: 11.61 (br s, 1H), 11.34 (br s, 1H), 7.78 (dd, J=9.3, 2.4 Hz, 1H), 7.65 (dd, J=8.8, 5.4 Hz, 1H), 7.60-7.54 (m, 2H), 7.19 (dd, J=9.9, 2.4 Hz, 1H), 6.92 (ddd, J=9.6, 8.8, 2.4 Hz, 1H), 6.44 (dd, J=9.3 Hz, 1H).

Example 70: N-(5-(6-fluoro-1H-indol-3-yl)pyridin-2-yl)-4-(methylsulfonamido)butanamide

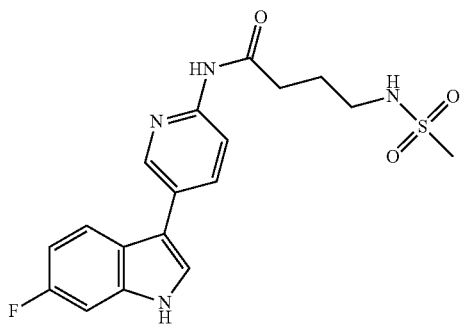 [SMILES: CS(=O)(=O)NCCCC(=O)Nc1ccc(-c2c[nH]c3cc(F)ccc23)cn1]

To a solution of 5-(6-fluoro-1H-indol-3-yl)pyridin-2-amine (Example 15; 120 mg; 0.53 mmol) in toluene (10 mL) was added trimethylaluminium (0.53 mL; 0.53 mmol; 1 M in hexanes) dropwise at 0° C. under nitrogen. The resulting solution was stirred at 0° C. for 20 minutes and a solution of 1-methylsulfonyl-2-pyrrolidinone (76 mg; 0.46 mmol; prepared as described in US2014163225) in toluene (2 mL) was added. The reaction mixture was allowed to warm to room temperature, stirred for 1 hour, then heated to reflux for 2.5 hours, cooled, and concentrated in vacuo. The residue was neutralized with citric acid and saturated aqueous sodium potassium tartrate, stirred vigorously for 45 minutes, and extracted with EtOAc (10 mL×3). The combined organic layers were dried over anhydrous $Na_2SO_4$, filtered, concentrated, and purified by preparative TLC (petroleum ether/EtOAc=1/1, v/v) to afford 20 mg (11%) of the title compound as a yellow solid. LC-MS: m/z 391.1 [M+H]$^+$. $^1$H NMR (400 MHz, MeOH-d$_4$) δ [ppm]: 8.58 (d, J=2.2 Hz, 1H), 8.13 (d, J=8.4 Hz, 1H), 8.04 (dd, J=8.4, 2.2 Hz, 1H), 7.76 (dd, J=8.7, 5.3 Hz, 1H), 7.53 (s, 1H), 7.14 (dd, J=9.9, 2.4 Hz, 1H), 6.91 (ddd, J=9.6, 8.7, 2.4 Hz, 1H), 3.17 (t, J=7.0 Hz, 2H), 2.95 (s, 3H), 2.57 (t, J=7.2 Hz, 2H), 1.95 (tt, J=7.2, 7.0 Hz, 2H).

Example 71: 6-(6-fluoro-1H-indol-3-yl)oxazolo[4,5-b]pyridin-2(3H)-one

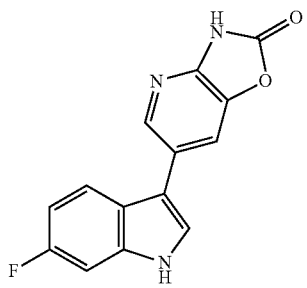 [SMILES: O=c1[nH]c2ncc(-c3c[nH]c4cc(F)ccc34)cc2o1]

Step 1: 6-(4,4,5,5-tetramethyl-1,3,2-dioxaborolan-2-yl)oxazolo[4,5-b]pyridin-2(3H)-one

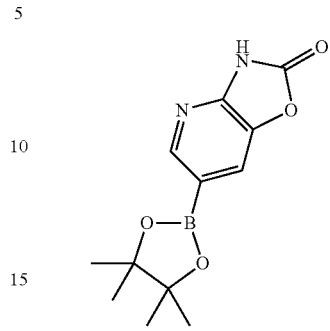

A mixture of 6-bromooxazolo[4,5-b]pyridin-2(3H)-one (3.00 g; 14.0 mmol; prepared as described in WO2010096389), bis(pinacolato)diboron (5.32 g; 20.9 mmol), Pd(dppf)Cl$_2$.DCM (1.14 g; 1.40 mmol), KOAc (4.19 g; 42.7 mmol) in 1,4-dioxane (50 mL) was stirred at 95° C. overnight under nitrogen. The mixture was filtered through Celite and washed with EtOAc (60 mL). The organic layer was concentrated and purified by a silica gel chromatography (petroleum ether/EtOAc=6/1-2/1, v/v) to afford 1.53 g (42%) of the title compound as a white solid. LC-MS: m/z 263.0 [M+H]$^+$.

Step 2: 6-(6-fluoro-1-(phenylsulfonyl)-1H-indol-3-yl)oxazolo[4,5-b]pyridin-2(3H)-one

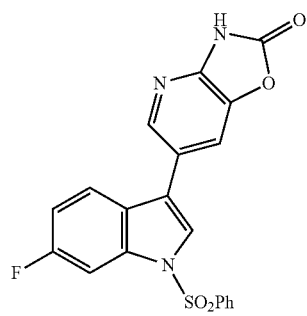

A mixture of 6-fluoro-3-iodo-1-(phenylsulfonyl)-1H-indole (prepared as described in WO2010/136491; 1.56 g; 3.89 mmol), 6-(4,4,5,5-tetramethyl-1,3,2-dioxaborolan-2-yl)oxazolo[4,5-b]pyridin-2(3H)-one (Step 1; 1.53 g; 5.84 mmol), Pd(dppf)Cl$_2$.DCM (300 mg; 0.37 mmol), and K$_2$CO$_3$ (3.76 g; 27.2 mmol) in dioxane (20 mL) and water (5 mL) was stirred at 100° C. for 3 hours under nitrogen. The mixture was filtered through Celite and diluted with EtOAc (100 mL) and aqueous of NH$_4$Cl (60 mL). The aqueous layer was extracted with EtOAc (70 mL×3). The combined organic layers were washed with brine, dried over anhydrous Na$_2$SO$_4$, filtered, concentrated, and purified by a silica gel chromatography (petroleum ether/EtOAc=6/1-1/1, v/v) to afford 329 mg (21%) of the title compound as a yellow solid. LC-MS: m/z 408.0 [M+H]$^+$.

Step 3

Following the general method as outlined in Example 1, starting from 6-(6-fluoro-1-(phenylsulfonyl)-1H-indol-3-yl)oxazolo[4,5-b]pyridin-2(3H)-one (Step 2; 179 mg; 0.44 mmol), 12 mg (10%) of the title compound was obtained as a red solid after purification by preparative HPLC. LC-MS: m/z 268.0 [M+H]+. 1H NMR (400 MHz, DMSO-d6) δ [ppm]: 12.41 (br s, 1H), 11.55 (br s, 1H), 8.36 (d, J=2.0 Hz, 1H), 7.93 (d, J=2.0 Hz, 1H), 7.83 (dd, J=8.8, 5.3 Hz, 1H), 7.76 (d, J=2.4 Hz, 1H), 7.24 (dd, J=9.9, 2.4 Hz, 1H), 6.96 (ddd, J=9.6, 8.8, 2.4 Hz, 1H).

Example 72: N-(1-(5-(6-chloro-1H-indol-3-yl)pyridin-2-yl)piperidin-4-yl)methanesulfonamide

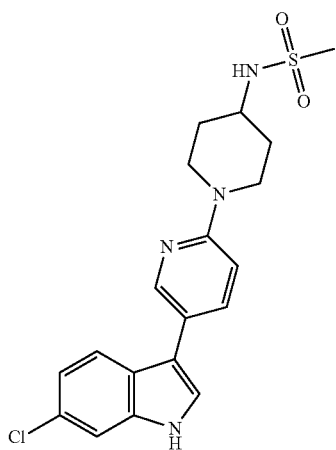 [SMILES: CS(=O)(=O)NC1CCN(c2ccc(-c3c[nH]c4cc(Cl)ccc34)cn2)CC1]

Following the general method as outlined in Example 14, the title compound was obtained as a white solid. LC-MS: m/z 405.1 [M+H]+. 1H NMR (400 MHz, DMSO-d6) δ [ppm]: 11.40 (br s, 1H), 8.42 (d, J=2.4 Hz, 1H), 7.80 (dd, J=8.6, 2.4 Hz, 1H), 7.76 (d, J=8.6 Hz, 1H), 7.63 (d, J=2.2 Hz, 1H), 7.46 (d, J=1.8 Hz, 1H), 7.10 (d, J=7.3 Hz, 1H), 7.07 (dd, J=8.6, 1.8 Hz, 1H), 6.94 (d, J=8.6 Hz, 1H), 4.27-4.18 (m, 2H), 3.49-3.35 (m, 1H), 3.03-2.92 (m, 2H), 2.95 (s, 3H), 1.95-1.85 (m, 2H), 1.51-1.38 (m, 2H).

Example 73: 6-(6-fluoro-1H-indol-3-yl)-1H-imidazo[4,5-b]pyridin-2(3H)-one

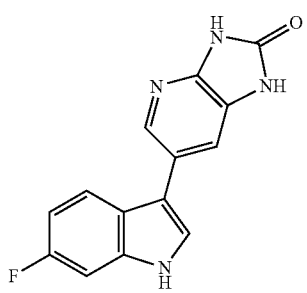 [SMILES: O=c1[nH]c2cc(-c3c[nH]c4cc(F)ccc34)cnc2[nH]1]

Step 1: 5-(4,4,5,5-tetramethyl-1,3,2-dioxaborolan-2-yl)pyridine-2,3-diamine

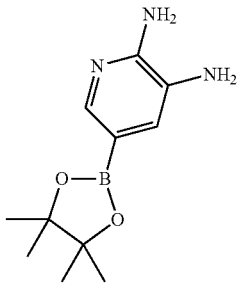 [SMILES: CC1(C)OB(c2cnc(N)c(N)c2)OC1(C)C]

A mixture of 5-bromopyridine-2,3-diamine (1.00 g; 5.3 mmol), bis(pinacolato)diboron (2.00 g; 7.9 mmol), Pd(dppf)Cl2.DCM (433 mg; 0.53 mmol), KOAc (1.55 g; 15.8 mmol) in 1,4-dioxane (100 mL) was stirred at 80° C. overnight under nitrogen. The mixture was filtered through Celite and washed with EtOAc (60 mL). The organic layer was concentrated to afford 1.24 g (99%) of the crude title compound as a yellow oil, which was used directly without further purification. LC-MS: m/z 236.2 [M+H]+.

Step 2: 5-(6-fluoro-1-(phenylsulfonyl)-1H-indol-3-yl)pyridine-2,3-diamine

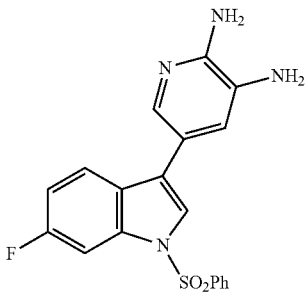

Following the general method as outlined in Example 2 Step 1, starting from 6-fluoro-3-iodo-1-(phenylsulfonyl)-1H-indole (prepared as described in WO2010/136491; 1.42 g; 3.54 mmol) and 5-(4,4,5,5-tetramethyl-1,3,2-dioxaborolan-2-yl)pyridine-2,3-diamine (Step 1; 1.24 g crude; 5.27 mmol), 650 mg (48%) of the title compound was obtained as a brown solid after purification by a silica gel chromatography (EtOAc). LC-MS: m/z 383.4 [M+H]+.

Step 3: 6-(6-fluoro-1-(phenylsulfonyl)-1H-indol-3-yl)-1H-imidazo[4,5-b]pyridin-2(3H)-one

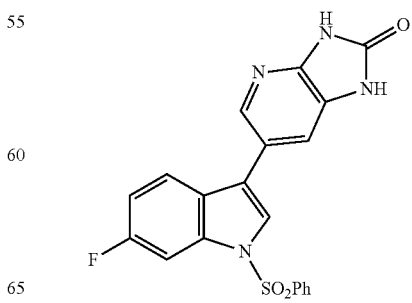

To a solution of 5-(6-fluoro-1-(phenylsulfonyl)-1H-indol-3-yl)pyridine-2,3-diamine (Step 2; 550 mg; 1.44 mmol) in THF (100 mL) was added CU (583 mg; 3.60 mmol). The reaction mixture was stirred at room temperature overnight, concentrated, diluted with water (100 mL), and extracted with EtOAc (50 mL×3). The combined organic layer was dried over anhydrous Na$_2$SO$_4$, filtered, concentrated, and washed with MeOH to afford 281 mg (48%) of the crude title compound as a grey solid, which was used directly without further purification. LC-MS: m/z 409.5 [M+H]$^+$.

Step 4

Following the general method as outlined in Example 1, starting from 6-(6-fluoro-1-(phenylsulfonyl)-1H-indol-3-yl)-1H-imidazo[4,5-b]pyridin-2(3H)-one (Step 3; 200 mg crude; 0.49 mmol), 45 mg (34%) of the title compound was obtained as a red solid after purification by preparative HPLC. LC-MS: m/z 269.1 [M+H]$^+$. $^1$H NMR (400 MHz, DMSO-d$_6$) δ [ppm]: 12.42 (br s, 1H), 11.29 (br s, 1H), 10.83 (br s, 1H), 8.16 (d, J=1.8 Hz, 1H), 7.75 (dd, J=8.8, 5.4 Hz, 1H), 7.67 (d, J=2.4 Hz, 1H), 7.42 (d, J=1.8 Hz, 1H), 7.22 (dd, J=9.9, 2.2 Hz, 1H), 6.95 (dd, J=9.6, 8.8, 2.2 Hz, 1H).

Example 74: 6-(6-fluoro-1H-indol-3-yl)-2-methyl-oxazolo[4,5-b]pyridine

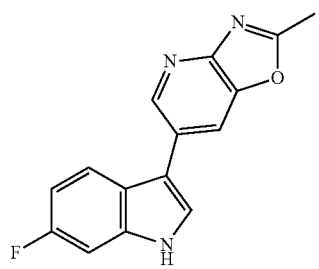 [SMILES: Cc1nc2ncc(-c3c[nH]c4cc(F)ccc34)cc2o1]

A mixture of 6-bromo-2-methyl-oxazolo[4,5-b]pyridine (700 mg; 3.29 mmol; prepared as described in WO2007045622), tert-butyl 6-fluoro-3-(4,4,5,5-tetramethyl-1,3,2-dioxaborolan-2-yl)-1H-indole-1-carboxylate (892 mg; 2.47 mmol), Pd(PPh$_3$)$_4$ (288 mg; 0.25 mmol) and Na$_2$CO$_3$ (913 mg; 8.61 mmol) in DME (10 mL) and water (1 mL) was stirred at 75° C. for 12 hours under nitrogen. The reaction mixture was concentrated, redissolved in EtOAc, filtered through a short plug of silica, concentrated, and purified by preparative HPLC to afford 12.6 mg (2%) of the title compound as a white solid. LC-MS: m/z 268.0 [M+H]$^+$. $^1$H NMR (400 MHz, DMSO-d$_6$) δ [ppm]: 11.60 (br s, 1H), 8.79 (d, J=2.0 Hz, 1H), 8.34 (d, J=2.0 Hz, 1H), 7.90 (dd, J=8.8, 5.5 Hz, 1H), 7.87 (d, J=2.4 Hz, 1H), 7.27 (dd, J=9.9, 2.4 Hz, 1H), 6.98 (ddd, J=9.7, 8.8, 2.4 Hz, 1H), 2.69 (s, 3H).

Example 75: 6-(6-fluoro-1H-indol-3-yl)-2-methyl-oxazolo[5,4-b]pyridine

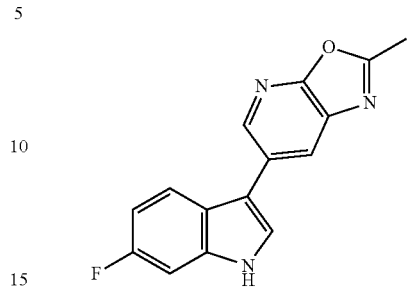

Step 1: 6-bromo-2-methyloxazolo[5,4-b]pyridine

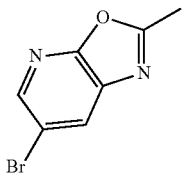

A mixture of 3-amino-5-bromopyridin-2-ol (1.00 g; 5.29 mmol) and trimethyl orthoacetate (5 mL) was stirred at 120° C. for 2 hours in a microwave reactor. The reaction mixture was concentrated and purified by a silica gel chromatography (petroleum ether/EtOAc=5/1-1/1) to afford 550 mg (49%) of the title compound as a white solid. LC-MS: m/z 212.8 [M+H]$^+$. $^1$H NMR (400 MHz, CDCl$_3$) δ [ppm]: 8.36 (d, J=2.1 Hz, 1H), 8.08 (d, J=2.1 Hz, 1H), 2.69 (s, 3H).

Step 2: tert-butyl 6-fluoro-3-(2-methyloxazolo[5,4-b]pyridin-6-yl)-1H-indole-1-carboxylate

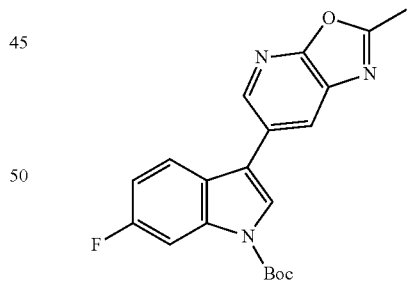

Following the general method as outlined in Example 74, starting from 6-bromo-2-methyloxazolo[5,4-b]pyridine (Step 1; 700 mg; 1.30 mmol) and tert-butyl 6-fluoro-3-(4,4,5,5-tetramethyl-1,3,2-dioxaborolan-2-yl)-1H-indole-1-carboxylate (609 mg; 2.47 mmol), 95 mg (20%) of the title compound was obtained as a white solid after purification by a silica gel chromatography (petroleum ether/EtOAc=5/1, v/v). LC-MS: m/z 367.9 [M+H]$^+$. $^1$H NMR (400 MHz, CDCl$_3$) δ [ppm]: 8.53 (d, J=2.0 Hz, 1H), 8.15 (d, J=2.0 Hz, 1H), 8.02-7.92 (m, 1H), 7.74 (s, 1H), 7.65 (dd, J=8.8, 5.3 Hz, 1H), 7.08 (ddd, J=9.5, 8.8, 2.3 Hz, 1H), 2.73 (s, 3H), 1.71 (s, 9H).

Step 3

To a solution of tert-butyl 6-fluoro-3-(2-methyloxazolo[5,4-b]pyridin-6-yl)-1H-indole-1-carboxylate (Step 2; 90 mg; 0.24 mmol) in DCM (2.5 mL) was added TFA (2.5 mL) dropwise. The reaction mixture was stirred at room temperature for 2 hours, poured into aqueous Na$_2$CO$_3$ (20 mL), and extracted with EtOAc (20 mL×3). The combined organic phase were concentrated and purified by preparative TLC (petroleum ether/EtOAc=1/1, v/v) to afford 30 mg (46%) of the title compound as a tan solid. LC-MS: m/z 268.1 [M+H]$^+$. $^1$H NMR (400 MHz, DMSO-d$_6$) δ [ppm]: 11.57 (br s, 1H), 8.60 (d, J=2.0 Hz, 1H), 8.33 (d, J=2.0 Hz, 1H), 7.86 (dd, J=8.8, 5.3 Hz, 1H), 7.84 (d, J=2.2 Hz, 1H), 7.25 (dd, J=9.9, 2.4 Hz, 1H), 6.98 (ddd, J=9.6, 8.8, 2.4 Hz, 1H), 2.67 (s, 3H).

Example 76: 6-(6-fluoro-1H-indol-3-yl)-1H-pyrrolo[3,2-b]pyridin-2(3H)-one

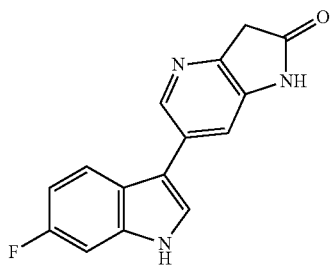 [SMILES: O=C1Cc2ncc(-c3c[nH]c4cc(F)ccc34)cc2N1]

Step 1: tert-butyl 6-fluoro-3-(2-oxo-2,3-dihydro-1H-pyrrolo[3,2-b]pyridin-6-yl)-1H-indole-1-carboxylate

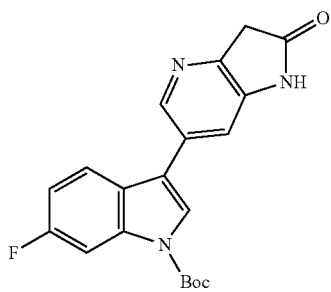 [SMILES: CC(C)(C)OC(=O)n1cc(-c2cnc3c(c2)NC(=O)C3)c2ccc(F)cc21]

Following the general method as outlined in Example 74, starting from 6-bromo-1H-pyrrolo[3,2-b]pyridin-2(3H)-one (200 mg; 0.55 mmol; prepared as described in *J. Med. Chem.* 2012, 55, 7667) and tert-butyl 6-fluoro-3-(4,4,5,5-tetramethyl-1,3,2-dioxaborolan-2-yl)-1H-indole-1-carboxylate (200 mg; 0.55 mmol), 150 mg (74%) of the title compound was obtained as a yellow solid after purification by a silica gel chromatography (DCM/MeOH=50/1, v/v). LC-MS: m/z 367.9 [M+H]$^+$.

Step 2

Following the general method as outlined in Intermediate 10 Step 2, starting from tert-butyl 6-fluoro-3-(2-oxo-2,3-dihydro-1H-pyrrolo[3,2-b]pyridin-6-yl)-1H-indole-1-carboxylate (Step 1; 150 mg; 0.41 mmol), 15 mg (14%) of the title compound was obtained as a brown solid after purification by preparative HPLC. LC-MS: m/z 268.1 [M+H]$^+$.

Example 77: N-(1-(5-(5-chloro-1H-indol-3-yl)pyridin-2-yl)piperidin-4-yl)methanesulfonamide

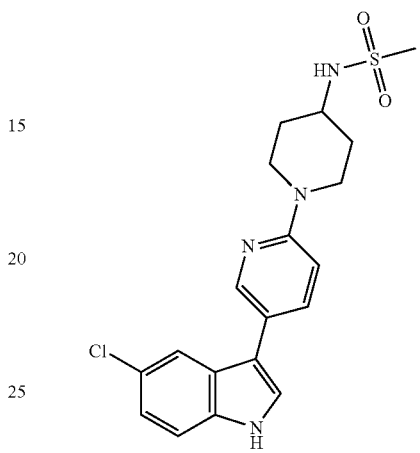

Following the general method as outlined in Example 14, the title compound was obtained as a white solid. LC-MS: m/z 405.1 [M+H]$^+$. $^1$H NMR (400 MHz, DMSO-d$_6$) δ [ppm]: 11.48 (br s, 1H), 8.40 (d, J=2.4 Hz, 1H), 7.81 (dd, J=8.6, 2.4 Hz, 1H), 7.71 (d, J=2.0 Hz, 1H), 7.67 (d, J=2.4 Hz, 1H), 7.45 (d, J=8.6 Hz, 1H), 7.14 (dd, J=8.6, 2.0 Hz, 1H), 7.11 (d, J=7.5 Hz, 1H), 6.94 (d, J=8.6 Hz, 1H), 4.28-4.18 (m, 2H), 3.49-3.38 (m, 1H), 3.04-2.94 (m, 2H), 2.95 (s, 3H), 1.96-1.86 (m, 2H), 1.52-1.38 (m, 2H).

Example 78: 1-(5-(6-fluoro-1H-indol-3-yl)pyridin-2-yl)imidazolidin-2-one

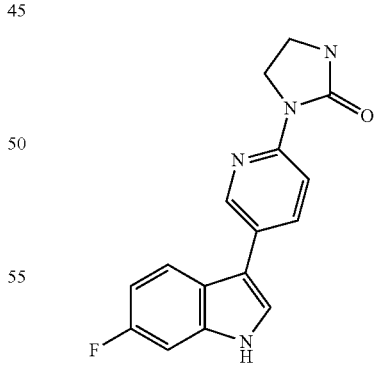

A mixture of N$^1$-(5-(6-fluoro-1H-indol-3-yl)pyridin-2-yl)ethane-1,2-diamine (Intermediate 15; 200 mg crude; 0.74 mmol) and CU (240 mg; 1.48 mmol) in THF (20 mL) was stirred at room temperature for 24 hours. The reaction mixture was concentrated, diluted with water (20 mL) and extracted with EtOAc (20 mL×3). The combined organic layers were dried over anhydrous Na$_2$SO$_4$, filtered, concentrated, and purified by preparative HPLC to afford 88 mg (40%) of the title compound as a yellow solid. LC-MS: m/z 297.1 [M+H]+. 1H NMR (400 MHz, DMSO-d6) δ [ppm]: 11.45 (br s, 1H), 8.60 (d, J=2.4 Hz, 1H), 8.24 (d, J=8.6 Hz, 1H), 8.00 (dd, J=8.6, 2.4 Hz, 1H), 7.82 (dd, J=8.8, 5.3 Hz, 1H), 7.71 (d, J=2.0 Hz, 1H), 7.23 (dd, J=9.9, 2.2 Hz, 1H), 7.18 (br s, 1H), 6.95 (ddd, J=9.6, 8.8, 2.2 Hz, 1H), 4.04 (t, J=7.9 Hz, 2H), 3.43 (d, J=7.9 Hz, 2H).

Example 79: N-(1-(5-(1H-indol-3-yl)pyridin-2-yl)piperidin-4-yl)methanesulfonamide

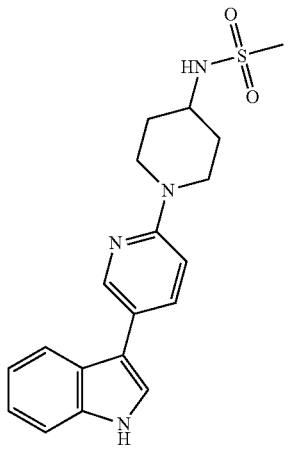 [SMILES: CS(=O)(=O)NC1CCN(c2ccc(-c3c[nH]c4ccccc34)cn2)CC1]

Following the general method as outlined in Example 14, the title compound was obtained as a white solid. LC-MS: m/z 371.1 [M+H]+. 1H NMR (400 MHz, DMSO-d6) δ [ppm]: 11.25 (br s, 1H), 8.44 (d, J=2.4 Hz, 1H), 7.82 (dd, J=8.6, 2.4 Hz, 1H), 7.76 (d, J=7.9 Hz, 1H), 7.58 (d, J=2.4 Hz, 1H), 7.43 (d, J=8.1 Hz, 1H), 7.18-7.03 (m, 3H), 6.94 (d, J=8.6 Hz, 1H), 4.28-4.18 (m, 2H), 3.49-3.37 (m, 1H), 3.04-2.93 (m, 2H), 2.95 (s, 3H), 1.97-1.85 (m, 2H), 1.55-1.38 (m, 2H).

Example 80: 5-(6-fluoro-1H-indol-3-yl)pyridine-2-sulfonamide hydrochloride

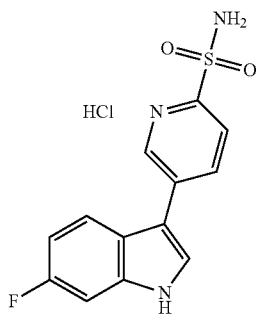 [SMILES: NS(=O)(=O)c1ccc(-c2c[nH]c3cc(F)ccc23)cn1 ; Cl]

Step 1: 5-bromopyridine-2-sulfonamide

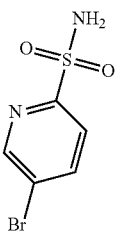

To a solution of 5-bromopyridine-2-sulfonyl chloride (750.0 mg; 2.92 mmol; prepared as described in WO2007039580) in DCM (10 mL) was added aqueous NH4OH (20 mL; 25% w/w). The reaction mixture was stirred at 70° C. for 12 hours and cooled to room temperature. The aqueous layer was extracted with EtOAc (50 mL×3) and the combined organic layers were dried over anhydrous Na2SO4, filtered, and concentrated to afford 400 mg (58%) of the crude title compound as a yellow solid, which was used directly without further purification. LC-MS: m/z 235.2 [M+H]+. 1H NMR (400 MHz, DMSO-d6) δ [ppm]: 8.87 (d, J=2.2 Hz, 1H), 8.33 (dd, J=8.4, 2.2 Hz, 1H), 7.87 (d, J=8.4 Hz, 1H), 7.58 (br s, 2H).

Step 2: tert-butyl 6-fluoro-3-(6-sulfamoylpyridin-3-yl)-1H-indole-1-carboxylate

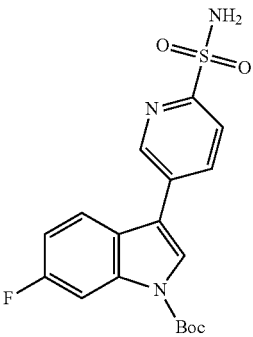 [SMILES: CC(C)(C)OC(=O)n1cc(-c2ccc(S(N)(=O)=O)nc2)c2ccc(F)cc21]

Following the general method as outlined in Example 74, starting from 5-bromopyridine-2-sulfonamide (Step 1; 175 mg; 0.74 mmol), tert-butyl 6-fluoro-3-(4,4,5,5-tetramethyl-1,3,2-dioxaborolan-2-yl)-1H-indole-1-carboxylate (320 mg; 0.89 mmol), 100 mg (35%) of the title compound was obtained as a white solid after purification by reverse phase flash chromatography. LC-MS: m/z 392.6 [M+H]+.

Step 3

To a solution of tert-butyl 6-fluoro-3-(6-sulfamoylpyridin-3-yl)-1H-indole-1-carboxylate (Step 2; 60 mg; 0.15 mmol) in EtOAc (5 mL) was added HCl/EtOAc (20 mL) slowly at room temperature. The reaction mixture was stirred overnight. Petroleum ether (40 mL) was added to the reaction mixture and the resulting precipitate was collected by vacuum filtration and washed with petroleum ether (40 mL) to afford 36 mg (81%) of the title compound as a yellow solid. LC-MS: m/z 292.0 [M+H]$^+$. $^1$H NMR (400 MHz, DMSO-d$_6$) δ [ppm]: 11.83 (br s, 1H), 9.04 (d, J=2.2 Hz, 1H), 8.33 (dd, J=8.4, 2.2 Hz, 1H), 8.04 (d, J=2.4 Hz, 1H), 7.95 (d, J=8.4 Hz, 1H), 7.94 (dd, J=8.7, 5.3 Hz, 1H), 7.42 (br s, 2H), 7.29 (dd, J=9.9, 2.2 Hz, 1H), 7.02 (ddd, J=9.5, 8.7, 2.2 Hz, 1H).

Example 81: N-(1-(5-(5-fluoro-1H-indol-3-yl)pyridin-2-yl)piperidin-4-yl)methanesulfonamide

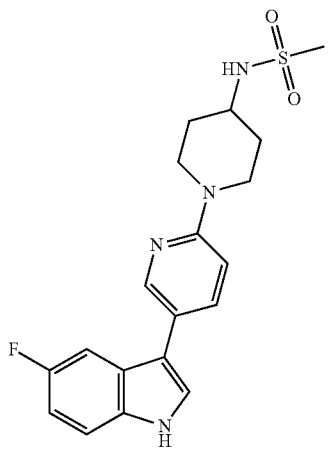 [SMILES: CS(=O)(=O)NC1CCN(c2ccc(-c3c[nH]c4ccc(F)cc34)cn2)CC1]

Following the general method as outlined in Example 14, the title compound was obtained as a white solid. LC-MS: m/z 389.1 [M+H]$^+$. $^1$H NMR (400 MHz, DMSO-d$_6$) δ [ppm]: 11.37 (br s, 1H), 8.41 (d, J=2.4 Hz, 1H), 7.81 (dd, J=8.8, 2.4 Hz, 1H), 7.67 (d, J=2.4 Hz, 1H), 7.46 (dd, J=10.1, 2.4 Hz, 1H), 7.43 (dd, J=8.8, 4.6 Hz, 1H), 7.10 (d, J=7.4 Hz, 1H), 6.98 (dd, J=9.6, 8.8, 2.4 Hz, 1H), 6.93 (d, J=8.8 Hz, 1H), 4.27-4.18 (m, 2H), 3.48-3.36 (m, 1H), 3.03-2.93 (m, 2H), 2.95 (s, 3H), 1.96-1.86 (m, 2H), 1.52-1.39 (m, 2H).

Example 82: 4-(5-(6-fluoro-1H-indol-3-yl)pyridin-2-yl)morpholin-3-one

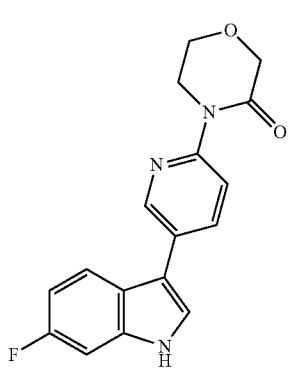 [SMILES: O=C1COCCN1c1ccc(-c2c[nH]c3cc(F)ccc23)cn1]

Step 1: tert-butyl 6-fluoro-3-(6-(3-oxomorpholino)pyridin-3-yl)-1H-indole-1-carboxylate

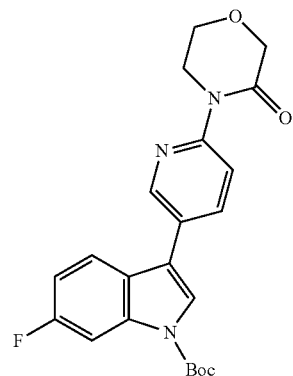 [SMILES: CC(C)(C)OC(=O)n1cc(-c2ccc(N3CCOCC3=O)nc2)c2ccc(F)cc21]

Following the general method as outlined in Example 74, starting from 4-(5-bromopyridin-2-yl)morpholin-3-one (317 mg; 1.23 mmol; prepared as described in *J. Med. Chem.* 2013, 56, 2642), tert-butyl 6-fluoro-3-(4,4,5,5-tetramethyl-1,3,2-dioxaborolan-2-yl)-1H-indole-1-carboxylate (400 mg; 1.11 mmol), 300 mg (66%) of the title compound was obtained as a yellow solid after purification by a silica gel chromatography (petroleum ether/EtOAc=10/1, v/v). LC-MS: m/z 412.6 [M+H]$^+$.

Step 2

Following the general method as outlined in Intermediate 10 Step 2, starting from tert-butyl 6-fluoro-3-(6-(3-oxomorpholino)pyridin-3-yl)-1H-indole-1-carboxylate (Step 1; 300 mg; 0.73 mmol), 110 mg (48%) of the title compound was obtained as a white solid after purification by preparative HPLC. LC-MS: m/z 312.1 [M+H]$^+$. $^1$H NMR (400 MHz, DMSO-d$_6$) δ [ppm]: 11.56 (br s, 1H), 8.78 (d, J=2.4 Hz, 1H), 8.14 (dd, J=8.6, 2.4 Hz, 1H), 8.04 (d, J=8.6 Hz, 1H), 7.88 (dd, J=8.8, 5.3 Hz, 1H), 7.83 (d, J=2.4 Hz, 1H), 7.25 (dd, J=9.9, 2.4 Hz, 1H), 6.97 (ddd, J=9.6, 8.8, 2.4 Hz, 1H), 4.28 (s, 2H), 4.07-3.97 (m, 4H).

Example 83: 1-(5-(6-fluoro-1H-indol-3-yl)pyridin-2-yl)piperazin-2-one

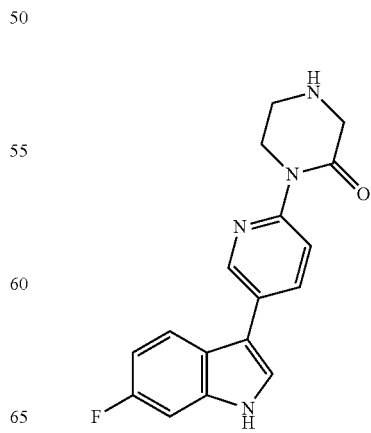

Step 1: tert-butyl 4-(5-bromopyridin-2-yl)-3-oxopiperazine-1-carboxylate

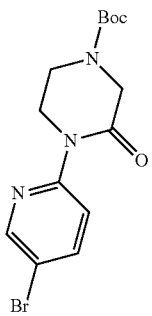 [SMILES: CC(C)(C)OC(=O)N1CCN(c2ccc(Br)cn2)C(=O)C1]

A mixture of 2,5-dibromopyridine (1.00 g; 4.22 mmol), tert-butyl 3-oxopiperazine-1-carboxylate (562 mg; 2.80 mmol) and Cs₂CO₃ (1.37 g; 4.20 mmol) in toluene (20 mL) was purged with nitrogen and added Pd₂(dba)₃ (129 mg; 0.14 mmol) and XantPhos (97 mg; 0.17 mmol). The reaction mixture was stirred at 100° C. overnight, cooled to room temperature, diluted with EtOAc (50 mL), filtered through Celite, washed with water (50 mL), brine (50 mL), dried over anhydrous Na₂SO₄, filtered, concentrated, and purified by a silica gel chromatography (petroleum ether/EtOAc=10/1, v/v) to afford 955 mg (96%) of the title compound as a yellow oil. LC-MS: m/z 355.8 [M+H]⁺.

Step 2: tert-butyl 3-(6-(4-(tert-butoxycarbonyl)-2-oxopiperazin-1-yl)pyridin-3-yl)-6-fluoro-1H-indole-1-carboxylate

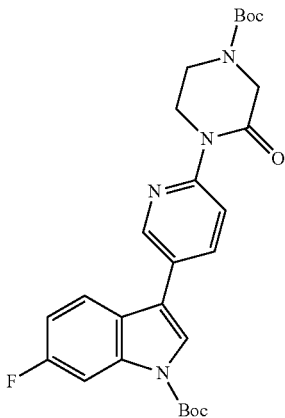 [SMILES: CC(C)(C)OC(=O)N1CCN(c2ccc(-c3cn(C(=O)OC(C)(C)C)c4cc(F)ccc34)cn2)C(=O)C1]

Following the general method as outlined in Example 74, starting from tert-butyl 4-(5-bromopyridin-2-yl)-3-oxopiperazine-1-carboxylate (Step 1; 427 mg; 1.20 mmol), tert-butyl 6-fluoro-3-(4,4,5,5-tetramethyl-1,3,2-dioxaborolan-2-yl)-1H-indole-1-carboxylate (400 mg; 1.11 mmol), 322 mg (57%) of the title compound was obtained as a yellow solid after purification by a silica gel chromatography (petroleum ether/EtOAc=10/1, v/v). LC-MS: m/z 511.8 [M+H]⁺.

Step 3

Following the general method as outlined in Intermediate 10 Step 2, starting from tert-butyl 3-(6-(4-(tert-butoxycarbonyl)-2-oxopiperazin-1-yl)pyridin-3-yl)-6-fluoro-1H-indole-1-carboxylate (Step 2; 320 mg; 0.63 mmol), 13 mg (7%) of the title compound was obtained as a white solid after purification by preparative HPLC. LC-MS: m/z 311.1 [M+H]⁺. ¹H NMR (400 MHz, DMSO-d₆) δ [ppm]: 11.55 (br s, 1H), 8.76 (d, J=2.4 Hz, 1H), 8.09 (dd, J=8.6, 2.4 Hz, 1H), 7.90 (d, J=8.6 Hz, 1H), 7.86 (dd, J=8.8, 5.3 Hz, 1H), 7.81 (d, J=2.4 Hz, 1H), 7.24 (dd, J=9.9, 2.4 Hz, 1H), 6.97 (ddd, J=9.6, 8.8, 2.4 Hz, 1H), 3.87 (t, J=5.4 Hz, 2H), 3.47 (s, 2H), 3.05 (t, J=5.4 Hz, 2H), 2.99 (br s, 1H).

Example 84: 2-(6-(6-fluoro-1H-indol-3-yl)-2-oxooxazolo[4,5-b]pyridin-3(2H)-yl)acetamide

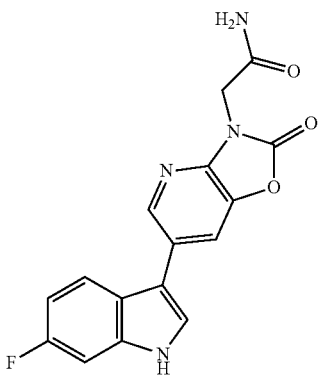 [SMILES: NC(=O)Cn1c(=O)oc2cc(-c3c[nH]c4cc(F)ccc34)cnc21]

Step 1: tert-butyl 3-(3-(2-amino-2-oxoethyl)-2-oxo-2,3-dihydrooxazolo[4,5-b]pyridin-6-yl)-6-fluoro-1H-indole-1-carboxylate

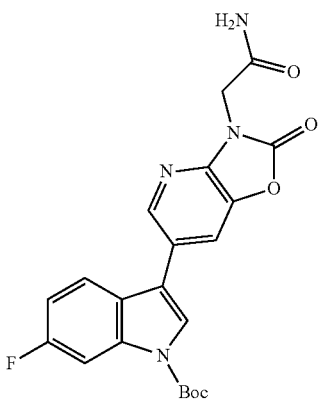 [SMILES: CC(C)(C)OC(=O)n1cc(-c2cnc3c(c2)oc(=O)n3CC(N)=O)c2ccc(F)cc21]

A mixture of: tert-butyl 6-fluoro-3-(2-oxo-2,3-dihydrooxazolo[4,5-b]pyridin-6-yl)-1H-indole-1-carboxylate (Intermediate 18; 320 mg; 0.87 mmol), 2-bromoacetamide (718 mg; 5.20 mmol), K₂CO₃ (359 mg; 2.60 mmol), and KI (144 mg; 0.87 mmol) in DMF (3 mL) was stirred at 80° C. for 16 hours. The reaction mixture was cooled to room temperature, diluted with water (50 mL) and extracted with EtOAc (50 mL×3). The combined organic layers were washed with brine (50 mL×2), dried over anhydrous Na₂SO₄, filtered, concentrated, and purified by a silica gel chromatography (petroleum ether/EtOAc=5/1-EtOAc, v/v) to afford 210 mg (57%) of the title compound as a yellow solid. LC-MS: m/z 427.7 [M+H]⁺.

Step 2

To a solution of tert-butyl 3-(3-(2-amino-2-oxoethyl)-2-oxo-2,3-dihydrooxazolo[4,5-b]pyridin-6-yl)-6-fluoro-1H-indole-1-carboxylate (Step 1; 110 mg; 0.26 mmol) in DCM (10 mL) and DMF (2 mL) was added TFA (3 mL) at 0° C. The mixture was stirred at room temperature for 16 hours, diluted with EtOAc (100 mL), basified with Et$_3$N (5 mL), filtered, concentrated, and purified by preparative HPLC to afford 10 mg (12%) of the title compound as a yellow solid. LC-MS: m/z 327.0 [M+H]$^+$. $^1$H NMR (400 MHz, DMSO-d$_6$) δ [ppm]: 11.57 (br s, 1H), 8.03 (s, 1H), 7.91 (dd, J=8.7, 5.3 Hz, 1H), 7.88-7.81 (m, 3H), 7.48 (br s, 1H), 7.24 (dd, J=9.9, 2.4 Hz, 1H), 6.99 (ddd, J=9.5, 8.7, 2.4 Hz, 1H), 5.07 (s, 2H).

Example 85: 2-(6-(6-fluoro-1H-indol-3-yl)-2-oxo-1H-imidazo[4,5-b]pyridin-3(2H)-yl)acetic acid

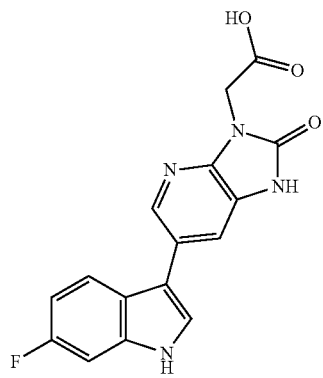 [SMILES: O=C(O)Cn1c(=O)[nH]c2cc(-c3c[nH]c4cc(F)ccc34)cnc21]

Step 1:
2-((5-bromo-3-nitropyridin-2-yl)amino)acetamide

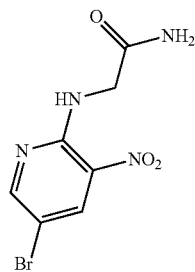 [SMILES: NC(=O)CNc1ncc(Br)cc1[N+](=O)[O-]]

A mixture of 5-bromo-2-chloro-3-nitropyridine (1.00 g; 4.21 mmol), glycinamide hydrochloride (666 mg; 6.02 mmol) and Et$_3$N (1.27 g; 12.6 mmol) in DMF (8 mL) was stirred at 80° C. for 16 hours. The reaction mixture was cooled, added to water (100 mL), and extracted with EtOAc (30 mL×2). The combined organic layers were washed with brine (30 mL×2), dried over anhydrous Na$_2$SO$_4$, filtered, concentrated, and purified by a silica gel chromatography (petroleum ether/EtOAc=5/1-2/1, v/v) to afford 460 mg (40%) of the title compound as a yellow solid. $^1$H NMR (400 MHz, DMSO-d$_6$) δ [ppm]: 8.73 (br t, J=5.2 Hz, 1H), 8.59 (d, J=2.2 Hz, 1H), 8.58 (d, J=2.2 Hz, 1H), 7.50 (br s, 1H), 7.14 (br s, 1H), 4.08 (d, J=5.2 Hz, 2H).

Step 2: tert-butyl 3-(6-((2-amino-2-oxoethyl)amino)-5-nitropyridin-3-yl)-6-fluoro-1H-indole-1-carboxylate

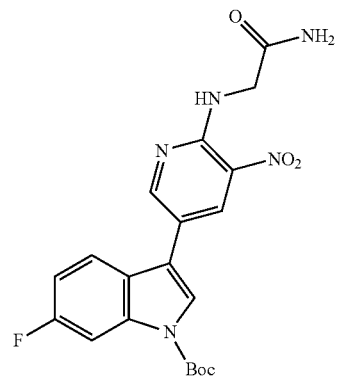

Following the general method as outlined in Example 74, starting from 2-((5-bromo-3-nitropyridin-2-yl)amino)acetamide (Step 1; 360 mg; 1.31 mmol) and tert-butyl 6-fluoro-3-(4,4,5,5-tetramethyl-1,3,2-dioxaborolan-2-yl)-1H-indole-1-carboxylate (724 mg; 2.00 mmol), 230 mg (41%) of the title compound was obtained as a white solid after purification by silica gel chromatography (petroleum ether/EtOAc=200/1-20/1, v/v). LC-MS: m/z 430.6 [M+H]$^+$. $^1$H NMR (400 MHz, DMSO-d$_6$) δ [ppm]: 8.85 (d, J=2.2 Hz, 1H), 8.77 (br t, J=5.3 Hz, 1H), 8.66 (d, J=2.2 Hz, 1H), 8.10 (s, 1H), 7.89 (dd, J=10.1, 2.4 Hz, 1H), 7.83 (dd, J=8.7, 5.3 Hz, 1H), 7.56 (br s, 1H), 7.24 (ddd, J=9.5, 8.7, 2.4 Hz, 1H), 7.15 (br s, 1H), 4.18 (d, J=5.3 Hz, 2H), 1.66 (s, 9H).

Step 3: tert-butyl 3-(5-amino-6-((2-amino-2-oxoethyl)amino)pyridin-3-yl)-6-fluoro-1H-indole-1-carboxylate

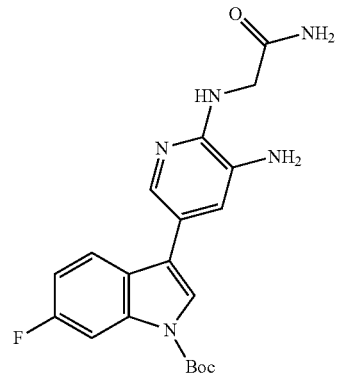 [SMILES: CC(C)(C)OC(=O)n1cc(-c2cnc(NCC(N)=O)c([N+](=O)[O-])c2)c2ccc(F)cc21]

To a mixture of tert-butyl 3-(6-((2-amino-2-oxoethyl)amino)-5-nitropyridin-3-yl)-6-fluoro-1H-indole-1-carboxylate (Step 2; 100 mg; 0.23 mmol) in MeOH (10 mL) was added Pd/C (10 mg; 5% w/w). The reaction, mixture was stirred at room temperature for 8 hours under hydrogen balloon, filtered and concentrated to afford 99 mg (>100%) of the crude title compound as a brown solid, which was used directly without further purification. LC-MS: m/z 400.1 [M+H]$^+$.

Step 4: tert-butyl 3-(3-(2-amino-2-oxoethyl)-2-oxo-2,3-dihydro-1H-imidazo[4,5-b]pyridin-6-yl)-6-fluoro-1H-indole-1-carboxylate

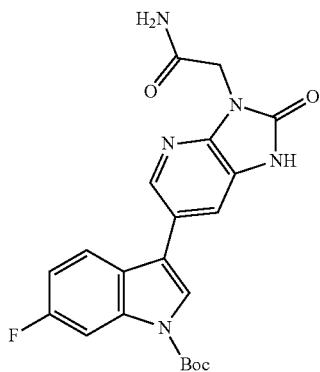 [SMILES: CC(C)(C)OC(=O)n1cc(-c2cnc3c(c2)[nH]c(=O)n3CC(N)=O)c2ccc(F)cc21]

To a stirred solution of tert-butyl 3-(5-amino-6-((2-amino-2-oxoethyl)amino)pyridin-3-yl)-6-fluoro-1H-indole-1-carboxylate (99 mg crude; 0.23 mmol) in THF (10 mL) was added Et₃N (83 mg; 0.82 mmol) and triphosgene (245 mg; 0.83 mmol) at 0° C. The reaction mixture was stirred at room temperature for 30 minutes, diluted with EtOAc (30 mL), filtered, concentrated, and purified by a silica gel chromatography (petroleum ether/EtOAc=3/1-EtOAc, v/v) to afford 48 mg (49%) of the title compound as a yellow solid. LC-MS: m/z 426.7 [M+H]⁺.

Step 5

A mixture of tert-butyl 3-(3-(2-amino-2-oxoethyl)-2-oxo-2,3-dihydro-1H-imidazo[4,5-b]pyridin-6-yl)-6-fluoro-1H-indole-1-carboxylate (48 mg; 0.11 mmol) in MeOH was added HCl/EtOAc (8 mL). The reaction mixture was stirred for 16 hours, concentrated, and purified by preparative HPLC (HCl as additive) to afford 1 mg (3%) of the title compound as a yellow solid. LC-MS: m/z 327.0 [M+H]⁺. ¹H NMR (400 MHz, MeOH-d₄) δ [ppm]: 8.26 (d, J=1.6 Hz, 1H), 7.77 (d, J=1.6 Hz, 1H), 7.76 (dd, J=8.8, 5.3 Hz, 1H), 7.57 (s, 1H), 7.16 (dd, J=9.9, 2.4 Hz, 1H), 6.92 (dd, J=9.6, 8.8, 2.4 Hz, 1H), 4.76 (s, 2H).

Example 86: ethyl 2-(6-(6-fluoro-1H-indol-3-yl)-2-oxo-1H-imidazo[4,5-b]pyridin-3(2H)-yl)acetate

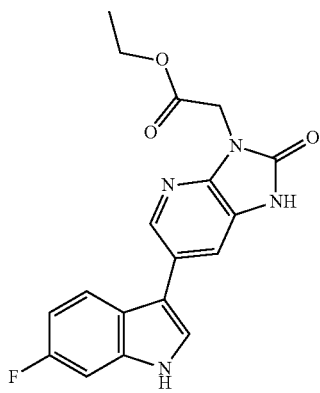 [SMILES: CCOC(=O)Cn1c(=O)[nH]c2cc(-c3c[nH]c4cc(F)ccc34)cnc21]

The title compound (3 mg, 7%) was isolated as a yellow solid in Step 5 of Example 85. LC-MS: m/z 355.1 [M+H]⁺. ¹H NMR (400 MHz, DMSO-d₆) δ [ppm]: 11.46 (br s, 1H), 11.25 (br s, 1H), 8.22 (d, J=1.8 Hz, 1H), 7.77 (dd, J=8.6, 5.3 Hz, 1H), 7.70 (d, J=2.4 Hz, 1H), 7.53 (d, J=1.8 Hz, 1H), 7.23 (dd, J=9.9, 2.2 Hz, 1H), 6.95 (ddd, J=9.5, 8.6, 2.2 Hz, 1H), 4.65 (s, 2H), 4.17 (q, J=7.0 Hz, 2H), 1.22 (t, J=7.0 Hz, 3H).

Example 87: 6-fluoro-3-(6-(piperazin-1-ylsulfonyl)pyridin-3-yl)-1H-indole

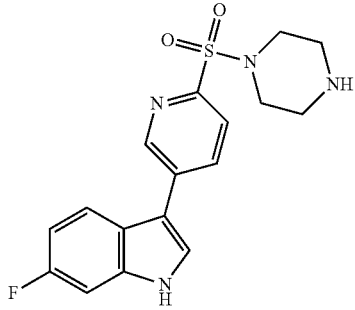 [SMILES: O=S(=O)(c1ccc(-c2c[nH]c3cc(F)ccc23)cn1)N1CCNCC1]

Step 1: tert-butyl 4-((5-bromopyridin-2-yl)sulfonyl)piperazine-1-carboxylate

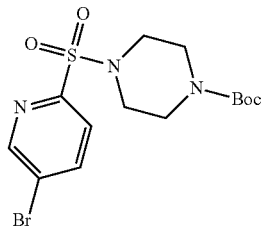 [SMILES: CC(C)(C)OC(=O)N1CCN(S(=O)(=O)c2ccc(Br)cn2)CC1]

To a mixture of tert-butyl piperazine-1-carboxylate (421 mg; 2.26 mmol) and Et₃N (229 mg; 2.26 mmol) in DCM (10 mL) was added 5-bromopyridine-2-sulfonyl chloride (290 mg; 1.13 mmol; prepared as described in WO2007039580) at room temperature. The reaction mixture was stirred for 30 minutes, concentrated, and purified by a silica gel chromatography (petroleum ether/EtOAc=20/1-5/1, v/v) to afford 160 mg (35%) of the title compound as a white solid. ¹H NMR (400 MHz, CDCl₃) δ [ppm]: 8.75 (d, J=2.2 Hz, 1H), 8.05 (dd, J=8.2, 2.2 Hz, 1H), 7.83 (d, J=8.2 Hz, 1H), 3.55-3.47 (m, 4H), 3.34-3.27 (m, 4H), 1.44 (s, 9H).

Step 2: tert-butyl 3-(6-((4-(tert-butoxycarbonyl)piperazin-1-yl)sulfonyl)pyridin-3-yl)-6-fluoro-1H-indole-1-carboxylate

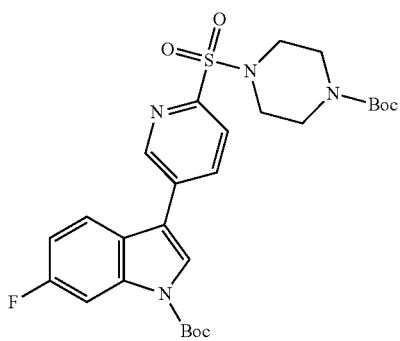 [SMILES: CC(C)(C)OC(=O)N1CCN(S(=O)(=O)c2ccc(-c3cn(C(=O)OC(C)(C)C)c4cc(F)ccc34)cn2)CC1]

Following the general method as outlined in Example 74, starting from tert-butyl 4-((5-bromopyridin-2-yl)sulfonyl)piperazine-1-carboxylate (Step 1; 106 mg; 0.26 mmol) and tert-butyl 6-fluoro-3-(4,4,5,5-tetramethyl-1,3,2-dioxaborolan-2-yl)-1H-indole-1-carboxylate (113 mg; 0.31 mmol), 79 mg (54%) of the title compound was obtained as a white solid after purification by silica gel chromatography (petroleum ether/EtOAc=50/1-10/1, v/v). LC-MS: m/z 561.8 [M+H]$^+$. $^1$H NMR (300 MHz, CDCl$_3$) δ [ppm]: 8.95 (d, J=2.2 Hz, 1H), 8.12 (dd, J=8.2, 2.2 Hz, 1H), 8.02 (d, J=8.2 Hz, 1H), 8.02-7.94 (m, 1H), 7.83 (s, 1H), 7.68 (dd, J=8.7, 5.3 Hz, 1H), 7.11 (ddd, J=9.5, 8.7, 2.4 Hz, 1H), 3.60-3.49 (m, 4H), 3.40-3.32 (m, 4H), 1.71 (s, 9H), 1.44 (s, 9H).

Step 3

Following the general method as outlined in Intermediate 10 Step 2, starting from tert-butyl 3-(6-((4-(tert-butoxycarbonyl)piperazin-1-yl)sulfonyl)pyridin-3-yl)-6-fluoro-1H-indole-1-carboxylate (Step 2; 108 mg; 0.19 mmol), 38 mg (55%) of the title compound was obtained as a white solid after purification by preparative TLC (EtOAc/MeOH/NH$_4$OH=10/1/0.1, v/v). LC-MS: m/z 361.1 [M+H]$^+$. $^1$H NMR (400 MHz, DMSO-d$_6$) δ [ppm]: 11.82 (br s, 1H), 9.12 (d, J=2.2 Hz, 1H), 8.38 (dd, J=8.4, 2.2 Hz, 1H), 8.08 (d, J=2.2 Hz, 1H), 7.97 (dd, J=8.8, 5.3 Hz, 1H), 7.91 (d, J=8.4 Hz, 1H), 7.29 (dd, J=9.7, 2.4 Hz, 1H), 7.03 (ddd, J=9.5, 8.8, 2.4 Hz, 1H), 3.10-3.05 (m, 4H), 2.75-2.69 (m, 4H).

Example 88: 5-(6-fluoro-1H-indol-3-yl)-N-(2-(methylsulfonamido)ethyl)pyridine-2-sulfonamide

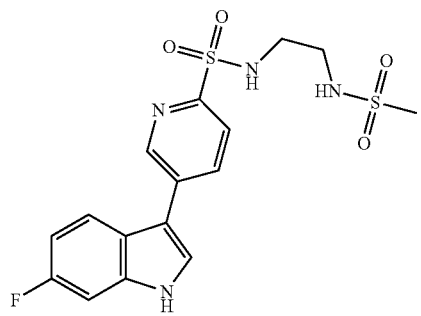 [SMILES: CS(=O)(=O)NCCNS(=O)(=O)c1ccc(-c2c[nH]c3cc(F)ccc23)cn1]

Step 1: 5-bromo-N-(2-(methylsulfonamido)ethyl)pyridine-2-sulfonamide

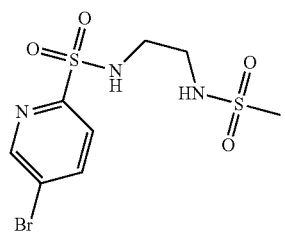 [SMILES: CS(=O)(=O)NCCNS(=O)(=O)c1ccc(Br)cn1]

Following the general method as outlined in Example 87 Step 1, starting from N-(2-aminoethyl)methanesulfonamide hydrochloride (192 mg; 1.10 mmol; prepared as described in EP2261213), 5-bromopyridine-2-sulfonyl chloride (256 mg; 1.00 mmol), 349 mg (98%) of the title compound was obtained as a white solid after purification by silica gel chromatography (petroleum ether/EtOAc=3/1-1/1, v/v). $^1$H NMR (300 MHz, DMSO-d$_6$) δ [ppm]: 8.90 (d, J=2.2 Hz, 1H), 8.35 (dd, J=8.4, 2.2 Hz, 1H), 8.11 (br s, 1H), 7.88 (d, J=8.4 Hz, 1H), 7.08 (br s, 1H), 3.15-2.96 (m, 4H), 2.88 (s, 3H).

Step 2: tert-butyl 6-fluoro-3-(6-(N-(2-(methylsulfonamido)ethyl)sulfamoyl)pyridin-3-yl)-1H-indole-1-carboxylate

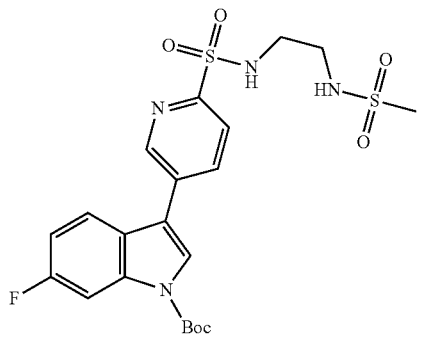 [SMILES: CC(C)(C)OC(=O)n1cc(-c2ccc(S(=O)(=O)NCCNS(C)(=O)=O)nc2)c2ccc(F)cc21]

Following the general method as outlined in Example 74, starting from 5-bromo-N-(2-(methylsulfonamido)ethyl)pyridine-2-sulfonamide (Step 1; 149 mg; 0.42 mmol) and tert-butyl 6-fluoro-3-(4,4,5,5-tetramethyl-1,3,2-dioxaborolan-2-yl)-1H-indole-1-carboxylate (150 mg; 0.42 mmol), 120 mg (56%) of the title compound was obtained as a brown oil after purification by silica gel chromatography (petroleum ether/EtOAc=3/1-1/1, v/v). LC-MS: m/z 513.5 [M+H]$^+$ Step 3

Following the general method as outlined in Intermediate 10 Step 2, starting from tert-butyl 6-fluoro-3-(6-(N-(2-(methylsulfonamido)ethyl)sulfamoyl)pyridin-3-yl)-1H-indole-1-carboxylate (Step 2; 120 mg; 0.23 mmol), 18 mg (19%) of the title compound was obtained as a white solid after purification by preparative TLC (DCM/MeOH=20/1, v/v) and preparative HPLC (NH$_4$HCO$_3$ as additive). LC-MS: m/z 412.8 [M+H]$^+$. $^1$H NMR (400 MHz, DMSO-d$_6$) δ [ppm]: 11.80 (br s, 1H), 9.07 (d, J=2.2 Hz, 1H), 8.36 (dd, J=8.4, 2.2 Hz, 1H), 8.06 (d, J=2.2 Hz, 1H), 7.99-7.91 (m, 3H), 7.29 (dd, J=9.9, 2.4 Hz, 1H), 7.09 (br t, 1H), 7.03 (ddd, J=9.6, 8.7, 2.4 Hz, 1H), 3.11-2.99 (m, 4H), 2.89 (s, 3H).

Example 89: 5-(6-fluoro-1H-indol-3-yl)-N-(2-(N-methylmethylsulfonamido)ethyl)pyridine-2-sulfonamide

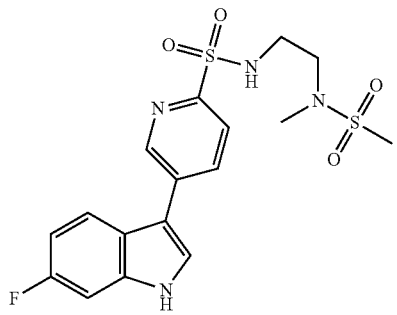 [SMILES: CN(CCNS(=O)(=O)c1ccc(-c2c[nH]c3cc(F)ccc23)cn1)S(C)(=O)=O]

Step 1: 5-bromo-N-(2-(N-methylmethylsulfona-mido)ethyl)pyridine-2-sulfonamide

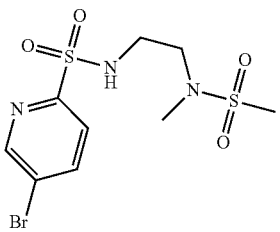 [SMILES: CN(CCNS(=O)(=O)c1ccc(Br)cn1)S(C)(=O)=O]

Following the general method as outlined in Example 87 Step 1, starting from N-(2-aminoethyl)-N-methylmethanesulfonamide hydrochloride (434 mg; 2.30 mmol), 5-bromopyridine-2-sulfonyl chloride (590 mg; 2.30 mmol), 690 mg (81%) of the title compound was obtained as a white solid after purification by a silica gel chromatography (petroleum ether/EtOAc=3/1-1/1, v/v). $^1$H NMR (400 MHz, CDCl$_3$) δ [ppm]: 8.74 (d, J=2.2 Hz, 1H), 8.05 (dd, J=8.4, 2.2 Hz, 1H), 7.88 (d, J=8.4 Hz, 1H), 5.26 (t, J=5.6 Hz, 1H), 3.42-3.35 (m, 2H), 3.35-3.29 (m, 2H), 2.90 (s, 3H), 2.85 (s, 3H).

Step 2: tert-butyl 6-fluoro-3-(6-(N-(2-(N-methylmethylsulfonamido)ethyl)sulfamoyl)pyridin-3-yl)-1H-indole-1-carboxylate

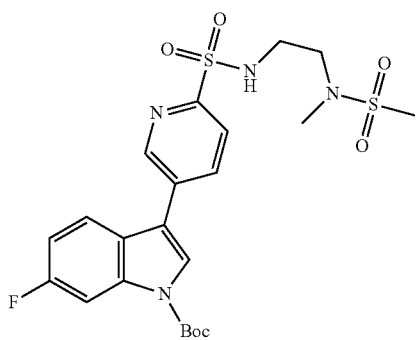 [SMILES: CN(CCNS(=O)(=O)c1ccc(-c2cn(C(=O)OC(C)(C)C)c3cc(F)ccc23)cn1)S(C)(=O)=O]

Following the general method as outlined in Example 74, starting from 5-bromo-N-(2-(N-methylmethylsulfonamido)ethyl)pyridine-2-sulfonamide (Step 1; 155 mg; 0.42 mmol) and tert-butyl 6-fluoro-3-(4,4,5,5-tetramethyl-1,3,2-dioxaborolan-2-yl)-1H-indole-1-carboxylate (150 mg; 0.42 mmol), 130 mg (59%) of the title compound was obtained as a brown solid after purification by a silica gel chromatography (petroleum ether/EtOAc=3/1-1/1, v/v). LC-MS: m/z 527.8 [M+H]$^+$.

Step 3

Following the general method as outlined in Intermediate 10 Step 2, starting from tert-butyl 6-fluoro-3-(6-(N-(2-(N-methylmethylsulfonamido)ethyl)sulfamoyl)pyridin-3-yl)-1H-indole-1-carboxylate (Step 2; 130 mg; 0.25 mmol), 25 mg (24%) of the title compound was obtained as a white solid after purification by preparative TLC (DCM/MeOH=20/1, v/v). LC-MS: m/z 426.8 [M+H]$^+$. $^1$H NMR (400 MHz, DMSO-d$_6$) δ [ppm]: 11.80 (br s, 1H), 9.07 (d, J=2.2 Hz, 1H), 8.36 (dd, J=8.4, 2.2 Hz, 1H), 8.06 (d, J=2.4 Hz, 1H), 8.02-7.91 (m, 3H), 7.29 (dd, J=9.7, 2.4 Hz, 1H), 7.03 (ddd, J=9.6, 8.7, 2.4 Hz, 1H), 3.20-3.12 (m, 4H), 2.88 (s, 3H), 2.77 (s, 3H).

Example 90: 6-fluoro-3-(6-((4-(methylsulfonyl)piperazin-1-yl)sulfonyl)pyridin-3-yl)-1H-indole

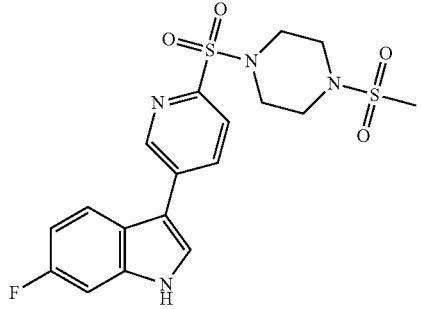 [SMILES: CS(=O)(=O)N1CCN(S(=O)(=O)c2ccc(-c3c[nH]c4cc(F)ccc34)cn2)CC1]

Step 1: 1-((5-bromopyridin-2-yl)sulfonyl)-4-(methylsulfonyl)piperazine

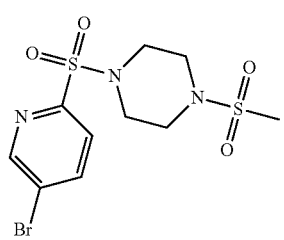 [SMILES: CS(=O)(=O)N1CCN(S(=O)(=O)c2ccc(Br)cn2)CC1]

Following the general method as outlined in Example 87 Step 1, starting from 1-(methylsulfonyl)piperazine (154 mg; 0.94 mmol), 5-bromopyridine-2-sulfonyl chloride (200 mg; 0.78 mmol), 280 mg (93%) of the title compound was obtained as a white solid after purification by reslurry with water/MeOH (5 mL/5 mL). LC-MS: m/z 383.7 [M+H]$^+$. $^1$H NMR (300 MHz, DMSO-d$_6$) δ [ppm]: 8.94 (d, J=2.2 Hz, 1H), 8.40 (dd, J=8.4, 2.2 Hz, 1H), 7.88 (d, J=8.4 Hz, 1H), 3.34-3.25 (m, 4H), 3.24-3.16 (m, 4H), 2.90 (s, 3H).

Step 2: tert-butyl 6-fluoro-3-(6-((4-(methylsulfonyl)piperazin-1-yl)sulfonyl)pyridin-3-yl)-1H-indole-1-carboxylate

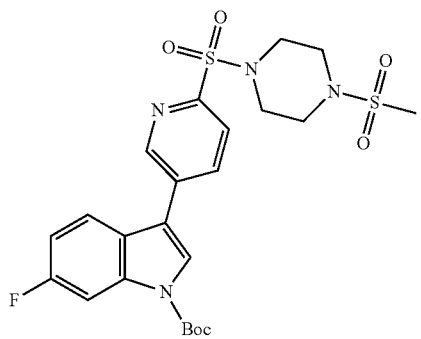 [SMILES: CC(C)(C)OC(=O)n1cc(-c2ccc(S(=O)(=O)N3CCN(S(C)(=O)=O)CC3)nc2)c2ccc(F)cc21]

Following the general method as outlined in Example 74, starting from 1-((5-bromopyridin-2-yl)sulfonyl)-4-(methylsulfonyl)piperazine (Step 1; 160 mg; 0.42 mmol) and tert-butyl 6-fluoro-3-(4,4,5,5-tetramethyl-1,3,2-dioxaborolan-2-yl)-1H-indole-1-carboxylate (150 mg; 0.42 mmol), 120 mg (54%) of the title compound was obtained as a brown oil after purification by a silica gel chromatography (petroleum ether/EtOAc=10/1-2/1, v/v). LC-MS: m/z 539.8 [M+H]$^+$.

Step 3

Following the general method as outlined in Intermediate 10 Step 2, starting from tert-butyl 6-fluoro-3-(6-((4-(methylsulfonyl)piperazin-1-yl)sulfonyl)pyridin-3-yl)-1H-indole-1-carboxylate (Step 2; 120 mg; 0.22 mmol), 24 mg (25%) of the title compound was obtained as a white solid after purification by preparative HPLC. LC-MS: m/z 438.8 [M+H]$^+$. $^1$H NMR (400 MHz, DMSO-d$_6$) δ [ppm]: 11.83 (br s, 1H), 9.12 (d, J=2.2 Hz, 1H), 8.40 (dd, J=8.4, 2.2 Hz, 1H), 8.08 (d, J=2.4 Hz, 1H), 7.98 (dd, J=8.8, 5.3 Hz, 1H), 7.94 (d, J=8.4 Hz, 1H), 7.29 (dd, J=10.0, 2.4 Hz, 1H), 7.03 (ddd, J=9.8, 8.8, 2.4 Hz, 1H), 3.36-3.30 (m, 4H), 3.26-3.19 (m, 4H), 2.90 (s, 3H).

Example 91: 5-(6-fluoro-1H-indol-3-yl)-N-methyl-N-(2-(methylsulfonamido)ethyl)pyridine-2-sulfonamide

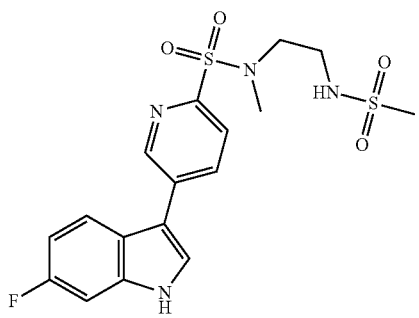 [SMILES: CN(CCNS(C)(=O)=O)S(=O)(=O)c1ccc(-c2c[nH]c3cc(F)ccc23)cn1]

Step 1: 5-bromo-N-methyl-N-(2-(methylsulfonamido)ethyl)pyridine-2-sulfonamide

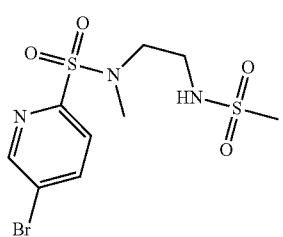 [SMILES: CN(CCNS(C)(=O)=O)S(=O)(=O)c1ccc(Br)cn1]

A mixture of 5-bromo-pyridine-2-sulfonyl chloride (257 mg; 1.00 mmol), N-(2-(methylamino)ethyl)methanesulfonamide hydrochloride (207 mg; 1.10 mmol) and Et$_3$N (152 mg; 1.50 mmol) in DCM (10 mL) was stirred at room temperature for 3 hours. The reaction mixture was concentrated and purified by a silica gel chromatography (petroleum ether/EtOAc=5/1-2/1, v/v) to afford 320 mg (86%) of the title compound as a yellow solid. $^1$H NMR (300 MHz, CDCl$_3$) δ [ppm]: 8.78 (d, J=2.2 Hz, 1H), 8.08 (dd, J=8.4, 2.2 Hz, 1H), 7.89 (d, J=8.4 Hz, 1H), 5.94 (br s, 1H), 3.60 (t, J=5.5 Hz, 2H), 3.48-3.35 (m, 2H), 3.02 (s, 3H), 2.91 (s, 3H).

Step 2: tert-butyl 6-fluoro-3-(6-(N-methyl-N-(2-(methylsulfonamido)ethyl)sulfamoyl)pyridin-3-yl)-1H-indole-1-carboxylate

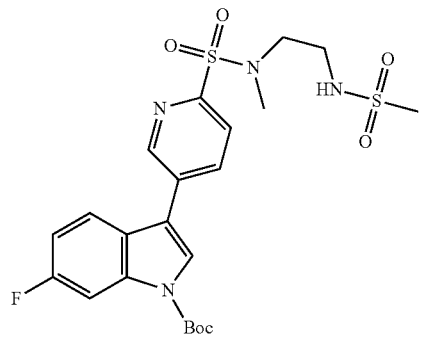 [SMILES: CN(CCNS(C)(=O)=O)S(=O)(=O)c1ccc(-c2cn(C(=O)OC(C)(C)C)c3cc(F)ccc23)cn1]

A mixture 5-bromo-N-methyl-N-(2-(methylsulfonamido)ethyl)pyridine-2-sulfonamide (Step 1; 154 mg; 0.41 mmol), tert-butyl 6-fluoro-3-(4,4,5,5-tetramethyl-1,3,2-dioxaborolan-2-yl)-1H-indole-1-carboxylate (150 mg; 0.42 mmol), K$_2$CO$_3$ (172 mg; 1.25 mmol) and Pd(dppf)Cl$_2$ (15.2 mg; 0.021 mmol) in dioxane (10 mL) and water (2 mL) was stirred at 100° C. for 3 hours under nitrogen. The mixture was cooled, diluted with EtOAc (60 mL), washed with brine (30 mL×2), dried over anhydrous Na$_2$SO$_4$, filtered, concentrated, and purified by a silica gel chromatography (petroleum ether/EtOAc=5/1 to EtOAc, v/v) to afford 66 mg (37%) of the title compound as a light yellow oil. LC-MS: m/z 426.8 [M+H]$^+$. $^1$H NMR (400 MHz, DMSO-d$_6$) δ [ppm]: 11.83 (br s, 1H), 9.10 (d, J=2.2 Hz, 1H), 8.38 (dd, J=8.3, 2.2 Hz, 1H), 8.08 (d, J=2.4 Hz, 1H), 7.97 (dd, J=8.8, 5.3 Hz, 1H), 7.94 (d, J=8.3 Hz, 1H), 7.29 (dd, J=9.8, 2.4 Hz, 1H), 7.21 (t, J=5.8 Hz, 1H), 7.03 (ddd, J=9.7, 8.8, 2.4 Hz, 1H), 3.32 (t, J=6.8 Hz, 2H), 3.17 (td, J=6.8, 5.8 Hz, 2H), 2.93 (s, 3H), 2.88 (s, 3H).

Example 92: N-(2-(5-(6-fluoro-1H-indol-3-yl)pyridine-2-sulfonamido)ethyl)acetamide

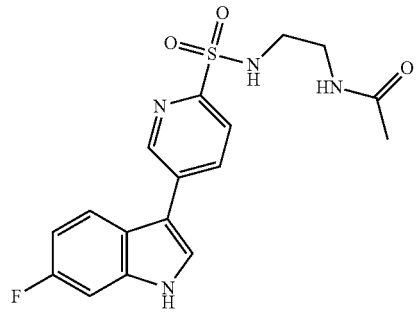 [SMILES: CC(=O)NCCNS(=O)(=O)c1ccc(-c2c[nH]c3cc(F)ccc23)cn1]

Step 1: N-(2-(5-bromopyridine-2-sulfonamido)ethyl)acetamide

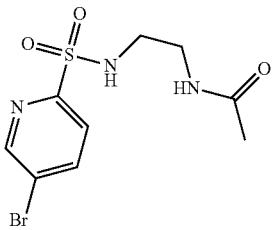 [SMILES: CC(=O)NCCNS(=O)(=O)c1ccc(Br)cn1]

A mixture of 5-bromo-pyridine-2-sulfonyl chloride (200 mg; 0.78 mmol), N-(2-aminoethyl)acetamide (95 mg; 0.93 mmol) and Et$_3$N (79 mg; 0.78 mmol) in DCM (10 mL) was stirred at room temperature for 3 hours. The resulting precipitate was collected by vacuum filtration, reslurried with MeOH/water (5 mL/5 mL), and filtered to afford 230 mg (92%) of the crude title compound as an off-white solid, which was used directly without further purification. $^1$H NMR (300 MHz, DMSO-d$_6$) δ [ppm]: 8.89 (d, J=2.2 Hz, 1H), 8.35 (dd, J=8.4, 2.2 Hz, 1H), 8.03 (br s, 1H), 7.86 (d, J=8.4 Hz, 1H), 7.87 (br s, 1H), 3.13-3.01 (m, 2H), 3.00-2.89 (m, 2H), 1.74 (s, 3H).

Step 2: tert-butyl 3-(6-(N-(2-acetamidoethyl)sulfamoyl)pyridin-3-yl)-6-fluoro-1H-indole-1-carboxylate

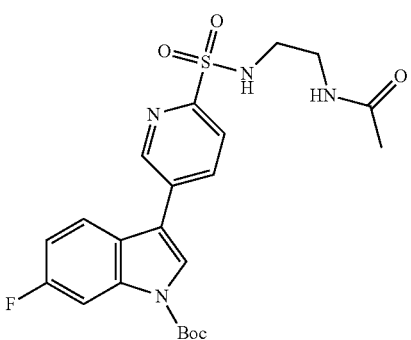 [SMILES: CC(=O)NCCNS(=O)(=O)c1ccc(-c2cn(C(=O)OC(C)(C)C)c3cc(F)ccc23)cn1]

A mixture N-(2-(5-bromopyridine-2-sulfonamido)ethyl) acetamide (Step 1; 140 mg crude; 0.43 mmol), tert-butyl 6-fluoro-3-(4,4,5,5-tetramethyl-1,3,2-dioxaborolan-2-yl)-1H-indole-1-carboxylate (189 mg; 0.52 mmol), K$_2$CO$_3$ (180 mg; 1.30 mmol) and Pd(dppf)Cl$_2$ (16 mg; 0.022 mmol) in dioxane (10 mL) and water (2 mL) was stirred at 100° C. for 2 hours under nitrogen. The mixture was cooled, diluted with EtOAc (60 mL), washed with brine (30 mL×2), dried over anhydrous Na$_2$SO$_4$, filtered, concentrated, and purified by a silica gel chromatography (petroleum ether/EtOAc=5/1 to EtOAc, v/v) to afford 105 mg (51%) of the title compound as a light yellow oil. LC-MS: m/z 477.2 [M+H]$^+$.

Step 3

Following the general method as outlined in Intermediate 10 Step 2, starting from tert-butyl 3-(6-(N-(2-acetamidoethyl)sulfamoyl)pyridin-3-yl)-6-fluoro-1H-indole-1-carboxylate (Step 2; 105 mg; 0.22 mmol), 48 mg (58%) of the title compound was obtained as a white solid after purification by preparative HPLC (NH$_4$HCO$_3$ additive). LC-MS: m/z 376.8 [M+H]$^+$. $^1$H NMR (400 MHz, DMSO-d$_6$) δ [ppm]: 11.79 (br s, 1H), 9.06 (d, J=2.2 Hz, 1H), 8.35 (dd, J=8.1, 2.2 Hz, 1H), 8.05 (s, 1H), 7.95 (dd, J=8.8, 5.3 Hz, 1H), 7.94 (d, J=8.4 Hz, 1H), 7.89-7.81 (m, 2H), 7.29 (dd, J=9.8, 2.4 Hz, 1H), 7.03 (ddd, J=9.7, 8.8, 2.4 Hz, 1H), 3.14-3.06 (m, 2H), 3.02-2.94 (m, 2H), 1.76 (s, 3H).

Example 93: 3-(6-(piperazin-1-ylsulfonyl)pyridin-3-yl)-1H-indole

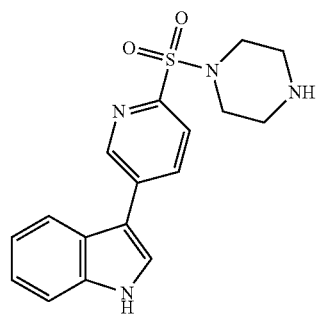 [SMILES: O=S(=O)(c1ccc(-c2c[nH]c3ccccc23)cn1)N1CCNCC1]

Following the general method as outlined in Example 87, the title compound was obtained as an off-white solid. LC-MS: m/z 342.9 [M+H]$^+$. $^1$H NMR (400 MHz, DMSO-d$_6$) δ [ppm]: 11.78 (br s, 1H), 9.14 (d, J=2.0 Hz, 1H), 8.40 (dd, J=8.1, 2.0 Hz, 1H), 8.09 (d, J=2.4 Hz, 1H), 7.98 (d, J=7.8 Hz, 1H), 7.91 (d, J=8.4 Hz, 1H), 7.51 (d, J=8.0 Hz, 1H), 7.28-7.14 (m, 2H), 3.15-3.02 (m, 4H), 2.79-2.67 (m, 4H).

Example 94: 5,6-difluoro-3-(6-(piperazin-1-ylsulfonyl)pyridin-3-yl)-1H-indole

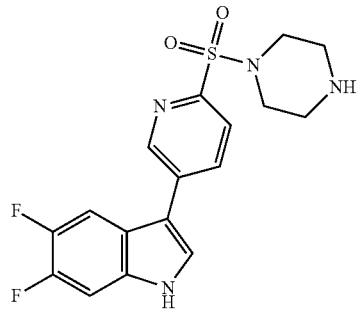 [SMILES: O=S(=O)(c1ccc(-c2c[nH]c3cc(F)c(F)cc23)cn1)N1CCNCC1]

Following the general method as outlined in Example 87, the title compound was obtained as a yellow solid. LC-MS: m/z 379.1 [M+H]$^+$. $^1$H NMR (400 MHz, DMSO-d$_6$) δ [ppm]: 11.93 (br s, 1H), 9.12 (d, J=2.2 Hz, 1H), 8.39 (dd, J=8.4, 2.2 Hz, 1H), 8.16 (s, 1H), 7.99 (d, J=11.6, 7.9 Hz, 1H), 7.90 (d, J=8.4 Hz, 1H), 7.53 (dd, J=10.8, 7.2 Hz, 1H), 3.15-3.02 (m, 4H), 2.80-2.67 (m, 4H), 2.41 (br s, 1H).

Example 95: 5-fluoro-3-(6-(piperazin-1-ylsulfonyl)pyridin-3-yl)-1H-indole

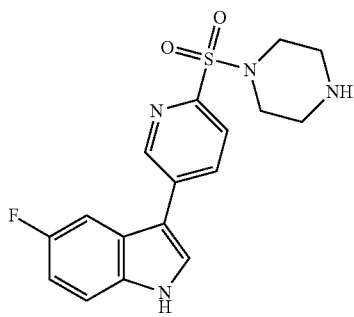 [SMILES: O=S(=O)(c1ccc(-c2c[nH]c3ccc(F)cc23)cn1)N1CCNCC1]

Following the general method as outlined in Example 87, the title compound was obtained as a white solid. LC-MS: m/z 361.1 [M+H]$^+$. $^1$H NMR (400 MHz, DMSO-d$_6$) δ [ppm]: 11.89 (br s, 1H), 9.12 (d, J=2.2 Hz, 1H), 8.39 (dd, J=8.4, 2.2 Hz, 1H), 8.17 (s, 1H), 7.90 (d, J=8.4 Hz, 1H), 7.75 (dd, J=10.6, 2.4 Hz, 1H), 7.52 (dd, J=8.8, 4.8 Hz, 1H), 7.08 (ddd, J=9.4, 8.8, 2.4 Hz, 1H), 3.14-3.03 (m, 4H), 2.80-2.67 (m, 4H), 2.36 (br s, 1H).

Example 96: 5-methyl-3-(6-(piperazin-1-ylsulfonyl)pyridin-3-yl)-1H-indole

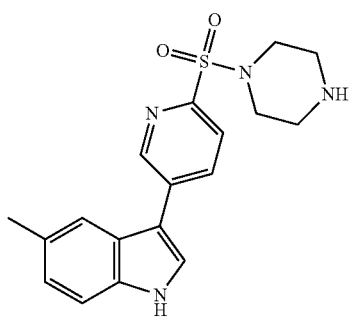 [SMILES: Cc1ccc2[nH]cc(-c3ccc(S(=O)(=O)N4CCNCC4)nc3)c2c1]

Following the general method as outlined in Example 87, the title compound was obtained as a white solid. LC-MS: m/z 357.2 [M+H]$^+$. $^1$H NMR (400 MHz, DMSO-d$_6$) δ [ppm]: 11.66 (br s, 1H), 9.12 (d, J=2.0 Hz, 1H), 8.38 (dd, J=8.4, 2.0 Hz, 1H), 8.02 (s, 1H), 7.91 (d, J=8.4 Hz, 1H), 7.78 (s, 1H), 7.39 (d, J=8.2 Hz, 1H), 7.05 (d, J=8.2 Hz, 1H), 3.10-3.05 (m, 4H), 2.80-2.66 (m, 4H), 2.44 (s, 3H), 2.24 (br s, 1H).

Example 97: 3-(6-(piperazin-1-ylsulfonyl)pyridin-3-yl)-1H-indole-5-carbonitrile

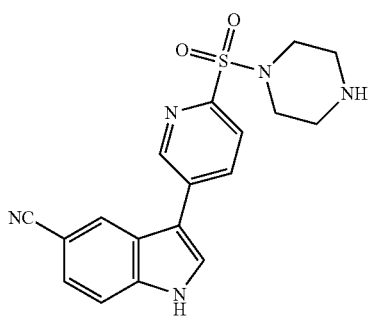 [SMILES: N#Cc1ccc2[nH]cc(-c3ccc(S(=O)(=O)N4CCNCC4)nc3)c2c1]

Following the general method as outlined in Example 87, the title compound was obtained as a white solid. LC-MS: m/z 367.8 [M+H]$^+$. $^1$H NMR (400 MHz, DMSO-d$_6$) δ [ppm]: 9.17 (d, J=2.0 Hz, 1H), 8.53 (s, 1H), 8.48 (dd, J=8.4, 2.0 Hz, 1H), 8.29 (s, 1H), 7.93 (d, J=8.4 Hz, 1H), 7.69 (d, J=8.4 Hz, 1H), 7.58 (d, J=8.4 Hz, 1H), 3.14-3.04 (m, 4H), 2.80-2.68 (m, 4H).

Example 98: 6-methyl-3-(6-(piperazin-1-ylsulfonyl)pyridin-3-yl)-1H-indole

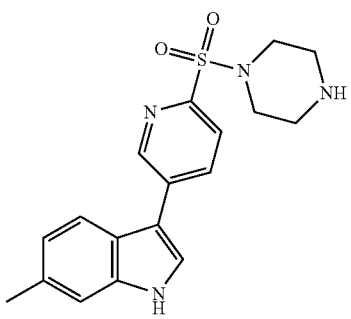 [SMILES: Cc1ccc2c(-c3ccc(S(=O)(=O)N4CCNCC4)nc3)c[nH]c2c1]

Following the general method as outlined in Example 87, the title compound was obtained as an off-white solid. LC-MS: m/z 356.9 [M+H]$^+$. $^1$H NMR (400 MHz, DMSO-d$_6$) δ [ppm]: 11.64 (br s, 1H), 9.12 (d, J=2.2 Hz, 1H), 8.38 (dd, J=8.4, 2.2 Hz, 1H), 8.01 (d, J=2.4 Hz, 1H), 7.90 (d, J=8.2 Hz, 1H), 7.86 (d, J=8.2 Hz, 1H), 7.29 (s, 1H), 7.01 (d, J=8.4 Hz, 1H), 3.14-3.02 (m, 4H), 2.80-2.65 (m, 4H), 2.43 (s, 3H), 2.33 (br s, 1H).

Example 99: 3-(5-(6-fluoro-1H-indol-3-yl)pyridine-2-sulfonamido)propanamide

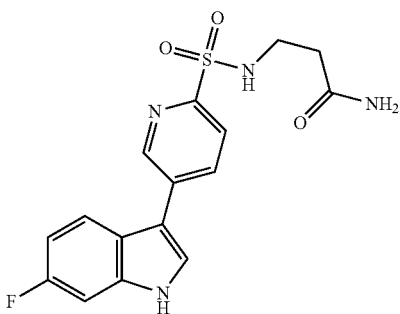 [SMILES: NC(=O)CCNS(=O)(=O)c1ccc(-c2c[nH]c3cc(F)ccc23)cn1]

Step 1:
3-(5-bromopyridine-2-sulfonamido)propanamide

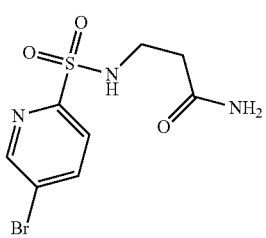 [SMILES: NC(=O)CCNS(=O)(=O)c1ccc(Br)cn1]

Following the general method as outlined in Example 87 Step 1, starting from 3-aminopropanamide (97 mg; 1.10 mmol) and 5-bromopyridine-2-sulfonyl chloride (256 mg; 1.00 mmol), 270 mg (88%) of the crude title compound was obtained as a white solid, which was used directly without further purification. ¹H NMR (400 MHz, DMSO-d₆) δ [ppm]: 8.90 (d, J=2.4 Hz, 1H), 8.35 (dd, J=8.4, 2.4 Hz, 1H), 7.97 (br s, 1H), 7.87 (d, J=8.4 Hz, 1H), 7.34 (br s, 1H), 6.85 (br s, 1H), 3.10 (t, J=7.2 Hz, 2H), 2.23 (t, J=7.2 Hz, 2H).

Step 2: tert-butyl 3-(6-(N-(3-amino-3-oxopropyl)sulfamoyl)pyridin-3-yl)-6-fluoro-1H-indole-1-carboxylate

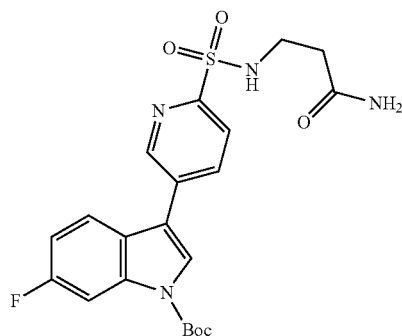 [SMILES: CC(C)(C)OC(=O)n1cc(-c2ccc(S(=O)(=O)NCCC(N)=O)nc2)c2ccc(F)cc21]

Following the general method as outlined in Example 74, starting from 3-(5-bromopyridine-2-sulfonamido)propanamide (Step 1; 170 mg crude; 0.55 mmol) and tert-butyl 6-fluoro-3-(4,4,5,5-tetramethyl-1,3,2-dioxaborolan-2-yl)-1H-indole-1-carboxylate (239 mg; 0.66 mmol), 110 mg (43%) of the title compound was obtained as a white solid after purification by a silica gel chromatography (petroleum ether/EtOAc=3/1-EtOAc, v/v). ¹H NMR (400 MHz, DMSO-d₆) δ [ppm]: 9.10 (d, J=2.2 Hz, 1H), 8.43 (dd, J=8.2, 2.2 Hz, 1H), 8.29 (s, 1H), 8.01 (d, J=8.2 Hz, 1H), 7.97 (dd, J=8.8, 5.3 Hz, 1H), 7.91 (dd, J=9.8, 2.2 Hz, 1H), 7.90 (br t, J=5.6 Hz, 1H), 7.34 (br s, 1H), 7.26 (ddd, J=9.7, 8.8, 2.2 Hz, 1H), 6.85 (br s, 1H), 3.15 (td, J=7.6, 5.6 Hz, 2H), 2.29 (t, J=7.6 Hz, 2H), 1.67 (s, 9H).

Step 3

Following the general method as outlined in Intermediate 10, starting from tert-butyl 3-(6-(N-(3-amino-3-oxopropyl)sulfamoyl)pyridin-3-yl)-6-fluoro-1H-indole-1-carboxylate (Step 2; 160 mg; 0.35 mmol), 46 mg (37%) of the title compound was obtained as a white solid after purification by preparative HPLC. LC-MS: m/z 362.8 [M+H]⁺. ¹H NMR (400 MHz, DMSO-d₆) δ [ppm]: 11.82 (br s, 1H), 9.08 (d, J=2.2 Hz, 1H), 8.36 (dd, J=8.2, 2.2 Hz, 1H), 8.07 (d, J=2.0 Hz, 1H), 7.97 (dd, J=8.8, 5.3 Hz, 1H), 7.95 (d, J=8.2 Hz, 1H), 7.82 (br t, J=5.6 Hz, 1H), 7.36 (br s, 1H), 7.29 (dd, J=9.8, 2.4 Hz, 1H), 7.03 (ddd, J=9.7, 8.8, 2.4 Hz, 1H), 6.87 (br s, 1H), 3.13 (td, J=7.6, 5.6 Hz, 2H), 2.28 (t, J=7.6 Hz, 2H).

Example 100: 5-(6-fluoro-1H-indol-3-yl)-N-(tetrahydro-2H-pyran-4-yl)pyridin-2-amine

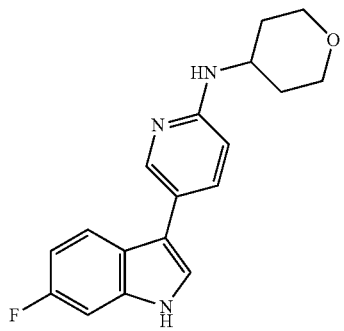

Step 1: 5-(6-fluoro-1-(phenylsulfonyl)-1H-indol-3-yl)-N-(tetrahydro-2H-pyran-4-yl)pyridin-2-amine

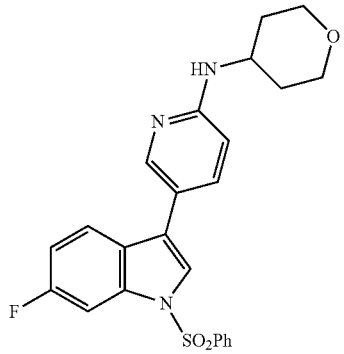

Following the general method as outlined in Example 23 Step 1, starting from 3-(6-bromopyridin-3-yl)-6-fluoro-1-(phenylsulfonyl)-1H-indole (Intermediate 11; 500 mg; 1.16 mmol) and tetrahydro-2H-pyran-4-amine (327 mg; 3.23 mmol), 582 mg (>100%) of the crude title compound was obtained as a brown oil, which was used directly without further purification. LC-MS: m/z 452.1. [M+H]⁺.

Step 2

Following the general method as outlined in Example 1, starting from 5-(6-fluoro-1-(phenylsulfonyl)-1H-indol-3-yl)-N-(tetrahydro-2H-pyran-4-yl)pyridin-2-amine (Step 1; 582 mg crude; 1.16 mmol), 52 mg (14%) of the title compound was obtained as an off-white solid after purification by preparative HPLC (NH₄HCO₃). LC-MS: m/z 311.9 [M+H]⁺. ¹H NMR (400 MHz, DMSO-d₆) δ [ppm]: 11.27 (br s, 1H), 8.26 (d, J=2.0 Hz, 1H), 7.71 (dd, J=8.8, 5.2 Hz, 1H), 7.65 (dd, J=8.4, 2.0 Hz, 1H), 7.50 (s, 1H), 7.17 (dd, J=9.9, 2.2 Hz, 1H), 6.90 (ddd, J=9.6, 8.8, 2.2 Hz, 1H), 6.57 (d, J=8.4 Hz, 1H), 6.46 (d, J=7.6 Hz, 1H), 4.00-3.88 (m, 1H), 3.93-3.87 (m, 2H), 3.47-3.36 (m, 2H), 1.95-1.86 (m, 2H), 1.51-1.37 (m, 2H).

Example 101: 3-(5-(6-fluoro-1H-indol-3-yl)-N-methylpyridine-2-sulfonamido)propanamide

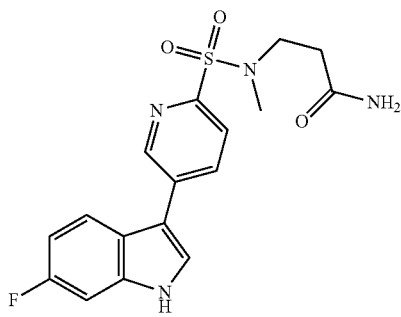 [SMILES: CN(CCC(N)=O)S(=O)(=O)c1ccc(-c2c[nH]c3cc(F)ccc23)cn1]

Step 1: 3-(5-bromo-N-methylpyridine-2-sulfonamido)propanamide

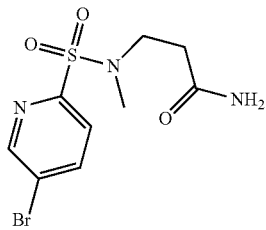 [SMILES: CN(CCC(N)=O)S(=O)(=O)c1ccc(Br)cn1]

Following the general method as outlined in Example 87 Step 1, starting from 3-(methylamino)propanamide (110 mg; 1.08 mmol; prepared as described in *Bio. Med. Chem.* 2001, 9, 665) and 5-bromopyridine-2-sulfonyl chloride (250 mg; 0.97 mmol), 300 mg (96%) of the title compound was obtained as a yellow solid after purification by a silica gel chromatography (petroleum ether/EtOAc=5/1, v/v). LC-MS: m/z 322.2 [M+H]+.

Step 2: tert-butyl 3-(6-(N-(3-amino-3-oxopropyl)-N-methylsulfamoyl)pyridin-3-yl)-6-fluoro-1H-indole-1-carboxylate

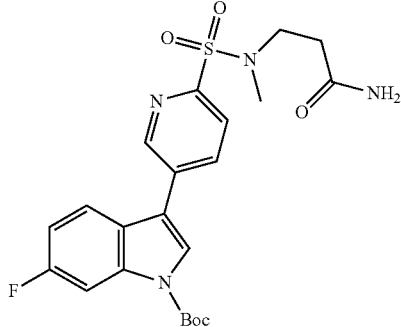 [SMILES: CN(CCC(N)=O)S(=O)(=O)c1ccc(-c2cn(C(=O)OC(C)(C)C)c3cc(F)ccc23)cn1]

Following the general method as outlined in Example 74, starting from 3-(5-bromo-N-methylpyridine-2-sulfonamido)propanamide (Step 1; 300 mg; 0.93 mmol) and tert-butyl 6-fluoro-3-(4,4,5,5-tetramethyl-1,3,2-dioxaborolan-2-yl)-1H-indole-1-carboxylate (506 mg; 1.40 mmol), 147 mg (33%) of the title compound was obtained as a yellow oil after purification by preparative TLC (EtOAc). LC-MS: m/z 477.1 [M+H]+. $^1$H NMR (400 MHz, DMSO-$d_6$) δ [ppm]: 9.14 (s, 1H), 8.45 (d, J=8.0 Hz, 1H), 8.30 (s, 1H), 8.04-7.95 (m, 2H), 7.94-7.87 (m, 1H), 7.43 (br s, 1H), 7.31-7.22 (m, 1H), 6.92 (br s, 1H), 2.87 (s, 3H), 3.42 (t, J=7.2 Hz, 2H), 2.39 (t, J=7.2 Hz, 2H), 1.67 (s, 9H).

Step 3

Following the general method as outlined in Intermediate 10, starting from tert-butyl 3-(6-(N-(3-amino-3-oxopropyl)-N-methylsulfamoyl)pyridin-3-yl)-6-fluoro-1H-indole-1-carboxylate (Step 2; 147 mg; 0.31 mmol), 29 mg (25%) of the title compound was obtained as a white solid after purification by preparative HPLC (NH$_4$HCO$_3$). LC-MS: m/z 376.9 [M+H]+. $^1$H NMR (400 MHz, DMSO-$d_6$) δ [ppm]: 11.83 (br s, 1H), 9.11 (d, J=2.2 Hz, 1H), 8.38 (dd, J=8.2, 2.2 Hz, 1H), 8.08 (d, J=2.0 Hz, 1H), 7.98 (dd, J=8.8, 5.3 Hz, 1H), 7.93 (d, J=8.2 Hz, 1H), 7.42 (br s, 1H), 7.29 (dd, J=9.9, 2.4 Hz, 1H), 7.03 (ddd, J=9.6, 8.8, 2.4 Hz, 1H), 6.91 (br s, 1H), 3.41 (t, J=7.2 Hz, 2H), 2.85 (s, 3H), 2.38 (t, J=7.2 Hz, 2H).

II. Biology Examples

II.1. Assay for TDO2 Enzymatic Activity Determination

The compounds of formula I inhibit the enzymatic activity of human TDO2.

To measure the TDO2 activity, the procedure described in Dolusic et al. *J. Med. Chem.;* 2011, 54, 5320-533 was adapted: the reaction mixture contained (final concentrations) potassium phosphate buffer (50 mM, pH 7.5), ascorbic acid (0.25 M), methylene blue (0.125 μM), catalase (40 units/mL, from bovine liver, Sigma), and human recombinant TDO2 enzyme (prepared as described in Dolusic et al. *J. Med. Chem.;* 2011, 54, 5320-5334; 0.9 μg) without or with the compounds of the present invention at the indicated concentrations (total volume 112.5 μL). The reaction was initiated by the addition of 37.5 μL of L-Trp (final concentration 1 mM) at room temperature. The reaction was conducted at room temperature during one hour and stopped by the addition of 30 μL of 30% (w/v) trichloroacetic acid.

To convert N-formylkynurenine into kynurenine, the reaction mixture was incubated at 65° C. for 30 min. Then 150 μL of the reaction mixture was mixed with 120 μL of 2.5% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The TDO activity was measured as described above using ten serial concentrations of the compounds of the present invention. Data were fitted using the Prism™ software (GraphPad Software, Inc.) using standard software configurations.

The biological activity of representative Examples is summarized in the following table:

| Example number | IC$_{50}$ (nM) |
|---|---|
| 1 | 370 |
| 2 | 560 |
| 3 | 1200 |
| 4 | 39000 |
| 5 | 730 |
| 6 | 1300 |
| 7 | 380 |
| 9 | 540 |

| Example number | IC$_{50}$ (nM) |
| --- | --- |
| 10 | 720 |
| 11 | 650 |
| 13 | 1700 |
| 14 | 970 |
| 15 | 1100 |
| 16 | 1600 |
| 17 | 870 |
| 18 | 4800 |
| 19 | 650 |
| 20 | 870 |
| 21 | 620 |
| 22 | 1200 |
| 25 | 540 |
| 26 | 710 |
| 27 | 490 |
| 28 | 1500 |
| 30 | 1600 |
| 31 | 790 |
| 34 | 290 |
| 40 | 1000 |
| 44 | 850 |
| 45 | 860 |
| 46 | 13000 |
| 47 | 2800 |
| 48 | 4500 |
| 49 | 11000 |
| 78 | 16000 |

In one embodiment, compounds having an 1050<2000 nm, preferably compound having an 1050<1000 nm are selected.

II.2. Cellular Assay for TDO2 Activity Determination

II.2.a hTDO2-Overexpressing P815 Cells

The compounds of Formula I inhibit the activity of human TDO2 in cells.

The assay (adapted from Pilotte L et al., Proc Natl Acad Sci USA, 2012, 109(7), 2497-502) was performed in 96-well flat bottom plates seeded with murine mastocytoma P815 cells overexpressing hTDO2 (prepared as described in Pilotte et al., PNAS, 2012, 109(7), 2497-2502), at a concentration of 5×10$^4$ cells/well in a final volume of 200 μL. To determine TDO or IDO activity, the cells were incubated overnight at 37° C. at 5% CO$_2$ in IMDM (Invitrogen) supplemented with 2% FBS and 2% penicillin/streptomycin in the presence of the compounds of the present invention, at different concentrations. The cells may be obtained from the American Type Cuylture Collecion [ATCC® TIB-64™ or commercially, e.g., from Sigma-Aldrich or Life Technologies.]

The plates were then centrifuged 5 min at 1000 rpm, and 100 μL of the supernatant were collected in a conical plate, 30 uL of TCA 30% were added and a further centrifugated at 3000×g for 10 minutes. 100 μL of the supernatant were collected in a flat bottomed plate and 100 μL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The TDO activity was measured as described above using ten serial concentrations of the compounds of the present invention. Data were fitted using the Prism™ software (GraphPad Software, Inc.) using standard software configurations.

The biological activity of representative Examples is summarized in the following table:

| Example number | IC$_{50}$ (nM) |
| --- | --- |
| 1 | 180 |
| 4 | 680 |
| 5 | 120 |
| 7 | 320 |
| 8 | 490 |
| 9 | 210 |
| 10 | 130 |
| 11 | 650 |
| 13 | 550 |
| 14 | 610 |
| 15 | 130 |
| 17 | 1300 |
| 21 | 350 |
| 22 | 400 |
| 23 | 430 |
| 25 | 140 |
| 27 | 190 |
| 28 | 1000 |
| 29 | 240 |
| 30 | 1500 |
| 31 | 120 |
| 34 | 240 |
| 35 | 250 |
| 37 | 450 |
| 39 | 350 |
| 40 | 150 |
| 44 | 68 |
| 45 | 220 |
| 46 | 670 |
| 47 | 240 |
| 48 | 620 |
| 50 | 1000 |
| 51 | 850 |
| 52 | 120 |
| 54 | 160 |
| 55 | 290 |
| 56 | 240 |
| 61 | 170 |
| 69 | 260 |

In one embodiment, compounds having an 1050<2000 nm are selected. In another embodiment, compounds having an 1050<1000 nm are selected.

II.2.b A172 Cells

The compounds of formula I inhibit the activity of human TDO2 in cells that constitutively express TDO2, such as A172 cells. A172 is a cell line derived from human brain glioblastoma cells. The cells are available from the American Type Culture Collection (ATCC®) as CRL-1620™.

The assay (adapted from Pilotte L et al., Proc Natl Acad Sci USA, 2012, 109(7), 2497-502) was performed in 96-well flat bottom plates seeded with human glioblastoma A172 cells, naturally expressing hTDO2 (prepared as described in Tilman et al., Mol Cancer, 2007, 17(6), 80), at a concentration of 1.25×10$^4$ cells/well in a final volume of 200 μL. To determine TDO, the cells were incubated overnight at 37° C. at 5% CO$_2$ in IMDM (Invitrogen) supplemented with 2% FBS and 2% penicillin/streptomycin in the presence of the compounds of the present invention, at different concentrations.

The plates were then centrifuged 5 min at 1000 rpm, and 100 μL of the supernatant were collected in a conical plate, 30 uL of TCA 30% were added and a further centrifugated at 3000×g for 10 minutes. 100 μL of the supernatant were collected in a flat bottomed plate and 100 μL of 2% (w/v) 4-(dimethylamino)-benzaldehyde in acetic acid and incubated for 5 min at room temperature. Kynurenine concentrations were determined by measuring the absorbance at 480 nm. A standard curve was made with pure kynurenine. The TDO activity was measured as described above using ten serial concentrations of the compounds of the present invention. Data were fitted using the Prism™ software (GraphPad Software, Inc.) using standard software configurations.

The biological activity of representative Examples is summarized in the following table:

| Example number | IC$_{50}$ (nM) |
| --- | --- |
| 14 | 1800 |
| 23 | 490 |
| 34 | 1600 |
| 35 | 530 |
| 36 | 1100 |
| 38 | 740 |
| 40 | 130 |
| 42 | 520 |
| 44 | 600 |
| 54 | 420 |
| 55 | 990 |
| 56 | 640 |
| 57 | 1400 |
| 58 | 810 |
| 59 | 1400 |
| 60 | 700 |
| 61 | 990 |
| 62 | 1300 |
| 63 | 360 |
| 64 | 870 |
| 65 | 820 |
| 66 | 440 |
| 67 | 460 |
| 68 | 480 |
| 69 | 370 |
| 70 | 720 |
| 71 | 1400 |
| 72 | 4700 |
| 73 | 600 |
| 74 | 400 |
| 75 | 500 |
| 76 | 4100 |
| 77 | 2800 |
| 78 | 490 |
| 79 | 1200 |
| 80 | 310 |
| 81 | 2000 |
| 82 | 590 |
| 83 | 1500 |
| 85 | 2300 |
| 86 | 610 |
| 87 | 230 |
| 88 | 350 |
| 89 | 350 |
| 90 | 1400 |
| 91 | 270 |
| 92 | 330 |
| 93 | 200 |
| 94 | 240 |
| 95 | 370 |
| 96 | 530 |
| 97 | 2400 |
| 98 | 1400 |
| 99 | 370 |
| 100 | 620 |
| 101 | 360 |

In one embodiment, compounds having an IC50<2000 nm are selected. In another embodiment, compounds having an 1050<1000 nm are selected.

II.3. Pharmacodynamic Assay for TDO2 In Vivo Activity Determination: Increase of Blood Tryptophan Levels in Mice The compounds of the present invention increase the amount of Tryptophan in mouse blood. Briefly, female BALB/c mice (7-8 weeks old) were treated with either a suspension of one of the compounds of the present invention in 0.5% hydroxypropyl methyl cellulose (HPMC) K4M (4000 mPa·s (cPs), Methocell™, Dow chemical)/0.25% Tween® 20 (Sigma Aldrich) at different doses (30, 60 and 100 mg/kg), or with a vehicle control (0.5% HPMC K4M/0.25% Tween 20), by the oral route by gavage (dosing volume 5 mL/kg, 10 mice per group). After two hours, blood was harvested, plasma was prepared and the amount of Tryptophan present was determined by LC-MS-MS (HPLC column Unison UK-Phenyl, 75×4.6, 3 µm, flow rate 0.8 mL/min, 8 minutes gradient from 95% water+0.1% formic acid/5% Acetonitrile+0.1% formic acid to 5% water+0.1% formic acid/95% Acetonitrile+0.1% formic acid, retention time 2.4 min; API4000 MS-MS system from AB Sciex, ESI+ mode, parent ion 205.1, daughter ion 146.1).

The compound of Example 14 increased circulating Tryptophan by 33% at 30 mg/kg (p<0.01), by 61% at 60 mg/kg (p<0.0001) and by 70% at 100 mg/kg (p<0.0001) compared to vehicle-treated controls, as evidenced in the table below.

The compound of Example 87 increased circulating Tryptophan by 89% at 30 mg/kg (p<0.0001), by 137% at 60 mg/kg (p<0.0001) and by 143% at 100 mg/kg (p<0.0001) compared to vehicle-treated controls, as evidenced in the table below.

Tryptophan concentration in plasma (average±standard error of the mean):

|  | Vehicle | 30 mg/kg | 60 mg/kg | 100 mg/kg |
| --- | --- | --- | --- | --- |
| Example 14 | 20970 ± 1104 | 27976 ± 1196 | 33862 ± 1529 | 35716 ± 1663 |
| Example 87 | 21982 ± 1072 | 41632 ± 1675 | 52146 ± 2042 | 53447 ± 1695 |

All publications cited in this specification and priority applications including U.S. Provisional Patent Application No. 61/996,974, filed Feb. 12, 2014, are incorporated herein by reference. While the invention has been described with reference to particular embodiments, it will be appreciated that modifications can be made without departing from the spirit of the invention. Such modifications are intended to fall within the scope of the appended claims.

The invention claimed is:

1. A compound of Formula I:

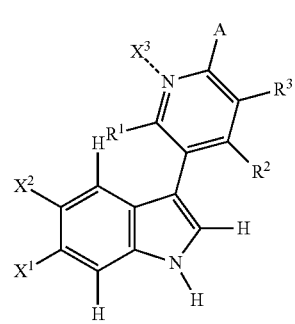

(I)

or a pharmaceutically acceptable enantiomer, salt or solvate thereof, wherein:
  $X^1$ and $X^2$ represent each independently H, halogen, C1-C6 alkyl, cyano, or haloalkyl;
  $X^3$ is absent or represents H, —O, or C1-C4 alkyl;
  $R^1$, $R^2$ and $R^3$ represent each independently H, halogen, C1-C6 alkyl, C1-C6 alkoxy, or C1-C6 haloalkyl, substituted C1-C6 alkyl, substituted C1-C6 alkoxy, or substituted C1-C6 haloalkyl, wherein the substituted alkyl, substituted alkoxy or substituted haloalkyl have one or more independently selected substituents consisting of halogen, hydroxyl, $OR^7$, $COOR^7$, $CONR^7R^8$, $NR^7COR^8$, $NR^7R^8$, $SO_2R^7$, $SO_2NR^7R^8$, $NR^7SO_2R^8$, $SO_2R^7$, aryl, CO—(C1-C6) alkyl, C1-C6 alkyl, or substituted C1-C6 alkyl which has one or more substituents selected from halogen, hydroxyl, amino or COOH; wherein $R^7$ and $R^8$ represent each independently a hydrogen atom or a group consisting of C1-C6 alkyl, C6-C12 aryl, arylalkyl, alkylaryl, C6 to C12 aryl, or amino;
  A represents
    $SO_2R^a$, wherein $R^a$ is amino, piperazine, piperazine substituted with $SO_2(C_1-C_4$ alkyl), or $NR^bR^{b''}$ wherein $R^b$ is H or $C_1-C_4$ alkyl and $R^{b''}$ is $CH_2CH_2CONH_2$, $CH_2$—$CH_2$—$N(H)(R^c)$—$R^d$ wherein $R^c$ is $SO_2$ or CO, and $R^d$ is $C_1-C_4$ alkyl or amino.

2. The compound according to claim 1, wherein when one or more of $R^4$, $R^5$ or $R^6$ is halogen, each is independently F, Cl or I.

3. The compound according to claim 2, wherein at least one of $R^4$, $R^5$ or $R^6$ is F.

4. The compound according to claim 1, wherein $X^3$ is absent or is C1 alkyl.

5. The compound according to claim 1, wherein X3 is absent.

6. A compound having Formula Ie:

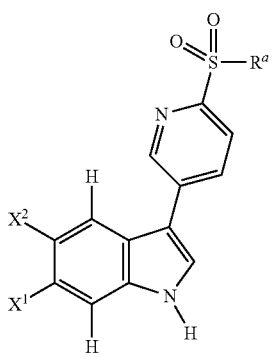

Ie or a pharmaceutically acceptable enantiomer, salt or solvate thereof, wherein
  X1 and X2 are each independently H, halogen, cyano, or C1-C4 alkyl and
  wherein $R^a$ is amino, piperazine, piperazine substituted with C1 alkyl, $SO_2(C_1-C_4$ alkyl), or $NR^bR^{b''}$ wherein $R^b$ is H or $C_1-C_4$ alkyl and $R^{b''}$ is $CH_2CH_2CONH_2$ or $CH_2$—$CH_2$—$N(H)(R^c)$—$R^d$, wherein $R^c$ is $SO_2$ or CO, and $R^d$ is $C_1-C_4$ alkyl or amino.

7. The compound according to claim 6, wherein $R^a$ is piperazine or piperazine substituted with C1 alkyl.

8. The compound according to claim 6, wherein $R^a$ is $NR^bR^{b''}$ wherein $R^b$ is H or $C_1-C_4$ alkyl and $R^{b''}$ is CH2-$CH_2$—$N(H)(R^c)$—$R^d$, wherein $R^c$ is $SO_2$ or CO, and $R^d$ is $C_1-C_4$ alkyl or amino.

9. The compound according to claim 6, wherein $R^b$ is C1 alkyl.

10. The compound according to claim 6, wherein $R^d$ is C1 alkyl or amino.

11. A compound selected from the group consisting of:
  6-fluoro-3-(6-(piperazin-1-ylsulfonyl)pyridin-3-yl)-1H-indole;
  5-(6-fluoro-1H-indol-3-yl)-N-(2-(methylsulfonamido)ethyl)pyridine-2-sulfonamide;
  5-(6-fluoro-1H-indol-3-yl)-N-(2-(N-methylmethylsulfonamido)ethyl)pyridine-2-sulfonamide;
  6-fluoro-3-(6-((4-(methylsulfonyl)piperazin-1-yl)sulfonyl)pyridin-3-yl)-1H-indole;
  5-(6-fluoro-1H-indol-3-yl)-N-methyl-N-(2-(methylsulfonamido)ethyl)pyridine-2-sulfonamide;
  N-(2-(5-(6-fluoro-1H-indol-3-yl)pyridine-2-sulfonamido)ethyl)acetamide;
  3-(6-(piperazin-1-yl sulfonyl)pyridin-3-yl)-1H-indole;
  5,6-difluoro-3-(6-(piperazin-1-ylsulfonyl)pyridin-3-yl)-1H-indole;
  5-fluoro-3-(6-(piperazin-1-ylsulfonyl)pyridin-3-yl)-1H-indole;
  5-methyl-3-(6-(piperazin-1-ylsulfonyl)pyridin-3-yl)-1H-indole;
  3-(6-(piperazin-1-yl sulfonyl)pyridin-3-yl)-1H-indole-5-carbonitrile;
  6-methyl-3-(6-(piperazin-1-ylsulfonyl)pyridin-3-yl)-1H-indole;
  3-(5-(6-fluoro-1H-indol-3-yl)pyridine-2-sulfonamido)propanamide;
  3-(5-(6-fluoro-1H-indol-3-yl)-N-methylpyridine-2-sulfonamido)-propanamide;
or a pharmaceutically acceptable enantiomer, salt or solvate thereof.

12. A pharmaceutical composition comprising a compound according to claim 1, or a pharmaceutically acceptable enantiomer, salt or solvate thereof, and at least one pharmaceutically acceptable carrier, diluent, excipient and/or adjuvant.

13. A pharmaceutical composition comprising a compound according to claim 11, or a pharmaceutically acceptable enantiomer, salt or solvate thereof, and at least one pharmaceutically acceptable carrier, diluent, excipient and/or adjuvant.

14. The composition according to claim 13, which comprises a free base form of the compound.

15. The composition according to claim 13, which comprises a salt form of the compound.

* * * * *